US012629370B2

(12) United States Patent
Rajasekhar et al.

(10) Patent No.: US 12,629,370 B2
(45) Date of Patent: *May 19, 2026

(54) TREATMENT OF PROSTATE CANCER

(71) Applicants: Sumitomo Pharma Co., Ltd., Osaka (JP); Takeda Pharmaceutical Company Limited, Osaka (JP)

(72) Inventors: Vijaykumar Reddy Rajasekhar, Apple Valley, CA (US); Brendan Mark Johnson, Chapel Hill, NC (US); David B. MacLean, Cambridge, MA (US); Lynn Seely, San Mateo, CA (US); Paul N. Mudd, Jr., Cary, NC (US); Hélène M. Faessel, Cambridge, MA (US)

(73) Assignees: Sumitomo Pharma Co., Ltd., Osaka (JP); Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/264,673

(22) Filed: Jul. 9, 2025

(65) Prior Publication Data

US 2025/0332166 A1 Oct. 30, 2025

Related U.S. Application Data

(63) Continuation of application No. 18/959,460, filed on Nov. 25, 2024, which is a continuation of application No. 18/937,891, filed on Nov. 5, 2024, now Pat. No. 12,336,990, which is a continuation of application No. 18/792,752, filed on Aug. 2, 2024, now abandoned, which is a continuation of application No. 17/866,203, filed on Jul. 15, 2022, now Pat. No. 12,097,198, which is a continuation of application No. 16/998,900, filed on Aug. 20, 2020, now Pat. No. 11,583,526, which is a continuation of application No. 16/563,161, filed on Sep. 6, 2019, now Pat. No. 10,786,501, which is a continuation of application No. 16/369,729, filed on Mar. 29, 2019, now Pat. No. 10,449,191, which is a continuation of application No. PCT/EP2017/074849, filed on Sep. 29, 2017.

(60) Provisional application No. 62/402,150, filed on Sep. 30, 2016, provisional application No. 62/402,004, filed on Sep. 30, 2016.

(51) Int. Cl.

| | |
|---|---|
| ***A61K 31/517*** | (2006.01) |
| ***A61K 9/00*** | (2006.01) |
| ***A61K 31/4164*** | (2006.01) |
| ***A61K 31/4166*** | (2006.01) |
| ***A61K 31/501*** | (2006.01) |
| ***A61K 31/513*** | (2006.01) |
| ***A61P 35/00*** | (2006.01) |

(52) U.S. Cl.

CPC .......... *A61K 31/501* (2013.01); *A61K 9/0053* (2013.01); *A61K 31/4166* (2013.01); *A61K 31/513* (2013.01); *A61P 35/00* (2018.01)

(58) Field of Classification Search

CPC .... A61K 31/517; A61K 31/4164; A61P 35/00
USPC .............................................. 514/260.1, 389
See application file for complete search history.

(56) References Cited

U.S. PATENT DOCUMENTS

| | | | |
|---|---|---|---|
| 5,573,777 | A | 11/1996 | Serpelloni et al. |
| 6,297,379 | B1 | 10/2001 | Furuya et al. |
| 6,340,686 | B1 | 1/2002 | Furuya et al. |
| 6,849,738 | B2 | 2/2005 | Fukuoka et al. |
| 7,056,927 | B2 | 6/2006 | Guo et al. |
| 7,176,211 | B2 | 2/2007 | Guo et al. |
| 7,300,935 | B2 | 11/2007 | Cho et al. |
| 7,419,983 | B2 | 9/2008 | Guo et al. |
| 7,569,570 | B2 | 8/2009 | Furuya et al. |
| 8,058,280 | B2 | 11/2011 | Cho et al. |
| 8,735,401 | B2 | 5/2014 | Cho et al. |
| 8,765,948 | B2 | 7/2014 | Gallagher et al. |
| 9,346,822 | B2 | 5/2016 | Cho et al. |
| 9,382,214 | B2 | 7/2016 | Gallagher et al. |
| 9,422,310 | B2 | 8/2016 | Beaton et al. |

(Continued)

FOREIGN PATENT DOCUMENTS

| | | | |
|---|---|---|---|
| CA | 2 978 223 | A1 | 9/2016 |
| CN | 115504994 | A | 12/2022 |

(Continued)

OTHER PUBLICATIONS

Albertsen, P.C. et al. (2014). "Cardiovascular morbidity associated with gonadotropin releasing hormone agonists and an antagonist," Europ. Urology 65:565-573.

(Continued)

*Primary Examiner* — Raymond J Henley, III
(74) *Attorney, Agent, or Firm* — Cooley LLP

(57) ABSTRACT

Methods for treating prostate cancer, including advanced prostate cancer, in a subject in need thereof, include administering once-daily to the subject, at least 80 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof. Another method includes: administering once-daily to the subject in need thereof, an oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; and thereafter administering once-daily to the subject, an oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]

(Continued)

pyrimidin-6-yl)phenyl)-N'-methoxyurea, or a corresponding amount of a pharmaceutically acceptable salt thereof.

20 Claims, 55 Drawing Sheets

(56) References Cited

U.S. PATENT DOCUMENTS

| | | | |
|---|---|---|---|
| 9,758,528 | B2 | 9/2017 | Fukuoka et al. |
| 10,150,778 | B2 | 12/2018 | Miwa |
| 10,350,170 | B2 | 7/2019 | Yamane et al. |
| 10,449,191 | B2 | 10/2019 | Rajasekhar et al. |
| 10,464,945 | B2 | 11/2019 | Miwa |
| 10,544,160 | B2 | 1/2020 | Miwa |
| 10,786,501 | B2 | 9/2020 | Rajasekhar et al. |
| 11,053,257 | B2 | 7/2021 | Miwa |
| 11,583,526 | B2 | 2/2023 | Rajasekhar et al. |
| 11,731,983 | B2 | 8/2023 | Miwa |
| 11,795,178 | B2 | 10/2023 | Fukuoka et al. |
| 12,097,198 | B2 | 9/2024 | Rajasekhar et al. |
| 12,144,809 | B1 | 11/2024 | Rajasekhar et al. |
| 12,180,224 | B2 | 12/2024 | Fukuoka et al. |
| 12,325,714 | B2 | 6/2025 | Miwa |
| 12,336,990 | B2 | 6/2025 | Rajasekhar et al. |
| 2003/0055269 | A1 | 3/2003 | Fukuoka et al. |
| 2005/0043315 | A1 | 2/2005 | Tsutsumi et al. |
| 2006/0160829 | A1 | 7/2006 | Cho et al. |
| 2009/0048273 | A1 | 2/2009 | Furuya et al. |
| 2009/0186890 | A1 | 7/2009 | Gellert et al. |
| 2009/0203622 | A1 | 8/2009 | Persson |
| 2011/0172249 | A1 | 7/2011 | Kamikawa et al. |
| 2017/0210753 | A1 | 7/2017 | Fukuoka et al. |
| 2019/0262346 | A1 | 8/2019 | Johnson et al. |
| 2020/0000730 | A1 | 1/2020 | Yamane et al. |
| 2024/0358700 | A1 | 10/2024 | Rajasekhar et al. |
| 2025/0051353 | A1 | 2/2025 | Miwa |
| 2025/0082632 | A1 | 3/2025 | Rajasekhar et al. |

FOREIGN PATENT DOCUMENTS

| | | | |
|---|---|---|---|
| CN | 115626933 | A | 1/2023 |
| EP | 1 319 409 | A1 | 6/2003 |
| EP | 2 329 823 | A1 | 6/2011 |
| WO | WO-00/56739 | A1 | 9/2000 |
| WO | WO-2004/067535 | A1 | 8/2004 |
| WO | WO-2010/026993 | A1 | 3/2010 |
| WO | WO-2014/051164 | A2 | 4/2014 |
| WO | WO-2016/030334 | A2 | 3/2016 |
| WO | WO-2016/136849 | A1 | 9/2016 |
| WO | WO-2017/040841 | A1 | 3/2017 |
| WO | WO-2018/060501 | A2 | 4/2018 |

OTHER PUBLICATIONS

Amin, M.L. (Aug. 2013). "P-glycoprotein Inhibition for Optimal Drug Delivery," Drug Target Insights 7:27-34.

Amory, J.K. et al. (2002). "Preoperative Supraphysiological Testosterone in Older Men Undergoing Knee Replacement Surgery," J Am Geriatr Soc. 50(10):1698-1701.

Maurice Ahsman, Hélène M. Faessel, Nelleke Snelder, David MacLean, and Peter Vis, *Modelling and Simulation of Oral GnRH Antagonist TAK-385 and Testosterone-Lowering Response in Prostate Cancer Patients to Optimized Trial Design and Dose Selection*, Annual Meeting of the Population Approach Group in Europe, Jun. 7-10, 2016; Abstract and Corresponding Poster.

Beckmann, W. (2000). "Seeding the desired polymorph: Background, possibilities, and case studies," Organic Process Research and Development 4(5):372-383.

Beer, T.M. et al. (Jul. 2014). "Enzalutamide in metastatic prostate cancer before chemotherapy," N. Engl. J. Med. 371(5):424-433.

Behre, H.M. et al. (May 1997). "High Loading and Low Maintenance Doses of a Gonadotropin-Releasing Hormone Antagonist Effectively Suppress Serum Luteinizing Hormone. Follicle-Stimulating Hormone, and Testosterone in Normal Men," Journal of Clinical Endocrinology and Metabolism 82(5):1403-1408.

Bernstein, J. (2002). "Polymorphism in molecular crystals," Clarendon Press, Oxford, p. 2 (11 total pages).

Brawer, M.K. et al. (2001). "Androgen deprivation and other treatments for advanced prostate cancer," Reviews in Urology 3 Suppl. 2(Suppl 2):S59-S68.

Breier, A. et al. (Sep. 2005). "P-glycoprotein—Implications of metabolism of neoplastic cells and cancer therapy," Curr. Cancer Drug Targets 5(6):457-468.

Brittain, H.G., ed. (1999). "Generation of polymorphs, hydrates, solvates, and amorphous solids," Polymorphism in Pharmaceutical Solids, pp. 183-226.

Byrn, S. et al. (1995). "Pharmaceutical solids: A strategic approach to regulatory considerations," Pharmaceutical Research 12(7):945-954.

Cancer.Org (2018). "Hormone therapy for prostate cancer," located at https://www.cancer.org/cancer/prostate-cancer/treating/hormone-therapy.html, 8 total pages.

ClinicalTrials.gov (2014). "Safety and Efficacy of TAK-385 for patients with localized prostate cancer," ID No. NCT02135445, located at https://clinicaltrials.gov/study/NCT02135445?term=NCT02135445&rank=1&tab=history&a=5, 13 total pages.

ClinicalTrials.gov (2014). "A Phase 2 Study to Evaluate the Safety and Efficacy of TAK-385, Together with a Leuprorelin Observational Cohort, in Participants with Prostate Cancer," ID No. NCT02083185, located at https://clinicaltrials.gov/study/NCT02083185?term=NCT02083185&rank=1&tab=history&a=8, 12 total pages.

ClinicalTrials.gov (2016). Bioavailability and Effect of Food on TAK-385 Tablet Formulations in Healthy Participants—Study Results—ClinicalTrials.gov, located at https://www.clinicaltrials.gov/ct2/show/results/NCT02396147?term=relugolix&rank=9.

ClinicalTrials.gov (2016). "Safety and Efficacy of TAK-385 for patients with localized prostate cancer," NCT02135445, located at https://clinicaltrials.gov/archive/NCT02135445/2016_06_02, 6 pages.

ClinicalTrials.gov (2017). NCT02135445, History of Changes for Study, Safety and Efficacy of TAK-385 for Patients with Localized Prostate Cancer, 20 total pages.

ClinicalTrials.gov (2016). "A Phase 2 Study to Evaluate the Safety and Efficacy of TAK-385, Together with a Leuprorelin Observational Cohort, in Participants with Prostate Cancer," NCT02083185, located at https://clinicaltrials.gov/archive/NCT02083185/2016_06_02, 4 pages.

*A Phase 1, Randomized, Open-Label Study of TAK-385, an Oral Gonadotropin-Releasing Hormone (GnRH) Antagonist in Japanese Patients with Androgen Deprivation Treatment-Naive Nonmetastatic Prostate Cancer*, Japan Registry of Clinical Trials (Jul. 9, 2015), https://jrct.niph.go.jp/pages/en-detail/49784/jRCT/3; jRCT Trial ID: jRCT2080222485; Japanese Publication and English Machine Translation.

A Study of TAK-385 in Hormone Treatment-naïve Participants with Prostate Cancer, Nat'l Inst. of Health, Dec. 15, 2015, https://clinicaltrials.gov/study/NCT02141659?term=NCT02141659%20&rank=1&tab=history&a=9; ClinicalTrials.gov ID NCT02141659.

Crawford (2011). "A Phase III Extension Trial With a 1-Arm Crossover from Leuprolide to Degarelix: Comparison of Gonadotropin-Releasing Hormone Agonist and Antagonist Effect on Prostate Cancer," J Urol. 186(3):889-897.

Crawford et al. (2014). "The Role of the FSH System in the Development and Progression of Prostate Cancer," The American Journal of Hematology/Oncology 10:5-13.

Crawford et al. (2017). "The potential role of follicle-stimulating hormone in the cardiovascular, metabolic, skeletal, and cognitive effects associated with androgen deprivation therapy," Urologic Oncology: Seminars and Original Investigations 35:183-191.

Dailymed (Jul. 15, 2013). Nilandron—Nilutamide Tablet. Located at https://dailymed.nlm.nih.gov/dailymed/drugInfo.cfm?setid=5ccf0e9a-8935-4c8c-b883-b4967281eb4a, retrieved on Feb. 10, 2025, 16 pages.

Dandona, P. et al. (2010). "A practical guide to male hypogonadism in the primary care setting," Int. J. Clin. Pract. 64:682-696.

(56) References Cited

OTHER PUBLICATIONS

D. Dearnaley, D.R. Saltzstein, J.E. Sylvester, L. Karsh, B.A. Mehlhaff, C. Pieczonka, J.L. Bailen, D.B. MacLean, H. Shi, H.M. Faessel, and N.D. Shore, *Phase 2 Study of Investigational Oral GnRH Antagonist TAK-385 (Relugolix) in Patients with Intermediate Risk Localized Prostate Cancer Requiring Neoadjuvant and Adjuvant Androgen Deprivation Therapy (ADT) with External Beam Radiation Therapy (EBRT): Results from the 12-Week Interim Analysis*, 7th European Multidisciplinary Meeting on Urological Cancers, Nov. 12-15, 2015; Abstract and Corresponding Poster.
De La Rosette, J. et al. (May 2011). "Efficacy and safety of androgen deprivation therapy after switching from monthly leuprolide to monthly degarelix in patients with prostate cancer," International Journal of Clinical Practice 65(5):559-566.
Épshtein, N.A. (2004). "Structure of chemical compounds, methods, of analysis and process control—Validation of HPLC Techniques for Pharmaceutical Analysis," Pharmaceutical Chemistry Journal 38(4):212-228.
Extended European Search Report mailed on Mar. 3, 2025, for EP Application No. 24 212 224.0, filed on Sep. 29, 2017, 17 pages.
H.M. Faessel, N. Snelder, M. Ahsman, D.B. MacLean, F. Saad, N.D. Shore, H. Shi, K. Venkatakrishnan, and P. Vis, *Quantitative Assessment of the Efficacy of TAK-385, an Investigational, Oral GnRH Antagonist in Prostate Cancer Patients (Pts) to Optimize Trial Design and Dose Selection*, 2016 Annual Meeting American Society for Clinical Pharmacology & Therapeutics (ASCPT), Mar. 8-12, 2016; Abstract and Corresponding Poster.
FDA Guidance for Industry (Feb. 2012). Drug Interaction Studies—Study Design, Data Analysis, Implication for Dosing, and Labeling Recommendations, Clinical Pharmacology, 79 pages.
Final Office Action mailed on Sep. 8, 2022, for U.S. Appl. No. 16/998,900, filed Aug. 20, 2020, 5 pages.
Finch, A. et al. (Aug. 2014). "P-glycoprotein and its role in drug-drug interactions" Aust. Prescr. 37(4):137-139.
Ganju, A. et al. (Apr. 2014). "Nanoways to overcome docetaxel resistance in prostate cancer," Drug Resistance Updates 17(1-2):13-23.
GenTech Scientific (Jul. 26, 2023). How does high-performance liquid chromatography work? The General Knowledge of a POSA regarding HPLC Located at https://gentechscientific.com/how-does-high-performance-liquid-chromatography-work-2/, retrieved on Feb. 10, 2025, 12 pages.
Giacomini, K.M. et al. (Mar. 2010). "Membrane transporters in drug development," Nat. Rev. Drug Discov. 9(3):215-236.
Gomella, L.G. (2009). "Effective Testosterone Suppression for Prostate Cancer: Is There a Best Castration Therapy?" Reviews in Urology 11(2):52-60.
Haleblian, J. et al. (Aug. 1969). "Pharmaceutical applications of polymorphism," J. Pharm. Sci. 58(8):911-929.
Hawach Scientific (Dec. 12, 2024). "Why is the C18 column mostly used in HPLC?" Located at https://www.hawachhplccolumn.com/news/why-is-c18-column-mostly-used-in-hplc/#:~:text=The%20C18%20column%20is%20popular,chemical%20stability%2C%20and%20widespread%20availability, retrieved on Feb. 10, 2025, 6 pages.
Hoare, D. et al. (2015). "Serum follicle-stimulating hormone levels predict time to development of castration-resistant prostate cancer," Can Urol Assoc J. 9:122-171.
ICH Impurities in New Drug Substances Q3A(R2) (Oct. 25, 2006). International Conference on Harmonization of Technical Requirements for Registration of Pharmaceuticals for Human Use, Geneva, Switzerland, EMEA, vol. 25, 15 pages.
ICH Impurities in New Drug Substances Q3B(R2) (2006). International Conference on Harmonization of Technical Requirements for Registration of Pharmaceuticals for Human Use, Geneva, Switzerland, EMEA, vol. 25, 16 pages.
ICH Tripartite (Nov. 2005). "Q2(R1) Validation of analytical procedures: Text and methodology," FDA, U.S. Department of Health and Human Services, 22 pages.
International Conference on Harmonisation (Dec. 2000). Guidance on Q6A Specifications: Test Procedures and Acceptance Criteria for New Drug Substances and New Drug Products: Chemical Substances Test Procedures and Acceptance Criteria for New Drug Substances and New Drug Products: Chemical Substances, FDA's Guidance for New Drug Substances, Federal Register, vol. 65, No. 251, 83041, 23 pages.
International Search Report mailed on Mar. 28, 2018, for PCT Application No. PCT/EP2017/074849, filed on Sep. 29, 2017, 5 pages.
Klotz, L. et al. (Dec. 2008). "The efficacy and safety of degarelix: a 12-month, comparative, randomized, open-label, parallel-group phase III study in patients with prostate cancer," BJU Int. 102(11):1531-1538.
Kostanski, J.W. et al. (2001). "Return to fertility after extended chemical castration with a GnRH antagonist," BMC Cancer 1:18, 7 pages.
David Burton MacLean, Hongliang Shi, Ajit Suri, Hélène Faessel, and Fred Saad, *Safety and Testosterone-Lowering Effects of the Investigational, Oral, GnRH Antagonist, TAK-385 in Healthy Male Volunteers: Results of a Phase 1 Inpatient/Outpatient Study*, Endocrine Society, Jun. 15-18, 2013, presentation No. SAT-318; Abstract and Corresponding Poster.
Maclean, D.B. et al. (2015). "Medical Castration Using the Investigational Oral GnRH Antagonist TAK-385 (Relugolix): Phase 1 Study in Healthy Males," Journal of Clinical Endocrinology and Metabolism 100:4579-4587.
Maggio, M. et al. (2012). "Effects of testosterone supplementation on clinical and rehabilitative outcomes in older men undergoing on-pump CABG," Conte. Clin. Trials 33:730-738.
Magnan, S. et al. (2015). "Intermittent vs Continuous Androgen Deprivation Therapy for Prostate Cancer: A Systematic Review and Meta-analysis," JAMA Oncol. 1:1261-1269.
Matrana, M.R. (2017). "Latitude and Stampede trials presented at ASCO 2017 offer refreshing, practicing-changing alternatives to upfront docetaxel for men with high-risk metastatic prostate cancer, but questions remain," Med. & Surg. Urol. 6:1000e120.
Mccutcheon, S.B. (May 2013). "Enzalutamide: a new agent for the prostate cancer treatment armamentarium," Journal of the Advanced Practitioner in Oncology 4(3):182-185.
Mealey, K.L. et al. (Jan. 2015). "P-Glycoprotein Mediated Drug Interactions in Animals and Humans with Cancer," J. Vet. Intern. Med. 29(1):1-6.
Mearini, L. et al. (Apr. 2011). "Intermittent Androgen Suppression in Prostate Cancer: Testosterone Levels and Its Implication," J. Sex. Med. 8(4):1218-1227.
Miranda, E.P. et al. (2017). "MP91-10 testosterone recovery profiles after cessation of androgen deprivation therapy," J. Urol. 197(4S):e1221-e1222, 2 total pages.
Miwa, K. et al. (2011). "Discovery of 1-{4-[1-(2,6-difluorobenzyl)-5-[(dimethylamino)methyl]-3-(6-methoxypyridazin-3-yl)-2,4-dioxo-1,2,3,4-tetrahydrothieno[2,3-d]pyrimidin-6-yl]phenyl}-3-methoxyurea (TAK-385) as a potent, orally active, non-peptide antagonist of the human gonadotropin-releasing hormone receptor," J. Med. Chem. 54:4998-5012.
Moul, J.W. (2015). "Hormone naïve prostate cancer: predicting and maximizing response intervals," Asian J Androl. 17:929-935.
Nakata, D. et al. (2014). "Suppression of the hypothalamic-pituitary-gonadal axis by TAK-385 (relugolix), a novel, investigational, orally active, small molecule gonadotropin-releasing hormone (GnRH) antagonist: studies in human GnRH receptor knock-in mice," Eurp. J. Pharmacol. 723:167-174.
Non-Final Office Action mailed on Feb. 12, 2020, for U.S. Appl. No. 16/563,161, filed Sep. 6, 2019, 6 pages.
Non-Final Office Action mailed on Apr. 8, 2022, for U.S. Appl. No. 16/998,900, filed Aug. 20, 2020, 6 pages.
Non-Final Office Action mailed on May 29, 2024, for U.S. Appl. No. 17/866,203, filed Jul. 15, 2022, 7 pages.
Non-Final Office Action mailed on Feb. 6, 2025, for U.S. Appl. No. 18/937,891, filed Nov. 5, 2024, 6 pages.
Notice of Allowance mailed on Jun. 18, 2019, for U.S. Appl. No. 16/369,729, filed Mar. 29, 2019, 7 pages.
Notice of Allowance Action mailed on May 21, 2020, for U.S. Appl. No. 16/563,161, filed Sep. 6, 2019, 5 pages.

(56) References Cited

OTHER PUBLICATIONS

Notice of Allowance mailed on Nov. 22, 2022, for U.S. Appl. No. 16/998,900, filed Aug. 20, 2020, 5 pages.
Notice of Allowance mailed on Jul. 18, 2024, for U.S. Appl. No. 17/866,203, filed Jul. 15, 2022, 5 pages.
Notice of Allowance mailed on Aug. 23, 2024, for U.S. Appl. No. 18/758,904, filed Jun. 28, 2024, 8 pages.
Notice of Allowance mailed on May 9, 2025, for U.S. Appl. No. 18/937,891, filed Nov. 5, 2024, 5 pages.
Orgovyx (2023). Highlights and Prescribing Information, located at https://www.myovant.com/wp-content/uploads/2022/10/NDA-214621-USPlandPI.pdf, 18 total pages.
Pahwa, R. et al. (2011). "Superdisintegrants in the development of orally disintegrating tablets: A review," IJPSR 2(11):2767-2780.
Paller, C.J. et al. (2013). "Management of biochemically recurrent prostate cancer after local therapy: Evolving standards of care and new directions," Clin. Adv. Hematol. Oncol. 11:14-23.
Papadasu, N. (Apr.-Jun. 2024). "A novel validated stability indicative UPLC method for Relugolix for the determination of process-related and degradation impurities," Rasayan Journal of Chemistry 17(2):325-336.
Pearlitol® 50 C Mannitol (2016-2025). Product Profile, located at https://www.roquette.com/innovation-hub/pharma/product-profile-pages/pearlitol-50c-mannitol, retrieved on Feb. 7, 2025, 4 pages.
Pham, T. et al. (Jun. 2016). "Advances in hormonal therapies for hormone naive and castration resistant prostate cancers with or without previous chemotherapy," Exp. Hematol. Oncol. 5:15, 11 pages.
Pilaniya, K. et al. (Jul. 2010). "Recent trends in the impurity profile of pharmaceuticals," Journal of Advanced Pharmaceutical Technology and Research 1(3):302-310.
Prostate Cancer UK (2018). Locally advanced prostate cancer, located at https://prostatecanceruk.org/media/2491080/locally_advanced_prostate_cancer-ifm.pdf, 12 total pages.
Pubchem (Feb. 23, 2016). Relugolix Impurity 17. PubChem CID 118378832. Located at https://pubchem.ncbi.nlm.nih.gov/compounds/118378832, retrieved on Feb. 10, 2025, 11 pages.
Rahman, N. et al. (Apr. 2006). "The importance of impurity analysis in pharmaceutical products: An integrated approach," Accreditation and Quality Assurance 11:69-74.
Request for Supplemental Examination of U.S. Pat. No. 10,449,191, Vijaykumar Reddy Rajasekhar et al., U.S. Appl. No. 96/050,044, filed Jun. 10, 2024, with Exhibits, 184 pages.—Terminated.
Request for Supplemental Examination of U.S. Pat. No. 10,786,501, Vijaykumar Reddy Rajasekhar et al., U.S. Appl. No. 96/050,045, filed Jun. 10, 2024, with Exhibits, 183 pages.—Terminated.
Request for Supplemental Examination of U.S. Pat. No. 11,583,526, Vijaykumar Reddy Rajasekhar et al., U.S. Appl. No. 96/050,046, filed Jun. 10, 2024, with Exhibits, 180 pages.—Terminated.
Saad, F. et al.: "Second interim analysis (IA2) results from a phase II trial of TAK-385, an oral GnRH antagonist, in prostate cancer patients (pts)", Journal of Clinical Oncology, Jan. 10, 2016.
Fred Saad, James L. Bailen, Christopher Michael Pieczonka, Daniel R. Saltzstein, Paul R. Sieber, David B. MacLean, Hongliang Shi, Hélène M. Faessel, and Neal D. Shore, *Second Interim Analysis (IA2) Results from a Phase II Trial of TAK-385, an Oral GnRH Antagonist, in Prostate Cancer Patients (Pts)*, American Society of Clinical Oncology Genitourinary Cancers Symposium, Jan. 7-9, 2016; Poster.
Shahidi, M. et al. (2001). "Recovery of serum testosterone, LH and FSH levels following neoadjuvant hormone cytoreduction and radical radiotherapy in localized prostate cancer," Clin. Oncol. 13:291-295.
Sharifi, N. et al. (Jul. 2005). "Androgen Deprivation Therapy for Prostate Cancer," JAMA 294(2):238-244.
Shore, N. et al. (2016). "PD28-01 testosterone lowering, PSA response and quality of life in patients with advanced hormone sensitive prostate cancer receiving TAK-385, an oral GNRH antagonist: phase 2 interim analysis," Journal of Urology 195(4S Suppl):e654, 1 total page.
Shore, N. et al. (2015). "S474 Abstracts 2502: TAK-385, an oral GnRH antagonist: efficacy and safety results from a randomized phase 2 trial in prostate cancer patients (pts)," 8049:31324-7.
Neal D. Shore, James L. Bailen, Christopher Pieczonka, David B. MacLean, Hongliang Shi, Hélène M. Faessel, Fred Saad, *TAK-385, an Oral GnRH Antagonist: Efficacy and Safety Results from a Randomized Phase 2 Trial in Prostate Cancer Patients*, Presentation at European Cancer Congress, Sep. 25-29, 2015.
Neal D. Shore, James L. Bailen, Christopher Pieczonka, David B. Maclean, Hongliang Shi, Hélène M. Faessel, and Fred Saad, TAK-385, *An Oral Gonadotropin-Releasing (GnRH) Antagonist: Efficacy and Safety Results from a Randomized Phase 2 Trial in Prostate Cancer Patients (Pts)*, Society of Urologic Oncology, Dec. 2-4, 2015; Abstract and Corresponding Poster.
Neal D. Shore, James L. Bailen, Christopher Pieczonka, Daniel R. Saltzstein, Paul R. Sieber, David B. MacLean, Hongliang Shi, Hélène M. Faessel, Huamao Mark Lin, Yanyan Zhu, and Fred Saad, *Testosterone Lowering, PSA Response and Quality of Life in Patients with Advanced Hormone-Sensitive Prostate Cancer Receiving TAK-385, an Oral GnRH Antagonist: Phase 2 Interim Analysis*, Presentation at American Urological Association 2016: Prostate Cancer: Advanced (Including Drug Therapy) I, May 6-10, 2016.
Shore, N.D. et al. (Feb. 2013). "Experience with degarelix in the treatment of prostate cancer," Ther. Adv. Urol. 5(1):11-24.
Spry, N.A. et al. (May 2006). "Adverse Effects to Quality of Life Arising from Treatment Can Recover with Intermittent Androgen Suppression in Men with Prostate Cancer," Eur. J. Cancer 42(8):1083-1092.
*Sumitomo Pharma Switzerland GmbH* et al v. *Apotex Inc.* et al, 1:25-cv-00311 (D. Del.), filed on Mar. 12, 2025.
*Sumitomo Pharma Switzerland GmbH* et al v. *Cipla Ltd.* et al, 1:25-cv-00312 (D. Del.), filed on Mar. 12, 2025.
*Sumitomo Pharma Switzerland GmbH* et al v. *Hetero Labs Ltd.* et al, 1:25-cv-00344 (D. Del.), filed on Mar. 19, 2025.
*Sumitomo Pharma Switzerland GmbH* et al v. *Aizant Drug Research Sols. Pvt. Ltd.*, 1:25-cv-00343 (D. Del.), filed on Mar. 19, 2025.
*Sumitomo Pharma Switzerland GmbH* et al v. *MSN Labs. Pvt. Ltd.*, et al, 1:25-cv-00345 (D. Del.), filed on Mar. 19, 2025.
*Sumitomo Pharma Switzerland GmbH* et al v. *Annora Pharma Pvt. Ltd.*, et al, 1:25-cv-00380 (D. Del.), filed on Mar. 27, 2025.
Supplemental Examination 96/050,044, Response to Notice of Non-Compliance with Exhibits 1-11, filed on Jul. 10, 2024, 414 pages.
Supplemental Examination 96/050,045, Response to Notice of Non-Compliance with Exhibits 1-11, filed on Jul. 10, 2024, 413 pages.
Supplemental Examination 96/050,046, Response to Notice of Non-Compliance with Exhibits 1-11, filed on Jul. 10, 2024, 406 pages.
Takeda Press Release. (2016). Roivant Sciences and Takeda launch Myovant Sciences to develop innovative therapeutics for women's health and prostate cancer, located at https://www.takeda.com/newsroom/newsreleases/2016/roivant-sciences-and-takeda-launch-myovant-sciences-to-develop-innovative-therapeutics-for-womens-health-and-prostate-cancer/, 2 total pages.
Takeda TAK-385 Clinical Study Report C27005 Synopsis (Nov. 25, 2014). "A Phase 1, Open-Label, Drug-Drug Interaction Study to Evaluate the Effects of Multiple Oral Doses of Fluconazole and Atorvastatin on the Pharmacokinetics of a Single Oral Dose of TAK-385 in Healthy Subjects," 5 pages.
Takeda TAK-385 Clinical Study Report TAK-385/CPH-010 (Jun. 21, 2013). "TAK-385/CPH-010: A phase 1, Open-Label, Drug-Drug Interaction Study to Evaluate the Effects of Multiple Oral Doses of Erythromycin on the Pharmacokinetics of a Single Oral Dose of TAK-385 in Healthy Adult Male and Female Subjects," 8 pages.
Tanaka, A. et al. (2009). "Pharmacological profile of TAK-385, an orally active gonadotropin releasing hormone (GNRH) antagonist," Fertility & Sterility P-86, p. S113.
Taylor, L.S. et al. (1999). "Amorphous solids," in Chapter 16: Polymorphism in Pharmaceutical Solids, pp. 587-629.
Texas Oncology (2019). Recurrent prostate cancer, located at https://www.texasoncology.com/types-of-cancer/prostate-cancer/recurrent-prostate-cancer, 5 total pages.

(56) References Cited

OTHER PUBLICATIONS

Threlfall, T.L. (Oct. 1995). "Analysis of organic polymorphs, A review," Analyst 120:2435-2460.
Tombal, B. et al. (2010). "Additional analysis of the secondary end point of biochemical recurrence rate in a phase 3 trial (CS21) comparing degarelix 80 mg versus leuprolide in prostate cancer patients segmented by baseline characteristics," Eur Urol 57(5):836-842.
Travison, T.G. et al. (2017). "Harmonized Reference Ranges for Circulating Testosterone Levels in Men of Four Cohort Studies in the United States and Europe," J. Clin. Endocrinol. Metab. 102:1161-1173.
Tsumura, H. et al. (2015). "Recovery of serum testosterone following neoadjuvant and adjuvant androgen deprivation therapy in men treated with prostate brachytherapy," World J. Radiol. 7:494-500.
Tukun, F-L. et al. (Dec. 2017). "Recent Development of Non-Peptide GnRH Antagonists," Molecules 22(12):2188, 25 pages.
Urology Care Foundation (2018). "What is advanced prostate cancer," located at https://www.urologyhealth.org/urologic-conditions/advanced-prostate-cancer, 15 total pages.
Van Poppel, H. et al. (Oct. 2008). "Degarelix: A novel gonadotropin-releasing hormone (GnRH) receptor blocker—results from a 1-year, multicentre, randomised, phase 2 dosage-finding study in the treatment of prostate cancer," Eur. Urol. 54(4):805-815.
Peter Vis, Nelleke Snelder, Maurice Ahsman, David MacLean, and Hélène Faessel, *Optimization of Trial Design and Dose Selection Based on the Quantitative Assessment of the Efficacy of TAK-385, an Investigational, Oral GnRH Antagonist, in Patients with Prostate Cancer*, World Conference on Pharmacometrics, Aug. 21-24, 2016; Abstract and Corresponding Presentation.
WebMD (2019). "Advanced prostate cancer: Frequently asked questions," 3 total pages.
Wessler, J.D. et al. (2013). "The P-glycoprotein transport system and cardiovascular drugs," JACC 61:2495-2502.
Written Opinion of the International Searching Authority mailed on Mar. 28, 2018, for PCT Application No. PCT/EP2017/074849, filed on Sep. 29, 2017, 8 pages.
U.S. Appl. No. 18/392,110, filed Dec. 21, 2023, by Migoya et al. (Copy not attached).
U.S. Appl. No. 18/792,752, filed Aug. 2, 2024, by Rajasekhar et al. (Copy not attached).
U.S. Appl. No. 18/797,045, filed Aug. 7, 2024, by Migoya et al. (Copy not attached).
U.S. Appl. No. 19/086,039, filed Mar. 20, 2025, by Migoya et al. (Copy not attached).
Amendment in Response to Non-Final Office Action for U.S. Appl. No. 13/242,541 (U.S. Pat. No. 8,735,401) dated Nov. 15, 2013, and Appendices, 43 pages.
Cannata, D.H. et al. (Feb. 2012). "Androgen deprivation therapy as primary treatment for prostate cancer," J. Clin. Endocrinol. Metab. 97(2):360-365.
ClinicalTrials.gov (Jul. 1, 2015). "Phase 2 Study to Evaluate the Safety and Efficacy of TAK-385, Together with a Leuprorelin Observational Cohort, in Participants with Prostate Cancer (C27002)," ID No. NCT02083185 version 8, 12 pages.
ClinicalTrials.gov (Jul. 1, 2015). Safety and Efficacy of TAK-385 for Patients with Localized Prostate Cancer (C27003), ID No. NCT02135445 version 5, 14 pages.
ClinicalTrials.gov (Aug. 11, 2015). "A Phase 1, Randomized, Open-Label Study of TAK-385, an Oral Gonadotropin-Releasing Hormone (GnRH) Antagonist in Japanese Patients with Androgen Deprivation Treatment-Naïve Nonmetastatic Prostate Cancer," Unique Protocol ID TAK-385/TB-AK160108, located at https://clinicaltrials.gov/study/NCT02141659?titles=NCT02141659&rank=1&tab=history&a=6, 9 total pages.
Degarelix Prescribing Information (2008). Tradename®, 16 pages.
European Association of Urology (EAU) (Mar. 2015). "Guidelines on prostate cancer," N. Mottet (Chair), 156 pages.
Federal Register (Dec. 29, 2000). "International Conference on Harmonisation; Guidance on Q6A Specifications: Test Procedures and Acceptance Criteria for New Drug Substances and New Drug Products: Chemical Substances," Food and Drug Administration, Federal Register 65(251):83041-83063.
ICH Harmonised Tripartite Guideline Q1A(R2) (Feb. 6, 2003). Stability testing of new drug substances and products, 20 pages.
Padiya, (2012). "Unprecedented "In Water" Imidazole Carbonylation: Paradigm Shift for Preparation of Urea and Carbamate," Org. Lett. 14(11):2814-2817.
Pulletikurthi, K.V.K.M. et al. (2022). "Force degradation studies of relugolix: identification, isolation and structure characterization of stress degradation products by using liquid chromatography-mass spectrometry, auto purification mass mediated preparative-high performance liquid chromatography, high resolution mass spectrometry, nuclear magnetic resonance spectroscopy," Spectroscopy Letters 55(2):128-137.
*Sumitomo Pharma Switzerland GmbH* et al. v. *Sandoz Inc.*, 1:25-cv-00970 (D. Del.), filed on Aug. 1, 2025.
Takeda Clinical Study Report C27001 Synopsis (Aug. 29, 2013). "Phase 1, Randomized, Double-Blind, Placebo-Controlled, Single and Multiple Dose, Inpatient and Outpatient Study in Healthy Men to Evaluate the Safety, Tolerability, Pharmacokinetics, and Efficacy for Testosterone Lowering of TAK 385, an Oral Gonadotropin-Releasing Hormone (GnRH) Antagonist," 7 pages.
Takeda Pharmaceutical Company Limited (2014). Financial Results for First Half of FY2014, Data Book, 31 pages.
Takeda Pharmaceutical Company Limited (Jul. 2015). Annual Report 2015, 84 pages.
U.S. Appl. No. 19/201,728, filed May 7, 2025, by Fukuoka et al. (Copy not attached).
Aulton's Pharmaceutics: The Design and Manufacture of Medicines, Fourth Edition, 2013, Eds., M.E. Aulton et al., Churchill Livingstone, Chapter 22—Dosage regimens, pp. 355-366.
ClinicalTrials.gov (May 6, 2016). "Safety and efficacy of TAK-385 for patients with localized prostate cancer," ID No. NCT02135445 V7, 14 pages.
ClinicalTrials.gov (May 6, 2016). "A Phase 2 Study to Evaluate the Safety and Efficacy of TAK-385, Together with a Leuprorelin Observational Cohort, in Participants with Prostate Cancer," ID No. NCT02083185 V9, 12 pages.
ClinicalTrials.gov (Jun. 9, 2016). "Bioavailability and Effect of Food on TAK-385 Tablet Formulations in Healthy Participants," ID No. NCT02396147 V3, 22 pages.
Maclean, D.B. et al. (2015). "Medical Castration Using the Investigational Oral GnRH Antagonist TAK-385 (Relugolix): Phase 1 Study in Healthy Males," Journal of Clinical Endocrinology and Metabolism 100:4579-4587, Supplemental Materials, 12 pages.
Notice of Opposition to a European Patent, Patent No. 3 518 932, Proprietor Sumitomo Pharma Switzerland GmbH and Takeda Pharmaceutical Company Limited, Opposition filed by ABG Intellectual Property Law, S.L. on Aug. 7, 2025, 31 pages.
Notice of Opposition to a European Patent, Patent No. 3 518 932, Proprietor Sumitomo Pharma Switzerland GmbH and Takeda Pharmaceutical Company Limited, Opposition filed by Sandoz AG on Aug. 7, 2025, 25 pages.
Presentation by Lawrence Drudge-Coates delivered at the British Ura-Oncology Group—British Association of Urological Nurses (BUG-BAUN) Joint Meeting, 2015, 27 pages.
Shore, N.D. (Jun. 4, 2020). "Oral relugolix for androgen-deprivation therapy in advanced prostate cancer," New Engl. J. Med. 382(23):2187-2196.
Submission by Patentee dated Dec. 15, 2021, in Response to the Communication Pursuant to Article 94(3) EPC dated Mar. 5, 2021, and Noting the Loss of Rights Pursuant to Rule 112(1) EPC dated Oct. 6, 2021, for EP Application No. 17 823 017.3, 7 pages.
Submission by Patentee dated Jul. 11, 2024, in Response to the Communication Pursuant to Article 94(3) EPC dated Jun. 3, 2024, for EP Application No. 17 823 017.3, 2 pages.
U.S. Appl. No. 62/402,004, filed Sep. 30, 2016, by Rajasekhar et al., 139 pages.
U.S. Appl. No. 62/402,150, filed Sep. 30, 2016, by Ditzler et al., 195 pages.

(56) References Cited

OTHER PUBLICATIONS

About ClinicalTrials. Gov (Jun. 7, 2024). National Library of Medicine (NIH), Retrieved on Dec. 4, 2025, located at https://clinicaltrials.gov/about-site/about-ctg, 6 pages.
About ClinicalTrials. Gov (Oct. 22, 2025). "Why should I register and submit results?" National Library of Medicine (NIH), Retrieved on Dec. 4, 2025, located at https://clinicaltrials.gov/policy/reporting-requirements, 8 pages.
FIRMAGON® Label (Feb. 2015). Degarelix for injection, 18 pages.
YouTube Video (Oct. 7, 2015). "Phase 2 trial of TAK-385, an oral GnRH antagonist, in prostate cancer," Video located at https://www.youtube.com/watch?v=4Y3tAL8Vnlo.

FIG. 2

| Variable / Visit | | Treatment | Summary Statistics | | | | | | | | 95%-CI | |
|---|---|---|---|---|---|---|---|---|---|---|---|---|
| | | | N | Mean | SD | Min | Q1 | Median | Q3 | Max | Lower | Upper |
| Serum Testosterone Concentrations (ng/ml) | Baseline | 80 mg | 15 | 6.367 | 1.9930 | 2.93 | 4.950 | 6.020 | 7.380 | 10.20 | 5.2630 | 7.4704 |
| | | 120 mg | 15 | 7.243 | 2.2424 | 3.17 | 5.540 | 7.240 | 9.800 | 10.70 | 6.0009 | 8.4844 |
| | WK1D2 | 80 mg | 15 | 0.975 | 0.5247 | 0.39 | 0.550 | 0.880 | 1.320 | 2.05 | 0.6841 | 1.2653 |
| | | 120 mg | 15 | 0.867 | 0.5835 | 0.43 | 0.560 | 0.670 | 0.900 | 2.66 | 0.5442 | 1.1905 |
| | WK1D4 | 80 mg | 15 | 0.384 | 0.0968 | 0.24 | 0.300 | 0.410 | 0.440 | 0.57 | 0.3304 | 0.4376 |
| | | 120 mg | 15 | 0.463 | 0.2313 | 0.28 | 0.360 | 0.400 | 0.470 | 1.25 | 0.3346 | 0.5907 |
| | WK2D1 | 80 mg | 15 | 0.285 | 0.0741 | 0.15 | 0.210 | 0.300 | 0.330 | 0.41 | 0.2443 | 0.3263 |
| | | 120 mg | 15 | 0.318 | 0.1165 | 0.17 | 0.230 | 0.300 | 0.430 | 0.59 | 0.2535 | 0.3825 |
| | WK3D1 | 80 mg | 15 | 0.207 | 0.0580 | 0.13 | 0.160 | 0.200 | 0.240 | 0.33 | 0.1752 | 0.2395 |
| | | 120 mg | 15 | 0.235 | 0.0925 | 0.13 | 0.150 | 0.220 | 0.280 | 0.44 | 0.1834 | 0.2859 |
| | WK5D1 | 80 mg | 15 | 0.213 | 0.0701 | 0.12 | 0.160 | 0.200 | 0.260 | 0.36 | 0.1745 | 0.2521 |
| | | 120 mg | 15 | 0.190 | 0.0670 | 0.09 | 0.140 | 0.170 | 0.240 | 0.33 | 0.1529 | 0.2271 |
| | WK9D1 | 80 mg | 15 | 0.195 | 0.0554 | 0.13 | 0.140 | 0.200 | 0.250 | 0.29 | 0.1647 | 0.2260 |
| | | 120 mg | 15 | 0.191 | 0.0818 | 0.10 | 0.130 | 0.170 | 0.240 | 0.39 | 0.1454 | 0.2360 |
| | WK13D1 | 80 mg | 12 | 0.216 | 0.0786 | 0.14 | 0.150 | 0.195 | 0.255 | 0.38 | 0.1659 | 0.2657 |
| | | 120 mg | 10 | 0.188 | 0.0634 | 0.13 | 0.140 | 0.175 | 0.200 | 0.33 | 0.1427 | 0.2333 |
| | WK17D1 | 80 mg | 8 | 0.210 | 0.0733 | 0.13 | 0.150 | 0.195 | 0.275 | 0.31 | 0.1487 | 0.2713 |
| | | 120 mg | 6 | 0.185 | 0.0712 | 0.13 | 0.130 | 0.150 | 0.260 | 0.29 | 0.1103 | 0.2597 |
| | WK21D1 | 80 mg | 4 | 0.180 | 0.0606 | 0.14 | 0.145 | 0.155 | 0.215 | 0.27 | 0.0836 | 0.2764 |
| | | 120 mg | 5 | 0.162 | 0.0507 | 0.13 | 0.130 | 0.140 | 0.160 | 0.25 | 0.0991 | 0.2249 |
| | WK25D1 | 80 mg | 3 | 0.143 | 0.0115 | 0.13 | 0.130 | 0.150 | 0.150 | 0.15 | 0.1146 | 0.1720 |
| | | 120 mg | 3 | 0.187 | 0.0814 | 0.13 | 0.130 | 0.150 | 0.280 | 0.28 | -0.0157 | 0.3890 |
| | WK37D1 | 80 mg | 0 | | | | | | | | | |
| | | 120 mg | 0 | | | | | | | | | |
| | WK49D1 | 80 mg | 0 | | | | | | | | | |
| | | 120 mg | 0 | | | | | | | | | |
| | WK61D1 | 80 mg | 0 | | | | | | | | | |
| | | 120 mg | 0 | | | | | | | | | |
| | WK73D1 | 80 mg | 0 | | | | | | | | | |
| | | 120 mg | 0 | | | | | | | | | |
| | WK85D1 | 80 mg | 0 | | | | | | | | | |
| | | 120 mg | 0 | | | | | | | | | |
| | WK97D1 | 80 mg | 0 | | | | | | | | | |
| | | 120 mg | 0 | | | | | | | | | |

FIG. 13

| Variable / Visit | | Treatment | Summary Statistics | | | | | | 95% CI | |
|---|---|---|---|---|---|---|---|---|---|---|
| | | | N | Mean | SD | Min | Median | Max | Lower | Upper |
| PSA (ng/mL) | Baseline | 80 mg | 3 | 6.7267 | 6.38138 | 0.990 | 5.5900 | 13.600 | -9.12556 | 22.57890 |
| | | 120 mg | 4 | 12.1325 | 5.29514 | 6.440 | 12.3450 | 17.400 | 3.70675 | 20.55825 |
| | | 160 mg | 3 | 8.4567 | 2.32707 | 5.770 | 9.7600 | 9.840 | 2.67592 | 14.23742 |
| | D28 | 80 mg | 3 | 1.7967 | 1.54085 | 0.080 | 2.2500 | 3.060 | -2.03103 | 5.62436 |
| | | 120 mg | 4 | 4.1825 | 2.64538 | 1.930 | 3.4900 | 7.820 | -0.02689 | 8.39139 |
| | | 160 mg | 3 | 4.9300 | 2.41156 | 2.570 | 4.8300 | 7.390 | -1.06064 | 10.92064 |
| Percent Change from Baseline in PSA (%) | D28 | 80 mg | 3 | -76.37 | 16.130 | -91.9 | -77.50 | -59.7 | -116.436 | -36.298 |
| | | 120 mg | 4 | -60.10 | 32.576 | -83.8 | -72.30 | -12.0 | -111.935 | -8.265 |
| | | 160 mg | 3 | -32.10 | 53.431 | -73.9 | -50.50 | 28.1 | -164.831 | 100.631 |

FIG. 14

| Variable / Visit | | Treatment | Summary Statistics | | | | | | 95% CI | |
|---|---|---|---|---|---|---|---|---|---|---|
| | | | N | Mean | SD | Min | Median | Max | Lower | Upper |
| PSA (ng/mL) | Baseline | 80 mg | 15 | 10.6004 | 14.56030 | 0.298 | 5.8400 | 54.200 | 2.53718 | 18.66362 |
| | | 120 mg | 15 | 6.6275 | 6.65774 | 0.434 | 4.7200 | 21.400 | 2.94054 | 10.31440 |
| | WK5D1 | 80 mg | 15 | 2.2865 | 2.60359 | 0.008 | 1.6500 | 9.990 | 0.84465 | 3.72829 |
| | | 120 mg | 15 | 1.9922 | 2.53302 | 0.029 | 0.7590 | 8.250 | 0.58946 | 3.39494 |
| | WK9D1 | 80 mg | 15 | 0.9600 | 1.63119 | 0.008 | 0.4110 | 6.390 | 0.07668 | 1.86332 |
| | | 120 mg | 15 | 0.6365 | 0.84759 | 0.008 | 0.2530 | 2.570 | 0.16709 | 1.10585 |
| | WK13D1 | 80 mg | 12 | 1.0823 | 1.89921 | 0.008 | 0.3305 | 6.670 | -0.12437 | 2.28903 |
| | | 120 mg | 10 | 0.5849 | 0.93700 | 0.008 | 0.1220 | 2.460 | -0.08539 | 1.25519 |
| | WK17D1 | 80 mg | 8 | 1.1209 | 1.96509 | 0.008 | 0.2380 | 5.730 | -0.52198 | 2.76373 |
| | | 120 mg | 6 | 0.4125 | 0.66581 | 0.008 | 0.0815 | 1.690 | -0.28623 | 1.11123 |
| | WK21D1 | 80 mg | 4 | 1.6148 | 2.70462 | 0.008 | 0.4055 | 5.640 | -2.68690 | 5.91840 |
| | | 120 mg | 5 | 0.4232 | 0.60005 | 0.008 | 0.1530 | 1.430 | -0.32186 | 1.16826 |
| | WK25D1 | 80 mg | 3 | 1.8270 | 3.12034 | 0.008 | 0.0430 | 5.430 | -5.92435 | 9.57835 |
| | | 120 mg | 3 | 0.5253 | 0.89605 | 0.008 | 0.0080 | 1.560 | -1.70057 | 2.75124 |
| | WK13D1 (LOCF) | 80 mg | 15 | 0.9098 | 1.72590 | 0.008 | 0.2790 | 6.670 | -0.04597 | 1.86557 |
| | | 120 mg | 15 | 0.6254 | 0.86640 | 0.008 | 0.2130 | 2.460 | 0.14560 | 1.10520 |
| | End of Study | 80 mg | 15 | 0.7853 | 1.41087 | 0.008 | 0.2190 | 5.430 | 0.00398 | 1.56658 |
| | | 120 mg | 15 | 0.5664 | 0.80460 | 0.008 | 0.2130 | 2.460 | 0.12083 | 1.01197 |
| Percent Change from Baseline in PSA (%) | WK5D1 | 80 mg | 15 | -73.57 | 20.242 | -98.0 | -79.20 | -25.4 | -84.776 | -62.357 |
| | | 120 mg | 15 | -75.87 | 17.063 | -97.3 | -83.80 | -36.5 | -85.316 | -66.417 |
| | WK9D1 | 80 mg | 15 | -88.32 | 13.589 | -98.9 | -94.30 | -58.1 | -95.845 | -80.795 |
| | | 120 mg | 15 | -92.53 | 5.762 | -99.2 | -94.40 | -79.9 | -95.718 | -89.338 |
| | WK13D1 | 80 mg | 12 | -88.77 | 15.424 | -98.9 | -97.35 | -51.0 | -98.567 | -78.967 |
| | | 120 mg | 10 | -93.17 | 5.554 | -99.3 | -95.55 | -80.8 | -97.143 | -89.197 |
| | WK17D1 | 80 mg | 8 | -88.74 | 14.657 | -98.9 | -96.55 | -61.2 | -100.991 | -76.484 |
| | | 120 mg | 6 | -95.42 | 2.583 | -98.4 | -96.35 | -92.1 | -98.127 | -92.706 |
| | WK21D1 | 80 mg | 4 | -95.80 | 4.290 | -99.2 | -97.20 | -89.6 | -102.626 | -88.974 |
| | | 120 mg | 5 | -96.04 | 2.489 | -98.4 | -96.80 | -93.3 | -99.130 | -92.950 |
| | WK25D1 | 80 mg | 3 | -95.83 | 5.107 | -99.5 | -98.00 | -90.0 | -108.520 | -83.146 |
| | | 120 mg | 3 | -96.43 | 3.235 | -98.4 | -98.20 | -92.7 | -104.469 | -88.398 |
| | WK13D1 (LOCF) | 80 mg | 15 | -89.47 | 13.849 | -98.9 | -97.20 | -51.0 | -97.142 | -81.804 |
| | | 120 mg | 15 | -93.11 | 5.671 | -99.3 | -95.80 | -80.8 | -96.254 | -89.973 |
| | End of Study | 80 mg | 15 | -90.69 | 11.709 | -99.5 | -96.80 | -61.2 | -97.171 | -84.203 |
| | | 120 mg | 15 | -94.12 | 5.577 | -99.3 | -95.90 | -80.8 | -97.206 | -91.032 |

FIG. 16

| | Cohort 1<br>80 mg<br>(N=3) | Cohort 2<br>120 mg<br>(N=3) | Cohort 3<br>160 mg<br>(N=3) |
|---|---|---|---|
| Day 1 (320 mg) | | | |
| $C_{max}$ (ng/mL) | 192 (49.3) | 198 (31.5) | 250 (83.0) |
| $t_{max}$ (hr) | 1.0 (0.5, 4.0) | 1.5 (1.0, 2.0) | 1.0 (0.5, 1.0) |
| $AUC_{24}$ (ng·hr/mL) | 686 (14.5) | 944 (65.3) | 770 (33.3) |
| Day 14 | | | |
| $C_{trough}$ (ng/mL) | 4.84 (40.3) | 8.76 (63.1) | 12.5 (25.0) |
| $C_{max}$ (ng/mL) | 23.5 (6.0) | 94.4 (121.9) | 216 (70.2) |
| $t_{max}$ (hr) | 0.5 (0.5, 1.0) | 0.5 (0.5, 1.0) | 0.5 (0.5, 1.0) |
| $AUC_{24}$ (ng·hr/mL) | 201 (25.1) | 368 (80.2) | 738 (51.4) |
| Day 28 | | | |
| $C_{trough}$ (ng/mL) | 6.07 (37.5) | 5.86 (67.7) | 10.6 (NE) [a] |
| $C_{max}$ (ng/mL) | 38.1 (57.1) | 34.4 (72.5) | 94.7 (NE) [a] |
| $t_{max}$ (hr) | 2.0 (1.0, 4.0) | 2.0 (1.0, 4.0) | 1.0 (1.0, 1.0) [a] |
| $AUC_{24}$ (ng·hr/mL) | 242 (31.5) | 329 (71.7) | 463 (NE) [a] |
| $t_{1/2}$ (hr) | 75.5 (14.4) | 78.1 (26.2) | 66.5 (NE) [a] |

FIG. 20

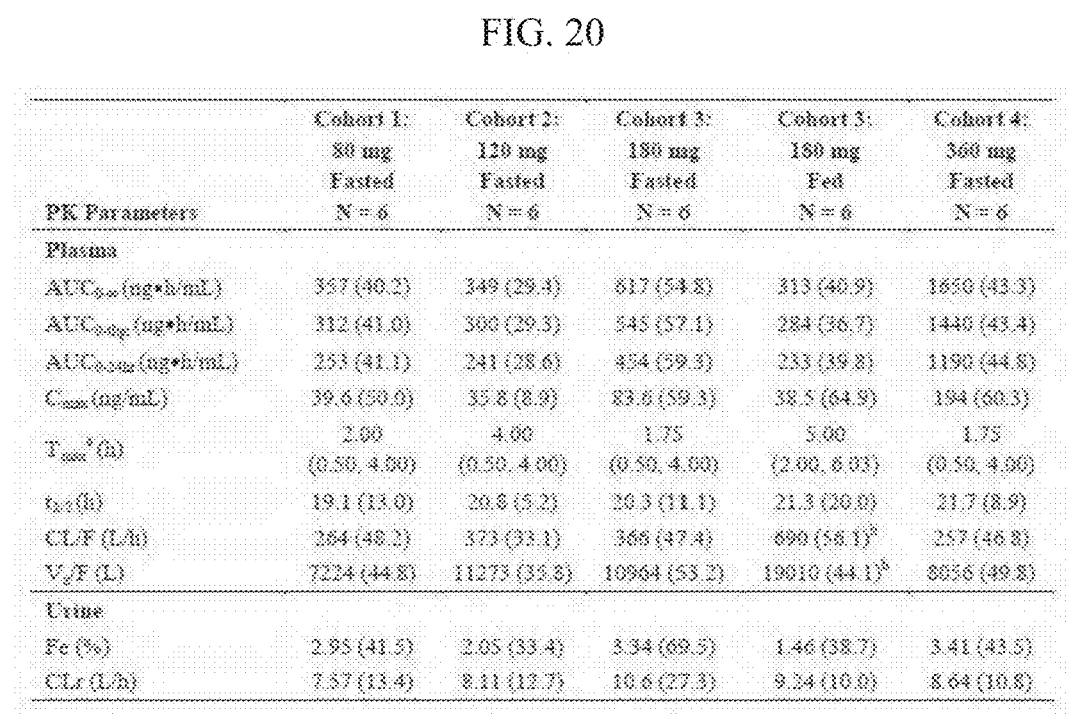

| PK Parameters | Cohort 1: 80 mg Fasted N = 6 | Cohort 2: 120 mg Fasted N = 6 | Cohort 3: 180 mg Fasted N = 6 | Cohort 3: 180 mg Fed N = 6 | Cohort 4: 360 mg Fasted N = 6 |
|---|---|---|---|---|---|
| Plasma | | | | | |
| $AUC_{0-\infty}$ (ng•h/mL) | 357 (40.2) | 349 (29.4) | 617 (54.8) | 313 (40.9) | 1650 (43.3) |
| $AUC_{0-t_{last}}$ (ng•h/mL) | 312 (41.0) | 300 (29.3) | 545 (57.1) | 284 (36.7) | 1440 (43.4) |
| $AUC_{0-24h}$ (ng•h/mL) | 253 (41.1) | 241 (28.6) | 454 (59.3) | 233 (39.8) | 1190 (44.8) |
| $C_{max}$ (ng/mL) | 39.6 (50.0) | 35.8 (8.9) | 83.6 (59.3) | 38.5 (64.9) | 194 (60.3) |
| $T_{max}^{a}$ (h) | 2.00 (0.50, 4.00) | 4.00 (0.50, 4.00) | 1.75 (0.50, 4.00) | 5.00 (2.00, 8.03) | 1.75 (0.50, 4.00) |
| $t_{1/2}$ (h) | 19.1 (13.0) | 20.8 (5.2) | 20.3 (11.1) | 21.3 (20.0) | 21.7 (8.9) |
| CL/F (L/h) | 284 (48.2) | 373 (33.1) | 368 (47.4) | 690 (58.1)[b] | 257 (46.8) |
| $V_z$/F (L) | 7224 (44.8) | 11275 (35.8) | 10964 (53.2) | 19010 (44.1)[b] | 8056 (49.8) |
| Urine | | | | | |
| Fe (%) | 2.95 (41.5) | 2.05 (33.4) | 3.34 (69.5) | 1.46 (38.7) | 3.41 (43.5) |
| CLr (L/h) | 7.57 (13.4) | 8.11 (12.7) | 10.6 (27.3) | 9.34 (10.0) | 8.64 (10.8) |

FIG. 22

| PK Parameters | Cohort 1: 80 mg N = 6 | Cohort 2: 180 mg N = 6 | Cohort 4: 320 mg N = 6 | Cohort 5: 320 mg N = 6 | Cohort 3: 360 mg N = 6 |
|---|---|---|---|---|---|
| **Plasma** | | | | | |
| $AUC_{0-24}$ (ng•h/mL) | 112 (42.6)[a] | 328 (42.9)[a] | 874 (72.0)[a] | 1358 (53.1) | 1878 (51.9) |
| $C_{max}$ (ng/mL) | 29.9 (67.5) | 84.1 (63.7) | 357 (73.6) | 400 (61.9) | 489 (60.7) |
| $T_{max}$[b] (h) | 1.00 (0.50, 2.00) | 1.00 (0.50, 1.50) | 1.50 (1.02, 12.0) | 1.50 (1.00, 2.00) | 2.00 (1.50, 2.00) |
| **Urine** | | | | | |
| Fe (%) | 0.934 (39.4) | 1.45 (35.6) | 2.20 (74.7) | 2.61 (62.3) | 3.43 (29.4) |
| CLr (L/h) | 7.29 (13.2) | 8.39 (18.5) | 7.25 (36.2) | 5.87 (30.6) | 7.38 (25.9) |

FIG. 23

| PK Parameters | Cohort 4: 20 mg N = 6 | Cohort 5: 20 mg N = 6 | Cohort 3: 40 mg N = 6 | Cohort 1: 80 mg N = 6 | Cohort 2: 180 mg N = 6 |
|---|---|---|---|---|---|
| **Plasma** | | | | | |
| $AUC_{0-\tau}$ (ng•h/mL) | 42.3 (24.9) | 49.8 (38.6) | 121 (55.5) | 203 (26.9) | 704 (50.8) |
| $C_{max}$ (ng/mL) | 3.91 (35.8) | 5.99 (43.8) | 20.8 (64.0) | 35.6 (54.0) | 168 (97.4) |
| $C_{min}$ (ng/mL) | 1.27 (25.4) | 1.35 (43.2) | 2.74 (46.0) | 3.48 (31.2) | 11.4 (42.8) |
| $T_{max}$[a] (h) | 1.01 (0.50, 1.50) | 1.50 (0.50, 2.00) | 1.59 (0.50, 2.00) | 1.26 (0.50, 4.00) | 1.50 (1.00, 4.00) |
| $t_{1/2}$(h) | 64.5 (52.6)[b] | 50.6 (20.2) | 49.4 (30.6) | 36.5 (17.4) | 35.8 (23.0) |
| $CL_{ss}/F$ (L/h) | 498 (25.0) | 458 (41.1) | 420 (47.9) | 424 (32.1) | 337 (62.5) |
| $V_z/F$ (L) | 43341 (34.4)[b] | 32108 (31.4) | 32753 (71.3) | 23144 (46.5) | 17344 (72.7) |
| R(AUC) | NA | NA | NA | 1.92 (23.5) | 2.16 (43.0) |
| R($C_{max}$) | NA | NA | NA | 1.52 (67.3) | 1.80 (37.0) |
| **Urine** | | | | | |
| Fe (%) | 1.44 (31.8) | 1.35 (40.0) | 1.76 (38.6) | 1.89 (20.2) | 2.88 (45.6) |
| CLr (L/h) | 6.92 (29.5) | 5.51 (26.7) | 6.42 (25.0) | 7.66 (17.4) | 7.43 (16.2) |

FIG. 24

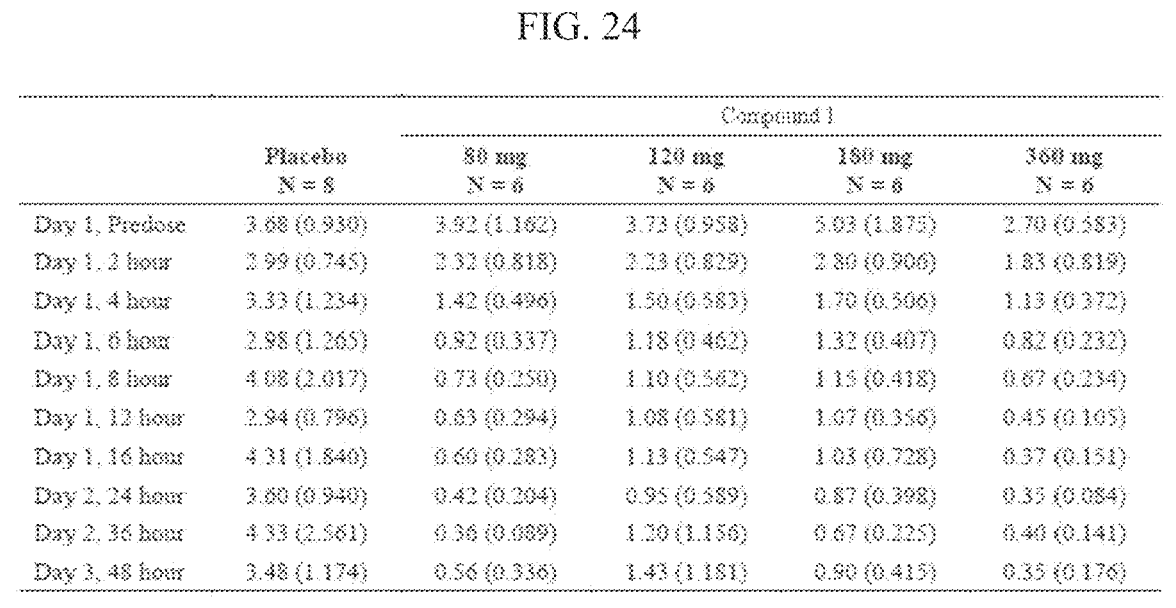

| | Placebo N = 8 | Compound 1 80 mg N = 6 | 120 mg N = 6 | 180 mg N = 8 | 360 mg N = 6 |
|---|---|---|---|---|---|
| Day 1, Predose | 3.68 (0.930) | 3.92 (1.162) | 3.73 (0.958) | 5.03 (1.875) | 2.70 (0.583) |
| Day 1, 2 hour | 2.99 (0.745) | 2.32 (0.818) | 2.23 (0.829) | 2.80 (0.906) | 1.83 (0.819) |
| Day 1, 4 hour | 3.33 (1.234) | 1.42 (0.496) | 1.50 (0.583) | 1.70 (0.506) | 1.13 (0.372) |
| Day 1, 6 hour | 2.98 (1.265) | 0.92 (0.337) | 1.18 (0.462) | 1.32 (0.407) | 0.82 (0.232) |
| Day 1, 8 hour | 4.08 (2.017) | 0.73 (0.250) | 1.10 (0.562) | 1.15 (0.418) | 0.67 (0.234) |
| Day 1, 12 hour | 2.94 (0.796) | 0.63 (0.294) | 1.08 (0.581) | 1.07 (0.356) | 0.45 (0.105) |
| Day 1, 16 hour | 4.31 (1.840) | 0.60 (0.283) | 1.13 (0.547) | 1.03 (0.728) | 0.37 (0.151) |
| Day 2, 24 hour | 3.60 (0.940) | 0.42 (0.204) | 0.95 (0.589) | 0.87 (0.398) | 0.35 (0.084) |
| Day 2, 36 hour | 4.33 (2.561) | 0.36 (0.089) | 1.20 (1.156) | 0.67 (0.225) | 0.40 (0.141) |
| Day 3, 48 hour | 3.48 (1.174) | 0.56 (0.336) | 1.43 (1.181) | 0.90 (0.415) | 0.35 (0.176) |

FIG. 26

| | | Compound 1 | | | |
|---|---|---|---|---|---|
| | **Placebo**<br>**N = 8** | **80 mg**<br>**N = 6** | **120 mg**<br>**N = 6** | **180 mg**<br>**N = 6** | **360 mg**<br>**N = 6** |
| Day 1, Predose | 10.40<br>(0.000) | 10.40<br>(0.000) | 10.40<br>(0.000) | 10.40<br>(0.000) | 10.40<br>(0.000) |
| Day 1, 2 hour | 10.40<br>(0.000) | 10.40<br>(0.000) | 10.40<br>(0.000) | 10.40<br>(0.000) | 10.40<br>(0.000) |
| Day 1, 4 hour | 10.40<br>(0.000) | 10.40<br>(0.000) | 10.40<br>(0.000) | 10.34<br>(0.161) | 9.407<br>(1.7175) |
| Day 1, 6 hour | 9.942<br>(1.1343) | 8.893<br>(1.8972) | 8.438<br>(1.8295) | 8.455<br>(1.9686) | 6.088<br>(2.4688) |
| Day 1, 8 hour | 10.24<br>(0.412) | 5.546<br>(1.5486) | 5.308<br>(1.6415) | 5.892<br>(2.1882) | 3.942<br>(1.4508) |
| Day 1, 12 hour | 10.24<br>(0.308) | 2.794<br>(0.7218) | 2.935<br>(0.9802) | 2.839<br>(0.5809) | 1.904<br>(0.7469) |
| Day 1, 16 hour | 10.40<br>(0.000) | 2.231<br>(0.8145) | 2.727<br>(0.9797) | 2.336<br>(0.7409) | 1.494<br>(0.4078) |
| Day 2, 24 hour | 10.40<br>(0.000) | 2.071<br>(0.7208) | 2.655<br>(0.8199) | 2.053<br>(0.5270) | 1.179<br>(0.2204) |
| Day 2, 36 hour | 9.958<br>(0.8694) | 0.9952<br>(0.25155) | 1.753<br>(1.3677) | 0.9730<br>(0.29733) | 0.7462<br>(0.10129) |
| Day 3, 48 hour | 10.40<br>(0.000) | 1.727<br>(1.0094) | 3.829<br>(3.3913) | 1.602<br>(0.6683) | 1.069<br>(0.2861) |

FIG. 27

| | | Compound 1 | | | |
|---|---|---|---|---|---|
| | Placebo<br>N = 8 | 80 mg<br>N = 6 | 120 mg<br>N = 6 | 180 mg<br>N = 6 | 360 mg<br>N = 6 |
| Day 1, Predose | 4.40 (2.104) | 2.90 (0.986) | 2.38 (1.284) | 4.60 (2.102) | 3.73 (1.155) |
| Day 1, 2 hours | 4.21 (1.746) | 2.72 (1.038) | 2.13 (1.174) | 4.12 (1.923) | 3.50 (1.064) |
| Day 1, 4 hours | 4.40 (2.055) | 2.55 (0.989) | 2.00 (0.867) | 3.95 (1.802) | 3.08 (0.968) |
| Day 1, 12 hours | 4.19 (1.938) | 2.02 (0.744) | 1.57 (0.650) | 3.07 (1.583) | 2.43 (0.692) |
| Day 2, 24 hours | 4.25 (1.858) | 1.60 (0.654) | 1.77 (0.981) | 2.63 (1.400) | 2.07 (0.731) |
| Day 3, 48 hours | 4.26 (2.049) | 1.13 (0.476) | 1.32 (0.598) | 1.93 (0.979) | 1.48 (0.531) |

FIG. 28

| | | Compound 1 | | | |
|---|---|---|---|---|---|
| | **Placebo**<br>**N = 8** | **80 mg**<br>**N = 6** | **120 mg**<br>**N = 6** | **180 mg**<br>**N = 6** | **360 mg**<br>**N = 6** |
| Day 1, Predose | 2.726 (1.1555) | 3.245 (0.6473) | 2.615 (0.2837) | 3.383 (1.4974) | 1.708 (0.2099) |
| Day 1, 2 hours | 2.589 (1.1444) | 3.158 (0.6161) | 2.352 (0.2363) | 2.714 (0.9308) | 1.748 (0.5755) |
| Day 1, 4 hours | 2.531 (1.0216) | 2.728 (0.5287) | 2.153 (0.2251) | 2.454 (0.8176) | 1.475 (0.4613) |
| Day 1, 12 hours | 1.811 (1.2582) | 1.552 (0.4034) | 1.250 (0.1964) | 1.183 (1.4652) | 0.827 (0.1880) |
| Day 2, 24 hours | 2.283 (1.3795) | 1.502 (0.4528) | 1.445 (0.2025) | 0.715 (0.4461) | 0.898 (0.1254) |
| Day 3, 48 hours | 2.146 (1.4958) | 1.415 (0.4148) | 1.558 (0.2014) | 0.768 (0.3568) | 0.853 (0.0944) |

FIG. 29

| | | Compound I | | | | |
|---|---|---|---|---|---|---|
| | Placebo N = 10 | 80 mg N = 6 | 180 mg N = 6 | 360/40 mg[a] N = 6 | 320/240/160/20 mg[b] N = 6 | 320/160/20 mg[c] N = 6 |
| Day 1, Predose | 3.70 (1.130) | 4.57 (1.694) | 3.90 (2.706) | 4.77 (1.376) | 5.53 (2.410) | 3.40 (1.722) |
| Day 1, 2 hour | 3.56 (1.622) | 2.58 (0.674) | 2.40 (1.444) | 2.37 (0.662) | 3.88 (1.609) | 1.57 (0.638) |
| Day 1, 4 hour | 3.63 (2.384) | 1.70 (0.469) | 1.55 (0.952) | 1.53 (0.501) | 2.40 (0.990) | 1.00 (0.620) |
| Day 1, 6 hour | 3.26 (1.161) | 1.47 (0.969) | 1.13 (0.835) | 1.18 (0.354) | 2.30 (1.436) | 0.72 (0.417) |
| Day 1, 8 hour | 2.85 (1.088) | 1.47 (1.498) | 1.00 (0.718) | 1.00 (0.276) | 1.60 (0.669) | 0.60 (0.335) |
| Day 1, 12 hour | 3.17 (1.546) | 1.10 (0.815) | 0.73 (0.367) | 0.72 (0.232) | 1.33 (0.568) | 0.58 (0.319) |
| Day 1, 16 hour | 3.62 (1.357) | 1.65 (1.019) | 0.87 (0.372) | 0.58 (0.214) | 1.63 (1.093) | 0.40 (0.228) |
| Day 2, 24 hour | 3.31 (1.438) | 1.38 (0.920) | 0.82 (0.232) | 0.52 (0.248) | 1.15 (0.672) | 0.45 (0.251) |
| Day 3, Predose | 3.29 (1.588) | 1.18 (1.192) | 0.35 (0.138) | 0.47 (0.258) | 0.55 (0.327) | 0.33 (0.082) |
| Day 7, Predose | 3.09 (1.873) | 1.13 (0.983) | 0.32 (0.147) | 0.73 (0.485) | 1.83 (1.229) | 1.23 (1.211) |
| Day 8, Predose | 2.58 (0.250) | NA | NA | NA | 1.67 (1.510) | 1.07 (0.816) |
| Day 11, Predose | 2.33 (0.880) | NA | NA | NA | 2.00 (2.097) | 1.32 (1.107) |
| Day 12, Predose | 3.64 (1.300) | 0.43 (0.524) | 0.27 (0.082) | 0.40 (0.190) | 1.95 (2.183) | 1.43 (1.597) |
| Day 13, Predose | 3.47 (1.619) | 0.38 (0.402) | 0.22 (0.041) | 0.42 (0.204) | 1.67 (1.659) | 1.42 (1.468) |
| Day 14, Predose | 3.15 (0.711) | 0.35 (0.321) | 0.22 (0.041) | 0.43 (0.207) | 2.03 (2.199) | 1.17 (1.169) |
| Day 14, 2 hour | 3.63 (1.306) | 0.30 (0.245) | 0.22 (0.041) | 0.30 (0.126) | 1.55 (1.571) | 1.13 (1.371) |
| Day 14, 4 hour | 3.26 (1.059) | 0.25 (0.122) | 0.22 (0.041) | 0.30 (0.167) | 1.68 (1.826) | 1.07 (1.255) |
| Day 14, 8 hour | 4.04 (1.973) | 0.28 (0.160) | 0.22 (0.041) | 0.32 (0.183) | 1.80 (2.105) | 0.98 (0.991) |
| Day 14, 12 hour | 2.97 (1.370) | 0.28 (0.204) | 0.22 (0.041) | 0.30 (0.126) | 2.07 (1.908) | 1.08 (1.361) |
| Day 15, 24 hour | 3.51 (1.065) | 0.33 (0.280) | 0.23 (0.082) | 0.40 (0.190) | 2.03 (2.129) | 1.48 (1.592) |
| Day 15, 36 hour | 3.31 (1.653) | 0.27 (0.163) | 0.20 (0.000) | 0.33 (0.197) | 2.23 (2.673) | 2.08 (1.517) |
| Day 16, 48 hour | 3.72 (1.451) | 0.33 (0.280) | 0.23 (0.052) | 0.43 (0.266) | 2.10 (1.899) | 1.50 (1.481) |

FIG. 31A

| | Placebo N = 10 | 80 mg N = 6 | 180 mg N = 6 | 360/40 mg[a] N = 6 | 320/240/160/ 20 mg[a] N = 6 | 320/160/ 20 mg[a] N = 6 |
|---|---|---|---|---|---|---|
| Day 1, Predose | 10.40 (0.000) | 10.40 (0.000) | 10.40 (0.000) | 10.40 (0.000) | 10.40 (0.000) | 9.981 (0.9249) |
| Day 1, 2 hour | 10.40 (0.000) | 10.40 (0.000) | 10.40 (0.000) | 10.31 (0.233) | 10.40 (0.000) | 9.452 (1.4867) |
| Day 1, 4 hour | 10.28 (0.385) | 10.40 (0.014) | 10.40 (0.000) | 8.368 (2.1854) | 10.28 (0.303) | 8.473 (1.6294) |
| Day 1, 6 hour | 10.40 (0.000) | 8.104 (2.5795) | 7.937 (2.1683) | 6.396 (2.5160) | 8.113 (2.1650) | 5.439 (0.9848) |
| Day 1, 8 hour | 10.30 (0.227) | 6.978 (3.0752) | 6.204 (2.4295) | 4.932 (2.4668) | 6.245 (2.4316) | 3.887 (0.9098) |
| Day 1, 12 hour | 9.963 (0.9452) | 4.376 (1.8784) | 3.019 (1.0295) | 2.651 (0.9647) | 3.801 (1.6254) | 2.555 (0.5386) |
| Day 1, 16 hour | 10.31 (0.297) | 3.604 (1.7200) | 2.602 (0.7410) | 1.770 (0.4960) | 2.761 (1.1640) | 1.791 (0.3205) |
| Day 2, 24 hour | 10.40 (0.012) | 5.910 (3.1307) | 2.779 (1.4823) | 1.495 (0.2748) | 2.914 (1.5102) | 1.552 (0.5156) |
| Day 3, Predose | 10.40 (0.000) | 3.705 (3.4236) | 1.421 (0.5044) | 1.126 (0.3027) | 1.312 (0.4639) | 1.082 (0.2278) |
| Day 7, Predose | 10.12 (0.875) | 2.573 (1.8408) | 0.9224 (0.23054) | 1.040 (0.4348) | 2.517 (1.5968) | 2.354 (2.4590) |
| Day 8, Predose | 10.40 (0.000) | NA | NA | NA | 2.266 (1.4202) | 2.628 (3.3226) |
| Day 11, Predose | 10.40 (0.000) | NA | NA | NA | 2.732 (2.0999) | 2.572 (3.8940) |
| Day 12, Predose | 10.40 (0.000) | 0.6281 (0.25253) | 0.5647 (0.26864) | 0.5692 (0.26992) | 2.770 (2.1199) | 2.405 (3.9437) |
| Day 13, Predose | 10.16 (0.635) | 0.5444 (0.20422) | 0.5164 (0.17481) | 0.5269 (0.15462) | 2.781 (2.4237) | 2.326 (3.9742) |
| Day 14, Predose | 10.33 (0.223) | 0.4367 (0.18193) | 0.4722 (0.23309) | 0.4736 (0.12379) | 2.808 (2.3716) | 2.249 (4.0088) |
| Day 14, 2 hour | 10.08 (0.809) | 0.2974 (0.07455) | 0.3284 (0.11020) | 0.4008 (0.11507) | 2.251 (1.8394) | 1.951 (3.5877) |
| Day 14, 4 hour | 10.28 (0.373) | 0.3299 (0.10565) | 0.3402 (0.11174) | 0.4166 (0.14217) | 2.458 (2.1101) | 2.177 (4.0429) |
| Day 14, 8 hour | 10.40 (0.000) | 0.3252 (0.13748) | 0.3136 (0.09694) | 0.3424 (0.11791) | 1.924 (1.4998) | 2.069 (4.0884) |
| Day 14, 12 hour | 10.10 (0.797) | 0.2198 (0.05308) | 0.2536 (0.05322) | 0.3047 (0.09957) | 1.819 (1.6463) | 1.713 (3.3795) |
| Day 15, 24 hour | 10.38 (0.067) | 0.4331 (0.15422) | 0.4612 (0.24051) | 0.4897 (0.18025) | 3.143 (2.8942) | 2.289 (3.9852) |

FIG. 31B

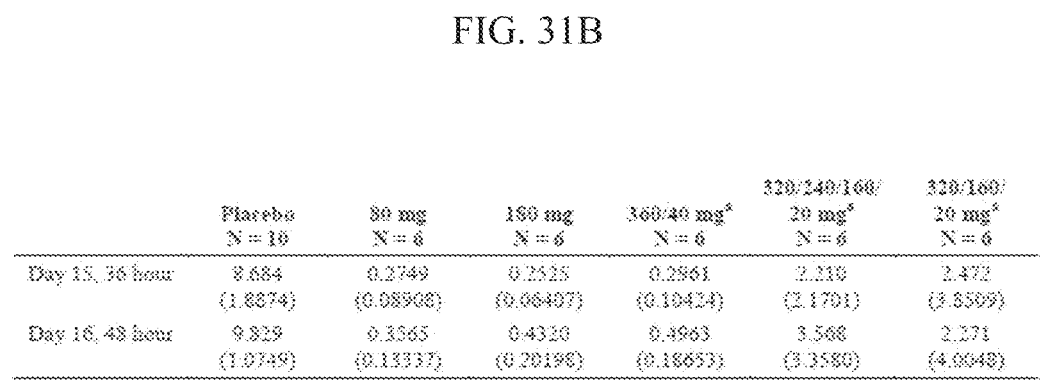

| | Placebo N = 10 | 80 mg N = 6 | 180 mg N = 6 | 360/40 mg[a] N = 6 | 320/240/160/ 20 mg[a] N = 6 | 320/160/ 20 mg[a] N = 6 |
|---|---|---|---|---|---|---|
| Day 15, 36 hour | 8.684 (1.8874) | 0.2749 (0.08908) | 0.2525 (0.06407) | 0.2861 (0.10424) | 2.210 (2.1701) | 2.472 (3.8509) |
| Day 16, 48 hour | 9.829 (1.0749) | 0.3565 (0.13337) | 0.4320 (0.20198) | 0.4963 (0.18653) | 3.568 (3.3580) | 2.271 (4.0048) |

FIG. 32

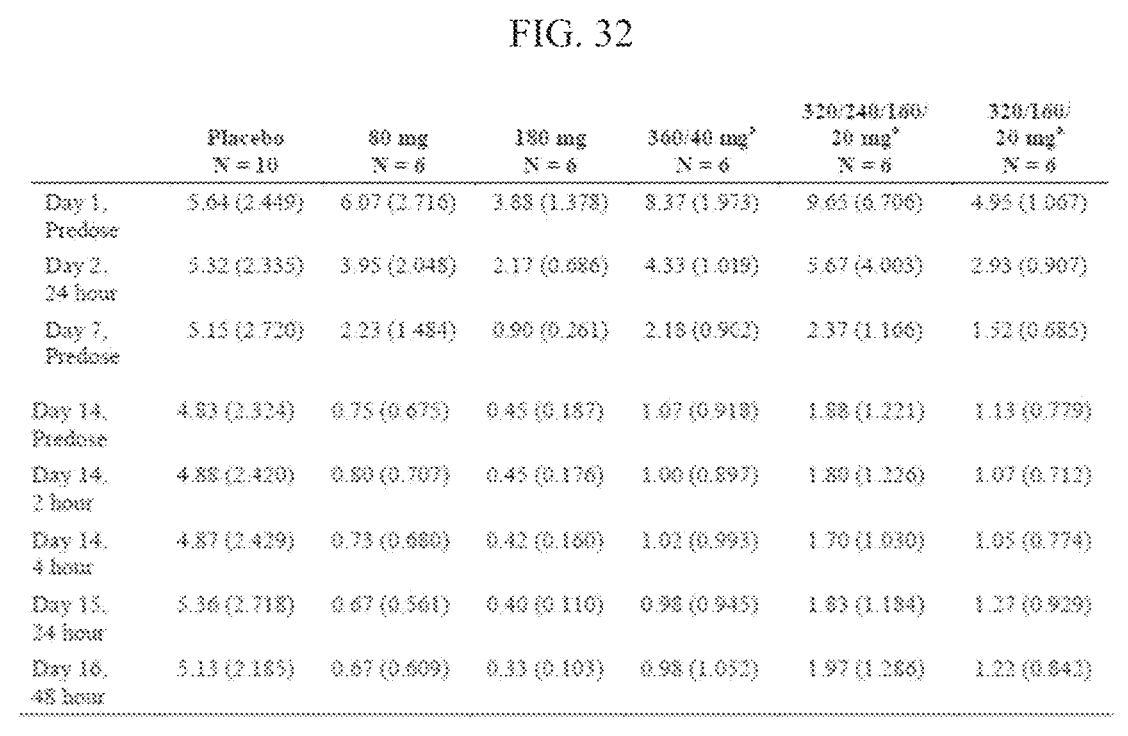

| | Placebo N = 10 | 80 mg N = 6 | 180 mg N = 6 | 360/40 mg[a] N = 6 | 320/240/180/ 20 mg[a] N = 6 | 320/180/ 20 mg[a] N = 6 |
|---|---|---|---|---|---|---|
| Day 1, Predose | 5.64 (2.449) | 6.07 (2.716) | 3.88 (1.378) | 8.37 (1.973) | 9.65 (6.706) | 4.95 (1.067) |
| Day 2, 24 hour | 5.32 (2.335) | 3.95 (2.048) | 2.17 (0.686) | 4.33 (1.019) | 5.67 (4.003) | 2.93 (0.907) |
| Day 7, Predose | 5.15 (2.720) | 2.23 (1.484) | 0.90 (0.261) | 2.18 (0.902) | 2.37 (1.166) | 1.52 (0.685) |
| Day 14, Predose | 4.83 (2.324) | 0.75 (0.675) | 0.48 (0.187) | 1.07 (0.918) | 1.88 (1.221) | 1.13 (0.779) |
| Day 14, 2 hour | 4.88 (2.420) | 0.80 (0.707) | 0.45 (0.176) | 1.00 (0.897) | 1.80 (1.226) | 1.07 (0.712) |
| Day 14, 4 hour | 4.87 (2.429) | 0.73 (0.680) | 0.42 (0.160) | 1.02 (0.993) | 1.70 (1.030) | 1.05 (0.774) |
| Day 15, 24 hour | 5.36 (2.718) | 0.67 (0.561) | 0.40 (0.110) | 0.98 (0.945) | 1.83 (1.184) | 1.27 (0.929) |
| Day 16, 48 hour | 5.13 (2.185) | 0.67 (0.609) | 0.33 (0.103) | 0.98 (1.052) | 1.97 (1.286) | 1.22 (0.842) |

FIG. 33

| | Placebo N = 10 | 80 mg N = 8 | 180 mg N = 6 | 360/40 mg[a] N = 6 | 320/240/160/ 20 mg[a] N = 8 | 320/160/ 20 mg[a] N = 8 |
|---|---|---|---|---|---|---|
| Day 1, Predose | 2.295 (0.9019) | 1.883 (0.6085) | 1.882 (0.6004) | 3.157 (2.5690) | 2.578 (1.3090) | 2.978 (1.1200) |
| Day 2, 24 hour | 2.178 (1.0653) | 1.198 (0.5137) | 1.177 (0.4642) | 1.757 (1.6372) | 1.237 (0.3702) | 1.582 (0.5295) |
| Day 7, Predose | 2.115 (0.7658) | 0.983 (0.4872) | 1.023 (0.4549) | 1.652 (1.4214) | 1.072 (0.4234) | 1.662 (0.8359) |
| Day 14, Predose | 2.008 (0.4845) | 0.883 (0.4489) | 0.953 (0.3888) | 1.378 (1.3521) | 1.248 (0.6892) | 1.820 (1.1129) |
| Day 14, 2 hour | 1.809 (0.4629) | 0.780 (0.3931) | 0.860 (0.3664) | 1.248 (1.1975) | 1.143 (0.5807) | 1.525 (0.9163) |
| Day 14, 4 hour | 1.889 (0.5316) | 0.840 (0.4128) | 0.887 (0.3778) | 1.277 (1.1130) | 1.098 (0.5098) | 1.640 (0.9514) |
| Day 15, 24 hour | 2.158 (0.9912) | 1.118 (0.7726) | 0.968 (0.3788) | 1.380 (1.4071) | 1.205 (0.7234) | 1.660 (0.9627) |
| Day 16, 48 hour | 2.137 (0.5961) | 1.093 (0.7712) | 0.865 (0.3086) | 1.348 (1.2425) | 1.365 (0.9330) | 1.748 (1.0694) |

FIG. 34

| | | Compound 1 | |
|---|---|---|---|
| | Placebo<br>N = 22 | 320/160/40 mg[a]<br>N = 22 | 160 mg<br>N = 20 |
| Day 1, Predose | 4.41 (2.869) | 3.89 (1.789) | 3.63 (2.211) |
| Day 1, 1 hour | 4.56 (2.694) | 3.38 (1.403) | 2.83 (1.305) |
| Day 1, 2 hour | 5.45 (2.875) | 2.26 (0.960) | 2.01 (0.941) |
| Day 1, 4 hour | 4.95 (2.776) | 1.47 (0.820) | 1.37 (0.726) |
| Day 1, 8 hour | 5.03 (3.158) | 0.95 (0.450) | 1.18 (0.919) |
| Day 2, 24 hour | 4.64 (2.779) | 0.54 (0.246) | 0.69 (0.385) |
| Day 7, Predose | 4.82 (3.386) | 1.18 (0.807) | 0.40 (0.304) |
| Day 14, Predose | 4.25 (3.287) | 1.13 (1.031) | 0.26 (0.188) |
| Day 21, Predose | 4.43 (2.447) | 1.09 (1.068) | 0.23 (0.091) |
| Day 28, Predose | 4.54 (2.280) | 1.30 (1.366) | 0.23 (0.112) |
| Day 28, 1 hour | 5.04 (2.869) | 1.27 (1.108) | 0.23 (0.091) |
| Day 28, 2 hour | 5.38 (3.415) | 1.06 (0.997) | 0.44 (0.982) |
| Day 28, 4 hour | 4.81 (2.389) | 0.94 (0.865) | 0.23 (0.091) |
| Day 28, 8 hour | 5.20 (2.474) | 1.04 (1.378) | 0.27 (0.187) |
| Day 29, 24 hour | 4.69 (2.711) | 1.18 (1.058) | 0.23 (0.113) |

FIG. 36

| | Placebo N = 22 | Compound 1 320/160/40 mg[a] N = 22 | Compound 1 160 mg N = 20 |
|---|---|---|---|
| Day 1, Predose | 10.33 (0.306) | 10.40 (0.029) | 10.40 (0.000) |
| Day 1, 1 hour | 10.38 (0.090) | 10.23 (0.815) | 10.39 (0.072) |
| Day 1, 2 hour | 10.28 (0.465) | 10.20 (0.779) | 10.28 (0.503) |
| Day 1, 4 hour | 10.31 (0.419) | 9.483 (1.7577) | 9.649 (1.1505) |
| Day 1, 8 hour | 10.22 (0.607) | 5.934 (2.5164) | 6.196 (2.6660) |
| Day 2, 24 hour | 10.40 (0.000) | 2.365 (1.1612) | 2.759 (1.3242) |
| Day 7, Predose | 10.27 (0.491) | 2.720 (2.4823) | 1.111 (0.5742) |
| Day 14, Predose | 10.33 (0.112) | 2.008 (2.2999) | 0.9140 (1.43914) |
| Day 21, Predose | 10.31 (0.299) | 2.217 (3.1365) | 0.7229 (0.97368) |
| Day 28, Predose | 10.37 (0.135) | 2.993 (3.4746) | 0.4949 (0.22777) |
| Day 28, 1 hour | 10.20 (0.681) | 2.687 (3.5239) | 0.4291 (0.22357) |
| Day 28, 2 hour | 10.18 (0.708) | 2.742 (3.4347) | 0.6790 (1.03855) |
| Day 28, 4 hour | 10.26 (0.472) | 2.719 (3.5361) | 0.9861 (1.80951) |
| Day 28, 8 hour | 10.24 (0.524) | 2.254 (3.2330) | 0.3870 (0.24450) |
| Day 29, 24 hour | 10.40 (0.000) | 2.675 (3.4580) | 0.4781 (0.22188) |
| End of Study (Day 56) | 10.28 (0.394) | 10.40 (0.000) | 8.180 (3.2445) |

FIG. 37

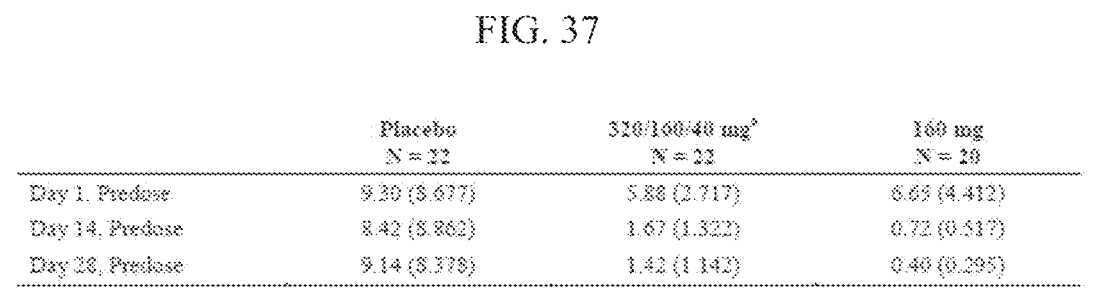

| | Placebo<br>N = 22 | 320/160/40 mg[a]<br>N = 22 | 160 mg<br>N = 20 |
|---|---|---|---|
| Day 1, Predose | 9.30 (8.677) | 5.88 (2.717) | 6.69 (4.412) |
| Day 14, Predose | 8.42 (8.862) | 1.67 (1.322) | 0.72 (0.517) |
| Day 28, Predose | 9.14 (8.378) | 1.42 (1.142) | 0.40 (0.295) |

FIG. 38

| | Placebo N = 22 | 320/160/40 mg[2] N = 22 | 160 mg N = 20 |
|---|---|---|---|
| Day 1, Predose | 2.510 (0.7979) | 3.182 (2.0511) | 3.396 (3.1601) |
| Day 14, Predose | 2.262 (0.6936) | 1.538 (0.8288) | 1.604 (1.5718) |
| Day 28, Predose | 2.650 (0.8370) | 1.505 (0.9282) | 1.449 (1.6542) |

FIG. 39

| | Placebo N = 8 | 60 mg N = 13 | 80 mg N = 14 |
|---|---|---|---|
| Day 1, Predose | 3.04 (1.536) | 3.91 (1.582) | 3.29 (2.282) |
| Day 1, 1 hour | 4.13 (1.990) | 3.68 (1.696) | 3.15 (1.436) |
| Day 1, 2 hour | 3.71 (0.866) | 2.78 (1.407) | 2.26 (1.115) |
| Day 1, 4 hour | 3.06 (1.585) | 1.96 (0.973) | 1.35 (0.612) |
| Day 1, 8 hour | 3.39 (1.835) | 1.85 (0.722) | 1.30 (0.732) |
| Day 2, 24 hour | 2.99 (1.237) | 1.32 (0.653) | 0.85 (0.433) |
| Day 7, Predose | 3.50 (1.587) | 2.03 (1.691) | 0.72 (0.560) |
| Day 14, Predose | 3.06 (1.683) | 0.76 (0.943) | 0.44 (0.386) |
| Day 21, Predose | 3.05 (1.683) | 0.66 (0.701) | 0.27 (0.188) |
| Day 28, Predose | 3.48 (1.543) | 0.29 (0.180) | 0.24 (0.109) |
| Day 28, 1 hour | 3.66 (1.549) | 0.30 (0.204) | 0.24 (0.109) |
| Day 28, 2 hour | 3.38 (0.835) | 0.26 (0.145) | 0.26 (0.116) |
| Day 28, 4 hour | 3.31 (0.946) | 0.36 (0.439) | 0.23 (0.107) |
| Day 28, 8 hour | 3.36 (1.336) | 0.23 (0.085) | 0.24 (0.134) |

FIG. 41

| | Placebo<br>N = 8 | 60 mg<br>N = 13 | 80 mg<br>N = 14 |
|---|---|---|---|
| Day 1, Predose | 10.40 (0.000) | 10.25 (0.559) | 10.40 (0.000) |
| Day 1, 1 hour | 10.40 (0.000) | 10.40 (0.000) | 10.40 (0.000) |
| Day 1, 2 hour | 10.40 (0.000) | 10.40 (0.000) | 10.33 (0.283) |
| Day 1, 4 hour | 10.40 (0.000) | 9.539 (2.1512) | 9.735 (1.5061) |
| Day 1, 8 hour | 10.40 (0.000) | 7.786 (2.9281) | 7.504 (2.7045) |
| Day 2, 24 hour | 10.40 (0.000) | 6.893 (3.5707) | 6.216 (3.2193) |
| Day 7, Predose | 10.40 (0.000) | 5.523 (3.9871) | 2.725 (2.6230) |
| Day 14, Predose | 10.30 (0.282) | 2.335 (2.9752) | 1.786 (2.7768) |
| Day 21, Predose | 10.40 (0.000) | 1.303 (2.7069) | 0.6715 (0.40817) |
| Day 28, Predose | 10.40 (0.000) | 0.8702 (1.15500) | 0.5327 (0.22539) |
| Day 28, 1 hour | 10.36 (0.117) | 0.8069 (1.15824) | 0.4877 (0.16698) |
| Day 28, 2 hour | 10.40 (0.000) | 0.7607 (1.12303) | 0.4902 (0.17801) |
| Day 28, 4 hour | 10.40 (0.000) | 1.025 (1.8005) | 0.4462 (0.13827) |
| Day 28, 8 hour | 10.40 (0.000) | 0.5276 (0.62607) | 0.7041 (1.19608) |
| Day 29, 24 hour | 10.40 (0.000) | 1.227 (1.6861) | 0.6297 (0.29079) |
| End of Study (Day 56) | 10.21 (0.532) | 10.40 (0.000) | 9.682 (1.8278) |

FIG. 42

| | Placebo<br>N = 8 | 60 mg<br>N = 13 | 80 mg<br>N = 14 |
|---|---|---|---|
| Day 1, Predose | 5.99 (3.154) | 6.32 (3.762) | 4.74 (1.644) |
| Day 14, Predose | 6.14 (3.873) | 1.53 (1.243) | 0.69 (0.363) |
| Day 28, Predose | 6.64 (4.759) | 0.52 (0.359) | 0.29 (0.103) |

FIG. 43

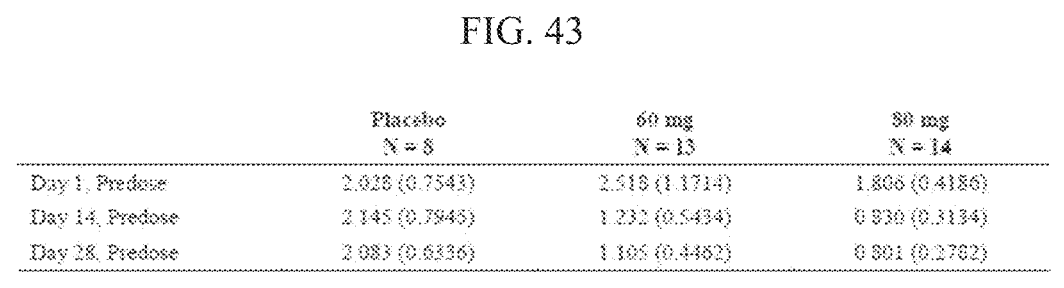

| | Placebo N = 8 | 60 mg N = 13 | 80 mg N = 14 |
|---|---|---|---|
| Day 1, Predose | 2.028 (0.7543) | 2.518 (1.1714) | 1.806 (0.4186) |
| Day 14, Predose | 2.145 (0.7946) | 1.232 (0.5434) | 0.830 (0.3134) |
| Day 28, Predose | 2.083 (0.6336) | 1.105 (0.4462) | 0.801 (0.2782) |

FIG. 49

| | Compound 1 **120 mg QD (N=65)** | Degarelix **80 mg Q4W (N=38)** |
|---|---|---|
| Patients with at least one dose of treatment | | |
| N | 65 | 38 |
| Castration rate[a] over 24 weeks | | |
| n | 62-(95) | 34-(89) |
| 95%-CI[b] | 87.1-99.0 | 75.2-97.1 |
| Profound castration rate[c] cover 24 weeks¤ | | |
| N | 53-(82) | 26-(68) |
| 95%-CI[b] | 70.0-90.1 | 51.3-82.5 |
| Patients who received at least 12 weeks of treatment | | |
| N | 64 | 38 |
| Castration rate[a] over 24 weeks | | |
| n | 61-(95) | 34-(89) |
| 95%-CI[b] | 86.9-99.0 | 75.2-97.1 |
| Profound castration rate[c] cover 24 weeks | | |
| n | 52-(81) | 26-(68) |
| 95%-CI[b] | 69.5-89.9 | 51.3-82.5 |
| Patients who received at least 24 weeks of treatment | | |
| N | 50 | 28 |
| Castration rate[a] over 24 weeks | | |
| n | 49-(98) | 24-(86) |
| 95%-CI[b] | 89.4-99.9 | 67.3-96.0 |
| Profound castration rate[c] cover 24 weeks | | |
| n | 42-(84) | 20-(71) |
| 95%-CI[b] | 70.9-92.8 | 51.3-86.8 |

FIG. 51

| | Compound 1<br>120 mg QD<br>(N=65) | Degarelix<br>80 mg Q4W<br>(N=38) |
|---|---|---|
| Time to testosterone recovery (days) | | |
| Number with events, n (%) | 34 (52) | 6 (16) |
| Number censored, n (%) | 30 (46) | 32 (84) |
| | | |
| $25^{th}$ percentile (95% CI) | 57 (43,62) | 100 (87,106) |
| Median (95% CI) | 91 (82,127) | 100 (100,106) |
| $75^{th}$ percentile (95% CI) | 127 (93,127) | 106 (100,106) |
| Min, Max | 7*,127 | 58,106 |
| | | |
| Kaplan-Meier estimates[a] (95% CI) | | |
| 4 weeks from last dose[c] | 0.03 (0.00,0.08) | 0.00 (0.00,0.00) |
| 8 weeks from last dose[c] | 0.24 (0.13,0.34) | 0.00 (0.00,0.00) |
| 12 weeks from last dose[c] | 0.45 (0.33,0.58) | 0.06 (0.00,0.13) |
| | | |
| Percent recovery (95% CI)[d] | | |
| 4 weeks from last dose[c] | 3.1 (0.4,10.7) | NE |
| 8 weeks from last dose[c] | 23.1 (13.5,35.2) | NE |
| 12 weeks from last dose[c] | 43.1 (30.8,56.0) | 5.3 (0.6,17.7) |

TREATMENT OF PROSTATE CANCER

CROSS-REFERENCE TO RELATED APPLICATIONS

This application is a continuation of U.S. patent application Ser. No. 18/959,460, filed Nov. 25, 2024, which is a continuation of U.S. patent application Ser. No. 18/937,891, filed Nov. 5, 2024, now issued as U.S. Pat. No. 12,336,990, which is a continuation of U.S. patent application Ser. No. 18/792,752, filed Aug. 2, 2024, which is a continuation of U.S. patent application Ser. No. 17/866,203, filed Jul. 15, 2022, now issued as U.S. Pat. No. 12,097,198, which is a continuation application of U.S. patent application Ser. No. 16/998,900, filed Aug. 20, 2020, now issued as U.S. Pat. No. 11,583,526, which is a continuation application of U.S. patent application Ser. No. 16/563,161, filed Sep. 6, 2019, now issued as U.S. Pat. No. 10,786,501, which is a continuation application of U.S. patent application Ser. No. 16/369,729, filed Mar. 29, 2019, now issued as U.S. Pat. No. 10,449,191, which is a continuation application of International Application No. PCT/EP2017/074849, filed Sep. 29, 2017, which claims priority to U.S. Provisional Application No. 62/402,150, filed Sep. 30, 2016, and U.S. Provisional Application No. 62/402,004, filed Sep. 30, 2016, the disclosures of which are incorporated herein by reference in their entireties.

FIELD

The present disclosure relates to methods for treating prostate cancer, including advanced prostate cancer and hormone dependent or sensitive prostate cancer, in a subject by an oral formulation. It also includes the treatment of men with castration-resistant prostate cancer. In particular, the present disclosure relates to methods for suppressing one or more sex hormones in a subject, by once-daily oral administration of a dosage form. The present disclosure also relates to a dosage pack having a separate oral load dose formulation and oral maintenance dose formulation.

BACKGROUND

Prostate cancer is the second most prevalent form of cancer in men and the second leading cause of death due to cancer in men in the United States. According to the National Cancer Institute, approximately 2.9 million men are currently living with prostate cancer in the United States, and approximately 180,000 men are newly diagnosed in the United States each year.

After diagnosis of prostate cancer, treatments generally include combinations of surgery and radiation therapy, but androgen deprivation therapies, or ADT, are also used. Prostate cancer is responsive to surgical castration and the effectiveness of this therapy results from the elimination of androgens. An androgen may refer to any natural or synthetic compound, usually a steroid hormone, which stimulates or controls the development and maintenance of male characteristics in vertebrates by binding to androgen receptors. Androgens include testosterone, dihydrotestosterone (DHT), dehydroepiandrosterone, and androstenedione. Most prostate cancers are androgen dependent and androgens, such as testosterone, promote the growth of cancerous prostate cells. ADT drastically reduces serum testosterone levels, blocks androgen receptor signaling, and delays prostate cancer progression. ADT serves as alternative to surgical castration and is valuable in the treatment of prostate cancer.

Castration by orchiectomy or a gonadotropin-releasing hormone (GnRH) agonist (GnRH receptor agonist) is the main mode of therapy for localized progressive and metastatic cancers, and GnRH agonists, such as leuprolide acetate, are widely used. When multiple doses of a GnRH agonist are administered, a temporary increase in gonadotropin secretion occurs. That is followed by a decrease in responsiveness (desensitization) in the pituitary gland and a decrease in secretion of the pituitary sex hormones, such as luteinizing hormone (LH) and follicle-stimulating hormone (FSH), which results in the decrease of sex hormones produced by the testes, such as testosterone and DHT. The initial increase in hormones caused by GnRH agonists leads to a temporary worsening of symptoms known as a clinical flare, such as an increase in bone pain and, more seriously, spinal cord compression. The effectiveness of GnRH agonist therapy does not begin to appear until about 3 to 4 weeks after the initial dose. In addition, known GnRH agonists are peptides that are unable to be administered orally and must be administered subcutaneously (SC), intravenously (IV), intramuscularly, or intranasally. Often these GnRH agonists are administered as depot formulation once every 1-3 months. Consequently, development is needed for a new treatment that is easy and convenient to administer, does not cause clinical flare, and which allows for suspension of treatment for a variety of time periods, and an increase in serum testosterone levels over a short period of time once treatment is suspended.

BRIEF SUMMARY OF THE DISCLOSURE

One aspect of the disclosure relates to a method for treating prostate cancer in a subject in need of an increase in serum testosterone levels to a level above 50 ng/dl, the method comprising administering to the subject once-daily an oral formulation comprising about 80 mg to about 480 mg of Compound 1: N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, wherein when the once-daily administration is suspended for a suspension period, the subject experiences an increase of serum testosterone levels.

Another aspect of the disclosure relates to a method for treating prostate cancer in a subject in need thereof, the method comprising administering to the subject once-daily an oral formulation comprising about 80 mg to about 480 mg of Compound 1, or a corresponding amount of a pharmaceutically acceptable salt thereof; suspending administration of the oral formulation for a suspension period to allow for an increase of serum testosterone levels; and resuming administering to the subject once-daily the oral formulation at the end of the suspension period.

One aspect of the disclosure relates to an oral formulation comprising about 80 mg to about 480 mg of Compound 1, or a corresponding amount of a pharmaceutically acceptable salt thereof, for use in a method of treating prostate cancer in a subject in need thereof.

Another aspect of the disclosure relates to an oral formulation comprising about 80 mg to about 480 mg of Compound 1, or a corresponding amount of a pharmaceutically acceptable salt thereof, for use in a method for treating prostate cancer in a subject in need thereof, the method comprising: administering the oral formulation to the subject once daily; suspending administration of the oral formulation for a suspension period to allow for an increase of serum testosterone levels; and resuming administering to the subject once daily the oral formulation at the end of the suspension period.

In certain embodiments of any of the foregoing or following, after the suspension period, once-daily administration of the oral formulation of the disclosure is not resumed.

In certain embodiments of any of the foregoing or following, the serum testosterone level increases to above medical castration level. In some embodiments, the serum testosterone level increases to greater than about 55 ng/dL or to greater than about 350 ng/dL. In certain embodiments, the serum testosterone level increases to about 300 ng/dL to about 600 ng/dL.

In some embodiments of any of the foregoing or following, the serum testosterone level increases to the subject's serum testosterone level prior to once-daily administration of the oral formulation of the disclosure. In certain embodiments of any of the foregoing or following, the serum testosterone level increases to the subject's serum testosterone level prior to once-daily administration of the oral formulation of the disclosure within 7 days of the beginning of the suspension period. In certain embodiments of any of the foregoing or following, the serum testosterone level increases to the subject's serum testosterone level prior to once-daily administration of the oral formulation of the disclosure within 45 days of the beginning of the suspension period.

In some embodiments of any of the foregoing or following, the prostate cancer is hormone dependent prostate cancer. In certain embodiments, the prostate cancer is advanced prostate cancer. In some embodiments, the prostate cancer is metastatic, non-metastatic, locally advanced, advanced hormone sensitive, advanced castration resistant, or recurrent. In certain embodiments, the prostate cancer is castration-resistant metastatic prostate cancer. In some embodiments, the prostate cancer is castration-resistant non-metastatic prostate cancer. In certain embodiments, the prostate cancer is hormone-sensitive metastatic prostate cancer. In some embodiments, the prostate cancer is hormone-sensitive non-metastatic prostate cancer.

In certain embodiments of any of the foregoing or following, said administering comprises administration once-daily of an oral load dose formulation of from about 240 mg to about 480 mg of Compound 1, or a corresponding amount of a pharmaceutically acceptable salt thereof, for 1-3 days at the beginning of treatment. In some embodiments, said administering comprises administration once-daily of an oral load dose formulation of from about 240 mg to about 480 mg of Compound 1, or a corresponding amount of a pharmaceutically acceptable salt thereof, for 1-3 days at the beginning of treatment after the suspension period. In certain embodiments, said administering comprises administration once-daily of an oral maintenance dose formulation of from about 80 mg to about 160 mg of Compound 1, or a corresponding amount of a pharmaceutically acceptable salt thereof. In certain embodiments of any of the foregoing or following, the once-daily oral maintenance dose formulation administration begins on the day after administering the last dose of the once-daily oral load dose formulation.

In certain embodiments of any of the foregoing or following, the suspension period is up to 52 weeks, up to 36 weeks, up to 24 weeks, up to 12 weeks, up to 8 weeks, or up to 4 weeks.

In certain embodiments of any of the foregoing or following, the suspension period is discontinued when the subject's prostate-specific antigen (PSA) level is ≥20% of the subject's PSA level of the nadir during treatment. In some embodiments, the suspension period is discontinued when the subject's PSA level is ≥50% of the subject's PSA level prior to treatment. In certain embodiments, the suspension period is discontinued when the subject's PSA level is greater than the subject's PSA level at the beginning of the suspension period. In certain embodiments, the suspension period is discontinued when the subject experiences return of symptoms of prostate cancer. In some embodiments, the suspension period may be discontinued when the subject's PSA level is ≥3 ng/ml, ≥10 ng/ml, ≥20 ng/ml, or ≥30 ng/mL.

In certain embodiments of any of the foregoing or following, the oral formulation is administered once-daily for 12 consecutive weeks or greater, for 24 consecutive weeks or greater, for 48 consecutive weeks or greater, for 52 consecutive weeks or greater, for 72 consecutive weeks or greater, or for 96 consecutive weeks or greater.

In certain embodiments of any of the foregoing or following, once-daily administration of an oral formulation of the disclosure is suspended after at least 24 consecutive weeks of treatment, at least 36 consecutive weeks of treatment, or at least 52 consecutive weeks of treatment.

In certain embodiments of any of the foregoing or following, the subject is in need of an increase in serum testosterone levels due to an intercurrent illness, receiving radiation therapy, while bedridden, having suffered an injury, having a surgical procedure or other invasive procedure, or a desire for a period of restored sexual function. In some embodiments, the subject is in need of an increase in serum testosterone levels due to an intercurrent illness or surgical or other invasive procedure with projected full recovery time of at least two weeks. In certain embodiments, once-daily administration of the oral formulation of the disclosure is suspended prior to a surgical or other invasive procedure or radiation therapy. In some embodiments, once-daily administration of the oral formulation of the disclosure is suspended after or during the surgical or other invasive procedure, injury, or radiation therapy. In certain embodiments of any of the foregoing or following, once-daily administration of the oral formulation of the disclosure occurs prior to and during the surgical or other invasive procedure or radiation therapy and once-daily administration of the oral formulation of the disclosure is suspended after the surgery or other invasive procedure or radiation therapy. In some embodiments, the surgical procedure is heart surgery, knee replacement, hip replacement, abdominal surgery, pelvic surgery, vascular surgery, spine surgery, or an emergency procedure due to injury. In certain embodiments of any of the foregoing or following, the subject is identified as at risk for acute postoperative frailty. In some embodiments, once-daily administration of the oral formulation of the disclosure is suspended during the intercurrent illness or while the subject is bedridden. In some embodiments, once-daily administration of the oral formulation of the disclosure is suspended following an accident or injury requiring prolonged recovery. In some embodiments, once-daily once-daily administration of the oral formulation of the disclosure is suspended following a stroke, cerebral hemorrhage, myocardial infarction, congestive heart failure, hip fracture or other event resulting in limited mobility and requiring prolonged recovery. In certain embodiments, once-daily administration of the oral formulation of the disclosure resumes after the subject is recovered from the intercurrent illness, is no longer bedridden, has resumed normal activities of daily living, or has regained a normal level of function. In some embodiments, the invasive procedure is a colonoscopy, angioplasty, stent placement, endovascular coil placement, endovascular aneurysm repair, endoscopy, laparoscopy, arthroscopy, coronary catheterization, or another catheter-based procedure.

In certain embodiments of any of the foregoing or following, the serum testosterone level is above medical castration levels within 7 days of the suspension of once-daily administration of the oral formulation of the disclosure.

In certain embodiments of any of the foregoing or following, the oral load dose formulation comprises about 240 mg, about 360 mg, or about 480 mg of Compound 1, or a corresponding amount of a pharmaceutically acceptable salt thereof. In certain such embodiments, the oral load dose formulation comprises about 360 mg of Compound 1, or a corresponding amount of a pharmaceutically acceptable salt thereof.

In certain embodiments of any of the foregoing or following, the oral maintenance dose formulation comprises about 80 mg, about 120 mg, or about 160 mg of Compound 1, or a corresponding amount of a pharmaceutically acceptable salt thereof. In certain such embodiments, the oral maintenance dose formulation comprises about 120 mg of Compound 1, or a corresponding amount of a pharmaceutically acceptable salt thereof.

In certain embodiments of any of the foregoing or following, the oral load dose formulation comprises about 360 mg of Compound 1, or a corresponding amount of a pharmaceutically acceptable salt thereof, and is administered once on day 1 of treatment, and the oral maintenance formulation comprises about 120 mg of Compound 1, or a corresponding amount of a pharmaceutically acceptable salt thereof, and is administered once-daily.

In certain embodiments of any of the foregoing or following, the oral formulation comprises about 80 mg to about 160 mg of Compound 1, or a corresponding amount of a pharmaceutically acceptable salt thereof.

In certain embodiments of any of the foregoing or following, the administering is pre-prandial. In some embodiments, the administering is at least 1 hour before eating or at least 2 hours after eating. In certain embodiments, the administering is at least 30 minutes before eating or while subject is fasting.

In certain embodiments of any of the foregoing or following, the oral formulation, oral load dose formulation and oral maintenance dose formulation are immediate release formulations.

In certain embodiments of any of the foregoing or following, the oral maintenance dose formulation comprises 102 mg to 204 mg of mannitol, 6 mg to 12 mg of hydroxypropyl cellulose, 10 mg to 20 mg of sodium starch glycolate, and 2 mg to 4 mg of magnesium stearate.

One aspect of the disclosure relates to any of the foregoing or following methods or uses further comprising administering an anti-androgen. In certain such embodiments, the anti-androgen is selected from the group consisting of flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine.

In certain embodiments of any of the foregoing or following methods or uses, the methods or uses further comprise administering a CYP17 lyase inhibitor. In certain such embodiments, the CYP17 lyase inhibitor is abiraterone.

In certain embodiments of any of the foregoing or following, the subject's serum testosterone level is suppressed prior to and after the suspension of once-daily administration of the oral formulation of the disclosure.

In certain embodiments of any of the foregoing or following, the method or use does not comprise administration of an anti-androgen.

In certain embodiments of any of the foregoing or following, the method or use does not comprise administration of prednisone. In some embodiments, the method or use further comprises administration of prednisone.

In certain embodiments of any of the foregoing or following, the method or use further comprises suspending once-daily administration of the oral formulation of the disclosure for a subsequent suspension period after completion of the suspension period and resumption of once-daily administration of the oral formulation of the disclosure. In some embodiments, the subsequent suspension period occurs at least 12 weeks after resuming once-daily administration of the oral formulation comprising about 80 mg to about 480 mg of Compound 1, or a corresponding amount of a pharmaceutically acceptable salt thereof.

In certain embodiments of any of the foregoing or following, within about 4 to about 8 days of first administering once-daily the oral formulation, or oral load dose formulation and oral maintenance dose formulation, the serum testosterone levels in the subject are at or below medical castration level. In some embodiments, within 4 days of first administering once-daily the oral formulation, or oral load dose formulation and oral maintenance dose formulation, the serum testosterone levels in the subject are at or below medical castration level.

One aspect of the disclosure relates to use of Compound 1, or a pharmaceutically acceptable salt thereof, for the manufacture of a medicament for the treatment of prostate cancer. In certain such embodiments, the prostate cancer is hormone dependent prostate cancer, advanced prostate cancer, metastatic, non-metastatic, locally advanced, advanced hormone sensitive, advanced castration resistant, recurrent, castration-resistant metastatic prostate cancer, castration-resistant non-metastatic prostate cancer, hormone-sensitive metastatic prostate cancer, or hormone-sensitive non-metastatic prostate cancer. In some embodiments, the medicament comprises 80 mg to about 480 mg of Compound 1, or a corresponding amount of the pharmaceutically acceptable salt thereof.

Other objects and advantages of the present disclosure will become apparent from the detailed description that follows.

BRIEF DESCRIPTION OF THE DRAWINGS

FIG. 2 is a table of individual changes in serum testosterone concentration of each Compound 1 dose level in accordance with Example 6 in which the serum testosterone concentrations are graphically depicted in FIGS. 1 and 7.

FIG. 13 is a table of serum prostate-specific antigen (PSA) and change from the subject's serum PSA level prior to treatment commencing with each Compound 1 dose level (Part A) in accordance with Example 6.

FIG. 14 is a table of serum PSA and change from the subject's serum PSA level prior to treatment commencing with each Compound 1 dose level (Part B) in accordance with Example 6.

FIG. 16 is a table of plasma pharmacokinetic (PK) parameters of Compound 1 for a treatment period (Part A) in accordance with Example 6.

FIG. 20 is a table of mean plasma and urine pharmacokinetic (PK) parameters following a single oral Compound 1 dose administration (Part 1) in accordance with Example 7.

FIG. 22 is a table of mean plasma and urine Compound 1 pharmacokinetic (PK) parameters obtained after day 1 after oral Compound 1 administration (Part 2) in accordance with Example 7.

FIG. 23 is a table of mean plasma and urine Compound 1 pharmacokinetic (PK) parameters obtained after day 14 after multiple oral Compound 1 administration (Part 2) in accordance with Example 7.

FIG. 24 is a table of mean serum LH concentration-time data (IU/L) for the treatment period (Part 1) in accordance with Example 7.

FIG. 26 is a table of mean serum testosterone concentration-time data (nmol/L) for the treatment period (Part 1) in accordance with Example 7.

FIG. 27 is a table of mean serum FSH concentration-time data (IU/L) for the treatment period (Part 1) in accordance with Example 7.

FIG. 28 is a table of mean serum dihydrotestosterone (DHT) concentration-time data (nmol/L) for the treatment period (Part 1) in accordance with Example 7.

FIG. 29 is a table of mean serum LH concentration-time data (IU/L) for the treatment period (Part 2) in accordance with Example 7.

FIGS. 31A and 31B are a table of mean serum testosterone concentration-time data (nmol/L) for the treatment period (Part 2) in accordance with Example 7.

FIG. 32 is a table of mean serum FSH concentration-time data (IU/L) for the treatment period (Part 2) in accordance with Example 7.

FIG. 33 is a table of mean serum dihydrotestosterone (DHT) concentration-time data (nmol/L) for the treatment period (Part 2) in accordance with Example 7.

FIG. 34 is a table of mean serum LH concentration-time data (IU/L) for the treatment period (Part 3) in accordance with Example 7.

FIG. 36 is a table of mean serum testosterone concentration-time data (nmol/L) for the treatment period (Part 3) in accordance with Example 7.

FIG. 37 is a table of mean serum FSH concentration-time data (IU/L) for the treatment period (Part 3) in accordance with Example 7.

FIG. 38 is a table of mean serum dihydrotestosterone (DHT) concentration-time data (nmol/L) for the treatment period (Part 3) in accordance with Example 7.

FIG. 39 is a table of mean serum LH concentration-time data (IU/L) for the treatment period (Part 4) in accordance with Example 7.

FIG. 41 is a table of mean serum testosterone concentration-time data (nmol/L) for the treatment period (Part 4) in accordance with Example 7.

FIG. 42 is a table of mean serum FSH concentration-time data (IU/L) for the treatment period (Part 4) in accordance with Example 7.

FIG. 43 is a table of mean serum dihydrotestosterone (DHT) concentration-time data (nmol/L) for the treatment period (Part 4) in accordance with Example 7.

FIG. 49 is a table of castration and profound castration rate data for Compound 1 compared to degarelix in accordance with Example 9. CI=confidence interval, Q4W=once every 4 weeks, QD=daily. (a) Castration rate was defined as the estimated proportion of patients who have serum testosterone concentrations <50 ng/dL at all scheduled visits Week 5, Day 1 to specific timepoint (Week 25, Day 1). (b) The 2-sided 95% CI was calculated using the normal approximation method, if the number of non-castration patients was =5 in any treatment arm, the exact CI was presented. (c) Profound castration rate was defined as the estimated proportion of patients who had serum testosterone concentrations <20 ng/dL at all scheduled visits Week 13, Day 1 through specific timepoint (Week 25, Day 1).

FIG. 51 is a table of time to serum testosterone recovery (i.e., the subject's serum testosterone level prior to treatment commencing or >280 ng/dL) in accordance with Example 9. CI=confidence interval, Max=maximum, Min=minimum, NE=not estimable, Q4W-once every 4 weeks, QD-daily. * indicates a censored observation. (a) Time to serum testosterone recovery was defined as the time from 1 day after the last dose of Compound 1 or 4 weeks plus 1 day after the last dose of degarelix to serum testosterone recovery. Serum testosterone recovery was defined as back to the subject's serum testosterone level prior to treatment commencing or >280 ng/dL whichever occurs first. It was censored for patients starting alternative ADT without recovery at the last serum testosterone lab assessment before the start of ADT. (b) Probability of event (n=number of subjects at risk). (c) 4, 8 or 12 weeks from 1 day after the last dose of Compound 1 or 4, 8 or 12 weeks plus 1 day after the last dose of degarelix. (d) The 2-sided 95% CI for proportion was calculated using the normal approximation method.

DETAILED DESCRIPTION

Figure 1:
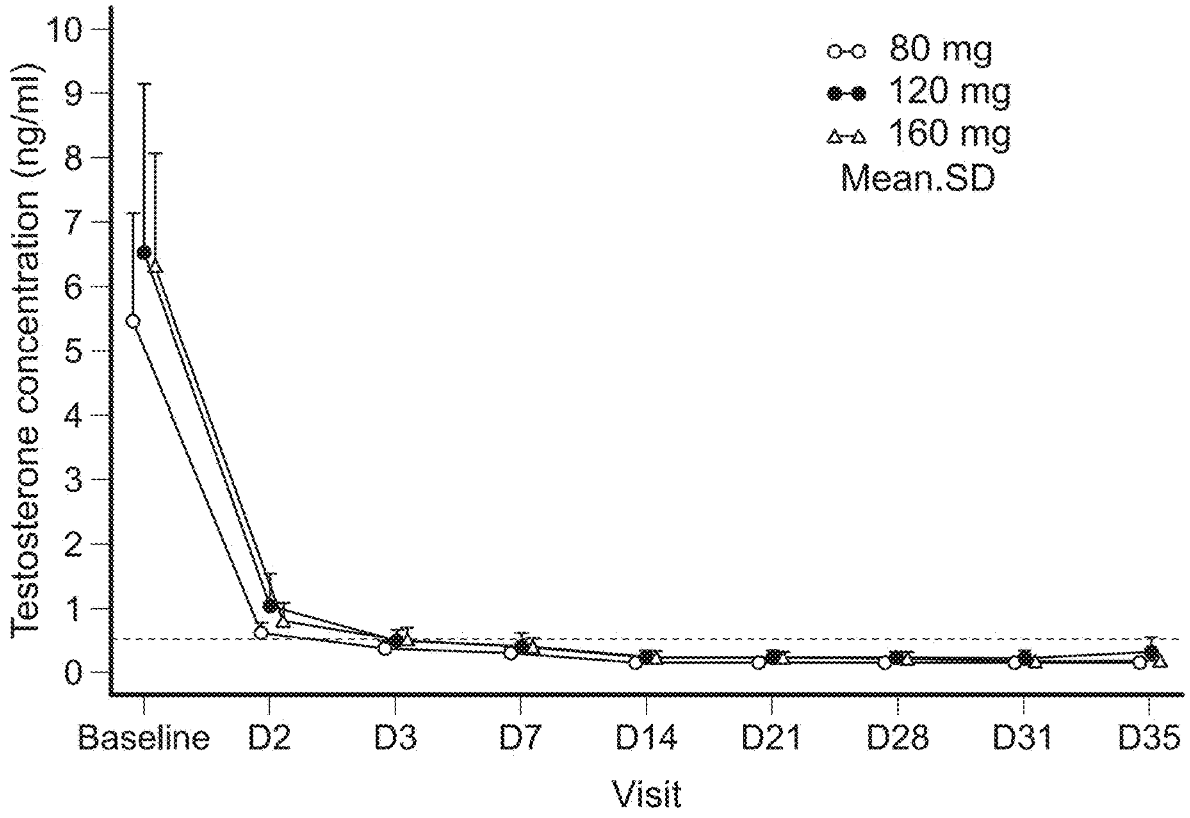
FIG. 1 graphically depicts mean serum testosterone concentrations for a treatment period of 28 days in accordance with Example 6.
Figure 3:
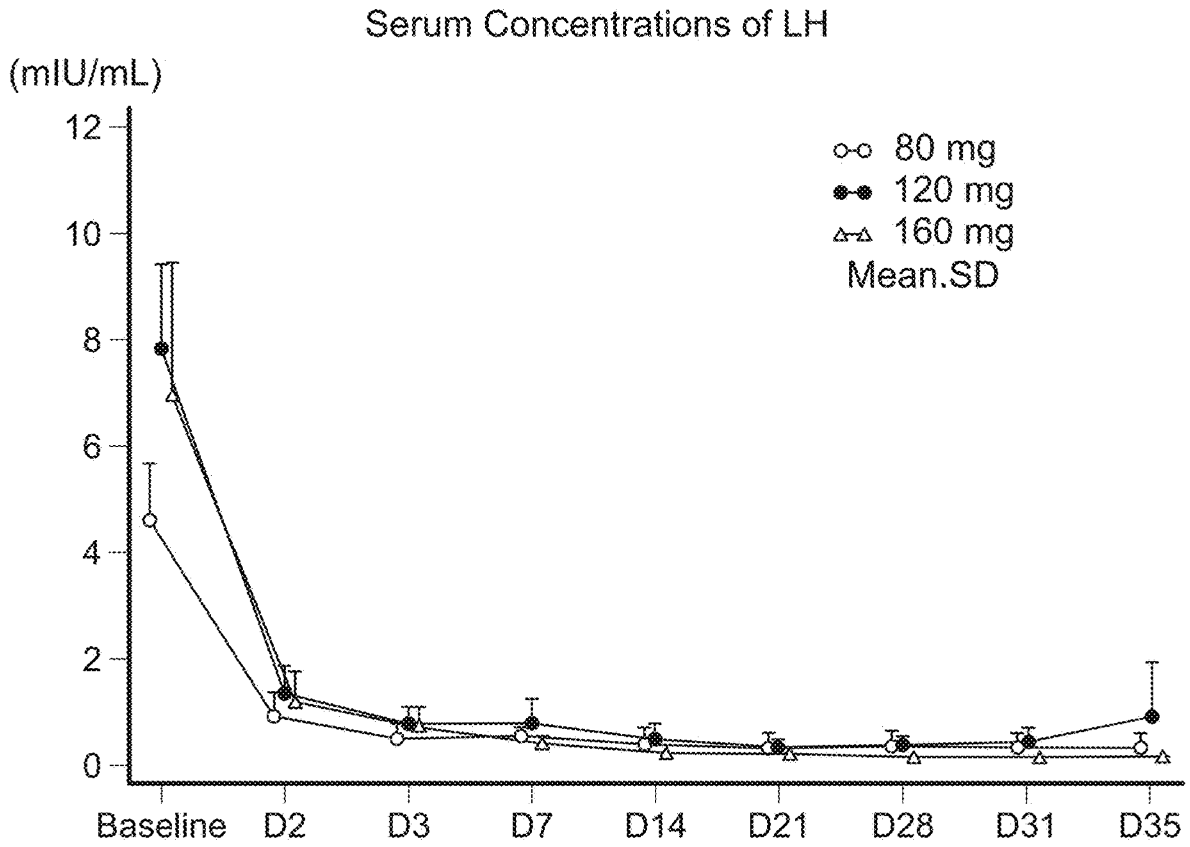
FIG. 3 graphically depicts mean serum LH concentrations for a treatment period (Part A) in accordance with Example 6.
Figure 4:
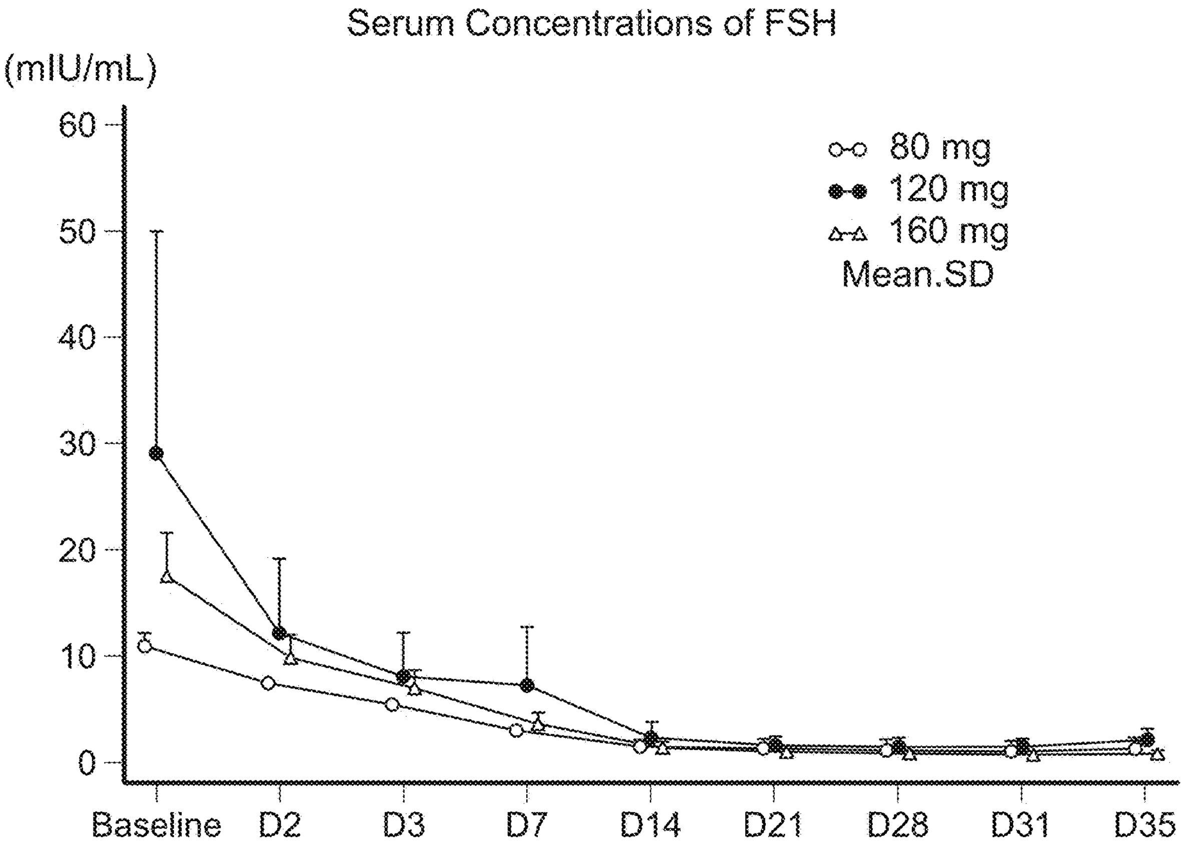
FIG. 4 graphically depicts mean serum FSH concentrations for a treatment period (Part A) in accordance with Example 6.
Figure 5:
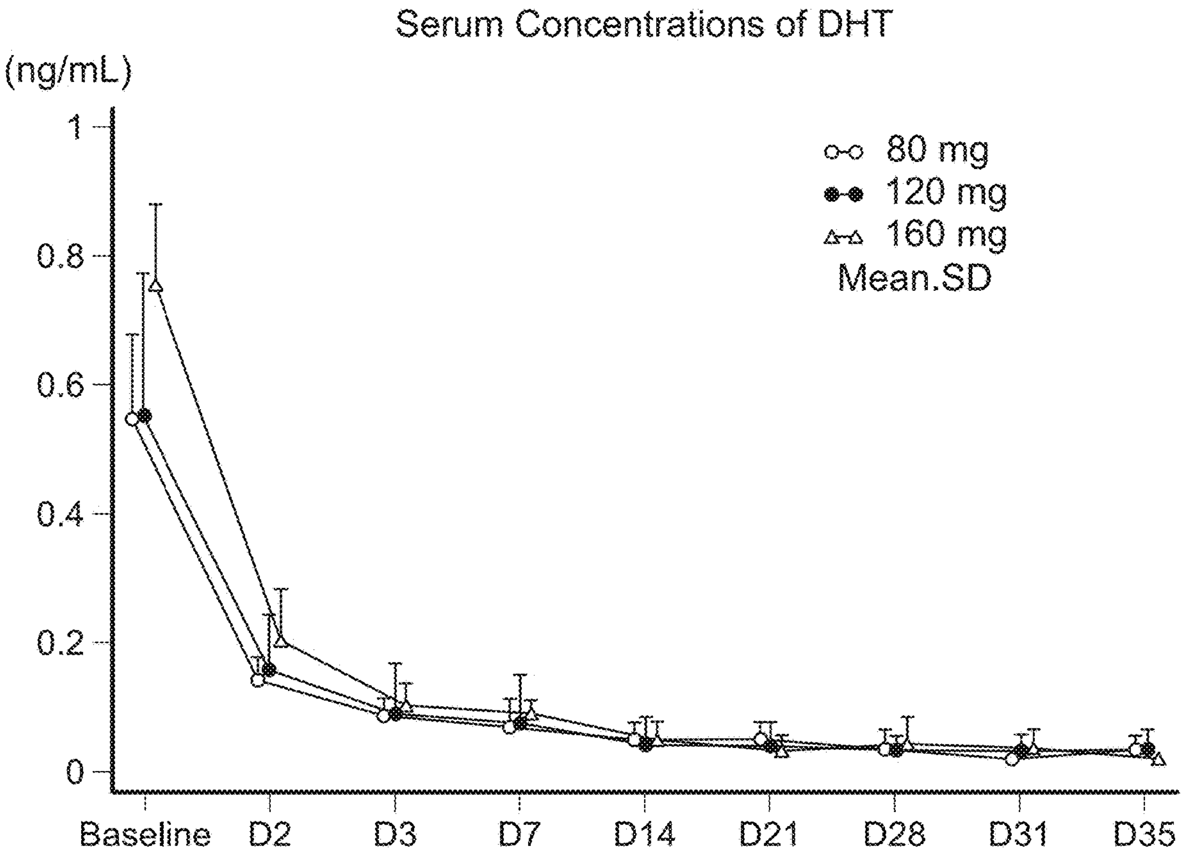
FIG. 5 graphically depicts mean serum dihydrotestosterone (DHT) concentrations for a treatment period (Part A) in accordance with Example 6.
Figure 6:
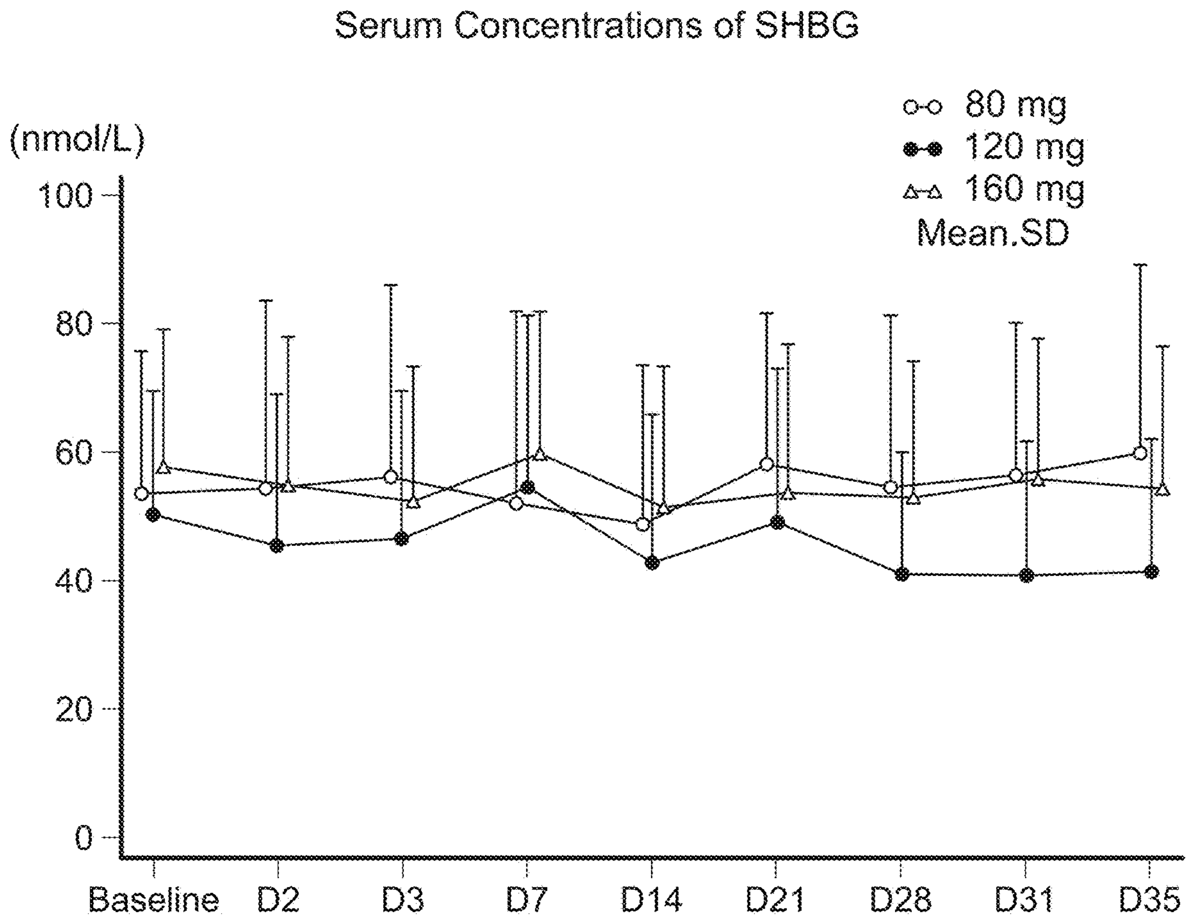
FIG. 6 graphically depicts mean serum sex hormone-binding globulin (SHBG) concentrations for a treatment period (Part A) in accordance with Example 6.

Disclosed herein are methods of using an orally active GnRH antagonist (GnRH receptor antagonist), Compound 1, or a pharmaceutically acceptable salt thereof, once-daily for the treatment of prostate cancer. The prostate cancer can be hormone dependent prostate cancer, advanced prostate cancer, advanced hormone sensitive prostate cancer, metastatic, non-metastatic, locally advanced, advanced hormone dependent, advanced castration resistant, recurrent, castration-resistant metastatic prostate cancer, castration-resistant non-metastatic prostate cancer, hormone-sensitive metastatic prostate cancer, or hormone-sensitive non-metastatic prostate cancer. After administration to a subject, formulations comprising Compound 1, or a pharmaceutically acceptable salt thereof, rapidly inhibit production of sex hormones, such as testosterone, LH, and FSH, and are not associated with an initial aggravation of symptoms, also known as clinical or hormonal flares.

Unlike GnRH agonists such as leuprolide acetate, Compound 1, or a pharmaceutically acceptable salt thereof, is present in an oral formulation and is not a depot, or a slow-release formulation and, once treatment is suspended, hormone levels increase and may return to the subject's serum hormone levels prior to treatment commencing (i.e., baseline levels) after once-daily administration of Compound 1, or a pharmaceutically acceptable salt thereof, is discontinued, thereby providing more control for patients and their physicians. Thus, in contrast to a treatment that uses depot injections, the treatment methods and uses of this disclosure allow for suspension periods in which subjects can stop treatment for a period of time and later restart treatment with no adverse effects. Suspension of treatment can be planned (e.g., in advance of, during or after a scheduled surgical or invasive procedure (e.g., knee replacement surgery or colonoscopy)) or can be implemented after the subject experiences, for example, intercurrent illness or injury. In either scenario (planned or unplanned), increasing the serum testosterone levels aids in recovery or helps to maintain the subject's physical health.

Additionally, in some patients receiving GnRH antagonists or GnRH agonists, even after treatment is discontinued for significant time periods, pre-treatment levels of serum testosterone are not achieved. Miranda et al., The Journal of Urology, May 16, 2017, Volume 197, Issue 4, e1221-e1222 (noting 23% of patients receiving ADT with a GnRH agonist maintained medical castration testosterone levels at 24 months after ADT cessation); Tsumura et al., World J. Radiol., Dec. 28, 2015; 7 (12): 494-500 (noting five years after the cessation of GnRH agonist therapy, approximately one-fifth of patients still had medical castration testosterone levels). One of the advantages of Compound 1, or a pharmaceutically acceptable salt thereof, is that, as shown in Example 9 and FIGS. 50 and 53, 43% of subjects achieve pre-treatment serum testosterone levels or a serum testosterone level at or above 280 ng/dl by 12 weeks versus only 5.3% with degarelix.

The disclosure provides methods and uses for treating prostate cancer in a subject in need thereof comprising administering, once-daily, formulations comprising Compound 1, or a pharmaceutically acceptable salt thereof. Subjects treated once-daily with oral formulations comprising Compound 1, or a pharmaceutically acceptable salt thereof, experience an increase in serum testosterone levels after the last dose of the formulation comprising Compound 1, or a pharmaceutically acceptable salt thereof. Accordingly, the disclosure provides methods of using oral formulations comprising Compound 1, or a pharmaceutically acceptable salt thereof, for treating prostate cancer in a subject in need of an increase in serum testosterone levels to a level above 50 ng/dL. Once-daily administration of formulations comprising Compound 1, or a pharmaceutically acceptable salt thereof, can be suspended for a suspension period, leading to an increase in the subject's serum testosterone levels shortly after the beginning of the suspension period. For example, for most subjects, serum testosterone levels will increase within 1 week of beginning a suspension period. An increase in a subject's serum testosterone level can be very beneficial for subjects experiencing an intercurrent illness, receiving radiation therapy, while bedridden, having suffered an injury, having a surgical procedure or other invasive procedure, or a desire for a period of restored sexual function (e.g., 25th wedding anniversary). Higher serum testosterone levels can be beneficial in such subjects because testosterone has an anabolic effect, helping to rebuild tissues, increase weight and muscle mass, and promote growth and mineralization of bone. Treatment can also be suspended to improve the subject's quality of life and energy levels; to help with healing after injury, illness, surgery, or radiation therapy; to aid subjects in remaining in control of their lifestyles; and to assist in regaining strength and mobility after intercurrent illness. Even before serum testosterone levels reach the subject's serum testosterone level prior to treatment commencing, the benefit of increased serum testosterone compared to a medical castration level may be important in a subject's recovery from, for example, surgery, such as knee replacement or hip surgery (whether planned or unplanned). The contribution of testosterone to rebuilding tissue and increasing muscle mass can be a factor for successful post-surgery physical therapy and regaining range of movement, mobility and strength. Once-daily administration of oral formulations comprising Compound 1, or a pharmaceutically acceptable salt thereof, can resume at the end of the suspension period. Alternatively, once-daily administration of oral formulations comprising Compound 1, or a pharmaceutically acceptable salt thereof, does not necessarily resume after suspension of once-daily administration, for example, if prostate-specific antigen (PSA) levels remain at an acceptable level during the suspension period.

Upon initial treatment or resumption of administration of Compound 1, or a pharmaceutically acceptable salt thereof, after a suspension period, serum testosterone levels typically fall to at or below medical castration levels within about 4 to about 8 days of first administering once-daily an oral formulation of the disclosure. This is in contrast with leuprolide and other GnRH agonists. If a subject stops and restarts treatment with leuprolide, or other GnRH agonists, it may take up to one month to observe a decrease in the subject's serum testosterone levels. Furthermore, the maximum decline in PSA, or PSA nadir, occurs more rapidly with once-daily administration of Compound 1, or a pharmaceutically acceptable salt thereof, than with GnRH agonists. Once-daily administration of Compound 1, or a pharmaceutically acceptable salt thereof, after a suspension period, also results in rapid (within days) and complete suppression of FSH unlike the GnRH agonists. There is a correlation between higher FSH levels and the progression of prostate cancer, as FSH stimulates FSH receptors expressed on the endothelial cells of tumor blood vessels in prostate cancer specimens. Further, patients with low FSH levels have a significantly longer time to castration resistance.

These advantages of the present methods and uses are important both in the treatment setting, for example, where a subject may be receiving radiation treatment or where there is the occurrence of a condition or procedure unrelated to the prostate cancer treatment. For example, as noted previously consider a subject undergoing prostate cancer treatment who is involved in a car accident. Whether or not a surgical procedure is required to aid in recovery from the car accident, higher serum testosterone levels will aid in the subject's recovery, such as in rebuilding damaged tissues or promoting the mineralization of bone in the case of fractures. Unlike in a treatment regimen involving a depot formulation, which is injected and requires a long period of time for a subject's serum testosterone levels to rise even after the nominal treatment period is complete, the present methods and uses allow for suspension of treatment by stopping the once-daily administration of the oral formulations, leading to an immediate rise in serum testosterone levels, without adverse effects in response to unexpected events. Additionally, where upcoming surgeries may be planned, for example a hip or knee replacement, the treatment can be suspended either shortly prior to or at the time of surgery to ensure optimal recovery of the patient after surgery and potentially better outcomes due to higher levels of the anabolic hormone testosterone. The methods and uses disclosed herein may allow for resumption of once-daily administration of Compound 1, or a pharmaceutically acceptable salt thereof, during the post-operative recovery stage if a subject's prostate cancer begins to worsen or spread. Upon resumption of administration of Compound 1, or a pharmaceutically acceptable salt thereof, after a suspension period for a surgery, serum testosterone levels typically fall to at or below medical castration levels within about 4 to about 8 days of first administering once-daily an oral formulation of the disclosure. As it may take up to one month to observe a decrease in a subject's serum testosterone levels after administering depot formulations of GnRH agonists, treatments involving these agonists may not have as much flexibility as treatments involving once-daily administration of Compound 1, or a pharmaceutically acceptable salt thereof. The maximum decline in PSA, or PSA nadir, may also occur more rapidly with once-daily administration of Compound 1, or a pharmaceutically acceptable salt thereof, after a suspension period than with GnRH agonists. Once-daily administration of Compound 1, or a pharmaceutically acceptable salt thereof, after a suspension period, may result in rapid (within days) and complete suppression of FSH unlike the GnRH agonists.

The intermittent therapy allowed by the methods, uses, and formulations of this disclosure may prevent the change from hormone dependent to androgen independent prostate cancer. Androgen independence may be an intrinsic, but dormant, property of some prostate cancer cells that is activated in response to androgen deprivation. The Compound 1, or a pharmaceutically acceptable salt thereof, intermittent therapy disclosed herein could be dosed so that a complete and continuous androgen deprivation does not happen, possibly preventing androgen independence. Rather than having a steady low level of serum testosterone, Compound 1, or a pharmaceutically acceptable salt thereof, can allow fluctuations back and forth (many peaks and valleys) with testosterone. "Intermittent treatment," intermittent therapy," or "intermittent dosing" may refer to on-again, off-again treatment or a "drug holiday." An example of intermittent treatment is stopping once-daily administration of oral formulations of the disclosure once the PSA drops to a very low level and if the PSA level begins to rise, restarting once-daily administration. Another form of intermittent therapy using the claimed methods and uses may employ therapy for fixed periods of time, for example, 6 months on followed by 6 months off.

Compound 1, or a pharmaceutically acceptable salt thereof, has a faster onset of action than currently available GnRH agonists, and unlike available peptide GnRH agonists that are given either subcutaneously or intranasally, Compound 1 is a non-peptide preparation that may be administered orally and once-daily. When compared to GnRH agonists, such as leuprolide acetate, which is typically administered as a depot formulation, Compound 1, or a pharmaceutically acceptable salt thereof, offers several advantages. Such advantages may include, but are not limited to, oral administration, rapid onset of serum testosterone suppression within four days, rapid onset of serum FSH suppression, rapid PSA depression, absence of clinical flare, no need for anti-androgen therapy to protect the patient from clinical flare symptoms. The ability to suspend treatment for periods of time can lead to an increase in serum testosterone levels shortly after treatment is suspended and may also return serum testosterone to the subject's serum testosterone level prior to treatment commencing after treatment is suspended, depending on the suspension period, and each of these outcomes may quickly result in improvements in quality of life, healing, and energy levels.

Compound 1, or a pharmaceutically acceptable salt thereof, also offers advantages over other GnRH antagonists. Once-daily oral administration of formulations comprising Compound 1, or a pharmaceutically acceptable salt thereof, allows hormone levels, such as serum testosterone levels, to return to the subject's serum hormone levels prior to treatment commencing more rapidly than a GnRH antagonist depot formulation, such as degarelix, after discontinuation. The option of increased serum testosterone levels, including a return to the subject's serum testosterone level prior to treatment commencing, is desirable for patients wanting to eliminate any unwanted effects of hormone suppression. The more rapid return of hormonal levels to the subject's serum hormone levels prior to treatment commencing is also advantageous in the restoration of energy levels and strength in men, for example, for the reasons such as described above. However, when the symptoms or markers (e.g., PSA levels) of the prostate cancer indicate a resumption of treatment is advisable, once-daily administration of Compound 1, or a pharmaceutically acceptable salt thereof, can resume at short notice, with a rapid onset of action, and without a clinical flare.

Provided herein is the use of oral formulations comprising Compound 1, or a pharmaceutically acceptable salt thereof, for the manufacture of a medicament for treatment according to any of methods described herein. Provided also are oral formulations comprising Compound 1, or a pharmaceutically acceptable salt thereof, for use in any of the methods described herein.

Further embodiments of the present disclosure are described hereinafter, in which some, but not all, embodiments of the disclosure are illustrated.

Each embodiment disclosed herein may be used individually or in combination with any other embodiment disclosed herein.

Publications, patents, and published patent applications referred to in this application are specifically incorporated by reference herein.

Compounds

As used herein, Compound 1, namely N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, is represented by the formula:

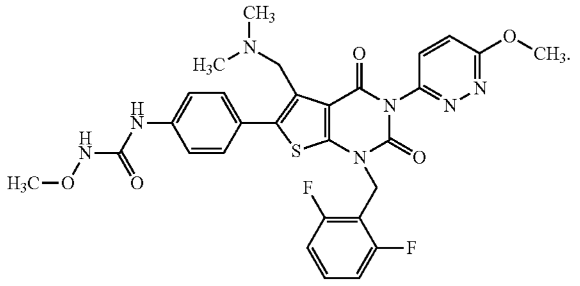 [SMILES: CONC(=O)Nc1ccc(-c2sc3c(c2CN(C)C)c(=O)n(-c2ccc(OC)nn2)c(=O)n3Cc2c(F)cccc2F)cc1]

Compound 1 and pharmaceutical compositions including Compound 1 can be produced by methods described in U.S. Pat. Nos. 7,300,935, 8,058,280, 9,346,822, 9,758,528, 8,735,401, and WO 2016136849, the disclosures of which are herein incorporated by reference.

In some embodiments, Compound 1 is a pharmaceutically acceptable salt. "Physiologically acceptable," "pharmaceutically acceptable," or "pharmacologically acceptable" compounds and compositions may include materials which are not biologically, or otherwise, undesirable. For example, the material may be administered to an individual without causing any substantially undesirable biological effects or interacting in a deleterious manner with any of the components of the composition in which it is contained. In certain such embodiments, the pharmaceutically acceptable salt of Compound 1 is a pharmaceutically acceptable acid addition salt. Such salts include, but are not limited to, salts with inorganic acids (e.g., hydrochloric acid, hydrobromic acid, nitric acid, sulfuric acid, phosphoric acid, and the like), and salts with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like).

Throughout the present disclosure, amounts of Compound 1 disclosed refer to the amount of Compound 1 free form present in the formulation. The term "corresponding amount" as used herein refers to the amount of a pharmaceutically acceptable salt of Compound 1 required to obtain the amount of Compound 1 free form recited in the formulation. It would be clear to one of skill in the art how to calculate the "corresponding amount" of the salt of a compound, such as the corresponding amount of the pharmaceutically acceptable salt of Compound 1, taking into account the difference in molecular weight between the free form of a compound and a salt form. For example, 80.0 mg of compound free base, would correspond to 84.7 mg of the HCl salt.

Compound 1 has been characterized as an orally active, nonpeptide, GnRH antagonist. Compound 1 has been shown to antagonize GnRH through the GnRH receptors, which are present in the pituitary anterior lobe basophiles (secretory cells), and inhibits the GnRH-stimulated secretion of LH and FSH from these cells. As a result, the drug decreases blood concentrations of hormones, including testosterone. Compound 1, or a pharmaceutically acceptable salt thereof, improves clinical symptoms observed in patients with prostate cancer. Administration of oral formulations comprising Compound 1, or a pharmaceutically acceptable salt thereof, also causes a rapid decline in serum PSA levels. As Compound 1 is a GnRH antagonist, it does not cause clinical flare and has a faster onset of action than GnRH agonists. Unlike GnRH agonists, Compound 1 is not a peptide preparation.

Therapeutic Uses and Methods of Treatment

Disclosed herein are methods of using an orally active, once-daily administered, GnRH antagonist, Compound 1, or a pharmaceutically acceptable salt thereof, for the treatment of prostate cancer.

The present disclosure provides oral formulations comprising at least 80 mg of Compound 1, or a corresponding amount of a pharmaceutically acceptable salt thereof, that can be employed in methods and uses for treating prostate cancer in a subject in need thereof. "Prostate cancer" may capture any cancer of the prostate, such as those described herein. Most prostate cancer is adenocarcinoma, but rarely can also include transitional cell (urothelial) cancer, squamous cell, small cell, carcinoid, or sarcomas. Prostate cancer can spread beyond the prostate (e.g., advanced prostate cancer) or it can be non-metastatic. "Non-metastatic prostate cancer" may refer to prostate cancer that has not spread from the primary site of the prostate and may be hormone-sensitive. Hormonal therapy is used to reduce the serum testosterone levels in prostate cancer. Hormonal therapy can also be used to reduce the serum PSA and FSH levels in prostate cancer. A "patient" or a "subject" may refer to a mammal or a non-mammal. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the present disclosure, the mammal is a human. In some embodiments of the present disclosure, the patient or subject is a human man.

In some embodiments of the methods and uses described herein, the prostate cancer is hormone dependent prostate cancer. "Hormone dependent prostate cancer," "hormone sensitive prostate cancer," "androgen dependent prostate cancer," or "androgen sensitive prostate cancer" may refer to prostate cancer needing relatively high levels of androgens to grow early in its development. Such prostate cancer may be referred to as androgen/hormone dependent or androgen/hormone sensitive because treatments that decrease androgen levels or block androgen activity can effectively inhibit its growth.

In some embodiments of the methods and uses described herein, the prostate cancer is advanced prostate cancer. Prostate cancer is typically considered "advanced" if it has spread beyond the prostate gland and the area around the prostate. It may spread to nearby tissues, lymph nodes, bones, or other parts of the body. When it spreads to tissues directly adjacent to the prostate gland, it is often referred to as "locally advanced prostate cancer." When it spreads beyond the tissues directly adjacent to the prostate gland, it is typically referred to as "metastatic prostate cancer." Metastatic prostate cancer typically may have spread to the bone, lung, liver, brain, lymph nodes outside the pelvis, or other organs, and may be hormone-sensitive. The following types of prostate cancer are also generally considered "advanced": PSA biochemical relapse following primary surgical or radiation therapy of curative intent; newly diagnosed metastatic prostate cancer; advanced localized disease for which immediate radiation or surgical therapy is not indicated, or men whose disease progresses after prostatectomy or radiation. The clinical recurrence of advanced prostate cancer occurs when it is associated with symptoms. Therefore, "advanced" prostate cancer may be present with or without evidence on diagnostic imaging tests and with or without clinical symptoms. The treatment methods and uses of this disclosure include palliative treatment of advanced prostate cancer.

In some embodiments of the methods and uses described herein, the prostate cancer is advanced hormone sensitive prostate cancer. "Advanced hormone dependent prostate cancer," "advanced hormone sensitive prostate cancer," "advanced androgen dependent prostate cancer," or "advanced androgen sensitive prostate cancer" as used herein may refer to prostate cancer that has spread beyond the prostate gland and the area around the prostate. The growth of prostate cancer is suppressed or the cancer may even shrink when androgen levels are suppressed (e.g., hormonal therapy that lowers serum testosterone below castration levels <50 ng/dL).

In some embodiments of the methods and uses described herein, the prostate cancer is locally advanced, advanced castration resistant, or recurrent. "Locally advanced prostate cancer" may refer to cancer that has started to break out of the prostate, or has spread to the area just outside, or nearby, the prostate. It may also be characterized as stage T3 or T4 prostate cancer. It may have spread to one or more of e.g., the prostate capsule, the seminal vesicles, the pelvic lymph nodes, the bladder, and the back passage (rectum). "Advanced castration-resistant prostate cancer" or "advanced hormone-resistant prostate cancer" may refer to castration-resistant prostate cancer that has spread beyond the prostate gland and the area around the prostate. This type of cancer continues to grow and progress even when androgen levels in the body are extremely low or undetectable. "Recurrent prostate cancer" may refer to prostate cancer that has been detected or has returned following initial treatment, such as after surgery, radiation therapy, and/or hormone therapy. Recurrent prostate cancer may have a biochemical and/or clinical recurrence. Some patients may only have a rise in PSA level as evidence of the recurrent prostate cancer (biochemical recurrence) and others will have evidence of recurrent prostate cancer on x-rays and scans (clinical recurrence). "Biochemical recurrence" may refer to the return of the prostate cancer after initial treatment, but the return cannot be measured by standard imaging methods. Therefore, prostate cancer may be present with or without evidence on diagnostic imaging tests and with or without clinical symptoms. The return of the prostate cancer is identified by a rise in PSA as determined by a blood test. The criteria for is biochemical recurrence may include a rise in PSA of "nadir+2 ng/mL" for relapse after radiation therapy, >0.2 ng/ml if recurrent after prostatectomy, and >2 ng/ml if recurrent after all other treatments. "Clinical recurrence" may refer to the return of clinical symptoms associated with growth or spread of prostate cancer after initial treatment of prostate cancer.

In some embodiments of the methods and uses described herein, the prostate cancer is castration-resistant prostate cancer. In some embodiments of the methods and uses described herein, the prostate cancer is castration-resistant metastatic prostate cancer. In some embodiments of the methods and uses described herein, the prostate cancer is castration-resistant non-metastatic prostate cancer. "Castration-resistant prostate cancer" or "hormone-resistant prostate cancer" may refer to prostate cancer that continues to grow even when androgen levels in the body are extremely low or undetectable. For example, with castration-resistant prostate cancer, PSA may increase or the cancer may show other signs of growing even after using hormone therapy to bring serum testosterone to castration levels (<50 ng/dL). For castration-resistant prostate cancer, hormonal therapy (e.g., suppression of serum testosterone levels) is continued, and additional therapies are added to the treatment protocol in addition to the continued administration of drugs used to lower serum testosterone. Castration-resistant prostate cancer may be either metastatic (castration-resistant metastatic prostate cancer) or non-metastatic (castration-resistant non-metastatic prostate cancer) prostate cancer. "Metastatic castration resistant prostate cancer" or "castration-resistant metastatic prostate cancer" may refer to prostate cancer that has spread beyond the prostate and continues to grow and progress (including but not limited to a rise in PSA) in the setting of suppressed androgen levels (i.e., hormonal therapy that lowers serum testosterone below castration levels <50 ng/dL). In some embodiments, once-daily administration of an oral formulation comprising Compound 1, or a pharmaceutically acceptable salt thereof, reduces serum FSH levels and, therefore, may reduce the rate of subjects who develop castration-resistant prostate cancer. In some embodiments, once-daily administration of an oral formulation comprising Compound 1, or a pharmaceutically acceptable salt thereof, reduces serum FSH levels and, therefore, may slow the development of castration-resistant prostate cancer. In some embodiments of the methods and uses described herein, the prostate cancer is hormone-sensitive metastatic prostate cancer. In some embodiments of the methods and uses described herein, the prostate cancer is hormone-sensitive non-metastatic prostate cancer.

In some embodiments of the methods and uses described herein, the prostate cancer is hormone naïve advanced prostate cancer. "Hormone naïve advanced prostate cancer" may be subdivided into two disease states: biochemical recurrence or traditional metastatic prostate cancer and may be characterized by no prior hormonal therapy or androgen deprivation therapy (ADT).

In some embodiments, the oral formulations of the methods and uses described herein comprise about 80 mg to about 480 mg of Compound 1, or a corresponding amount of a pharmaceutically acceptable salt thereof. As used herein, "oral formulation" encompasses the terms "oral load dose formulation," "oral load dosage," "oral load dose," "oral maintenance dose formulation," "oral maintenance dosage," and the like, unless clearly dictated otherwise by context. An "oral load dose formulation," "oral load dosage," or "oral load dose" is an initial dose of a Compound 1, or a pharmaceutically acceptable salt thereof, that may be given at the beginning of a course of treatment before changing to a different maintenance dose. As described herein, it is typically a larger initial dose of Compound 1, or a pharmaceutically acceptable salt thereof, or series of such doses given to rapidly achieve a therapeutically effective amount of drug in the body. A "therapeutically effective amount" may refer to an amount of a compound sufficient to treat a specified disorder or disease or one or more of its symptoms and/or to prevent the occurrence of the disease or disorder. For example, a therapeutically effective dose for prostate cancer treatment includes where the treatment brings about an amelioration of one or more symptoms of the prostate cancer, slows the progression of the prostate cancer, results in remission, etc. An "oral maintenance dose formulation," "oral maintenance dosage," or "oral maintenance dose" is the dose of Compound 1, or a pharmaceutically acceptable salt thereof, given after a certain period of taking the load dosage and is typically a lower amount of Compound 1, or a pharmaceutically acceptable salt thereof, than the load dosage yet maintains the desired therapeutic effect.

In some embodiments, the oral formulations of the methods and uses described herein comprise about 80 mg to about 160 mg of Compound 1, or a corresponding amount of a pharmaceutically acceptable salt thereof. In some embodiments, the oral formulations of the methods and uses described herein comprise about 120 mg of Compound 1, or a corresponding amount of a pharmaceutically acceptable salt thereof. In some embodiments, the oral formulations of the methods and uses described herein comprise about 360 mg of Compound 1, or a corresponding amount of a pharmaceutically acceptable salt thereof. In some embodiments, the oral formulations of the methods and uses described herein comprise about 240 mg of Compound 1, or a corresponding amount of a pharmaceutically acceptable salt thereof. In some embodiments, the oral formulations of the methods and uses described herein comprise about 180 mg of Compound 1, or a corresponding amount of a pharmaceutically acceptable salt thereof.

The methods and uses described herein also include treating prostate cancer in a subject in need thereof by administering to the subject once-daily for at least 12 consecutive weeks, an oral formulation comprising at least 80 mg of Compound 1, or a corresponding amount of a pharmaceutically acceptable salt thereof. In certain such embodiments, the oral formulation comprises about 120 mg, about 180 mg, about 240 mg, or about 360 mg of Compound 1, or a corresponding amount of a pharmaceutically acceptable salt thereof. In certain such embodiments, the oral formulation comprises about 120 mg or about 360 mg of Compound 1, or a corresponding amount of a pharmaceutically acceptable salt thereof. The methods and uses described herein also include treating prostate cancer in a subject in need thereof by administering to the subject once-daily for at least 4 consecutive weeks, at least 8 consecutive weeks, at least 12 consecutive weeks, at least 16 consecutive weeks, at least 20 consecutive weeks, or at least 24 consecutive weeks an oral formulation comprising at least 80 mg of Compound 1, or a corresponding amount of a pharmaceutically acceptable salt thereof.

Several benefits may result from treating prostate cancer by administering Compound 1, or a pharmaceutically acceptable salt thereof, thereby suppressing one or more sex hormones, to a subject in need of treatment as described herein. "Suppression" as used herein may occur by inhibiting the production of luteinizing hormone (LH) and follicle-stimulating hormone (FSH) by the pituitary gland, a hormone required by the testes to make testosterone and other androgens or sex hormones. Follicle-stimulating hormone (FSH) stimulates FSH receptors expressed on the endothelial cells of tumor blood vessels in prostate cancer specimens. FSH signaling in prostate cancer may contribute to the progression of castration resistant prostate cancer. Suppression of serum testosterone levels may mean that the testes are not producing testosterone at the levels normally observed in the absence of treatment for an oral formulation comprising Compound 1, or a pharmaceutically acceptable salt thereof. The degree of suppression is measured by serum testosterone, or other sex hormone, levels in the blood. Sex hormones may refer to any glandular secretions that are responsible for controlling sexual development and reproductive function in males. Such sex hormones include, for example, testosterone, dihydrotestosterone, follicle-stimulating hormone (FSH), LH, GnRH, androsterone, and inhibin. In accordance with this disclosure, one or more sex hormones, including testosterone, FSH, and LH, may be suppressed by the once-daily administration of Compound 1, or a pharmaceutically acceptable salt thereof, to a subject having prostate cancer. In particular, medical castration levels of less than or equal to 50 ng/dL (1.73 nmol/L) serum testosterone may be achieved and maintained from day 14 to day 28 after beginning once-daily administration. Also, following once-daily administration of an oral formulation of 180 mg on day 1 of Compound 1, or a corresponding amount of a pharmaceutically acceptable salt thereof, medical castration levels of less than or equal to 50 ng/dL (1.73 nmol/L) serum testosterone may be achieved within 24 to 48 hours. Further, following once-daily administration of a single oral load dose formulation of 360 mg and once-daily administration of oral maintenance dose formulations of 120 mg of Compound 1, or a corresponding amount of a pharmaceutically acceptable salt thereof, for 48 consecutive weeks, medical castration levels of less than or equal to 50 ng/dL (1.73 nmol/L) serum testosterone are achieved by the beginning of week 5 and maintained through the end of week 48. Further, following once-daily administration of a single oral load dose formulation of 240 mg and once-daily administration of oral maintenance dose formulations of 120 mg of Compound 1, or a corresponding amount of a pharmaceutically acceptable salt thereof, for 48 consecutive weeks, medical castration levels of less than or equal to 50 ng/dL (1.73 nmol/L) serum testosterone are achieved by the beginning of week 5 and maintained through the end of week 48. As used herein, "medical castration" generally refers to serum testosterone levels of about ≤50 ng/dL and "profound castration" generally refers to serum testosterone levels of about ≤20 ng/dL.

In accordance with this disclosure, methods and uses are provided for suppressing one or more sex hormones, including testosterone, LH, and FSH, in a subject having prostate cancer. Additionally, in accordance with this disclosure, methods and uses are provided for suppressing serum PSA levels. In some embodiments, the methods and uses include: administering to the subject once-daily for at least one day, an oral dosage form that includes at least one oral load dose formulation, wherein the oral load dose formulation comprises about 240 mg to about 480 mg of Compound 1, or a corresponding amount of a pharmaceutically acceptable salt thereof; and administering once-daily to the subject for at least 4 consecutive weeks, at least 8 consecutive weeks, at least 12 consecutive weeks, at least 16 consecutive weeks, at least 20 consecutive weeks, or at least 24 consecutive weeks, an oral maintenance dose formulation, in which the oral maintenance dose formulation comprise about 80 mg to about 160 mg of Compound 1, or a corresponding amount of a pharmaceutically acceptable salt thereof. In some embodiments, the methods and uses include administering to the subject once-daily for at least 24 consecutive weeks, in an oral maintenance dose formulation, at least 80 mg of Compound 1, or a corresponding amount of a pharmaceutically acceptable salt thereof.

In the methods and uses of this disclosure, serum testosterone may be suppressed in the subject to a level less than or equal to 50 ng/dL (1.73 nmol/L) or less than or equal to 20 ng/dL (0.69 nmol/L). In some embodiments, following once-daily administration of an oral formulation of 180 mg on day 1 of Compound 1, or a corresponding amount of a pharmaceutically acceptable salt thereof, medical castration levels of less than or equal to 50 ng/dL (1.73 nmol/L) serum testosterone may be achieved within 24 to 48 hours after commencing administration. In some embodiments, following once-daily administration of a single oral load dose formulation of 360 mg and oral maintenance dose formulations of 120 mg of Compound 1, or a corresponding amount of a pharmaceutically acceptable salt thereof, for 48 consecutive weeks, medical castration levels of less than or equal to 50 ng/dl (1.73 nmol/L) serum testosterone may be achieved by the beginning of week 5 and maintained through the end of week 48. In some embodiments, following once-daily administration of a single oral load dose formulation of 240 mg and oral maintenance dose formulations of 120 mg of Compound 1, or a corresponding amount of a pharmaceutically acceptable salt thereof, for 48 consecutive weeks, medical castration levels of less than or equal to 50 ng/dl (1.73 nmol/L) serum testosterone may be achieved by the beginning of week 5 and maintained through the end of week 48.

The treatment methods and uses of this disclosure may provide fast onset and fast offset for subjects. With respect to offset, unlike GnRH agonists, such as leuprolide acetate, Compound 1, or a pharmaceutically acceptable salt thereof, is neither a depot or a slow-release formulation, and hormone levels, particularly serum testosterone levels, increase and may return to the subject's serum hormone levels prior to treatment commencing more rapidly after once-daily administration is discontinued, providing more control and treatment options for patients and their physicians. For example, a more rapid increase of hormone levels, including increases in serum testosterone levels, in some cases to the subject's serum hormone levels prior to treatment commencing (pre-treatment levels), may be advantageous in the management of an intercurrent illness, among other conditions and procedures, and for the restoration of sexual function and energy levels in men. Methods and uses described herein may permit more rapid recovery from short-term medical castration, when used for neoadjuvant/adjuvant therapy or intermittent ADT. As noted previously, this flexibility is important in both the treatment setting, for example, where a subject may be receiving radiation treatment or where there is the occurrence of a condition or procedure unrelated to the prostate cancer treatment. For example, as noted previously consider a subject undergoing prostate cancer treatment who is involved in a car accident. Whether or not a surgical procedure is required to aid in recovery from the car accident, higher serum testosterone levels will aid in the subject's recovery because testosterone has an anabolic effect, helping to rebuild tissues and increase weight and muscle mass. Unlike in a treatment regimen involving a depot formulation, the present methods and uses allow for suspension of treatment without adverse effects in response to unexpected events (e.g., illness, injury, etc.). Additionally, where upcoming surgeries may be planned, for example a hip or knee replacement, the treatment may be suspended either shortly prior to or at the time of surgery to ensure optimal recovery of the patient after surgery and potentially better outcomes due to higher serum testosterone levels.

Subjects undergoing treatment in accordance with this disclosure may be able to remain in control of their lifestyle and quality of life. In contrast to conventional treatments which use depot injections, treatment with formulations of this disclosure allows for suspension periods, or intermittent treatment, in which subjects can stop treatment for a period of time and later restart treatment with no adverse effects, including no incidence of clinical flare. "Clinical" or "hormonal flare" may refer to a temporary increase in serum testosterone levels from complete serum testosterone suppression levels in the body caused by certain types of hormone therapy (e.g., androgen deprivation therapy) used to treat prostate cancer. Clinical flare can be serious in nature, for example, causing exacerbation of bone pain and urinary problems. The treatment methods and uses of this disclosure may provide a desirable quick on/off option for subjects. The treatment methods and uses of this disclosure allow maintenance of sexual activity by subjects at certain times during the treatment period. Increases in serum testosterone levels can also promote an increase in energy levels, which may have a positive impact on the subject's (and the subject's family's) quality of life. For example, for important life events (e.g., attending one's daughter's wedding, walking her down the aisle, and dancing with the mother of the bride or celebrating an important wedding anniversary), the present methods and uses can incorporate suspension period allowing for increased energy levels or improvement in sexual function and therefore greater enjoyment of such events, without the potential adverse impact on the control of the prostate cancer related to the clinical flare associated with restarting treatment after the suspension period.

The disclosure provides methods of using oral formulations comprising Compound 1, or a pharmaceutically acceptable salt thereof, for treating prostate cancer in a subject in need of an increase in serum testosterone levels to a level above 50 ng/dL. The disclosure also provides methods and uses for treating prostate cancer in a subject in need thereof comprising administering once-daily formulations comprising Compound 1, or a pharmaceutically acceptable salt thereof. Once-daily administration of formulations comprising Compound 1, or a pharmaceutically acceptable salt thereof, can be suspended for a suspension period, leading to an increase in the subject's serum testosterone levels. In certain embodiments, once-daily administration of oral formulations comprising Compound 1, or a pharmaceutically acceptable salt thereof, resumes at the end of the suspension period. In some embodiments, once-daily administration of oral formulations comprising Compound 1, or a pharmaceutically acceptable salt thereof, does not resume after it is suspended.

The present disclosure further provides that, after suspending once-daily administration of oral formulations of the disclosure for a suspension period, the subject may experience an increase in serum testosterone levels. In some embodiments after stopping once-daily administration of oral formulations comprising Compound 1, or a pharmaceutically acceptable salt thereof, for a suspension period, a subject's serum testosterone level may increase within 1 day of the beginning of the suspension period. In some embodiments after stopping once-daily administration of oral formulations of the disclosure for a suspension period, a subject's serum testosterone level may increase within 2 days of the beginning of the suspension period. In some embodiments after stopping once-daily administration of oral formulations of the disclosure for a suspension period, a subject's serum testosterone level may increase within 3 days of the beginning of the suspension period. In some embodiments after stopping once-daily administration of oral formulations of the disclosure for a suspension period, a subject's serum testosterone level may increase within 4 days of the beginning of the suspension period. In some embodiments after stopping once-daily administration of oral formulations of the disclosure for a suspension period, a subject's serum testosterone level may increase within 5 days of the beginning of the suspension period. In some embodiments after stopping once-daily administration of oral formulations of the disclosure for a suspension period, a subject's serum testosterone level may increase within 6 days of the beginning of the suspension period. In some embodiments after stopping once-daily administration of oral formulations of the disclosure for a suspension period, a subject's serum testosterone level may increase within 7 days of the beginning of the suspension period. In some embodiments after stopping once-daily administration of oral formulations of the disclosure for a suspension period, a subject's serum testosterone level may increase within 10 days of the beginning of the suspension period.

During a suspension period, a subject's serum testosterone level may increase to the subject's serum testosterone level prior to once-daily administration of an oral formulation of the disclosure comprising Compound 1, or a pharmaceutically acceptable salt thereof. With respect to offset, after stopping once-daily administration for a suspension period, the serum testosterone level may increase to the subject's serum testosterone level prior to administration of the oral formulation of the disclosure within 4 weeks, or within 8 weeks, or within 12 weeks, or within 16 weeks, or within 24 weeks, after the last dose administered prior to the suspension period. In some embodiments, the serum testosterone level may increase to the subject's serum testosterone level prior to once-daily administration of the oral formulation of the disclosure within 4 weeks to 12 weeks after the last dose. In some embodiments after stopping once-daily administration of oral formulations of the disclosure for a suspension period, the serum testosterone level may increase to the subject's serum testosterone level prior to administration of the oral formulations comprising Compound 1, or a pharmaceutically acceptable salt thereof, within 1 day of the suspension of administration. In some embodiments after stopping once-daily administration of oral formulations of the disclosure for a suspension period, the serum testosterone level may increase to the subject's serum testosterone level prior to administration of the oral formulations within 2 days of the suspension of administration. In some embodiments after stopping once-daily administration of oral formulations of the disclosure for a suspension period, the serum testosterone level may increase to the subject's serum testosterone level prior to administration of the oral formulations of the disclosure within 3 days of the suspension of administration. In some embodiments after stopping once-daily administration of oral formulations of the disclosure for a suspension period, the serum testosterone level may increase to the subject's serum testosterone level prior to administration of the oral formulations of the disclosure within 4 days of the suspension of administration. In some embodiments after stopping once-daily administration of oral formulations of the disclosure for a suspension period, the serum testosterone level may increase to the subject's serum testosterone level prior to administration of the oral formulations of the disclosure within 5 days of the suspension of administration. In some embodiments after stopping once-daily administration of oral formulations of the disclosure for a suspension period, the serum testosterone level may increase to the subject's serum testosterone level prior to administration of the oral formulations of the disclosure within 6 days of the suspension of administration. In some embodiments after stopping once-daily administration of oral formulations of the disclosure for a suspension period, the serum testosterone level may increase to the subject's serum testosterone level prior to administration of the oral formulations of the disclosure within 7 days of the suspension of administration. In some embodiments after stopping once-daily administration of oral formulations of the disclosure for a suspension period, the serum testosterone level may increase to the subject's serum testosterone level prior to administration of the oral formulations of the disclosure within 8 days of the suspension of administration. In some embodiments after stopping once-daily administration of oral formulations of the disclosure for a suspension period, the serum testosterone level may increase to the subject's serum testosterone level prior to administration of the oral formulations of the disclosure within 9 days of the suspension of administration. In some embodiments after stopping once-daily administration of oral formulations of the disclosure for a suspension period, the serum testosterone level may increase to the subject's serum testosterone level prior to administration of the oral formulations of the disclosure within 10 days of the suspension of administration. In some embodiments after stopping once-daily administration of oral formulations of the disclosure for a suspension period, the serum testosterone level may increase to the subject's serum testosterone level prior to administration of the oral formulations of the disclosure within 15 days of the suspension of administration. In some embodiments after stopping once-daily administration of oral formulations of the disclosure for a suspension period, the serum testosterone level may increase to the subject's serum testosterone level prior to administration of the oral formulations of the disclosure within 20 days of the suspension of administration. In some embodiments after stopping once-daily administration of oral formulations of the disclosure for a suspension period, the serum testosterone level may increase to the subject's serum testosterone level prior to administration of the oral formulations of the disclosure within 30 days of the suspension of administration. In some embodiments after stopping once-daily administration of oral formulations of the disclosure for a suspension period, the serum testosterone level may increase to the subject's serum testosterone level prior to administration of the oral formulations of the disclosure within 35 days of the suspension of administration. In some embodiments after stopping once-daily administration of oral formulations of the disclosure for a suspension period, the serum testosterone level may increase to the subject's serum testosterone level prior to administration of the oral formulations of the disclosure within 40 days of the suspension of administration. In some embodiments after stopping once-daily administration of oral formulations of the disclosure for a suspension period, the serum testosterone level may increase to the subject's serum testosterone level prior to administration of the oral formulations of the disclosure within 45 days of the suspension of administration. In some embodiments after stopping once-daily administration of oral formulations of the disclosure for a suspension period, the serum testosterone level may increase to the subject's serum testosterone level prior to administration of the oral formulations of the disclosure within 50 days of the suspension of administration. In some embodiments after stopping once-daily administration of oral formulations of the disclosure for a suspension period, the serum testosterone level may increase to the subject's serum testosterone level prior to administration of the oral formulations of the disclosure within 55 days of the suspension of administration. In some embodiments after stopping once-daily administration of oral formulations of the disclosure for a suspension period, the serum testosterone level may increase to the subject's serum testosterone level prior to administration of the oral formulations of the disclosure within 60 days of the suspension of administration. In some embodiments after stopping once-daily administration of oral formulations of the disclosure for a suspension period, the serum testosterone level may increase to the subject's serum testosterone level prior to administration of the oral formulations of the disclosure within 65 days of the suspension of administration. In some embodiments after stopping once-daily administration of oral formulations of the disclosure for a suspension period, the serum testosterone level may increase to the subject's serum testosterone level prior to administration of the oral formulations of the disclosure within 70 days of the suspension of administration. In some embodiments after stopping once-daily administration of oral formulations of the disclosure for a suspension period, the serum testosterone level may increase to the subject's serum testosterone level prior to administration of the oral formulations of the disclosure within 75 days of the suspension of administration. In some embodiments after stopping once-daily administration of oral formulations of the disclosure for a suspension period, the serum testosterone level may increase to the subject's serum testosterone level prior to administration of the oral formulations of the disclosure within 80 days of the suspension of administration. In some embodiments after stopping once-daily administration of oral formulations of the disclosure for a suspension period, the serum testosterone level may increase to the subject's serum testosterone level prior to administration of the oral formulations of the disclosure within 85 days of the suspension of administration. In some embodiments after stopping once-daily administration of oral formulations of the disclosure for a suspension period, the serum testosterone level may increase to the subject's serum testosterone level prior to administration of the oral formulations of the disclosure within 90 days of the suspension of administration. In some embodiments after stopping once-daily administration of oral formulations of the disclosure for a suspension period, the serum testosterone level may increase to the subject's serum testosterone level prior to administration of the oral formulations of the disclosure within 95 days of the suspension of administration. In some embodiments after stopping once-daily administration of oral formulations of the disclosure for a suspension period, the serum testosterone level may increase to the subject's serum testosterone level prior to administration of the oral formulations of the disclosure within 100 days of the suspension of administration.

The disclosure provides for increases in a subject's serum testosterone level to greater than medical castration levels. In some embodiments after stopping once-daily administration of oral formulations of the disclosure comprising Compound 1, or a pharmaceutically acceptable salt thereof, for a suspension period, a subject's serum testosterone level may increase to greater than medical castration levels within 1 day of the beginning of the suspension period. In some embodiments after stopping once-daily administration of oral formulations of the disclosure for a suspension period, a subject's serum testosterone level may increase to greater than medical castration levels within 2 days of the beginning of the suspension period. In some embodiments after stopping once-daily administration of oral formulations of the disclosure for a suspension period, a subject's serum testosterone level may increase to greater than medical castration levels within 3 days of the beginning of the suspension period. In some embodiments after stopping once-daily administration of oral formulations of the disclosure for a suspension period, a subject's serum testosterone level may increase to greater than medical castration levels within 4 days of the beginning of the suspension period. In some embodiments after stopping once-daily administration of oral formulations of the disclosure for a suspension period, a subject's serum testosterone level may increase to greater than medical castration levels within 5 days of the beginning of the suspension period. In some embodiments after stopping once-daily administration of oral formulations of the disclosure for a suspension period, a subject's serum testosterone level may increase to greater than medical castration levels within 6 days of the beginning of the suspension period. In some embodiments after stopping once-daily administration of oral formulations of the disclosure for a suspension period, a subject's serum testosterone level may increase to greater than medical castration levels within 7 days of the beginning of the suspension period. In some embodiments after stopping once-daily administration of oral formulations of the disclosure for a suspension period, a subject's serum testosterone level may increase to greater than medical castration levels within 10 days of the beginning of the suspension period. In some embodiments after stopping once-daily administration of oral formulations of the disclosure for a suspension period, a subject's serum testosterone level may increase to greater than medical castration levels within 15 days of the beginning of the suspension period. In some embodiments after stopping once-daily administration of oral formulations of the disclosure for a suspension period, a subject's serum testosterone level may increase to greater than medical castration levels within 20 days of the beginning of the suspension period. In some embodiments after stopping once-daily administration of oral formulations of the disclosure for a suspension period, a subject's serum testosterone level may increase to greater than medical castration levels within 25 days of the beginning of the suspension period. In some embodiments after stopping once-daily administration of oral formulations of the disclosure for a suspension period, a subject's serum testosterone level may increase to greater than medical castration levels within 30 days of the beginning of the suspension period.

In some embodiments after stopping once-daily administration of oral formulations of the disclosure comprising Compound 1, or a pharmaceutically acceptable salt thereof, for a suspension period, a subject's serum testosterone level may increase to greater than about 55 ng/dL within 1 day of the beginning of the suspension period. In some embodiments after stopping once-daily administration of oral formulations of the disclosure for a suspension period, a subject's serum testosterone level may increase to greater than about 55 ng/dl within 2 days of the beginning of the suspension period. In some embodiments after stopping once-daily administration of oral formulations of the disclosure for a suspension period, a subject's serum testosterone level may increase to greater than about 55 ng/dL within 3 days of the beginning of the suspension period. In some embodiments after stopping once-daily administration of oral formulations of the disclosure for a suspension period, a subject's serum testosterone level may increase to greater than about 55 ng/dL within 4 days of the beginning of the suspension period. In some embodiments after stopping once-daily administration of oral formulations of the disclosure for a suspension period, a subject's serum testosterone level may increase to greater than about 55 ng/dL within 5 days of the beginning of the suspension period. In some embodiments after stopping once-daily administration of oral formulations of the disclosure for a suspension period, a subject's serum testosterone level may increase to greater than about 55 ng/dL within 6 days of the beginning of the suspension period. In some embodiments after stopping once-daily administration of oral formulations of the disclosure for a suspension period, a subject's serum testosterone level may increase to greater than about 55 ng/dL within 7 days of the beginning of the suspension period. In some embodiments after stopping once-daily administration of oral formulations of the disclosure for a suspension period, a subject's serum testosterone level may increase to greater than about 55 ng/dL within 10 days of the beginning of the suspension period. In some embodiments after stopping once-daily administration of oral formulations of the disclosure for a suspension period, a subject's serum testosterone level may increase to greater than about 55 ng/dL within 15 days of the beginning of the suspension period. In some embodiments after stopping once-daily administration of oral formulations of the disclosure for a suspension period, a subject's serum testosterone level may increase to greater than about 55 ng/dL within 20 days of the beginning of the suspension period. In some embodiments after stopping once-daily administration of oral formulations of the disclosure for a suspension period, a subject's serum testosterone level may increase to greater than about 55 ng/dL within 25 days of the beginning of the suspension period. In some embodiments after stopping once-daily administration of oral formulations of the disclosure for a suspension period, a subject's serum testosterone level may increase to greater than about 55 ng/dl within 30 days of the beginning of the suspension period.

Normal serum testosterone levels for European and American men, 19 to 39 years, are variable and are reported to be between about 250 ng/dl to about 920 ng/dL (see, The Journal of Clinical Endocrinology & Metabolism, Volume 102, Issue 4, 1 Apr. 2017, Pages 1161-1173). Suspension of once-daily administration of the oral formulations of the disclosure may allow for increases in a subject's serum testosterone levels to a range between about 250 ng/dL to about 920 ng/dL, or to "normal" serum testosterone levels. The Endocrine Society recommends about 300 ng/dL as the lower limit of "normal" serum testosterone levels. Other medical societies recommend 150 ng/dL, 200 ng/dL, or 230 ng/dL as the lower limit of "normal" serum testosterone levels. The methods and uses of the disclosure may allow for a return to "normal" serum testosterone levels. In some embodiments after stopping once-daily administration of oral formulations of the disclosure comprising Compound 1, or a pharmaceutically acceptable salt thereof, for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 1 day of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dl, about 550 ng/dL, or about 600 ng/dL within 2 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 3 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dl, about 400 ng/dL, about 450 ng/dL, about 500 ng/dL, about 550 ng/dL, or about 600 ng/dL within 4 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 5 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dl, about 500 ng/dL, about 550 ng/dL, or about 600 ng/dL within 6 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dl within 7 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 10 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 15 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dl, about 400 ng/dL, about 450 ng/dL, about 500 ng/dL, about 550 ng/dL, or about 600 ng/dl within 20 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dl, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 25 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 30 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dl within 35 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dl, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 40 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 45 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 50 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dl, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 55 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 60 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dl, about 400 ng/dL, about 450 ng/dL, about 500 ng/dL, about 550 ng/dL, or about 600 ng/dL within 65 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 70 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dl, about 280 ng/dL, about 300 ng/dL, about 350 ng/dL, about 400 ng/dL, about 450 ng/dL, about 500 ng/dL, about 550 ng/dL, or about 600 ng/dL within 75 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 80 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 85 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dL, about 100 ng/dL, about 150 ng/dL, about 200 ng/dL, about 250 ng/dl, about 280 ng/dL, about 300 ng/dL, about 350 ng/dL, about 400 ng/dL, about 450 ng/dL, about 500 ng/dL, about 550 ng/dL, or about 600 ng/dL within 90 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dl, about 80 ng/dL, about 85 ng/dL, about 90 ng/dL, about 95 ng/dL, about 100 ng/dl, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 95 days of the beginning of the suspension period. In some embodiments after stopping once-daily administration of oral formulations of the disclosure for a suspension period, a subject's serum testosterone level may increase to greater than or about 60 ng/dL, about 65 ng/dL, about 70 ng/dL, about 75 ng/dL, about 80 ng/dL, about 85 ng/dL, about 90 ng/dL, about 95 ng/dl, about 100 ng/dL, about 150 ng/dL, about 200 ng/dL, about 250 ng/dL, about 280 ng/dL, about 300 ng/dL, about 350 ng/dL, about 400 ng/dL, about 450 ng/dL, about 500 ng/dL, about 550 ng/dL, or about 600 ng/dL within 100 days of the beginning of the suspension period. In some embodiments after stopping once-daily administration of oral formulations of the disclosure for a suspension period, a subject's serum testosterone level may increase to greater than or about 350 ng/dL after the beginning of the suspension period.

In some embodiments after stopping once-daily administration of oral formulations comprising Compound 1, or a pharmaceutically acceptable salt thereof, for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 1 day of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dl to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 2 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dl, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dl to about 550 ng/dL, about 550 ng/dL to about 600 ng/dL, or about 300 ng/dL to about 600 ng/dl within 3 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dl to about 600 ng/dL within 4 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dl to about 500 ng/dL, about 500 ng/dL to about 550 ng/dL, about 550 ng/dL to about 600 ng/dL, or about 300 ng/dl to about 600 ng/dL within 5 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dl to about 600 ng/dL, or about 300 ng/dL to about 600 ng/dL within 6 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dl, about 150 ng/dL to about 200 ng/dL, about 200 ng/dL to about 250 ng/dL, about 250 ng/dL to about 300 ng/dl, about 300 ng/dL to about 350 ng/dL, about 350 ng/dL to about 400 ng/dL, about 400 ng/dl to about 450 ng/dL, about 450 ng/dL to about 500 ng/dL, about 500 ng/dL to about 550 ng/dL, about 550 ng/dl to about 600 ng/dL, or about 300 ng/dL to about 600 ng/dL within 7 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dl to about 200 ng/dL, about 200 ng/dl to about 250 ng/dL, about 250 ng/dl to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dl to about 550 ng/dL, about 550 ng/dL to about 600 ng/dL, or about 300 ng/dL to about 600 ng/dl within 10 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dl to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dl to about 600 ng/dL within 15 days of the beginning of the suspension period. In some embodiments after stopping once-daily administration of oral formulations of the disclosure for a suspension period, a subject's serum testosterone level may increase to about 50 ng/dl to about 100 ng/dl, about 100 ng/dL to about 150 ng/dL, about 150 ng/dL to about 200 ng/dL, about 200 ng/dl to about 250 ng/dL, about 250 ng/dL to about 300 ng/dL, about 300 ng/dL to about 350 ng/dl, about 350 ng/dL to about 400 ng/dL, about 400 ng/dL to about 450 ng/dL, about 450 ng/dl to about 500 ng/dL, about 500 ng/dL to about 550 ng/dL, about 550 ng/dL to about 600 ng/dL, or about 300 ng/dL to about 600 ng/dL within 20 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dl to about 200 ng/dl, about 200 ng/dL to about 250 ng/dL, about 250 ng/dL to about 300 ng/dL, about 300 ng/dl to about 350 ng/dL, about 350 ng/dL to about 400 ng/dL, about 400 ng/dL to about 450 ng/dL, about 450 ng/dl to about 500 ng/dL, about 500 ng/dL to about 550 ng/dL, about 550 ng/dl to about 600 ng/dL, or about 300 ng/dL to about 600 ng/dL within 25 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dl to about 450 ng/dL, about 450 ng/dL to about 500 ng/dL, about 500 ng/dL to about 550 ng/dL, about 550 ng/dl to about 600 ng/dL, or about 300 ng/dL to about 600 ng/dl within 30 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dl to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dl to about 550 ng/dL, about 550 ng/dL to about 600 ng/dL, or about 300 ng/dL to about 600 ng/dL within 35 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dl to about 500 ng/dL, about 500 ng/dL to about 550 ng/dL, about 550 ng/dL to about 600 ng/dL, or about 300 ng/dL to about 600 ng/dL within 40 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dl to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 45 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dl to about 200 ng/dL, about 200 ng/dL to about 250 ng/dL, about 250 ng/dL to about 300 ng/dl, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 50 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dl to about 550 ng/dL, about 550 ng/dL to about 600 ng/dL, or about 300 ng/dL to about 600 ng/dL within 50 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dl to about 250 ng/dL, about 250 ng/dL to about 300 ng/dL, about 300 ng/dL to about 350 ng/dl, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 60 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dl to about 200 ng/dL, about 200 ng/dL to about 250 ng/dL, about 250 ng/dL to about 300 ng/dL, about 300 ng/dl to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 65 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dl to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 70 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dl to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 75 days of the beginning of the suspension period. In some embodiments after stopping once-daily administration of oral formulations of the disclosure for a suspension period, a subject's serum testosterone level may increase to about 50 ng/dl to about 100 ng/dl, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dl to about 600 ng/dL within 80 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dl to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 85 days of the beginning of the suspension period. In some embodiments after stopping once-daily administration of oral formulations of the disclosure for a suspension period, a subject's serum testosterone level may increase to about 50 ng/dl to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dl to about 450 ng/dL, about 450 ng/dL to about 500 ng/dL, about 500 ng/dL to about 550 ng/dL, about 550 ng/dL to about 600 ng/dL, or about 300 ng/dL to about 600 ng/dL within 90 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dL, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dl to about 600 ng/dL within 95 days of the beginning of the suspension period. In some embodiments after stopping once-daily administration of oral formulations of the disclosure for a suspension period, a subject's serum testosterone level may increase to about 50 ng/dL to about 100 ng/dL, about 100 ng/dL to about 150 ng/dL, about 150 ng/dL to about 200 ng/dL, about 200 ng/dL to about 250 ng/dL, about 250 ng/dL to about 300 ng/dL, about 300 ng/dL to about 350 ng/dl, about 350 ng/dL to about 400 ng/dL, about 400 ng/dL to about 450 ng/dL, about 450 ng/dL to about 500 ng/dL, about 500 ng/dL to about 550 ng/dL, about 550 ng/dL to about 600 ng/dL, or about 300 ng/dl to about 600 ng/dL within 100 days of the beginning of the suspension period. In some embodiments after stopping once-daily administration of oral formulations of the disclosure for a suspension period, a subject's serum testosterone level may increase to about 300 ng/dl to about 600 ng/dL after the beginning of the suspension period.

In some embodiments, a subject's serum testosterone level may be suppressed prior to and after the suspension of administration (e.g., the serum testosterone level is below the medical castration level, profound medical castration level, significantly lower than the subject's level prior to treatment (e.g., less than 50% of pre-treatment level, less than 40%, less than 30%, less than 20%, less than 10%, less than 5%, or less than 1%)).

With respect to onset, the present disclosure also provides for resuming once-daily administration of an oral formulation of the disclosure or an oral load dose formulation and an oral maintenance dose formulation of the disclosure after a suspension period to achieve a return to medical castration levels of serum testosterone. As noted previously, resuming once-daily administration with Compound 1, or a pharmaceutically acceptable salt thereof, does not include the disadvantageous clinical flare associated with GnRH agonists and therefore should not lead to worsening of symptoms or erosion of prior gains in treatment as would restarting treatment after a suspension period when treating with GnRH agonists. In some embodiments, within about 4 to about 8 days of first administering once-daily an oral formulation of the disclosure or an oral load dose formulation and an oral maintenance dose formulation of the disclosure after a suspension period, the serum testosterone levels in the subject may be at or below medical castration level. In some embodiments, within 4 days of first administering once-daily an oral formulation of the disclosure or an oral load dose formulation and an oral maintenance dose formulation of the disclosure after a suspension period, the serum testosterone levels in the subject may be at or below medical castration level. In some embodiments, within 5 days of first administering once-daily an oral formulation of the disclosure or an oral load dose formulation and an oral maintenance dose formulation of the disclosure after a suspension period, the serum testosterone levels in the subject may be at or below medical castration level. In some embodiments, within 6 days of first administering once-daily an oral formulation of the disclosure or an oral load dose formulation and an oral maintenance dose formulation of the disclosure after a suspension period, the serum testosterone levels in the subject may be at or below medical castration level. In some embodiments, within 7 days of first administering once-daily an oral formulation of the disclosure or an oral load dose formulation and an oral maintenance dose formulation of the disclosure after a suspension period, the serum testosterone levels in the subject may be at or below medical castration level. In some embodiments, within 8 days of first administering once-daily an oral formulation of the disclosure or an oral load dose formulation and an oral maintenance dose formulation of the disclosure after a suspension period, the serum testosterone levels in the subject may be at or below medical castration level. In some embodiments, within 3 days of first administering once-daily an oral formulation of the disclosure or an oral load dose formulation and an oral maintenance dose formulation of the disclosure after a suspension period, the serum testosterone levels in the subject may be at or below medical castration level.

In some embodiments, after resuming once-daily administration of an oral formulation of the disclosure comprising about 180 mg of Compound 1, or a corresponding amount of a pharmaceutically acceptable salt thereof, after a suspension period, serum testosterone levels in a subject may be at or below medical castration level within 24 hours to 48 hours after commencing administration. In some embodiments, after resuming once-daily administration of an oral formulation of the disclosure comprising about 180 mg of Compound 1, or a corresponding amount of a pharmaceutically acceptable salt thereof, after a suspension period, serum testosterone levels in a subject may be at or below medical castration level within 3 days after commencing administration. In some embodiments, after resuming once-daily administration of an oral formulation of the disclosure comprising about 180 mg of Compound 1, or a corresponding amount of a pharmaceutically acceptable salt thereof, after a suspension period, serum testosterone levels in a subject may be at or below medical castration level within 4 days after commencing administration. In some embodiments, after resuming once-daily administration of an oral formulation of the disclosure comprising about 180 mg of Compound 1, or a corresponding amount of a pharmaceutically acceptable salt thereof, after a suspension period, serum testosterone levels in a subject may be at or below medical castration level within 5 days after commencing administration. In some embodiments, after resuming once-daily administration of an oral formulation of the disclosure comprising about 180 mg of Compound 1, or a corresponding amount of a pharmaceutically acceptable salt thereof, after a suspension period, serum testosterone levels in a subject may be at or below medical castration level within 6 days after commencing administration. In some embodiments, after resuming once-daily administration of an oral formulation of the disclosure comprising about 180 mg of Compound 1, or a corresponding amount of a pharmaceutically acceptable salt thereof, after a suspension period, serum testosterone levels in a subject may be at or below medical castration level within 1 week after commencing administration.

In some embodiments, after resuming once-daily administration of an oral formulation of the disclosure comprising about 80 mg to about 160 mg of Compound 1, or a corresponding amount of a pharmaceutically acceptable salt thereof, after a suspension period, serum testosterone levels in a subject may be at or below medical castration level within 24 hours to 48 hours after commencing administration. In some embodiments, after resuming once-daily administration of an oral formulation of the disclosure comprising about 80 mg to about 160 mg of Compound 1, or a corresponding amount of a pharmaceutically acceptable salt thereof, after a suspension period, serum testosterone levels in a subject may be at or below medical castration level within 3 days after commencing administration. In some embodiments, after resuming once-daily administration of an oral formulation of the disclosure comprising about 80 mg to about 160 mg of Compound 1, or a corresponding amount of a pharmaceutically acceptable salt thereof, after a suspension period, serum testosterone levels in a subject may be at or below medical castration level within 4 days after commencing administration. In some embodiments, after resuming once-daily administration of an oral formulation of the disclosure comprising about 80 mg to about 160 mg of Compound 1, or a corresponding amount of a pharmaceutically acceptable salt thereof, after a suspension period, serum testosterone levels in a subject may be at or below medical castration level within 5 days after commencing administration. In some embodiments, after resuming once-daily administration of an oral formulation of the disclosure comprising about 80 mg to about 160 mg of Compound 1, or a corresponding amount of a pharmaceutically acceptable salt thereof, after a suspension period, serum testosterone levels in a subject may be at or below medical castration level within 6 days after commencing administration. In some embodiments, after resuming once-daily administration of an oral formulation of the disclosure comprising about 80 mg to about 160 mg of Compound 1, or a corresponding amount of a pharmaceutically acceptable salt thereof, after a suspension period, serum testosterone levels in a subject may be at or below medical castration level within 1 week after commencing administration.

In some embodiments, after resuming once-daily administration of an oral formulation of the disclosure comprising about 120 mg of Compound 1, or a corresponding amount of a pharmaceutically acceptable salt thereof, after a suspension period, serum testosterone levels in a subject may be at or below medical castration level within 24 hours to 48 hours after commencing administration. In some embodiments, after resuming once-daily administration of an oral formulation of the disclosure comprising about 120 mg of Compound 1, or a corresponding amount of a pharmaceutically acceptable salt thereof, after a suspension period, serum testosterone levels in a subject may be at or below medical castration level within 3 days after commencing administration. In some embodiments, after resuming once-daily administration of an oral formulation of the disclosure comprising about 120 mg of Compound 1, or a corresponding amount of a pharmaceutically acceptable salt thereof, after a suspension period, serum testosterone levels in a subject may be at or below medical castration level within 4 days after commencing administration. In some embodiments, after resuming once-daily administration of an oral formulation of the disclosure comprising about 120 mg of Compound 1, or a corresponding amount of a pharmaceutically acceptable salt thereof, after a suspension period, serum testosterone levels in a subject may be at or below medical castration level within 5 days after commencing administration. In some embodiments, after resuming once-daily administration of an oral formulation of the disclosure comprising about 120 mg of Compound 1, or a corresponding amount of a pharmaceutically acceptable salt thereof, after a suspension period, serum testosterone levels in a subject may be at or below medical castration level within 6 days after commencing administration. In some embodiments, after resuming once-daily administration of an oral formulation of the disclosure comprising about 120 mg of Compound 1, or a corresponding amount of a pharmaceutically acceptable salt thereof, after a suspension period, serum testosterone levels in a subject may be at or below medical castration level within 1 week after commencing administration.

In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), medical castration levels of less than or equal to 50 ng/dl (1.73 nmol/L) serum testosterone may be achieved within 24 to 48 hours after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 days after commencing administration and maintained until the end of administration. In some embodiments, following administration of an oral load dose formulation of the disclosure comprising 240 mg of Compound 1, or a corresponding amount of a pharmaceutically acceptable salt thereof, on once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 5 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 6 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 1 week after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 2 weeks after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 weeks after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 weeks after commencing administration and maintained until the end of administration.

In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), medical castration levels of less than or equal to 50 ng/dl (1.73 nmol/L) serum testosterone may be achieved within 24 to 48 hours after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 days after commencing administration and maintained until the end of administration. In some embodiments, following administration of an oral load dose formulation of the disclosure comprising 360 mg of Compound 1, or a corresponding amount of a pharmaceutically acceptable salt thereof, on once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 5 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 6 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 1 week after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 2 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 weeks after commencing administration and maintained until the end of administration.

In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), profound castration levels of less than or equal to 20 ng/dl (1.73 nmol/L) serum testosterone may be achieved within 24 to 48 hours after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 3 days after commencing administration and maintained until the end of administration. In some embodiments, following administration of an oral load dose formulation of the disclosure comprising 360 mg of Compound 1, or a corresponding amount of a pharmaceutically acceptable salt thereof, on once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 4 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 5 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 6 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 1 week after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 2 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 3 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment after a suspension period, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 4 weeks after commencing administration and maintained until the end of administration.

In some embodiments, after resuming once-daily administration of an oral formulation of the disclosure after a suspension period, median time from administration of the first oral formulation after the suspension period to PSA nadir may be less than 5 weeks, less than 6 weeks, less than 7, weeks, less than 8 weeks, less than 9 weeks, less than 10 weeks, less than 11 weeks, less than 12 weeks, less than 13 weeks, less than 14 weeks, less than 15 weeks, less than 16 weeks, less than 17 weeks, less than 18 weeks, less than 19 weeks, less than 20 weeks, less than 21 weeks, less than 22 weeks, less than 23 weeks, less than 24 weeks, or less than 25 weeks. In some embodiments, after resuming once-daily administration of an oral formulation of the disclosure after a suspension period, median time from administration of the first oral formulation after the suspension period to PSA nadir may be about 5 weeks to about 10 weeks, about 5 weeks to about 15 weeks, about 5 weeks to about 20 weeks, about 5 weeks to about 25 weeks, about 10 weeks to about 15 weeks, about 10 weeks to about 20 weeks, about 10 weeks to about 25 weeks, or about 15 weeks to about 20 weeks. In some embodiments, after resuming once-daily administration of an oral formulation of the disclosure after a suspension period, median time from administration of the first oral formulation after the suspension period to PSA nadir may be about 10 weeks to about 20 weeks. In some embodiments, after resuming once-daily administration of oral formulations of the disclosure for 4 weeks following a suspension period, serum PSA levels are reduced by greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, or greater than or equal to about 90% of the subject's serum PSA levels prior to treatment commencing. In some embodiments, after resuming once-daily administration of oral formulations of the disclosure for 4 weeks following a suspension period, serum PSA levels are reduced by greater than or equal to about 50% of the subject's serum PSA levels prior to treatment commencing.

In some embodiments, following administration of an oral load dose formulation of the disclosure once-daily for 1-3 days at the beginning of treatment after a suspension period, and once-daily administration of an oral maintenance dose formulation of the disclosure starting on the day after administering the last dose of the oral load dose formulation, and continuing for a set treatment period, median time from commencing treatment to PSA nadir may be less than 5 weeks, less than 6 weeks, less than 7, weeks, less than 8 weeks, less than 9 weeks, less than 10 weeks, less than 11 weeks, less than 12 weeks, less than 13 weeks, less than 14 weeks, less than 15 weeks, less than 16 weeks, less than 17 weeks, less than 18 weeks, less than 19 weeks, less than 20 weeks, less than 21 weeks, less than 22 weeks, less than 23 weeks, less than 24 weeks, or less than 25 weeks. In some embodiments, following administration of an oral load dose formulation of the disclosure once-daily for 1-3 days at the beginning of treatment after a suspension period, and once-daily administration of an oral maintenance dose formulation of the disclosure starting on the day after administering the last dose of the oral load dose formulation, and continuing for a set treatment period, median time from commencing treatment to PSA nadir may be about 5 weeks to about 10 weeks, about 5 weeks to about 15 weeks, about 5 weeks to about 20 weeks, about 5 weeks to about 25 weeks, about 10 weeks to about 15 weeks, about 10 weeks to about 20 weeks, about 10 weeks to about 25 weeks, or about 15 weeks to about 20 weeks. In some embodiments, following administration of an oral load dose formulation of the disclosure once-daily for 1-3 days at the beginning of treatment after a suspension period, and once-daily administration of an oral maintenance dose formulation of the disclosure starting on the day after administering the last dose of the oral load dose formulation, and continuing for a set treatment period, median time from commencing treatment to PSA nadir may be about 10 weeks to about 20 weeks. In some embodiments, 4 weeks after commencing administration of an oral load dose formulation of the disclosure once-daily for 1-3 days after a suspension period, and once-daily administration of an oral maintenance dose formulation of the disclosure starting on the day after administering the last dose of the oral load dose formulation, serum PSA levels are reduced by greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, or greater than or equal to about 90% of the subject's serum PSA levels prior to treatment commencing. In some embodiments, 4 weeks after commencing administration of an oral load dose formulation of the disclosure once-daily for 1-3 days after a suspension period, and once-daily administration of an oral maintenance dose formulation of the disclosure starting on the day after administering the last dose of the oral load dose formulation, serum PSA levels are reduced by greater than or equal to about 50% of the subject's serum PSA levels prior to treatment commencing.

In some embodiments, after resuming once-daily administration of an oral formulation of the disclosure for 1 week, 4 weeks, 12 weeks, 24 weeks, or 48 weeks after a suspension period, serum FSH levels may be less than or equal to about 7.2 mIU/mL, about 4.8 mIU/mL, about 2.4 mIU/mL, or about 1.2 mIU/mL. In certain such embodiments, once-daily administration of oral formulations comprising Compound 1, or a pharmaceutically acceptable salt thereof, may result in sustained suppression of serum FSH levels. Normal FSH levels in adult males are typically between 1.5 to 12.4 mIU/mL, but are elevated in subjects with prostate cancer. In some embodiments, after resuming once-daily administration of an oral formulation of the disclosure for 1 week after a suspension period, serum FSH levels may be less than or equal to about 7.2 mIU/mL, about 4.8 mIU/mL, about 2.4 mIU/mL, or about 1.2 mIU/mL. In some embodiments, resuming once-daily administration of an oral formulation of the disclosure for 1 week, 4 weeks, 12 weeks, 24 weeks, or 48 weeks after a suspension period may suppress serum FSH levels by greater than or equal to about 80% or about 90% of the subject's serum FSH levels prior to treatment commencing.

In some embodiments, following administration of an oral load dose formulation of the disclosure once-daily for 1-3 days at the beginning of treatment after a suspension period, and once-daily administration of an oral maintenance dose formulation of the disclosure starting on the day after administering the last dose of the oral load dose formulation, serum FSH levels may be less than or equal to about 7.2 mIU/mL, about 4.8 mIU/mL, about 2.4 mIU/mL, or about 1.2 mIU/mL 1 week, 4 weeks, 12 weeks, 24 weeks, or 48 weeks after commencing treatment. In certain such embodiments, once-daily administration of oral formulations comprising Compound 1, or a pharmaceutically acceptable salt thereof, may result in sustained suppression of serum FSH levels. In some embodiments, following administration of an oral load dose formulation of the disclosure once-daily for 1-3 days at the beginning of treatment after a suspension period, and once-daily administration of an oral maintenance dose formulation of the disclosure starting on the day after administering the last dose of the oral load dose formulation, serum FSH levels may be less than or equal to about 7.2 mIU/mL, about 4.8 mIU/mL, about 2.4 mIU/mL, or about 1.2 mIU/mL 1 week after commencing treatment. In some embodiments, following administration of an oral load dose formulation of the disclosure once-daily for 1-3 days at the beginning of treatment after a suspension period, and once-daily administration of an oral maintenance dose formulation of the disclosure starting on the day after administering the last dose of the oral load dose formulation, serum FSH levels may be suppressed by greater than or equal to about 80% or about 90% of the subject's serum FSH levels prior to treatment commencing 1 week, 4 weeks, 12 weeks, 24 weeks, or 48 weeks after commencing treatment.

Because of the return to serum testosterone levels to a level above 50 ng/dL after the last dose of an oral formulation comprising Compound 1, or a pharmaceutically acceptable salt thereof, and the rapid onset of the oral formulations of the disclosure once once-daily administration is restarted after a suspension period, administration may be suspended for a suspension period as necessary to allow for an increase in serum testosterone levels. In certain embodiments, the subject is in need of an increase in serum testosterone levels to a level above 50 ng/dL. Increases in serum testosterone level may be needed due to an intercurrent illness, receiving radiation therapy, while bedridden, having suffered an injury, having a surgical procedure or other invasive procedure, or a desire for a period of restored sexual function. An "intercurrent illness" may refer to an illness occurring during the course of another illness, not related to the primary illness process (e.g., the illness is not prostate cancer or a symptom of prostate cancer but can be, for example pneumonia, etc.). In some embodiments, an intercurrent illness is an acute illness—an illness with an abrupt onset. An intercurrent illness can result in loss of physical function or in muscle wasting, prolonged periods of time in bed, prolonged inflammation, infection, or prolonged physical therapy. An "injury" may impair the structure or function of the body and can result in loss of physical function or in muscle wasting, prolonged periods of time in bed, prolonged inflammation, infection, prolonged physical therapy, or recovery from a surgical or invasive procedure. Injury includes, but is not limited to, wounds, fractures, and burns. A "surgical procedure" or "other invasive procedure" may refer to a procedure that is carried out by entering the body through the skin or through a body cavity or anatomical opening, and includes procedures carried out in an operating room, surgical suite or procedure room. A "surgical procedure" can include, but is not limited to, heart surgery, knee replacement, hip replacement, abdominal surgery, pelvic surgery, vascular surgery, spine surgery, or an emergency procedure due to injury. An "invasive procedure" may include, but is not limited to, a colonoscopy, angioplasty, stent placement, endovascular coil placement, endovascular aneurysm repair, endoscopy, laparoscopy, arthroscopy, coronary catheterization, or another catheter-based procedure. As noted previously, increased serum testosterone levels can be beneficial in such subjects because testosterone has an anabolic effect, helping to rebuild tissues, increase weight and muscle mass, and promote growth and mineralization of bone, thus may help in counteracting the deliterious impact of the surgical procedure, intercurrent illness, injury, etc. discussed above. "Restored sexual function" or "recovery of sexual function" may refer to an improvement in sexual function observed as sex hormone levels increase after suspension of once-daily administration of oral formulations comprising Compound 1, or a pharmaceutically acceptable salt thereof. For example, when serum testosterone levels are normalized to above medical castration levels of >50 ng/dL because once-daily administration of oral formulations comprising Compound 1, or a pharmaceutically acceptable salt thereof, is suspended, sexual function is improved. Sexual function and libido will continue to improve as serum testosterone levels increase to above 50 ng/dL and return to normal (pre-treatment) levels. Improvement of sexual function may include, but is not limited to, improvements in libido, erectile dysfunction, arousal, orgasm, nocturnal erections, sexual desire, penile morphology, ejaculation, quality of life, overall self-esteem, and overall relationships.

Once-daily administration may also be suspended to improve the subject's quality of life and energy levels; to help with healing after injury, intercurrent illness, surgery, or radiation therapy; to aid subjects in remaining in control of their lifestyles, including an improvement in sexual function; and to assist in regaining strength and mobility after intercurrent illness or injury. Once administration is suspended, it may or may not resume as needed. In some embodiments, once-daily administration resumes after the subject is recovered from an intercurrent illness, is no longer bedridden, has resumed normal activities of daily living, or has regained a normal level of function (e.g., returns to the level of function the subject experience prior to the illness).

The present disclosure provides for suspension of the once-daily administration of oral formulations of the disclosure prior to a surgical procedure or other invasive procedure or radiation therapy. In some embodiments, once-daily administration may be suspended prior to a surgical procedure or other invasive procedure. In some embodiments, once-daily administration of oral formulations of the disclosure may be suspended after a surgical procedure or other invasive procedure, injury, or radiation therapy. In certain embodiments, once-daily administration of oral formulations of the disclosure occurs prior to and during the surgical procedure or other invasive procedure or radiation therapy and once-daily administration may be suspended after the surgical procedure or other invasive procedure or radiation therapy. In some embodiments, once-daily administration of oral formulations of the disclosure may be suspended during a surgical procedure or other invasive procedure, injury, or radiation therapy. In certain embodiments, once-daily administration of the oral formulations of the disclosure may be suspended because the subject is in need of an increase in serum testosterone levels due to a surgical procedure or other invasive procedure with a projected full recovery time of at least about 1 week, about 2 weeks, about 3 weeks, about 4 weeks, about 5 weeks, about 6 weeks, about 7 weeks, about 8 weeks, about 9 weeks, about 10 weeks, about 12 weeks, about 16 weeks, about 20 weeks, about 24 weeks, about 36 weeks, about 48 weeks, or about 52 weeks. In certain such embodiments, the recovery time is about 2 weeks. In some embodiments, once-daily administration of oral formulations of the disclosure is not resumed after a suspension of administration prior to, after, or during a surgical procedure or other invasive procedure. In certain such embodiments, once-daily administration is not resumed after a suspension of administration after a surgical procedure or other invasive procedure. In some embodiments, the surgical procedure is heart surgery, knee replacement, hip replacement, abdominal surgery, pelvic surgery, vascular surgery, spine surgery, or an emergency procedure due to injury. In certain embodiments of the methods and uses described herein, the subject receiving prostate cancer treatment is identified as at risk for acute postoperative frailty.

The present disclosure provides for suspension of once-daily administration of oral formulations of the disclosure prior to radiation therapy. In some embodiments, once-daily administration of oral formulations of the disclosure may be suspended after radiation therapy. Suspension of once-daily administration of oral formulations of the disclosure after radiation therapy may aid in recovery from the radiation therapy yet permit therapeutic treatment with oral formulations comprising Compound 1, or a pharmaceutically acceptable salt thereof, during radiation therapy, enabling intensive treatment of prostate cancer. In certain embodiments, once-daily administration of oral formulations of the disclosure occurs prior to and during radiation therapy and administration may be suspended after radiation therapy. In some embodiments, once-daily administration of oral formulations of the disclosure may be suspended during radiation therapy. In certain embodiments, once-daily administration of the oral formulations of the disclosure may be suspended because the subject is in need of an increase in serum testosterone levels due to radiation therapy for at least about 1 week, about 2 weeks, about 3 weeks, about 4 weeks, about 5 weeks, about 6 weeks, about 7 weeks, about 8 weeks, about 9 weeks, about 10 weeks, about 12 weeks, about 16 weeks, about 20 weeks, about 24 weeks, about 36 weeks, about 48 weeks, or about 52 weeks. In some embodiments, once-daily administration of oral formulations of the disclosure is not resumed after a suspension of administration prior to, after, or during radiation therapy. In certain such embodiments, once-daily administration is not resumed after a suspension of administration after radiation therapy. In some embodiments, once-daily administration may be resumed when there is rise in PSA of "nadir+2 ng/mL" after radiation therapy. In some embodiments, once-daily administration may be resumed after radiation therapy when the subject's PSA level rises to ≥3 ng/ml, ≥10 ng/ml, ≥20 ng/ml, or ≥30 ng/mL.

In some embodiments, once-daily administration may be suspended during an intercurrent illness or while the subject is bedridden. In some embodiments, once-daily administration may be suspended after an intercurrent illness. In certain embodiments, once-daily administration of the oral formulations of the disclosure may be suspended because the subject is in need of an increase in serum testosterone levels due to an intercurrent illness with a projected full recovery time of at least about 1 week, about 2 weeks, about 3 weeks, about 4 weeks, about 5 weeks, about 6 weeks, about 7 weeks, about 8 weeks, about 9 weeks, about 10 weeks, about 12 weeks, about 16 weeks, about 20 weeks, about 24 weeks, about 36 weeks, about 48 weeks, or about 52 weeks. In certain such embodiments, the recovery time is about 2 weeks. In some embodiments, once-daily administration of oral formulations of the disclosure is not resumed after a suspension of administration after or during an intercurrent illness. In certain such embodiments, once-daily administration is not resumed after a suspension of administration after an intercurrent illness. In some embodiments, once-daily administration of oral formulations of the disclosure may be suspended for an intercurrent illness, wherein the illness is stroke or cerebral hemorrhage. In certain embodiments, once-daily administration may be suspended for an intercurrent illness, wherein the illness is myocardial infarction or congestive heart failure. In some embodiments, once-daily administration is suspended following an accident or injury requiring prolonged recovery. In some embodiments, once-daily administration is suspended following a stroke, cerebral hemorrhage, myocardial infarction, congestive heart failure, hip fracture or other event resulting in limited mobility and requiring prolonged recovery.

In certain embodiments, once-daily administration of the oral formulations of the disclosure may be suspended because the subject is in need of an increase in serum testosterone levels due to an injury with a projected full recovery time of at least about 1 week, about 2 weeks, about 3 weeks, about 4 weeks, about 5 weeks, about 6 weeks, about 7 weeks, about 8 weeks, about 9 weeks, about 10 weeks, about 12 weeks, about 16 weeks, about 20 weeks, about 24 weeks, about 36 weeks, about 48 weeks, or about 52 weeks. In certain such embodiments, the recovery time is about 2 weeks. In some embodiments, once-daily administration of oral formulations of the disclosure may be suspended for an injury, wherein the injury is a bone fracture. In certain embodiments, once-daily administration may be suspended for an injury, wherein the injury is a hip fracture. In some embodiments, once-daily administration of oral formulations of the disclosure may be suspended for an injury, wherein the injury is a knee injury.

The formulations of this disclosure may allow for a rise of serum testosterone when medically needed. Stopping once-daily administration of the oral formulations of the disclosure comprising Compound 1, or a pharmaceutically acceptable salt thereof, may decrease the catabolic effect of intercurrent/acute illness and bedrest in men with prostate cancer, thereby allowing for serum testosterone levels to rise to assist in regaining strength and mobility after an intercurrent/acute illness. This benefit cannot be achieved with the depot GnRH agonist/antagonist formulations. This intermittent androgen deprivation therapy may minimize adverse events associated with continuous androgen deprivation therapy while providing comparable efficacy for patients with prostate cancer.

The duration of the suspension period should be such that there is minimal adverse effect on the treatment due to the temporary stoppage of once-daily administration of oral formulations of the disclosure. In some embodiments, the suspension period is from 4 weeks or less to 12 weeks or greater. Longer suspension periods may be possible as long as the subject's PSA levels remain low, such as <4 ng/ml or <0.2 ng/mL. In some embodiments, once-daily administration may be resumed when there is rise in PSA of "nadir+2 ng/ml" during the suspension period. In some embodiments, once-daily administration may be resumed when the subject's PSA level rises to ≥3 ng/mL, ≥10 ng/ml, ≥20 ng/ml, or ≥30 ng/ml during the suspension period. In some embodiments, the suspension period may be up to 60 weeks. In some embodiments, the suspension period may be up to 52 weeks. In some embodiments, the suspension period may be up to 48 weeks. In some embodiments, the suspension period may be up to 36 weeks. In some embodiments, the suspension period may be up to 24 weeks. In some embodiments, the suspension period may be up to 20 weeks. In some embodiments, the suspension period may be up to 16 weeks. In some embodiments, the suspension period may be up to 12 weeks. In some embodiments, the suspension period may be up to 4 weeks. In some embodiments, the suspension period may be up to 8 weeks.

Depending on one or more of the following: symptom severity, subject age, weight and sensitivity, the duration of the suspension period can be altered. In some embodiments, as long as the PSA level is <4 ng/mL or <0.2 ng/mL, the subject may be off therapy. In some embodiments, the suspension period is discontinued when the subject's prostate-specific antigen (PSA) level is ≥20% of the subject's PSA level of the nadir during treatment. In some embodiments, the suspension period is discontinued when the subject's PSA level is ≥50% of the subject's PSA level prior to treatment. In certain embodiments, the suspension period is discontinued when the subject's PSA level is greater than the subject's PSA level at the beginning of the suspension period. In some embodiments, the suspension period is discontinued when the subject experiences return of symptoms of prostate cancer. In certain embodiments, the suspension period is discontinued when the subject's PSA level is ≥3 ng/mL. In other embodiments, the suspension period is discontinued when the subject's PSA level is ≥ 10 ng/mL. In some embodiments, the suspension period is discontinued when the subject's PSA level is ≥20 ng/mL. In other embodiments, the suspension period is discontinued when the subject's PSA level is ≥30 ng/mL.

In some embodiments, the time as to when a suspension period during the treatment period can be taken by a subject should be such that there is a minimal adverse effect on the treatment due to the suspension period. In some embodiments, before a suspension period can be taken, a subject must have completed at least 4 consecutive weeks, at least 8 consecutive weeks, at least 12 consecutive weeks, at least 16 consecutive weeks, at least 20 consecutive weeks, at least 24 consecutive weeks, at least 36 consecutive weeks, at least 48 consecutive weeks, at least 52 consecutive weeks, at least 72 consecutive weeks, or at least 96 consecutive weeks of treatment. In some embodiments, before a suspension period can be taken, a subject must have completed at least 24 consecutive weeks of treatment. In some embodiments, before a suspension period can be taken, a subject must have completed at least 48 consecutive weeks of treatment. As with duration, depending on one or more of the following: symptom severity, subject age, weight and sensitivity, the time for taking the suspension period during the treatment period can be altered.

With respect to onset, within about 4 to about 8 days of first administering once-daily an oral formulation of the disclosure or an oral load dose formulation and an oral maintenance dose formulation of the disclosure, the serum testosterone levels in the subject may be at or below medical castration level. In some embodiments, within 4 days of first administering once-daily an oral formulation of the disclosure or an oral load dose formulation and an oral maintenance dose formulation of the disclosure, the serum testosterone levels in the subject may be at or below medical castration level. In some embodiments, within 5 days of first administering once-daily an oral formulation of the disclosure or an oral load dose formulation and an oral maintenance dose formulation of the disclosure, the serum testosterone levels in the subject may be at or below medical castration level. In some embodiments, within 6 days of first administering once-daily an oral formulation of the disclosure or an oral load dose formulation and an oral maintenance dose formulation of the disclosure, the serum testosterone levels in the subject may be at or below medical castration level. In some embodiments, within 7 days of first administering once-daily an oral formulation of the disclosure or an oral load dose formulation and an oral maintenance dose formulation of the disclosure, the serum testosterone levels in the subject may be at or below medical castration level. In some embodiments, within 8 days of first administering once-daily an oral formulation of the disclosure or an oral load dose formulation and an oral maintenance dose formulation of the disclosure, the serum testosterone levels in the subject may be at or below medical castration level. In some embodiments, within 3 days of first administering once-daily an oral formulation of the disclosure or an oral load dose formulation and an oral maintenance dose formulation of the disclosure, the serum testosterone levels in the subject may be at or below medical castration level.

With further respect to onset, in some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), medical castration levels of less than or equal to 50 ng/dL (1.73 nmol/L) serum testosterone may be achieved within 24 to 48 hours after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 3 days after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 4 days after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 5 days after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 6 days after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 1 week after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 2 weeks after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 3 weeks after commencing administration and maintained until the end of administration. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, serum testosterone levels in a subject may be at or below medical castration level within 4 weeks after commencing administration and maintained until the end of administration.

With further respect to onset, as described herein, following once-daily administration of an oral formulation comprising about 180 mg of Compound 1, or a corresponding amount of a pharmaceutically acceptable salt thereof, medical castration levels of less than or equal to 50 ng/dL (1.73 nmol/L) serum testosterone may be achieved within 24 to 48 hours after commencing administration. In some embodiments, following once-daily administration of an oral formulation of the disclosure comprising about 180 mg of Compound 1, or a corresponding amount of a pharmaceutically acceptable salt thereof, serum testosterone levels in a subject may be at or below medical castration level within 3 days after commencing administration. In some embodiments, following once-daily administration of an oral formulation of the disclosure comprising about 180 mg of Compound 1, or a corresponding amount of a pharmaceutically acceptable salt thereof, serum testosterone levels in a subject may be at or below medical castration level within 4 days after commencing administration. In some embodiments, following once-daily administration of an oral formulation of the disclosure comprising about 180 mg of Compound 1, or a corresponding amount of a pharmaceutically acceptable salt thereof, serum testosterone levels in a subject may be at or below medical castration level within 5 days after commencing administration. In some embodiments, following once-daily administration of an oral formulation of the disclosure comprising about 180 mg of Compound 1, or a corresponding amount of a pharmaceutically acceptable salt thereof, serum testosterone levels in a subject may be at or below medical castration level within 6 days after commencing administration. In some embodiments, following once-daily administration of an oral formulation of the disclosure comprising about 180 mg of Compound 1, or a corresponding amount of a pharmaceutically acceptable salt thereof, serum testosterone levels in a subject may be at or below medical castration level within 1 week after commencing administration.

With further respect to onset, as described herein, following once-daily administration of an oral formulation comprising about 80 mg to about 160 mg of Compound 1, or a corresponding amount of a pharmaceutically acceptable salt thereof, medical castration levels of less than or equal to 50 ng/dL (1.73 nmol/L) serum testosterone may be achieved within 24 to 48 hours after commencing administration. In some embodiments, following once-daily administration of an oral formulation of the disclosure comprising about 80 mg to about 160 mg of Compound 1, or a corresponding amount of a pharmaceutically acceptable salt thereof, serum testosterone levels in a subject may be at or below medical castration level within 3 days after commencing administration. In some embodiments, following once-daily administration of an oral formulation of the disclosure comprising about 80 mg to about 160 mg of Compound 1, or a corresponding amount of a pharmaceutically acceptable salt thereof, serum testosterone levels in a subject may be at or below medical castration level within 4 days after commencing administration. In some embodiments, following once-daily administration of an oral formulation of the disclosure comprising about 80 mg to about 160 mg of Compound 1, or a corresponding amount of a pharmaceutically acceptable salt thereof, serum testosterone levels in a subject may be at or below medical castration level within 5 days after commencing administration. In some embodiments, following once-daily administration of an oral formulation of the disclosure comprising about 80 mg to about 160 mg of Compound 1, or a corresponding amount of a pharmaceutically acceptable salt thereof, serum testosterone levels in a subject may be at or below medical castration level within 6 days after commencing administration. In some embodiments, following once-daily administration of an oral formulation of the disclosure comprising about 80 mg to about 160 mg of Compound 1, or a corresponding amount of a pharmaceutically acceptable salt thereof, serum testosterone levels in a subject may be at or below medical castration level within 1 week after commencing administration.

With further respect to onset, as described herein, following once-daily administration of an oral formulation comprising about 120 mg of Compound 1, or a corresponding amount of a pharmaceutically acceptable salt thereof, medical castration levels of less than or equal to 50 ng/dL (1.73 nmol/L) serum testosterone may be achieved within 24 to 48 hours after commencing administration. In some embodiments, following once-daily administration of an oral formulation of the disclosure comprising about 120 mg of Compound 1, or a corresponding amount of a pharmaceutically acceptable salt thereof, serum testosterone levels in a subject may be at or below medical castration level within 3 days after commencing administration. In some embodiments, following once-daily administration of an oral formulation of the disclosure comprising about 120 mg of Compound 1, or a corresponding amount of a pharmaceutically acceptable salt thereof, serum testosterone levels in a subject may be at or below medical castration level within 4 days after commencing administration. In some embodiments, following once-daily administration of an oral formulation of the disclosure comprising about 120 mg of Compound 1, or a corresponding amount of a pharmaceutically acceptable salt thereof, serum testosterone levels in a subject may be at or below medical castration level within 5 days after commencing administration. In some embodiments, following once-daily administration of an oral formulation of the disclosure comprising about 120 mg of Compound 1, or a corresponding amount of a pharmaceutically acceptable salt thereof, serum testosterone levels in a subject may be at or below medical castration level within 6 days after commencing administration. In some embodiments, following once-daily administration of an oral formulation of the disclosure comprising about 120 mg of Compound 1, or a corresponding amount of a pharmaceutically acceptable salt thereof, serum testosterone levels in a subject may be at or below medical castration level within 1 week after commencing administration.

With further respect to onset, in some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), medical castration levels of less than or equal to 50 ng/dl (1.73 nmol/L) serum testosterone may be achieved within 24 to 48 hours after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 5 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 6 days after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 1 week after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 2 weeks after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 weeks after commencing administration and maintained until the end of administration. In some embodiments, following administration of an oral load dose formulation of the disclosure comprising 240 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 weeks after commencing administration and maintained until the end of administration.

With further respect to onset, in some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), medical castration levels of less than or equal to 50 ng/dl (1.73 nmol/L) serum testosterone may be achieved within 24 to 48 hours after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 5 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 6 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 1 week after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 2 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 3 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below medical castration level within 4 weeks after commencing administration and maintained until the end of administration.

With further respect to onset, in some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater), profound castration levels of less than or equal to 20 ng/dl (1.73 nmol/L) serum testosterone may be achieved within 24 to 48 hours after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 3 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 4 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 5 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 6 days after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 1 week after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 2 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 3 weeks after commencing administration and maintained until the end of administration. In some embodiments, following administration of an oral load dose formulation of the disclosure comprising 360 mg of Compound 1, or a corresponding amount of a pharmaceutically acceptable salt thereof, once-daily for 1-3 days at the beginning of treatment, and once-daily administration of an oral maintenance dose formulation of the disclosure comprising 120 mg of Compound 1, or a corresponding amount of a pharmaceutically acceptable salt thereof, starting on the day after administering the last dose of the oral load dose formulation, and continuing for a set treatment period, serum testosterone levels in a subject may be at or below profound castration level within 4 weeks after commencing administration and maintained until the end of administration.

In some embodiments of the methods and uses described herein, PSA may be suppressed in the subject to a level less than or equal to 4 ng/ml or less than or equal to 2 ng/mL.

During a treatment period (e.g., at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater) of once-daily administration of oral formulations comprising Compound 1, or a pharmaceutically acceptable salt thereof, median time from administration of the first oral formulation to PSA nadir may be less than 5 weeks, less than 6 weeks, less than 7, weeks, less than 8 weeks, less than 9 weeks, less than 10 weeks, less than 11 weeks, less than 12 weeks, less than 13 weeks, less than 14 weeks, less than 15 weeks, less than 16 weeks, less than 17 weeks, less than 18 weeks, less than 19 weeks, less than 20 weeks, less than 21 weeks, less than 22 weeks, less than 23 weeks, less than 24 weeks, or less than 25 weeks. In some embodiments, during a treatment period of once-daily administration of oral formulations comprising Compound 1, or a pharmaceutically acceptable salt thereof, median time from administration of the first oral formulation to PSA nadir may be about 5 weeks to about 10 weeks, about 5 weeks to about 15 weeks, about 5 weeks to about 20 weeks, about 5 weeks to about 25 weeks, about 10 weeks to about 15 weeks, about 10 weeks to about 20 weeks, about 10 weeks to about 25 weeks, or about 15 weeks to about 20 weeks. In some embodiments, during a treatment period of once-daily administration of oral formulations comprising Compound 1, or a pharmaceutically acceptable salt thereof, median time from administration of the first oral formulation to PSA nadir may be about 10 weeks to about 20 weeks. In some embodiments, after once-daily administration of oral formulations of the disclosure for 4 weeks, serum PSA levels are reduced by greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, or greater than or equal to about 90% of the subject's serum PSA levels prior to treatment commencing. In some embodiments, after once-daily administration of oral formulations of the disclosure for 4 weeks, serum PSA levels are reduced by greater than or equal to about 50% of the subject's serum PSA levels prior to treatment commencing.

In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, median time from commencing treatment to PSA nadir may be less than 5 weeks, less than 6 weeks, less than 7, weeks, less than 8 weeks, less than 9 weeks, less than 10 weeks, less than 11 weeks, less than 12 weeks, less than 13 weeks, less than 14 weeks, less than 15 weeks, less than 16 weeks, less than 17 weeks, less than 18 weeks, less than 19 weeks, less than 20 weeks, less than 21 weeks, less than 22 weeks, less than 23 weeks, less than 24 weeks, or less than 25 weeks. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, median time from commencing treatment to PSA nadir may be about 5 weeks to about 10 weeks, about 5 weeks to about 15 weeks, about 5 weeks to about 20 weeks, about 5 weeks to about 25 weeks, about 10 weeks to about 15 weeks, about 10 weeks to about 20 weeks, about 10 weeks to about 25 weeks, or about 15 weeks to about 20 weeks. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, and continuing for a set treatment period, median time from commencing treatment to PSA nadir may be about 10 weeks to about 20 weeks. In some embodiments, 4 weeks after commencing administration of an oral load dose formulation of the disclosure once-daily for 1-3 days, and once-daily administration of an oral maintenance dose formulation of the disclosure starting on the day after administering the last dose of the oral load dose formulation, serum PSA levels are reduced by greater than or equal to about 5%, greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, or greater than or equal to about 90% of the subject's serum PSA levels prior to treatment commencing. In some embodiments, 4 weeks after commencing administration of an oral load dose formulation of the disclosure once-daily for 1-3 days, and once-daily administration of an oral maintenance dose formulation of the disclosure starting on the day after administering the last dose of the oral load dose formulation, serum PSA levels are reduced by greater than or equal to about 50% of the subject's serum PSA levels prior to treatment commencing.

After once-daily administration of oral formulations comprising Compound 1, or a pharmaceutically acceptable salt thereof, for 1 week, 4 weeks, 12 weeks, 24 weeks, or 48 weeks, serum FSH levels may be less than or equal to about 7.2 mIU/mL, about 4.8 mIU/mL, about 2.4 mIU/mL, or about 1.2 mIU/mL. In certain such embodiments, once-daily administration of oral formulations comprising Compound 1, or a pharmaceutically acceptable salt thereof, may result in sustained suppression of serum FSH levels. Normal FSH levels in adult males are typically between 1.5 to 12.4 mIU/mL, but are elevated in subjects with prostate cancer. In some embodiments, after once-daily administration of oral formulations comprising Compound 1, or a pharmaceutically acceptable salt thereof, for 1 week, serum FSH levels may be less than or equal to about 7.2 mIU/mL, about 4.8 mIU/mL, about 2.4 mIU/mL, or about 1.2 mIU/mL. In some embodiments, once-daily administration of oral formulations comprising Compound 1, or a pharmaceutically acceptable salt thereof, for 1 week, 4 weeks, 12 weeks, 24 weeks, or 48 weeks, may suppress serum FSH levels by greater than or equal to about 80% or about 90% of the subject's serum FSH levels prior to treatment commencing.

In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, serum FSH levels may be less than or equal to about 7.2 mIU/mL, about 4.8 mIU/mL, about 2.4 mIU/mL, or about 1.2 mIU/mL 1 week, 4 weeks, 12 weeks, 24 weeks, or 48 weeks after commencing treatment. In certain such embodiments, once-daily administration of oral formulations comprising Compound 1, or a pharmaceutically acceptable salt thereof, may result in sustained suppression of serum FSH levels. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, serum FSH levels may be less than or equal to about 7.2 mIU/mL, about 4.8 mIU/mL, about 2.4 mIU/mL, or about 1.2 mIU/mL 1 week after commencing treatment. In some embodiments, following administration of an oral load dose formulation of the disclosure once-daily for 1-3 days at the beginning of treatment, and once-daily administration of an oral maintenance dose formulation of the disclosure starting on the day after administering the last dose of the oral load dose formulation, serum FSH levels may be suppressed by greater than or equal to about 80% or about 90% of the subject's serum FSH levels prior to treatment commencing 1 week, 4 weeks, 12 weeks, 24 weeks, or 48 weeks after commencing treatment.

The disclosure also provides oral formulations comprising about 80 mg to about 480 mg of Compound 1, or a corresponding amount of a pharmaceutically acceptable salt thereof, for use in a method of treating prostate cancer in a subject in need thereof.

The disclosure provides oral formulations comprising about 80 mg to about 480 mg of Compound 1, or a corresponding amount of a pharmaceutically acceptable salt thereof, for use in a method for treating prostate cancer in a subject in need thereof, the method comprising: administering the oral formulation to the subject once daily; suspending administration of the oral formulation for a suspension period to allow for an increase of serum testosterone levels; and resuming administering to the subject once daily the oral formulation at the end of the suspension period.

The disclosure also provides for use of Compound 1, or a pharmaceutically acceptable salt thereof, for the manufacture of a medicament for the treatment of prostate cancer. In certain such embodiments, the prostate cancer is hormone dependent prostate cancer, advanced prostate cancer, metastatic, non-metastatic, locally advanced, advanced hormone sensitive, advanced castration resistant, recurrent, castration-resistant metastatic prostate cancer, castration-resistant non-metastatic prostate cancer, hormone-sensitive metastatic prostate cancer, or hormone-sensitive non-metastatic prostate cancer. In some embodiments, the medicament comprises 80 mg to about 480 mg of Compound 1, or a corresponding amount of the pharmaceutically acceptable salt thereof.

Methods and uses described herein may provide androgen deprivation in prostate cancer without increasing risk of hyperglycemia and diabetes as compared to GnRH agonists (e.g., Lupron). Unlike other GnRH antagonists (e.g., degarelix), oral formulations of the disclosure provide androgen deprivation without need for injection.

Methods and uses described herein may delay progression of castration resistant disease. In particular, Compound 1, or a pharmaceutically acceptable salt thereof, may offer improved disease control when compared with a GnRH agonist in terms of superior FSH suppression and PSA progression-free survival.

Methods and uses described herein may be used to achieve the anti-androgen withdrawal syndrome. An "anti-androgen" may refer to any drug or substance that decreases the levels or activity of androgens. Anti-androgens tend to inhibit the production, activity, or effects of a male sex hormone or prevent androgens like testosterone or dihydrotestosterone from mediating their biological effects in the body. The anti-androgen withdrawal syndrome is a well-established phenomenon in prostate cancer. It is widely accepted that a subset of patients will benefit from the withdrawal of anti-androgen or steroidal hormone from hormonal therapy, exhibiting decreasing PSA values and clinical improvement.

Methods and uses described herein may be employed to provide heart benefits. The cardiac benefits may be linked to better FSH suppression compared to agonists. Methods and uses described herein may be employed to provide ADT with lower rates of cardiovascular side effects compared to agonists. Also, the formulations of the present disclosure may be useful in sexual reassignment/cross gender transition protocols. Further, the formulations of the present disclosure may be useful in preserving fertility during chemotherapy.

Dosing and Administration

Although GnRH agonists and antagonists are typically given either subcutaneously, intramuscularly or intranasally, including by depot formulations, Compound 1, or a pharmaceutically acceptable salt thereof, may be administered orally and once-daily, making dose administration easier and more convenient.

For treatment of prostate cancer, Compound 1, or a pharmaceutically acceptable salt thereof, may be administered orally once-daily, and formulated with a pharmaceutically acceptable carrier or excipients. In some embodiments, the dosage formulation is a solid preparation, such as a tablet, capsule, granule, or powder, for oral administration.

In some embodiments, the oral formulations comprising Compound 1, or a pharmaceutically acceptable salt thereof, have an immediate release profile. However, the oral formulation may have other release profiles including, for example, sustained release, controlled release, delayed release and extended release.

In some embodiments, the periods of once-daily administration for oral formulations comprising Compound 1, or a pharmaceutically acceptable salt thereof, in the methods and uses described herein are: at least 4 consecutive weeks or greater, at least 8 consecutive weeks or greater, at least 12 consecutive weeks or greater, at least 16 consecutive weeks or greater, at least 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater. In some embodiments, the periods of once-daily administration are 4 consecutive weeks or greater. In some embodiments, the periods of once-daily administration are 8 consecutive weeks or greater. In some embodiments, the periods of once-daily administration are 12 consecutive weeks or greater. In some embodiments, the periods of once-daily administration are 16 consecutive weeks or greater. In some embodiments, the periods of once-daily administration are 20 consecutive weeks or greater. In some embodiments, the periods of once-daily administration are 24 consecutive weeks or greater. In some embodiments, the periods of once-daily administration are 36 consecutive weeks or greater. In some embodiments, the periods of daily administration are 48 consecutive weeks or greater. In some embodiments, the periods of once-daily administration are 52 consecutive weeks or greater. In some embodiments, the periods of once-daily administration are 72 consecutive weeks or greater. In some embodiments, the periods of once-daily administration are 96 consecutive weeks or greater.

The methods and uses described herein include chronic administration. For example, the treatment periods using oral formulations comprising Compound 1, or a pharmaceutically acceptable salt thereof, for treating prostate cancer in a subject and suppressing PSA and/or one or more sex hormones in a subject, including testosterone, LH, and FSH, may be of a long duration, such as, once-daily administration for consecutive day periods of 48 weeks or greater, once-daily administration for consecutive day periods of 52 consecutive weeks or greater, once-daily administration for consecutive day periods of 72 consecutive weeks or greater, once-daily administration for consecutive day periods of 76 weeks or greater, once-daily administration for consecutive day periods of 96 weeks or greater, once-daily administration for consecutive day periods of 104 weeks or greater, or once-daily administration for consecutive day periods of 128 weeks or greater. In certain such embodiments, the treatment period is once-daily administration for consecutive day periods of 48 weeks or greater.

The methods and uses described herein include administering, once-daily, oral formulations comprising Compound 1, or a pharmaceutically acceptable salt thereof, to a subject in need thereof for the treatment of prostate cancer. In certain such embodiments, the oral formulation comprises at least about 80 mg to about 480 mg of Compound 1, or a corresponding amount of a pharmaceutically acceptable salt thereof. In some embodiments, the oral formulation comprises about 80 mg, about 120 mg, about 160 mg, about 180 mg, or about 360 mg of Compound 1, or a corresponding amount of a pharmaceutically acceptable salt thereof. In some embodiments, the oral formulation comprises about 80 mg to about 160 mg of Compound 1, or a corresponding amount of a pharmaceutically acceptable salt thereof. In certain embodiments, the oral formulation comprises about 240 mg to about 480 mg of Compound 1, or a corresponding amount of a pharmaceutically acceptable salt thereof. In some embodiments, the oral formulation comprises about 80 mg of Compound 1, or a corresponding amount of a pharmaceutically acceptable salt thereof. In some embodiments, the oral formulation comprises about 120 mg of Compound 1, or a corresponding amount of a pharmaceutically acceptable salt thereof. In some embodiments, the oral formulation comprises about 160 mg of Compound 1, or a corresponding amount of a pharmaceutically acceptable salt thereof. In some embodiments, the oral formulation comprises about 180 mg of Compound 1, or a corresponding amount of a pharmaceutically acceptable salt thereof. In some embodiments, the oral formulation comprises about 360 mg of Compound 1, or a corresponding amount of a pharmaceutically acceptable salt thereof. In some embodiments, the oral formulation comprises about 240 mg of Compound 1, or a corresponding amount of a pharmaceutically acceptable salt thereof.

The present disclosure provides once-daily administration of oral formulations such as an oral load dose formulation comprising Compound 1, or a pharmaceutically acceptable salt thereof, and an oral maintenance dose formulation comprising Compound 1, or a pharmaceutically acceptable salt thereof, to a subject in need of treatment for prostate cancer. In some embodiments, the oral load dose formulation is a tablet or capsule and the oral maintenance dose formulations are a tablet or capsule. In some embodiments, the oral load dose formulation has an immediate release profile. However, the oral load dose formulation can have other release profiles including, for example, sustained release, controlled release, delayed release and extended release. In some embodiments, the oral maintenance dose formulation has an immediate release profile. However, the oral maintenance dose formulation can have other release profiles including, for example, sustained release, controlled release, delayed release and extended release. In some embodiments, both the oral load and oral maintenance dose formulations are immediate release formulations.

In some embodiments, an oral load dose formulation comprising Compound 1, or a pharmaceutically acceptable salt thereof, may be administered once-daily to begin treatment of prostate cancer and the duration of administration is between 1 and 3 days. In some embodiments, an oral load dose formulation comprising Compound 1, or a pharmaceutically acceptable salt thereof, may be administered once-daily to begin treatment of prostate cancer and the duration of administration is 1 day. In some embodiments, an oral load dose formulation comprising Compound 1, or a pharmaceutically acceptable salt thereof, may be administered once-daily to begin treatment of prostate cancer and the duration of administration is 2 days. In some embodiments, an oral load dose formulation comprising Compound 1, or a pharmaceutically acceptable salt thereof, may be administered once-daily to begin treatment of prostate cancer and the duration of administration is 3 days.

Oral load dose formulations of the disclosure may comprise about 240 to about 480 mg of Compound 1, or a corresponding amount of a pharmaceutically acceptable salt thereof, such as about 320 mg to about 400 mg. In some embodiments, the oral load dose formulation of the disclosure comprises about 240 mg, about 320 mg, about 360 mg, or about 480 mg of Compound 1, or a corresponding amount of a pharmaceutically acceptable salt thereof. In some embodiments, the oral load dose formulation of the disclosure comprises about 360 mg of Compound 1, or a corresponding amount of a pharmaceutically acceptable salt thereof. In some embodiments, the oral load dose formulation of the disclosure comprises about 240 mg of Compound 1, or a corresponding amount of a pharmaceutically acceptable salt thereof. In some embodiments, the oral load dose formulation of the disclosure comprises about 320 mg of Compound 1, or a corresponding amount of a pharmaceutically acceptable salt thereof. In some embodiments, the oral load dose formulation of the disclosure comprises about 480 mg of Compound 1, or a corresponding amount of a pharmaceutically acceptable salt thereof.

Thereafter, and sometimes combined during the duration of the oral load dose formulation, there is once-daily administration of an oral maintenance dose formulation. In some embodiments, the oral maintenance dose formulation once-daily administration begins on the day after administering the last dose of the oral load dose formulation. In some embodiments, the oral maintenance dose formulation of the disclosure comprises about 80 mg to about 160 mg of Compound 1, or a corresponding amount of a pharmaceutically acceptable salt thereof, such as about 100 mg to about 140 mg. In some embodiments, the oral maintenance dose formulation of the disclosure comprises about 120 mg of Compound 1, or a corresponding amount of a pharmaceutically acceptable salt thereof. In some embodiments, the oral maintenance dose formulation of the disclosure comprises about 160 mg of Compound 1, or a corresponding amount of a pharmaceutically acceptable salt thereof. In some embodiments, the oral maintenance dose formulation of the disclosure comprises about 80 mg of Compound 1, or a corresponding amount of a pharmaceutically acceptable salt thereof. In some embodiments, the oral maintenance dose formulation of the disclosure comprises about 180 mg of Compound 1, or a corresponding amount of a pharmaceutically acceptable salt thereof.

In some embodiments, the oral load dose formulation of the disclosure may be administered once-daily for 1-3 days at the beginning of treatment and each dose comprises about 240 to about 480 mg of Compound 1, or a corresponding amount of a pharmaceutically acceptable salt thereof, such as about 320 mg to about 400 mg. In some embodiments, the oral load dose formulation of the disclosure may be administered once-daily for 1-3 days at the beginning of treatment and each dose comprises about 240 mg, about 320 mg, about 360 mg, or about 480 mg of Compound 1, or a corresponding amount of a pharmaceutically acceptable salt thereof. In some embodiments, the oral load dose formulation of the disclosure may be administered once-daily for 1-3 days at the beginning of treatment and each dose comprises about 360 mg of Compound 1, or a corresponding amount of a pharmaceutically acceptable salt thereof. In some embodiments, the oral load dose formulation of the disclosure may be administered once-daily for 1-3 days at the beginning of treatment and each dose comprises about 240 mg of Compound 1, or a corresponding amount of a pharmaceutically acceptable salt thereof. In some embodiments, the oral load dose formulation of the disclosure may be administered once-daily for 1-3 days at the beginning of treatment and each dose comprises about 320 mg of Compound 1, or a corresponding amount of a pharmaceutically acceptable salt thereof. In some embodiments, the oral load dose formulation of the disclosure may be administered once-daily for 1-3 days at the beginning of treatment and each dose comprises about 480 mg of Compound 1, or a corresponding amount of a pharmaceutically acceptable salt thereof.

In some embodiments, the oral load dose formulation of the disclosure may be administered once-daily for 1 day at the beginning of treatment and each dose comprises about 240 to about 480 mg of Compound 1, or a corresponding amount of a pharmaceutically acceptable salt thereof, such as about 320 mg to about 400 mg. In some embodiments, the oral load dose formulation of the disclosure may be administered once-daily for 1 day at the beginning of treatment and each dose comprises about 240 mg, about 320 mg, about 360 mg, or about 480 mg of Compound 1, or a corresponding amount of a pharmaceutically acceptable salt thereof. In some embodiments, the oral load dose formulation of the disclosure may be administered once-daily for 1 day at the beginning of treatment and each dose comprises about 360 mg of Compound 1, or a corresponding amount of a pharmaceutically acceptable salt thereof. In some embodiments, the oral load dose formulation of the disclosure may be administered once-daily for 1 day at the beginning of treatment and each dose comprises about 240 mg of Compound 1, or a corresponding amount of a pharmaceutically acceptable salt thereof. In some embodiments, the oral load dose formulation of the disclosure may be administered once-daily for 1 day at the beginning of treatment and each dose comprises about 320 mg of Compound 1, or a corresponding amount of a pharmaceutically acceptable salt thereof. In some embodiments, the oral load dose formulation of the disclosure may be administered once-daily for 1 day at the beginning of treatment and each dose comprises about 480 mg of Compound 1, or a corresponding amount of a pharmaceutically acceptable salt thereof.

In some embodiments, the oral load dose formulation of the disclosure may be administered once-daily for 2 days at the beginning of treatment and each dose comprises about 240 to about 480 mg of Compound 1, or a corresponding amount of a pharmaceutically acceptable salt thereof, such as about 320 mg to about 400 mg. In some embodiments, the oral load dose formulation of the disclosure may be administered once-daily for 2 days at the beginning of treatment and each dose comprises about 240 mg, about 320 mg, about 360 mg, or about 480 mg of Compound 1, or a corresponding amount of a pharmaceutically acceptable salt thereof. In some embodiments, the oral load dose formulation of the disclosure may be administered once-daily for 2 days at the beginning of treatment and each dose comprises about 360 mg of Compound 1, or a corresponding amount of a pharmaceutically acceptable salt thereof. In some embodiments, the oral load dose formulation of the disclosure may be administered once-daily for 2 days at the beginning of treatment and each dose comprises about 240 mg of Compound 1, or a corresponding amount of a pharmaceutically acceptable salt thereof. In some embodiments, the oral load dose formulation of the disclosure may be administered once-daily for 2 days at the beginning of treatment and each dose comprises about 320 mg of Compound 1, or a corresponding amount of a pharmaceutically acceptable salt thereof. In some embodiments, the oral load dose formulation of the disclosure may be administered once-daily for 2 days at the beginning of treatment and each dose comprises about 480 mg of Compound 1, or a corresponding amount of a pharmaceutically acceptable salt thereof.

In some embodiments, the oral load dose formulation of the disclosure may be administered once-daily for 3 days at the beginning of treatment and each dose comprises about 240 to about 480 mg of Compound 1, such as about 320 mg to about 400 mg, or a corresponding amount of a pharmaceutically acceptable salt thereof. In some embodiments, the oral load dose formulation of the disclosure may be administered once-daily for 3 days at the beginning of treatment and each dose comprises about 240 mg, about 320 mg, about 360 mg, or about 480 mg of Compound 1, or a corresponding amount of a pharmaceutically acceptable salt thereof. In some embodiments, the oral load dose formulation of the disclosure may be administered once-daily for 3 days at the beginning of treatment and each dose comprises about 360 mg of Compound 1, or a corresponding amount of a pharmaceutically acceptable salt thereof. In some embodiments, the oral load dose formulation of the disclosure may be administered once-daily for 3 days at the beginning of treatment and each dose comprises about 240 mg of Compound 1, or a corresponding amount of a pharmaceutically acceptable salt thereof. In some embodiments, the oral load dose formulation of the disclosure may be administered once-daily for 3 days at the beginning of treatment and each dose comprises about 320 mg of Compound 1, or a corresponding amount of a pharmaceutically acceptable salt thereof. In some embodiments, the oral load dose formulation of the disclosure may be administered once-daily for 3 days at the beginning of treatment and each dose comprises about 480 mg of Compound 1, or a corresponding amount of a pharmaceutically acceptable salt thereof.

In some embodiments, an oral maintenance dose formulation of the disclosure may be administered once-daily and comprises about 80 mg to about 160 mg of Compound 1, or a corresponding amount of a pharmaceutically acceptable salt thereof, such as about 100 mg to about 140 mg. In some embodiments, the oral maintenance dose formulation of the disclosure may be administered once-daily and comprises about 120 mg of Compound 1, or a corresponding amount of a pharmaceutically acceptable salt thereof. In some embodiments, the oral maintenance dose formulation of the disclosure may be administered once-daily and comprises about 160 mg of Compound 1, or a corresponding amount of a pharmaceutically acceptable salt thereof. In some embodiments, the oral maintenance dose formulation of the disclosure may be administered once-daily and comprises about 80 mg of Compound 1, or a corresponding amount of a pharmaceutically acceptable salt thereof. In some embodiments, the oral maintenance dose formulation of the disclosure may be administered once-daily and comprises about 180 mg of Compound 1, or a corresponding amount of a pharmaceutically acceptable salt thereof.

In some embodiments, the oral maintenance dose formulations of the disclosure may be administered once-daily for 4 consecutive weeks or greater, 8 consecutive weeks or greater, 12 consecutive weeks or greater, 16 consecutive weeks or greater, 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater. In some embodiments, the oral maintenance dose formulations of the disclosure may be administered once-daily for 4 consecutive weeks or greater. In some embodiments, the oral maintenance dose formulations of the disclosure may be administered once-daily for 8 consecutive weeks or greater. In some embodiments, the oral maintenance dose formulations of the disclosure may be administered once-daily for 12 consecutive weeks or greater. In some embodiments, the oral maintenance dose formulations of the disclosure may be administered once-daily for 16 consecutive weeks or greater. In some embodiments, the oral maintenance dose formulations of the disclosure may be administered once-daily for 20 consecutive weeks or greater. In some embodiments, the oral maintenance dose formulations of the disclosure may be administered once-daily for 24 consecutive weeks or greater. In some embodiments, the oral maintenance dose formulations of the disclosure may be administered once-daily for 36 consecutive weeks or greater. In some embodiments, the oral maintenance dose formulations of the disclosure may be administered once-daily for 48 consecutive weeks or greater. In some embodiments, the oral maintenance dose formulations of the disclosure may be administered once-daily for 52 consecutive weeks or greater. In some embodiments, the oral maintenance dose formulations of the disclosure may be administered once-daily for 72 consecutive weeks or greater. In some embodiments, the oral maintenance dose formulations of the disclosure may be administered once-daily for 96 consecutive weeks or greater. For chronic administration, the oral maintenance dose formulations of the disclosure may be administered once-daily for: consecutive day periods of 48 weeks or greater, consecutive day periods of 52 consecutive weeks or greater, consecutive day periods of 72 consecutive weeks or greater, consecutive day periods of 76 weeks or greater, consecutive day periods of 96 weeks or greater, consecutive day periods of 104 weeks or greater, or consecutive day periods of 128 weeks or greater. In certain such embodiments, the oral maintenance dose formulations of the disclosure may be administered once-daily for consecutive day periods of 48 weeks or greater.

In some embodiments, the oral load dose formulation of the disclosure comprises about 360 mg of Compound 1, or a corresponding amount of a pharmaceutically acceptable salt thereof, and may be administered once on day 1 of the treatment period, and the oral maintenance dose formulations of the disclosure comprise about 120 mg of Compound 1, or a corresponding amount of a pharmaceutically acceptable salt thereof, and may be administered once-daily starting on day 2 of the treatment period. In certain such embodiments, the daily oral maintenance dose formulations may be administered once-daily for a 12 consecutive weeks or greater treatment period. In some embodiments, the daily oral maintenance dose formulations of the disclosure may be administered once-daily for a 48 consecutive weeks or greater treatment period.

In some embodiments, the oral load dose formulation of the disclosure comprises about 240 mg of Compound 1, or a corresponding amount of a pharmaceutically acceptable salt thereof, and may be administered once on day 1 of the treatment period, and the oral maintenance dose formulations of the disclosure comprise about 120 mg of Compound 1, or a corresponding amount of a pharmaceutically acceptable salt thereof, and may be administered once-daily starting on day 2 of the treatment period. In certain such embodiments, the daily oral maintenance dose formulations may be administered once-daily for a 12 consecutive weeks or greater treatment period. In some embodiments, the daily oral maintenance dose formulations of the disclosure may be administered once-daily for a 48 consecutive weeks or greater treatment period.

In some embodiments, the oral load dose formulation of the disclosure comprises about 360 mg of Compound 1, or a corresponding amount of a pharmaceutically acceptable salt thereof, and may be administered once on day 1 of a first treatment period, and the oral maintenance dose formulations of the disclosure comprise about 120 mg of Compound 1, or a corresponding amount of a pharmaceutically acceptable salt thereof, and may be administered once-daily starting on day 1 or day 2 of a second treatment period. In certain such embodiments, the daily oral maintenance dose formulations may be administered once-daily for a 12 consecutive weeks or greater treatment period. In some embodiments, the daily oral maintenance dose formulations of the disclosure may be administered once-daily for a 48 consecutive weeks or greater treatment period.

In some embodiments, the oral load dose formulation of the disclosure comprises about 240 mg of Compound 1, or a corresponding amount of a pharmaceutically acceptable salt thereof, and may be administered once on day 1 of a first treatment period, and the oral maintenance dose formulations of the disclosure comprise about 120 mg of Compound 1, or a corresponding amount of a pharmaceutically acceptable salt thereof, and may be administered once-daily starting on day 1 or day 2 of a second treatment period. In certain such embodiments, the daily oral maintenance dose formulations may be administered once-daily for a 12 consecutive weeks or greater treatment period. In some embodiments, the daily oral maintenance dose formulations of the disclosure may be administered once-daily for a 48 consecutive weeks or greater treatment period.

The present disclosure further provides that once-daily administration of oral formulations comprising Compound 1, or a pharmaceutically acceptable salt thereof, can be suspended for a suspension period, thereby allowing for an increase in a subject's serum testosterone levels. Increased serum testosterone levels during the suspension period may enable subjects to remain in control of their lifestyle and quality of life (e.g., maintenance of sexual activity). In some embodiments, the suspension occurs after the oral formulation of the disclosure is administered once-daily for 4 consecutive weeks or greater. In some embodiments, the suspension occurs after the oral formulation of the disclosure is administered once-daily for 8 consecutive weeks or greater. In some embodiments, the suspension occurs after the oral formulation of the disclosure is administered once-daily for 12 consecutive weeks or greater. In some embodiments, the suspension occurs after the oral formulation of the disclosure is administered once-daily for 16 consecutive weeks or greater. In some embodiments, the suspension occurs after the oral formulation of the disclosure is administered once-daily for 20 consecutive weeks or greater. In some embodiments, the suspension occurs after the oral formulation of the disclosure is administered once-daily for 24 consecutive weeks or greater. In some embodiments, the suspension occurs after the oral formulation of the disclosure is administered once-daily for 36 consecutive weeks or greater. In some embodiments, the suspension occurs after the oral formulation of the disclosure is administered once-daily for 48 consecutive weeks or greater. In some embodiments, the suspension occurs after the oral formulation of the disclosure is administered once-daily for 52 consecutive weeks or greater. In some embodiments, the suspension occurs after the oral formulation of the disclosure is administered once-daily for 72 consecutive weeks or greater. In some embodiments, the suspension occurs after the oral formulation of the disclosure is administered once-daily for 96 consecutive weeks or greater. In some embodiments, the administration of the oral formulation of the disclosure is suspended after at least 24 consecutive weeks of once-daily administration. In some embodiments, the administration of the oral formulation of the disclosure is suspended after at least 48 consecutive weeks of once-daily administration.

The suspension period may last until the desired increase in a subject's serum testosterone levels is achieved or may last as long as required. In some embodiments, the suspension period may last until the PSA begins to rise. In some embodiments, once-daily administration may be resumed when there is rise in PSA of "nadir+2 ng/ml." In some embodiments, once-daily administration may be resumed when the subject's PSA level is ≥3 ng/ml, ≥10 ng/mL, ≥20 ng/ml, or ≥30 ng/ml. In some embodiments, the suspension period may be up to 60 weeks. In some embodiments, the suspension period may be up to 52 weeks. In some embodiments, the suspension period may be up to 48 weeks. In some embodiments, the suspension period may be up to 36 weeks. In some embodiments, the suspension period may be up to 24 weeks. In some embodiments, the suspension period may be up to 20 weeks. In some embodiments, the suspension period may be up to 16 weeks. In some embodiments, the suspension period may be up to 12 weeks. In some embodiments, the suspension period may be up to 4 weeks. In some embodiments, the suspension period may be up to 8 weeks.

In some embodiments, the once-daily administration of oral formulations of the disclosure comprising Compound 1, or a pharmaceutically acceptable salt thereof, for all methods and uses disclosed herein can be suspended for a period of 4 weeks or less, after at least 24 consecutive weeks of once-daily administration. In some embodiments, the once-daily administration of oral formulations of the disclosure comprising Compound 1, or a pharmaceutically acceptable salt thereof, for all methods and uses disclosed herein can be suspended for a period of 4 weeks or less to 8 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 12 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 16 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 20 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 24 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 36 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 48 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 52 weeks or greater, after at least 24 consecutive weeks of once-daily administration. In some embodiments, the once-daily administration of oral formulations comprising Compound 1, or a pharmaceutically acceptable salt thereof, for all methods and uses disclosed herein can be suspended for a period of 4 weeks or less to 60 weeks or greater, after at least 24 consecutive weeks of once-daily administration.

The present disclosure provides for resumption of once-daily administration of oral formulations of the disclosure following a suspension period. In some embodiments, once-daily administration of oral formulations of the disclosure comprising about 80 mg to about 480 mg of Compound 1, or a corresponding amount of a pharmaceutically acceptable salt thereof, is resumed at the end of the suspension period.

The present disclosure also provides for once-daily administration of oral load dose formulations after a suspension period. In some embodiments, an oral load dose formulation of the disclosure comprising about 240 mg to about 480 mg of Compound 1, or a corresponding amount of a pharmaceutically acceptable salt thereof, may be administered once-daily for 1-3 days at the beginning of the treatment period after the suspension period. In some embodiments, the oral load dose formulation of the disclosure may be administered once-daily for 1 day after the suspension period. In some embodiments, the oral load dose formulation of the disclosure may be administered once-daily for 2 days after the suspension period. In some embodiments, the oral load dose formulation of the disclosure may be administered once-daily for 3 days after the suspension period.

After a suspension period, the present disclosure provides for administration of a once-daily oral maintenance dose formulation of the disclosure comprising about 80 mg to about 160 mg of Compound 1, or a corresponding amount of a pharmaceutically acceptable salt thereof, beginning after administering the last dose of the oral load dose formulation of the disclosure. In some embodiments following a suspension period, administration of the once-daily oral maintenance dose formulation of the disclosure comprising about 80 mg to about 160 mg of Compound 1, or a corresponding amount of a pharmaceutically acceptable salt thereof, begins on the day after administering the last dose of the oral load dose formulation of the disclosure.

In certain embodiments with intermittent dosing involving separate treatment periods, the oral load dose formulation of the disclosure may be administered once-daily for 1-3 days at the beginning of each treatment period. In certain embodiments with intermittent dosing involving separate treatment periods, the oral maintenance dose formulation of the disclosure may be administered once-daily at the beginning of each treatment period.

After resuming administration of oral formulations or oral maintenance dose formulations of the disclosure following a suspension period, the oral formulations or oral maintenance dose formulations may be administered once-daily for 4 consecutive weeks or greater, 8 consecutive weeks or greater, 12 consecutive weeks or greater, 16 consecutive weeks or later, 20 consecutive weeks or greater, 24 consecutive weeks or greater, 36 consecutive weeks or greater, 48 consecutive weeks or greater, 52 consecutive weeks or greater, 72 consecutive weeks or greater, or 96 consecutive weeks or greater. In some embodiments, the oral formulations or oral maintenance dose formulations of the disclosure may be administered once-daily for 4 consecutive weeks or greater following a suspension period. In some embodiments, the oral formulations or oral maintenance dose formulations of the disclosure may be administered once-daily for 8 consecutive weeks or greater following a suspension period. In some embodiments, the oral formulations or oral maintenance dose formulations of the disclosure may be administered once-daily for 12 consecutive weeks or greater following a suspension period. In some embodiments, the oral formulations or oral maintenance dose formulations of the disclosure may be administered once-daily for 16 consecutive weeks or greater following a suspension period. In some embodiments, the oral formulations or oral maintenance dose formulations of the disclosure may be administered once-daily for 20 consecutive weeks or greater following a suspension period. In some embodiments, the oral formulations or oral maintenance dose formulations of the disclosure may be administered once-daily for 24 consecutive weeks or greater following a suspension period. In some embodiments, the oral formulations or oral maintenance dose formulations of the disclosure may be administered once-daily for 36 consecutive weeks or greater following a suspension period. In some embodiments, the oral formulations or oral maintenance dose formulations of the disclosure may be administered once-daily for 48 consecutive weeks or greater following a suspension period. In some embodiments, the oral formulations or oral maintenance dose formulations of the disclosure may be administered once-daily for 52 consecutive weeks or greater following a suspension period. In some embodiments, the oral formulations or oral maintenance dose formulations of the disclosure may be administered once-daily for 72 consecutive weeks or greater following a suspension period. In some embodiments, the oral formulations or oral maintenance dose formulations of the disclosure may be administered once-daily for 96 consecutive weeks or greater following a suspension period. For chronic administration after a suspension period, the oral formulations or oral maintenance dose formulations of the disclosure may be administered once-daily for: consecutive day periods of 48 weeks or greater, consecutive day periods of 52 consecutive weeks or greater, consecutive day periods of 72 consecutive weeks or greater, consecutive day periods of 76 weeks or greater, consecutive day periods of 96 weeks or greater, consecutive day periods of 104 weeks or greater, or consecutive day periods of 128 weeks or greater. In certain such embodiments, the oral formulations or oral maintenance dose formulations of the disclosure may be administered once-daily for consecutive day periods of 48 weeks or greater.

In some embodiments, the once-daily administration of oral formulations comprising Compound 1, or a pharmaceutically acceptable salt thereof, is suspended for a subsequent suspension period after completion of an initial suspension period and resumption of administration. In certain such embodiments, the subsequent suspension period occurs at least 12 weeks after resuming once-daily administration of an oral formulation comprising about 80 mg to about 480 mg of Compound 1, or a corresponding amount of a pharmaceutically acceptable salt thereof.

The present disclosure also provides for not resuming administration once it is suspended. For example, in some embodiments, administration may be suspended after radiation therapy is completed and not resumed. In some embodiments, administration after radiation therapy is completed will not be resumed until the PSA rises. In some embodiments, once-daily administration may be resumed when there is rise in PSA of "nadir+2 ng/mL" after radiation therapy. In some embodiments, once-daily administration may resumed after radiation therapy when the subject's PSA level is ≥3 ng/ml, ≥10 ng/mL, ≥20 ng/ml, or ≥30 ng/ml.

In some embodiments, administration of the oral formulations of the present disclosure is food dependent. In certain such embodiments, administration is preferably before any meal. In some embodiments, the oral formulation comprising Compound 1, or a pharmaceutically acceptable salt thereof, may be administered pre-prandial. In some embodiments, administration is at least 1 hour before eating or at least 2 hours after eating. In other embodiments, administration can also be at least 30 minutes before eating or while the subject is fasting. In some embodiments, administration is about 2 hours before eating or 1 hour after eating. In some embodiments, administration is at least 30 minutes before eating, 1 hour before eating, or 2 hours before eating. In some embodiments, administration is at least 30 minutes after eating, 1 hour after eating, or 2 hours after eating.

In some embodiments, the administration of the oral formulations of the disclosure is without any fasting or eating schedule requirement. In some embodiments, the administration is without any fasting requirement. In certain such embodiments, the administration of the oral formulation can be food independent. In some embodiments, administration can be during a meal.

The present disclosure provides that the administration for all methods and uses described herein is such that there is no stimulation of sex hormones, and thereby flare is prevented or minimized in subjects.

Depending on one or more of the following: symptom severity, subject age, weight and sensitivity, and risk factors, such as whether a smoker, and existing medications, the duration and intervals of administration can be altered.

Dosage Forms of the Disclosure

As used herein, the oral formulations of the disclosure may include, but are not limited to, tablets, capsules, caplets, pills, oral dissolving films, lozenges, gums, granules, and powders. In some embodiments, the oral formulation is a tablet or a capsule.

In some embodiments, the oral formulations, including the oral load and maintenance dose formulations, disclosed herein have an immediate release profile. However, the oral formulations can have other release profiles including, for example, sustained release, controlled release, delayed release and extended release. In some embodiments, the oral formulations disclosed herein have a sustained release profile. In some embodiments, the oral formulations disclosed herein have controlled release profile. In some embodiments, the oral formulations disclosed herein have a delayed release profile. In some embodiments, the oral formulations disclosed herein have an extended release profile.

The excipients of the oral formulations of the disclosure are a blend of excipients, and amounts, that help to optimize the efficacy of the formulation. The following are core excipients and include various organic or inorganic excipients or carrier substances, including, but not limited to, one or more fillers or diluents, lubricants, binders, surfactants, pH adjusters, sweeteners, flavors, and disintegrants. There can be a film coat with pharmaceutical additives, including, but not limited to, one or more film formers, coating bases, coating additives, plasticizers, organic acids, pigments or antioxidants, light shielding agents, flow-aids or polishing agents, and colorants.

Diluents or fillers for use in the present disclosure include organic materials and inorganic materials including, but not limited to, dextrose, lactose, mannitol, D-mannitol (e.g., PEARLITOL 50C, PEARLITOL 100SD, PEARLITOL 200SD, PEARLITOL 300 DC, and PEARLITOL 400DC), sodium starch, sucrose, calcium phosphate, anhydrous calcium phosphate, precipitated calcium carbonate, calcium sulfate, calcium carbonate, calcium silicate, sorbitol, corn starch, potato starch, wheat starch, rice starch, partly pregelatinized starch, pregelatinized starch, porous starch, and calcium carbonate starch. In some embodiments, the diluent is mannitol. Diluents or fillers for use in the present disclosure include organic materials and inorganic materials also include, but are not limited to, hydroxypropyl cellulose, crystalline cellulose (e.g., CEOLUS KG-802 (grade: KG-802) and CEOLUS PH-302 (grade: PH-302)), crystalline cellulose (particles), crystalline cellulose (fine particles), microcrystalline cellulose, hydroxypropyl methylcellulose (e.g., hypromellose 2910), starch, gelatin, sucrose, dextrin, lactose, povidone (polyvinylpyrrolidone), copolyvidone, acacia, sodium alginate, and carboxymethylcellulose. In some embodiments, the diluent is D-mannitol. In some embodiments, the diluent is microcrystalline cellulose. In some embodiments, the diluent is lactose.

Binders for use in the present disclosure include, but are not limited to, hydroxypropyl cellulose, crystalline cellulose (e.g., CEOLUS KG-802 (grade: KG-802) and CEOLUS PH-302 (grade: PH-302)), crystalline cellulose (particles), crystalline cellulose (fine particles), microcrystalline cellulose, hydroxypropyl methylcellulose (e.g., hypromellose 2910), starch, gelatin, sucrose, dextrin, lactose, povidone (polyvinylpyrrolidone), and copolyvidone. Natural and synthetic gums that can be used as binders include, but are not limited to, acacia, sodium alginate, and carboxymethylcellulose. In some embodiments, the binder is hydroxypropyl methylcellulose. In some embodiments, the binder is hydroxypropyl cellulose.

Disintegrants for use in the present disclosure include, but are not limited to, crosslinked polymers, such as crosslinked polyvinylpyrrolidone (crospovidone), crosslinked sodium carboxylmethyl cellulose (croscarmellose sodium), crosslinked carmellose sodium, microcrystalline cellulose, carboxymethyl cellulose, carboxylmethyl cellulose calcium, carboxylmethyl starch sodium, and sodium starch glycolate. Additional disintegrants for use in the present disclosure include, but are not limited to, corn starch, sodium carboxymethyl starch, low-substituted hydroxypropylcellulose (L-HPC), hydroxypropyl starch, and magnesium alumino metasilicate. In some embodiments, the disintegrant is sodium starch glycolate. In some embodiments, the disintegrant is crosslinked sodium carboxylmethyl cellulose.

Lubricants for use in the present disclosure include, but are not limited to, magnesium stearate; stearic acid; sodium stearyl fumarate; triethyl citrate; inorganic lubricants, namely talc, colloidal silica and fumed silicon dioxide; polymeric lubricants, such as polyethylene glycol, PEG 4000, and PEG 6000; mineral oils; and hydrogenated vegetable oils. However, other compounds, such as fatty acids and metallic salts thereof, fatty acid esters and salts thereof, organic waxes, polymers and inorganic substances, can be employed. Useful fatty acids include, but are not limited to, lauric acid, palmitic acid and stearic acid. Useful metallic salts include, but are not limited to, those of calcium, magnesium and zinc. Useful fatty acid esters include, but are not limited to, glyceride esters, such as glyceryl monostearate, glyceryl tribehenate, glyceryl palmitostearate and glyceryl dibehenate. Useful sugar esters include, but are not limited to, sucrose esters of fatty acids, sorbitan monostearate, and sucrose monopalmitate. Useful salts thereof include, but are not limited to, sodium oleate, sodium benzoate, sodium acetate, magnesium lauryl sulfate, and sodium lauryl sulfate. In some embodiments, lubricants include magnesium stearate, calcium stearate, talc, and colloidal silica. In some embodiments, the lubricant is magnesium stearate. As used herein, polyethylene glycol is a generic term of compounds represented by the formula $H(OCH_2CH_2)_nOH$ wherein n is a natural number (compound wherein n is not less than 2000 is sometimes referred to as polyethylene oxide).

Examples of colorants used in the formulations of the disclosure include, but are not limited to, food colors such as Food Color Yellow No. 5, Food Color Red No. 2, Food Color Blue No. 2 and the like, food lake colors, red ferric oxide, and yellow ferric oxide.

Examples of pH adjusters used in the formulations of the disclosure include, but are not limited to, citric acid or a salt thereof, phosphoric acid or a salt thereof, carbonic acid or a salt thereof, tartaric acid or a salt thereof, fumaric acid or a salt thereof, acetic acid or a salt thereof, and amino acid or a salt thereof.

Examples of surfactants used in the formulations of the disclosure include, but are not limited to, sodium lauryl sulfate, polysorbate 80, and polyoxyethylene(160) polyoxypropylene(30)glycol.

Examples of sweeteners used in the formulations of the disclosure include, but are not limited to, aspartame (trade name), acesulfame potassium, sucralose, thaumatin, saccharin sodium, and dipotassium glycyrrhizinate.

Examples of the flavors used in the formulations of the disclosure include, but are not limited to, menthol, peppermint oil, lemon oil, and vanillin.

In some embodiments, the pigments for use herein include, but are not limited to, titanium dioxide.

In some embodiments, the film former/film coating base is a sugar coating base. Sugar coating bases for use herein include, but are not limited to, sucrose in combination with one or more of talc, precipitated calcium carbonate, gelatin, gum arabic, pullulan, or carnauba wax.

In some embodiments, the film former/film coating base is a water-soluble film coating base. Water-soluble film coating bases for use herein include, but are not limited to, cellulose polymers such as hydroxypropylcellulose, hydroxypropyl methylcellulose (e.g., hypromellose 2910, TC-5), hydroxyethylcellulose, methylhydroxyethylcellulose and the like; synthetic polymers such as polyvinyl acetaldiethylaminoacetate, aminoalkylmethacrylate copolymer E, polyvinylpyrrolidone and the like; and polysaccharides such as pullulan and the like. In some embodiments, the water-soluble film coating base is hydroxypropyl methylcellulose (e.g., hypromellose 2910, TC-5). In some embodiments, the film former/film coating base is hydroxypropyl methylcellulose (HPMC). In some embodiments, the hydroxypropyl methylcellulose is hypromellose 2910.

In some embodiments, the film former/film coating base comprises cellulose polymers such as hydroxypropylmethylcellulose phthalate, ethylcellulose, hydroxypropylmethylcellulose acetate succinate, carboxymethylethylcellulose, cellulose acetate phthalate and the like; acrylic acid polymers such as methacrylic acid copolymer L, methacrylic acid copolymer LD, methacrylic acid copolymer S, aminoalkylmethacrylate copolymer RS, ethyl acrylate-methyl methacrylate copolymer suspension, and the like; and naturally occurring substances such as shellac and the like.

In some embodiments, the flow aid/polishing agent is carnauba wax. In some embodiments, the flow aid/polishing agent is talc.

In some embodiments, colorants for use herein include, but are not limited to, ferric oxide. In some embodiments, the colorant is red ferric oxide. In some embodiments, the colorant is yellow ferric oxide. In some embodiments, the colorant is a combination of yellow ferric oxide and red ferric oxide.

In some embodiments, the plasticizers for use herein include, but are not limited to, polyethylene glycol (e.g., macrogol 6000), triethyl citrate, castor oil, polysorbates, and the like.

In some embodiments, the organic acids for use herein include, but are not limited to, citric acid, tartaric acid, malic acid, ascorbic acid, and the like.

In some embodiments, the oral formulations of the disclosure, including the oral load dose formulations and the oral maintenance dose formulations, comprise at least one excipient that improves stability while maintaining load capacity. It has been found that for the treatment of prostate cancer, the oral formulations provided by this disclosure that include sodium starch glycolate have improved stability and greater load capacity of Compound 1, or a pharmaceutically acceptable salt thereof, so that Compound 1, or a corresponding amount of a pharmaceutically acceptable salt thereof, can be as high as about 360 mg in an oral load dose formulation and about 120 mg in an oral maintenance dose formulation.

The present disclosure provides oral formulations comprising Compound 1, or a pharmaceutically acceptable salt thereof, for the treatment of prostate cancer. In certain such embodiments, the oral formulations comprise about 80 mg or about 120 mg or about 160 mg or about 180 mg of Compound 1, or a corresponding amount of a pharmaceutically acceptable salt thereof, and core excipients, such as one or more diluents, one or more binders, one or more disintegrants, one or more lubricants, or combinations thereof. In certain such embodiments, the diluent comprises mannitol, the binder comprises hydroxypropyl cellulose, the disintegrant comprises sodium starch glycolate, and the lubricant comprises hydroxypropyl cellulose. In some embodiments, the oral formulations further comprise one or more film formers/film coating bases, one or more pigments, one or more colorants, one or more flow aids/polishing agents, or combinations thereof. In certain such embodiments, the film former/film coating base comprises hypromellose 2910, the pigment comprises titanium dioxide, the colorant comprises ferric oxide, and the flow aid/polishing agent comprises carnauba wax.

In some embodiments, the oral formulations of the disclosure comprise about 240 mg to about 480 mg of Compound 1, or a corresponding amount of a pharmaceutically acceptable salt thereof, such as about 360 mg or about 240 mg, and core excipients such as one or more diluents, one or more binders, one or more disintegrants, one or more lubricants, or combinations thereof. In certain such embodiments, the diluent comprises mannitol, the binder comprises hydroxypropyl cellulose, the disintegrant comprises sodium starch glycolate, and the lubricant comprises hydroxypropyl cellulose. In some embodiments, the oral formulations of the disclosure further comprise one or more film formers/film coating bases, one or more pigments, one or more colorants, one or more flow aids/polishing agents, or combinations thereof. In certain such embodiments, the film formers/film coating base comprises hypromellose 2910, the pigment comprises titanium dioxide, the colorant comprises ferric oxide, and the flow aid/polishing agent comprises carnauba wax.

In some embodiments, the present disclosure provides oral formulations comprising about 80 mg or about 120 mg or about 160 mg or about 180 mg of Compound 1, or a corresponding amount of a pharmaceutically acceptable salt thereof, and core excipients, namely, 51 mg to 244 mg of mannitol, 3 mg to 12 mg of hydroxypropyl cellulose, 10 mg to 20 mg of sodium starch glycolate, and 2 mg to 4 mg of magnesium stearate. In some embodiments, the oral formulations of the disclosure can comprise 80 mg or 120 mg or 160 mg of Compound 1, or a corresponding amount of a pharmaceutically acceptable salt thereof, and core excipients, namely, 51 mg to 244 mg of mannitol, 3 mg to 12 mg of hydroxypropyl cellulose, 10 mg to 20 mg of sodium starch glycolate, and 2 mg to 4 mg of magnesium stearate. The present disclosure still further provides that such oral formulations include a film coat having film excipients, namely, 7.12 to 14.24 mg of hypromellose 2910 (i.e., hydroxypropyl methylcellulose), 0.8 mg to 1.6 mg of titanium dioxide, a sufficient quantity of carnauba wax, and 0.08 mg to 0.16 mg of ferric oxide.

In some embodiments, the oral formulations of the disclosure comprise 80 mg or 120 mg or 160 mg of Compound 1, or a corresponding amount of a pharmaceutically acceptable salt thereof, and core excipients, namely, 102 mg to 204 mg of mannitol, 6 mg to 12 mg of hydroxypropyl cellulose, 10 mg to 20 mg of sodium starch glycolate, and 2 mg to 4 mg of magnesium stearate. The present disclosure still further provides that such oral formulations include a film coat having film excipients, namely, 7.12 to 14.24 mg of hypromellose 2910 (i.e., hydroxypropyl methylcellulose), 0.8 mg to 1.6 mg of titanium dioxide, a sufficient quantity of carnauba wax, and 0.08 mg to 0.16 mg of ferric oxide.

In some embodiments, the oral formulations of the disclosure comprise about 240 mg to about 480 mg of Compound 1, or a corresponding amount of a pharmaceutically acceptable salt thereof. Further, in certain such embodiments, the oral formulations of the disclosure can include: from 306 mg to 612 mg of mannitol (including D-mannitol); from 30 mg to 60 mg of sodium starch glycolate; from 18 mg to 36 mg of hydroxypropyl cellulose; and from 6 mg to 12 mg of magnesium stearate, as core excipients; as well as from 21.36 mg to 42.72 mg of hypromellose 2910; from 2.4 mg to 4.8 mg of titanium dioxide; from 0.24 mg to 0.48 mg of ferric oxide; and a sufficient quantity of carnauba wax.

In some embodiments, the oral formulations of the disclosure comprise about 240 mg to about 480 mg of Compound 1, or a corresponding amount of a pharmaceutically acceptable salt thereof. Further, in certain such embodiments, the oral formulations of the disclosure can include: from 306 mg to 612 mg of mannitol (including D-mannitol); from 30 mg to 60 mg of sodium starch glycolate; from 18 mg to 36 mg of hydroxypropyl cellulose; and from 6 mg to 12 mg of magnesium stearate. In certain such embodiments, the oral formulations of the disclosure further comprise from 21.36 mg to 42.72 mg of hypromellose 2910; from 2.4 mg to 4.8 mg of titanium dioxide; from 0.24 mg to 0.48 mg of ferric oxide; and a sufficient quantity of carnauba wax.

In some embodiments, the oral load dose formulations of the disclosure comprise about 240 mg, about 320 mg, about 360 mg, or about 480 mg of Compound 1, or a corresponding amount of a pharmaceutically acceptable salt thereof, and may be administered once-daily. In some embodiments, the oral load dose formulations comprise about 360 mg of Compound 1, or a corresponding amount of a pharmaceutically acceptable salt thereof. About 360 mg of Compound 1, or a corresponding amount of a pharmaceutically acceptable salt thereof, is used because it optimizes stability in the composition, as well as maintains an efficacious load dose. In some embodiments, the oral maintenance dose formulations of the disclosure comprise about 80 mg, about 120 mg, about 160 mg, or about 180 mg of Compound 1, or a corresponding amount of a pharmaceutically acceptable salt thereof, and may be administered once-daily. In some embodiments, the oral maintenance dose formulations of the disclosure comprise about 120 mg of Compound 1, or a corresponding amount of a pharmaceutically acceptable salt thereof. About 120 mg of Compound 1, or a corresponding amount of a pharmaceutically acceptable salt thereof, is used because it optimizes stability in the composition, as well as maintains an efficacious load dose.

Oral maintenance dose formulations of the disclosure comprising Compound 1, or a pharmaceutically acceptable salt thereof, can be used for treating prostate cancer. In certain such embodiments, the oral maintenance dose formulations of the disclosure comprise about 80 mg to about 160 mg of Compound 1, or a corresponding amount of a pharmaceutically acceptable salt thereof, such as about 120 mg, and core excipients, such as one or more diluents, one or more binders, one or more disintegrants, one or more lubricants, or combinations thereof. In certain such embodiments, the diluent comprises mannitol, the binder comprises hydroxypropyl cellulose, the disintegrant comprises sodium starch glycolate, and the lubricant comprises hydroxypropyl cellulose. In some embodiments, the oral maintenance dose formulations further comprise one or more film formers/film coating bases, one or more pigments, one or more colorants, one or more flow aids/polishing agents, or combinations thereof. In certain such embodiments, the film former/film coating base comprises hypromellose 2910, the pigment comprises titanium dioxide, the colorant comprises ferric oxide, and the flow aid/polishing agent comprises carnauba wax. Further, in some embodiments, the oral maintenance dose formulations of the disclosure can include: from 244 mg to 488 mg of mannitol (including D-mannitol); from 80 mg to 160 mg of microcrystalline cellulose; from 12 mg to 24 mg of hydroxypropyl cellulose; from 20 mg to 40 mg of croscarmellose sodium; from 4 mg to 8 mg of magnesium stearate; from 14.24 mg to 28.48 mg of hypromellose 2910; from 1.6 mg to 3.2 mg of titanium dioxide; and from 0.16 mg to 0.32 mg of ferric oxide. With this and other oral formulations of the disclosure, water is removed during processing of the oral maintenance dose formulation.

In some embodiments, the oral maintenance dose formulation of the disclosure includes: 17.54 wt % of Compound 1, or a corresponding amount of a pharmaceutically acceptable salt thereof; 53.51 wt % of mannitol; 17.54 wt % of microcrystalline cellulose; 2.63 wt % of hydroxypropyl cellulose; 4.39 wt % of croscarmellose sodium, and 0.88 wt % of magnesium stearate, as core excipients. In certain such embodiments, the oral maintenance dose formulation of the disclosure also includes the following other excipients: 3.12 wt % of hypromellose 2910; 0.35 wt % of titanium dioxide; and 0.04 wt % of ferric oxide.

In some embodiments, the oral maintenance dose formulations provided by this disclosure comprise about 80 mg to about 160 mg of Compound 1, or a corresponding amount of a pharmaceutically acceptable salt thereof. Further, in certain such embodiments, the oral maintenance dose formulations of the disclosure can include: from 102 mg to 204 mg of mannitol (including D-mannitol); from 10 mg to 20 mg of sodium starch glycolate; from 6 mg to 12 mg of hydroxypropyl cellulose; from 2 mg to 4 mg of magnesium stearate; from 7.12 mg to 14.24 mg of hypromellose 2910; from 0.8 mg to 1.6 mg of titanium dioxide; from 0.08 mg to 0.16 mg of ferric oxide; and a sufficient quantity of carnauba wax.

In some embodiments, the oral maintenance dose formulations provided by this disclosure comprise about 80 mg to about 160 mg of Compound 1, or a corresponding amount of a pharmaceutically acceptable salt thereof. Further, in certain such embodiments, the oral maintenance dose formulations of the disclosure can include: from 102 mg to 204 mg of mannitol (including D-mannitol); from 10 mg to 20 mg of sodium starch glycolate; from 6 mg to 12 mg of hydroxypropyl cellulose; and from 2 mg to 4 mg of magnesium stearate. In certain such embodiments, the oral maintenance dose formulations of the disclosure further comprise from 7.12 mg to 14.24 mg of hypromellose 2910; from 0.8 mg to 1.6 mg of titanium dioxide; from 0.08 mg to 0.16 mg of ferric oxide; and a sufficient quantity of carnauba wax.

In some embodiments, the oral maintenance dose formulations of the disclosure include: 38.46 wt % of Compound 1, or a corresponding amount of a pharmaceutically acceptable salt thereof; 49.04 wt % of mannitol; 4.81 wt % of sodium starch glycolate (Type A); 2.88 wt % of hydroxypropyl cellulose; and 0.96 wt % of magnesium stearate, as core excipients. In certain such embodiments, the oral maintenance dose formulations of the disclosure also include the following other excipients: 3.42 wt % of hypromellose 2910; 0.38 wt % of titanium dioxide; 0.04 wt % of ferric oxide; and a sufficient quantity of carnauba wax.

In some embodiments, the oral maintenance dose formulations of the disclosure include: 80 mg of Compound 1, or a corresponding amount of a pharmaceutically acceptable salt thereof; 244 mg of mannitol; 80 mg of microcrystalline cellulose; 12 mg of hydroxypropyl cellulose; 20 mg of croscarmellose sodium; 4 mg of magnesium stearate as core excipients. In certain such embodiments, the oral maintenance dose formulations of the disclosure also include a film coat including 14.24 mg of hypromellose 2910; 1.6 mg of titanium dioxide; and 0.16 mg of ferric oxide.

In some embodiments, the oral maintenance dose formulations of the disclosure include: 120 mg of Compound 1, or a corresponding amount of a pharmaceutically acceptable salt thereof; 366 mg of mannitol (filler/diluent); 120 mg of microcrystalline cellulose (filler/diluent); 18 mg of hydroxypropyl cellulose (binder); 30 mg of croscarmellose sodium (disintegrant), and 6 mg of magnesium stearate (lubricant), as core excipients. In certain such embodiments, the oral maintenance dose formulations of the disclosure also include the following other excipients: 21.36 mg of hypromellose 2910 (film coating base); 2.4 mg of titanium dioxide (pigment); and 0.24 mg of ferric oxide (colorant).

In some embodiments, the oral maintenance dose formulations of the disclosure include: 160 mg of Compound 1, or a corresponding amount of a pharmaceutically acceptable salt thereof; 488 mg of mannitol; 160 mg of microcrystalline cellulose; 24 mg of hydroxypropyl cellulose; 40 mg of croscarmellose sodium; 8 mg of magnesium stearate as core excipients. In certain such embodiments, the maintenance dose formulations of the disclosure also include as a film coat 28.48 mg of hypromellose 2910; 3.2 mg of titanium dioxide; and 0.32 mg of ferric oxide.

In some embodiments, the oral maintenance dose formulations provided by this disclosure include: 80 mg of Compound 1, or a corresponding amount of a pharmaceutically acceptable salt thereof; 102 mg of mannitol; 10 mg of sodium starch glycolate; 6 mg of hydroxypropyl cellulose; 2 mg of magnesium stearate; 7.12 mg of hypromellose 2910; 0.8 mg of titanium dioxide; 0.08 mg of ferric oxide; and a sufficient quantity of carnauba wax.

In some embodiments, the oral maintenance dose formulations provided by this disclosure include: 120 mg of Compound 1, or a corresponding amount of a pharmaceutically acceptable salt thereof; 153 mg of mannitol (filler/diluent); 15 mg of sodium starch glycolate (disintegrant); 9 mg of hydroxypropyl cellulose (binder); 3 mg of magnesium stearate (lubricant); 10.68 mg of hypromellose 2910 (film coating base); 1.2 mg of titanium dioxide (pigment); 0.12 mg of ferric oxide (colorant); and a sufficient quantity of carnauba wax (tablet flow aid/polishing agent).

In some embodiments, the oral maintenance dose formulations provided by this disclosure include: 160 mg of Compound 1, or a corresponding amount of a pharmaceutically acceptable salt thereof; 204 mg of mannitol; 20 mg of sodium starch glycolate; 12 mg of hydroxypropyl cellulose; 4 mg of magnesium stearate; 14.24 mg of hypromellose 2910; 1.6 mg of titanium dioxide; 0.16 mg of ferric oxide; and a sufficient quantity of carnauba wax.

The disclosure provides oral load dose formulations comprising Compound 1, or pharmaceutically acceptable salt thereof, for treatment of prostate cancer. In certain such embodiments, the oral load dose formulations of the disclosure comprise about 240 mg to about 480 mg of Compound 1, or a corresponding amount of a pharmaceutically acceptable salt thereof, such as about 360 mg or 240 mg, and core excipients such as one or more diluents, one or more binders, one or more disintegrants, one or more lubricants, or combinations thereof. In certain such embodiments, the diluent comprises mannitol, the binder comprises hydroxypropyl cellulose, the disintegrant comprises sodium starch glycolate, and the lubricant comprises hydroxypropyl cellulose. In some embodiments, the oral load dose formulations of the disclosure further comprise one or more film formers/film coating bases, one or more pigments, one or more colorants, one or more flow aids/polishing agents, or combinations thereof. In certain such embodiments, the film former/film coating base comprises hypromellose 2910, the pigment comprises titanium dioxide, the colorant comprises ferric oxide, and the flow aid/polishing agent comprises carnauba wax. Further, in some embodiments the oral load dose formulations of the disclosure can include: from 732 mg to 1464 mg of mannitol (including D-mannitol); from 240 mg to 480 mg of microcrystalline cellulose; from 36 mg to 72 mg of hydroxypropyl cellulose; from 60 mg to 120 mg of croscarmellose sodium; from 12 mg to 24 mg of magnesium stearate; from 42.72 mg to 85.44 mg of hypromellose 2910; from 4.8 mg to 9.6 mg of titanium dioxide; and from 0.48 mg to 0.96 mg of ferric oxide. With this and other oral formulations of the disclosure, water is removed during processing of the oral load dose formulation.

In some embodiments, the oral load dose formulations of the disclosure include: 17.54 wt % of Compound 1, or a corresponding amount of a pharmaceutically acceptable salt thereof; 53.51 wt % of mannitol; 17.54 wt % of microcrystalline cellulose; 2.63 wt % of hydroxypropyl cellulose; 4.39 wt % of croscarmellose sodium; and 0.88 wt % of magnesium stearate, as core excipients. In certain such embodiments, the oral load dose formulations of the disclosure also include the following other excipients: 3.12 wt % of hypromellose 2910; 0.35 wt % of titanium dioxide; and 0.04 wt % of ferric oxide.

In some embodiments, the oral load dose formulations of the disclosure comprise about 240 mg to about 480 mg of Compound 1, or a corresponding amount of a pharmaceutically acceptable salt thereof. In certain such embodiments, the oral load dose formulations of the disclosure can include: from 306 mg to 612 mg of mannitol (including D-mannitol); from 30 mg to 60 mg of sodium starch glycolate; from 18 mg to 36 mg of hydroxypropyl cellulose; and from 6 mg to 12 mg of magnesium stearate, as core excipients; as well as from 21.36 mg to 42.72 mg of hypromellose 2910; from 2.4 mg to 4.8 mg of titanium dioxide; from 0.24 mg to 0.48 mg of ferric oxide; and a sufficient quantity of carnauba wax.

In some embodiments, the oral load dose formulations of the disclosure comprise about 240 mg to about 480 mg of Compound 1, or a corresponding amount of a pharmaceutically acceptable salt thereof. In certain such embodiments, the oral load dose formulations of the disclosure can include: from 306 mg to 612 mg of mannitol (including D-mannitol); from 30 mg to 60 mg of sodium starch glycolate; from 18 mg to 36 mg of hydroxypropyl cellulose; and from 6 mg to 12 mg of magnesium stearate. In certain such embodiments, the oral load dose formulations of the disclosure further comprise from 21.36 mg to 42.72 mg of hypromellose 2910; from 2.4 mg to 4.8 mg of titanium dioxide; from 0.24 mg to 0.48 mg of ferric oxide; and a sufficient quantity of carnauba wax.

In some embodiments, the oral load dose formulations of the disclosure include: 38.46 wt % of Compound 1, or a corresponding amount of a pharmaceutically acceptable salt thereof; 49.04 wt % of mannitol; 4.81 wt % of sodium starch glycolate (Type A); 2.88 wt % of hydroxypropyl cellulose; and 0.96 wt % of magnesium stearate, as core excipients. In certain such embodiments, the oral load dose formulations of the disclosure also include the following other excipients: 3.42 wt % of hypromellose 2910; 0.38 wt % of titanium dioxide; 0.04 wt % of ferric oxide; and a sufficient quantity of carnauba wax.

In some embodiments, the oral load dose formulations of the disclosure include: 240 mg of the Compound 1, or a corresponding amount of a pharmaceutically acceptable salt thereof; 732 mg of mannitol; 240 mg of microcrystalline cellulose; 36 mg of hydroxypropyl cellulose; 60 mg of croscarmellose sodium; 12 mg of magnesium stearate; 42.72 mg of hypromellose 2910; 4.8 mg of titanium dioxide; and 0.48 mg of ferric oxide.

In some embodiments, the oral load dose formulations of the disclosure include: 360 mg of Compound 1, or a corresponding amount of a pharmaceutically acceptable salt thereof; 1098 mg of mannitol (filler/diluent); 360 mg of microcrystalline cellulose (filler/diluent); 54 mg of hydroxypropyl cellulose (binder); 90 mg of croscarmellose sodium (disintegrant); and 18 mg of magnesium stearate (lubricant), as core excipients. In certain such embodiments, the oral load dose formulations of the disclosure also include the following other excipients: 64.08 mg of hypromellose 2910 (film coating base); 7.2 mg of titanium dioxide (pigment); and 0.72 mg of ferric oxide (colorant).

In some embodiments, the oral load dose formulation of the disclosure include: 480 mg of the Compound 1, or a corresponding amount of a pharmaceutically acceptable salt thereof; 1464 mg of mannitol; 480 mg of microcrystalline cellulose; 72 mg of hydroxypropyl cellulose; 120 mg of croscarmellose sodium; 24 mg of magnesium stearate; 85.44 mg of hypromellose 2910; 9.6 mg of titanium dioxide; and 0.96 mg of ferric oxide.

In some embodiments, the oral load dose formulations provided by this disclosure include: 240 mg of Compound 1, or a corresponding amount of a pharmaceutically acceptable salt thereof; 306 mg of mannitol; 30 mg of sodium starch glycolate; 18 mg of hydroxypropyl cellulose; 6 mg of magnesium stearate; 21.36 mg of hypromellose 2910; 2.4 mg of titanium dioxide; 0.24 mg of ferric oxide; and a sufficient quantity of carnauba wax.

In some embodiments, the oral load dose formulations provided by this disclosure include: 360 mg of Compound 1, or a corresponding amount of a pharmaceutically acceptable salt thereof; 459 mg of mannitol (filler/diluent); 45 mg of sodium starch glycolate (disintegrant); 27 mg of hydroxypropyl cellulose (binder); 9 mg of magnesium stearate (lubricant); 32.04 mg of hypromellose 2910 (film coating base); 3.6 mg of titanium dioxide (pigment); 0.36 mg of ferric oxide (colorant); and a sufficient quantity of carnauba wax (tablet flow aid/polishing agent).

In some embodiments, the oral load dose formulations provided by this disclosure include: 480 mg of Compound 1, or a corresponding amount of a pharmaceutically acceptable salt thereof; 612 mg of mannitol; 60 mg of sodium starch glycolate; 36 mg of hydroxypropyl cellulose; 12 mg of magnesium stearate; 42.72 mg of hypromellose 2910; 4.8 mg of titanium dioxide; 0.48 mg of ferric oxide; and a sufficient quantity of carnauba wax.

Dosage Packs of the Disclosure

The present disclosure provides for dosage packs comprising the oral load and maintenance dose formulations disclosed herein. The dosage pack of the disclosure includes an oral load dose formulation that is separate from an oral maintenance dose formulation. In certain such embodiments, the dosage pack is used for treating prostate cancer. In some embodiments, the oral load dose formulation in the dosage pack has a different color, shape, and/or size than the oral maintenance dose formulation.

In some embodiments, the dosage pack provided by this disclosure includes: an oral load dose formulation comprising excipients and from about 240 mg to about 480 mg of Compound 1, or a corresponding amount of a pharmaceutically acceptable salt thereof; and an oral maintenance dose formulation comprising excipients and about 80 mg to about 160 mg of Compound 1, or a corresponding amount of a pharmaceutically acceptable salt thereof. In certain such embodiments, the oral load dose and maintenance formulations independently comprise excipients such as one or more diluents, one or more binders, one or more disintegrants, one or more lubricants, or combinations thereof. In certain such embodiments, the diluent comprises mannitol, the binder comprises hydroxypropyl cellulose, the disintegrant comprises sodium starch glycolate, and the lubricant comprises hydroxypropyl cellulose. In some embodiments, the oral load dose and maintenance formulations independently further comprise one or more film formers/film coating bases, one or more pigments, one or more colorants, one or more flow aids/polishing agents, or combinations thereof. In certain such embodiments, the film former/film coating base comprises hypromellose 2910, the pigment comprises titanium dioxide, the colorant comprises ferric oxide, and the flow aid/polishing agent comprises carnauba wax.

In some embodiments, the oral load dose formulation of the dosage pack of the disclosure comprises 306 mg to 612 mg of mannitol, 18 mg to 36 mg of hydroxypropyl cellulose, 30 mg to 60 mg of sodium starch glycolate, and 6 mg to 12 mg of magnesium stearate.

In some embodiments, the oral load dose formulation of the dosage pack of the disclosure further comprises 21.36 mg to 42.72 mg of hypromellose 2910, 2.4 mg to 4.8 mg of titanium dioxide, 0.24 mg to 0.48 mg of ferric oxide, and a sufficient quantity of carnauba wax.

In some embodiments, the oral maintenance dose formulation of the dosage pack of the disclosure comprises 102 mg to 204 mg of mannitol, 6 mg to 12 mg of hydroxypropyl cellulose, 10 mg to 20 mg of sodium starch glycolate, and 2 mg to 4 mg of magnesium stearate.

In some embodiments, the oral maintenance dose formulation of the dosage pack of the disclosure further comprises 7.12 mg to 14.24 mg of hypromellose 2910, 0.8 mg to 1.6 mg of titanium dioxide, 0.08 mg to 0.16 mg of ferric oxide, and a sufficient quantity of carnauba wax.

In certain aspects of the disclosure, the oral load dose formulation and the oral maintenance dose formulation of the dosage pack include at least one excipient that improves stability while maintaining load capacity. In some embodiments, the sodium starch glycolate in the oral load dose formulation and the oral maintenance dose formulation of the dosage pack of the disclosure improves stability and load capacity of Compound 1, or a pharmaceutically acceptable salt thereof, in the oral load dose formulation and the oral maintenance dose formulation.

In some embodiments, the oral load dose formulation of the dosage pack of the disclosure comprises about 240 mg, about 320 mg, about 360 mg, or about 480 mg of Compound 1, or a corresponding amount of a pharmaceutically acceptable salt thereof. In some embodiments, the oral load dose formulation of the dosage pack of the disclosure comprises about 360 mg of Compound 1, or a corresponding amount of a pharmaceutically acceptable salt thereof. In some embodiments, the oral load dose formulation of the dosage pack of the disclosure comprises about 240 mg of Compound 1, or a corresponding amount of a pharmaceutically acceptable salt thereof.

In some embodiments, the oral maintenance dose formulation of the dosage pack of the disclosure comprises about 80 mg, about 120 mg, or about 160 mg of Compound 1, or a corresponding amount of a pharmaceutically acceptable salt thereof. In some embodiments, the oral maintenance dose formulation of the dosage pack of the disclosure comprises about 120 mg of Compound 1, or a corresponding amount of a pharmaceutically acceptable salt thereof.

In some embodiments, the oral load dose formulation of the dosage pack of the disclosure comprises about 360 mg of Compound 1, or a corresponding amount of a pharmaceutically acceptable salt thereof, and the oral maintenance dose formulation comprises about 120 mg of Compound 1, or a corresponding amount of a pharmaceutically acceptable salt thereof.

In some embodiments, the oral load dose formulation of the dosage pack of the disclosure comprises about 240 mg of Compound 1, or a corresponding amount of a pharmaceutically acceptable salt thereof, and the oral maintenance dose formulation comprises about 120 mg of Compound 1, or a corresponding amount of a pharmaceutically acceptable salt thereof.

In some embodiments, the oral load dose formulation and the oral maintenance dose formulation of the dosage pack of the disclosure are tablets.

In some embodiments, the oral load dose formulation and the oral maintenance dose formulation of the dosage pack of the disclosure have an immediate release profile.

In some embodiments, the dosage pack of the disclosure further comprises at least one of an anti-androgen or CYP17 lyase inhibitor. In certain such embodiments, the anti-androgen comprises enzalutamide, bicalutamide, enzalutamide or flutamide, and the CYP17 lyase inhibitor comprises abiraterone.

Combination Therapy

The administration mode of oral formulations of the disclosure comprising Compound 1, or a pharmaceutically acceptable salt thereof, and a concomitant medicament can, for example, be (1) an administration of a single oral formulation obtained by formulating Compound 1, or a pharmaceutically acceptable salt thereof, and a concomitant medicament, simultaneously, (2) a simultaneous administration via an identical route of two formulations obtained by formulating Compound 1, or a pharmaceutically acceptable salt thereof, and a concomitant medicament separately, and (3) a sequential and intermittent administration via an identical route of two formulations obtained by formulating Compound 1, or a pharmaceutically acceptable salt thereof, and a concomitant medicament separately.

In accordance with this disclosure, methods and uses comprising administration of oral formulations of the disclosure comprising Compound 1, or a pharmaceutically acceptable salt thereof, can further comprise radiation therapy.

In accordance with this disclosure, methods and uses comprising administration of oral formulations of the disclosure comprising Compound 1, or a pharmaceutically acceptable salt thereof, can further comprise administration of chemotherapy. "Chemotherapy" may refer to a category of treatment using agents/drugs that are destructive to tumor cells and certain tissues. Examples of such agents/drugs include small molecule compounds and biologic drugs, such as an antibody or a polypeptide. Chemotherapy drugs that can be used with the methods and uses described herein include, but are not limited to, alkylating agents, antimetabolites, anti-tumor antibiotics, topoisomerase inhibitors, mitotic inhibitors, corticosteroids, differentiating agents, proteasome inhibitors, immunotherapeutics, and hormone therapeutics. Chemotherapy drugs may include, but are not limited to, abiraterone acetate with or without prednisone, enzalutamide, docetaxel, cabazitaxel, mitoxantrone, estramustine, doxorubicin, etoposide, vinblastine, and inhibitors of the enzyme poly adenosine diphosphate ribose polymerase (PARP).

In accordance with this disclosure, oral formulations of the disclosure comprising Compound 1, or a pharmaceutically acceptable salt thereof, can be given daily together with an anti-androgen. The anti-androgen can be given on and off throughout treatment to provide benefit of an anti-androgen withdrawal syndrome. Alternatively, oral formulations comprising Compound 1, or a pharmaceutically acceptable salt thereof, can be given on and off throughout the treatment cycle to provide an anti-androgen withdrawal syndrome by itself. To help treat clinical flare in subjects with prostate cancer, an anti-androgen can be co-administered with an oral formulation of the disclosure comprising Compound 1, or a pharmaceutically acceptable salt thereof. Illustrative anti-androgens include, but are not limited to, flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine. Such anti-androgens are typically administered for the first 2 to 4 weeks of treatment. An illustrative dosage is an oral formulation comprising about 120 mg of Compound 1, or a corresponding amount of a pharmaceutically acceptable salt thereof, and 160 mg of enzalutamide.

In some embodiments, an oral formulation of the disclosure comprising Compound 1, or a pharmaceutically acceptable salt thereof, may be administered with a CYP17 lyase inhibitor. In some embodiments, the CYP17 lysase inhibitor is abiraterone or salts thereof, galeterone or salts thereof, ketoconazole or salts thereof, or seviteronel or salts thereof. In certain such embodiments, the CYP17 lyase inhibitor comprises abiraterone or salts thereof. In some embodiments, the CYP17 lyase inhibitor and oral formulation comprising Compound 1, or a pharmaceutically acceptable salt thereof, may be administered with a glucocorticoid. In certain such embodiments, the glucocorticoid is prednisone. An illustrative dosing regime is abiraterone acetate given daily in combination with prednisone given daily. In certain such embodiments, 1000 mg of abiraterone acetate is given orally once-daily in combination with 5 mg prednisone given orally twice daily. In some embodiments, the CYP17 lyase inhibitor and oral formulation comprising Compound 1, or a pharmaceutically acceptable salt thereof, may be administered in the absence of a glucocorticoid.

In accordance with the treatment methods and uses of this disclosure, if a prostate cancer is growth hormone dependent, an oral formulation of the disclosure comprising Compound 1, or a pharmaceutically acceptable salt thereof, may be administered in combination with a growth hormone (receptor) antagonist, or Prolactin (receptor) antagonist, or other drugs that may decrease growth hormone or IGF-1.

Still another benefit of this disclosure is that an oral formulation of the disclosure comprising Compound 1, or a pharmaceutically acceptable salt thereof, may be administered to a subject in conjunction with one or more interventions that mitigate or avoid side-effects normally associated with a GnRH antagonist, such as bone mineral density (BMD) loss. Interventions include life style interventions and pharmacologic interventions. Such life style interventions include, but are not limited to, exercise, smoking abstinence, and alcohol abstinence. Such pharmacologic interventions include, but are not limited to, calcium supplementation, vitamin D supplementation, bisphosphonates, denosumab, calcitonin, SERMs, and strontium.

In some embodiments, the methods and uses provided herein do not include administering Compound 1 or a pharmaceutically acceptable salt thereof within 6 hours of administering a P-glycoprotein (P-gp) inhibitor, CYP3A inducer, or a P-gp inducer, or any combinations thereof. P-gp mediates the export of drugs from certain cells, such as those located in the small intestine, blood-brain barrier, hepatocytes, and kidney proximal tube. P-gp may be affected by P-gp inducers or inhibitors, which impair P-gp mediated uptake or efflux, or enhance P-gp activity, respectively. CYP3A is a subfamily of monooxygenases which may be involved in drug metabolism. P-gp or CYP3A inducers may include carbamazepine, rifampin, St. John's wort, bosentan, efavirenz, mitotane, modafinil, or nafcillin. P-gp inhibitors may include amiodarone, azithromycin, captopril, carvedilol, clarithromycin, conivaptan, cyclosporine, diltiazem, dronedarone, eliglustat, erythromycin, felodipine, itraconazole, ketoconazole, lapatinib, lopinavir/ritonavir, propafenone, quercetin, quinidine, reserpine, ranolazine, saquinavir, telaprevir, tipranavir, ticagrelor, tacrolimus, and verapamil. A discussion of the P-gp transport system may be found in J. D. Wesslery, et al. JACC (2013) 61(25): 2495-502. In some embodiments, Compound 1 or a pharmaceutically acceptable salt thereof is administered no less than 6 hours, no less than 8 hours, no less than 10 hours, or no less than 12 hours before a P-gp inhibitor, CYP3A inducer, or a P-gp inducer, or any combinations thereof is administered. In some embodiments, Compound 1 or a pharmaceutically acceptable salt thereof is administered no less than 6 hours, no less than 8 hours, no less than 10 hours, or no less than 12 hours after a P-gp inhibitor, CYP3A inducer, or a P-gp inducer, or any combinations thereof is administered. In certain embodiments, for example when beginning a treatment comprising administration of Compound 1 or a pharmaceutically acceptable salt thereof, Compound 1 or a pharmaceutically acceptable salt thereof is administered no less than 16 hours, no less than 20 hours, or no less than 24 hours before a P-gp inhibitor, CYP3A inducer, or a P-gp inducer, or any combinations thereof is administered. In other embodiments, for example when beginning a treatment comprising administration of Compound 1 or a pharmaceutically acceptable salt thereof, Compound 1 or a pharmaceutically acceptable salt thereof is administered no less than 16 hours, no less than 20 hours, or no less than 24 hours after a P-gp inhibitor, CYP3A inducer, or a P-gp inducer, or any combinations thereof is administered.

Pharmacokinetics

In some embodiments, Compound 1, or a pharmaceutically acceptable salt thereof, is formulated to achieve a desired PK profile, such as effective plasma levels for once-daily treatment with a low dose of Compound 1, or a pharmaceutically acceptable salt thereof. Pharmacokinetic characteristics were determined in healthy subjects after single or repeat-dose administration (once per day, until pharmacokinetic steady-state is reached, at least as long as 5 half-lives). The effect of food or meals was determined after a single-dose administration, where the pharmacokinetics of Compound 1 before/with/after food is compared to administration in the fasted state (no food for at least 8 hours prior to dosing and for 4 hours after dosing). After administration of Compound 1, blood samples at prespecified intervals were collected, plasma is harvested, and the concentration of Compound 1 is determined using analytical methods such as high-performance liquid chromatography with tandem mass-spectrometry. Pharmacokinetic parameters (such as $C_{max}$, AUC and half-life) were determined from plasma concentration-time data for each individual subject using noncompartmental analysis methods, as implemented in software such as Phoenix WinNonlin. These parameters may then be summarized or compared using statistical methods.

In some embodiments, a "high-bioavailability formulation" dosage form comprising about 120 mg of Compound 1, or a corresponding amount of a pharmaceutically acceptable salt thereof, taken orally pre-prandially may provide a blood plasma concentration of at least about 22.68 ng/ml at 1 hour after dose administration. In some embodiments, it may provide a blood plasma concentration of about 48.6 ng/ml at 1 hour after dose administration. In certain embodiments, it may provide a blood plasma concentration of about 84 ng/ml at 1 hour after dose administration. In some embodiments, the high-bioavailability formulation may have a lower dose of Compound 1, or a pharmaceutically acceptable salt thereof, yet may achieve the same average drug exposure in subjects.

In some embodiments, Compound 1, or a pharmaceutically acceptable salt thereof, may be formulated to achieve a low variability of pharmacokinetic and pharmacodynamic effects in subjects. In some embodiments, a "low variability formulation" dosage form comprising about 40 mg of Compound 1, or a corresponding amount of a pharmaceutically acceptable salt thereof, taken orally pre-prandially may provide pharmacodynamic effects that are less subject to variation in subjects, yet may achieve the same average drug exposure in subjects as in other embodiments described herein.

In some embodiments, an oral load dose formulation tablet comprising about 240 mg to about 480 mg of Compound 1, or a corresponding amount of a pharmaceutically acceptable salt thereof, and an oral maintenance dose formulation tablet comprising about about 80 mg to about 160 mg of Compound 1, or a corresponding amount of a pharmaceutically acceptable salt thereof, are formulated so that both are high-bioavailability and food-independent, and may provide pharmacokinetic and pharmacodynamic effects that are less subject to variation in subjects.

In some embodiments, an oral load dose formulation tablet comprising about 360 mg of Compound 1, or a corresponding amount of a pharmaceutically acceptable salt thereof, and an oral maintenance dose formulation tablet comprising about 120 mg of Compound 1, or a corresponding amount of a pharmaceutically acceptable salt thereof, are formulated so that both are high-bioavailability and food-independent, and may provide pharmacokinetic and pharmacodynamic effects that are less subject to variation in subjects.

In some embodiments, a patient can take an oral formulation comprising Compound 1, or a pharmaceutically acceptable salt thereof, before or after a meal, which requires that consuming a meal has a minimum effect on the mean plasma AUC relative to the fasting state. In some embodiments, a "food-independent formulation" oral maintenance dose formulation comprising about 120 mg of Compound 1, or a corresponding amount of a pharmaceutically acceptable salt thereof, taken orally may have a ratio of the mean plasma AUC for fed-state administration relative to fasted-state administration [mean plasma $AUC_{(fed)}$/mean plasma $AUC_{(fasted)}$] that is 0.9 to 1.1, such as 0.95 to 1.05 or 1. In some embodiments, the mean plasma $AUC_{(fed)}$/mean plasma $AUC_{(fasted)}$ is 0.8 to 1.25.

The present disclosure provides a method or use for treating prostate cancer that includes administering to the subject at least once daily for 24 consecutive weeks or greater for a treatment period, an oral formulation comprising at least about 80 mg of Compound 1, or a corresponding amount of a pharmaceutically acceptable salt thereof, in a dosage form that may achieve a pharmacokinetic (PK) profile in which the area under the plasma drug concentration-time curve ($AUC_{(0\text{-}tau)}$) increases at least 1.5 fold or 2 fold or greater when measured from the first to last day of the treatment period. In certain such embodiments, the $AUC_{(0\text{-}tau)}$ may increase at least 1.5 fold when measured from the first to last day of the treatment period. In certain such embodiments, the $AUC_{(0\text{-}tau)}$ may increase at least 2 fold or greater when measured from the first to last day of the treatment period.

The present disclosure also provides a method or use for treating prostate cancer in a subject, the method or use including: administering to the subject for at least one day for a first treatment period, an oral load dose formulation comprising about 240 mg to about 480 mg of Compound 1, or a corresponding amount of a pharmaceutically acceptable salt thereof; and administering to the subject at least once daily for 24 consecutive weeks or greater for a second treatment period, an oral maintenance dose formulation having about 80 mg to about 160 mg of Compound 1, or a corresponding amount of a pharmaceutically acceptable salt thereof, and the oral maintenance dose formulation has a PK profile in which mean plasma $AUC_{(0\text{-}tau)}$ may increase at least 1.5 fold or 2 fold or greater when measured from the first day of the first treatment period to last day of the second treatment period. In certain such embodiments, the oral maintenance dose formulation has a PK profile in which mean plasma $AUC_{(0\text{-}tau)}$ may increase at 2 fold or greater when measured from the first to last day of the treatment period.

The present disclosure still further provides a method or use for suppressing one or more sex hormones in a subject having prostate cancer that includes: administering to the subject at least once daily for 24 consecutive weeks or greater for a treatment period, an oral formulation comprising at least about 80 mg of Compound 1, or a corresponding amount of a pharmaceutically acceptable salt thereof, in a dosage form that may achieve a PK profile in which mean plasma $AUC_{(0\text{-}tau)}$ may increase at least 1.5 fold or 2 fold or greater when measured from the first to last day of the treatment period. In certain such embodiments, the $AUC_{(0\text{-}tau)}$ may increase at least 1.5 fold when measured from the first to last day of the treatment period. In certain such embodiments, the $AUC_{(0\text{-}tau)}$ may increase at least 2 fold or greater when measured from the first to last day of the treatment period.

The present disclosure provides a method or use for suppressing one or more sex hormones in a subject having prostate cancer that includes: administering to the subject for at least one day for a first treatment period, an oral load dose formulation comprising about 240 mg to about 480 mg of Compound 1, or a corresponding amount of a pharmaceutically acceptable salt thereof; and administering to the subject at least once daily for 24 consecutive weeks or greater for a second treatment period, an oral maintenance dose formulation having about 80 mg to about 160 mg of Compound 1, or a corresponding amount of a pharmaceutically acceptable salt thereof, and the oral maintenance dose formulation has a PK profile in which mean plasma $AUC_{(0\text{-}tau)}$ may increase at least 1.5 fold or 2 fold or greater, when measured from the first day of the first treatment period to last day of the second treatment period. In certain such embodiments, the $AUC_{(0\text{-}tau)}$ may increase at least 2 fold or greater when measured from the first to last day of the treatment period.

The present disclosure further provides a method or use for treating prostate cancer that includes administering to the subject at least once daily for 24 consecutive weeks or greater for the treatment period, an oral formulation comprising at least about 80 mg of Compound 1, or a corresponding amount of a pharmaceutically acceptable salt thereof, in a dosage form to achieve a PK profile in which mean $C_{max}$ may increase at least 2 fold when measured from the first to last day of the treatment period.

The present disclosure further provides a method or use for treating prostate cancer that includes: administering to the subject for at least one day for a first treatment period, an oral formulation comprising about 240 mg to about 480 mg of Compound 1, or a corresponding amount of a pharmaceutically acceptable salt thereof; and administering to the subject at least once daily for 24 consecutive weeks or greater for a second treatment period, the oral maintenance dose formulation comprising about 80 mg to about 160 mg of Compound 1, or a corresponding amount of a pharmaceutically acceptable salt thereof, and the oral maintenance dose formulation has a PK profile in which mean $C_{max}$ may increase at least 2 fold when measured from the first day of the first treatment period to last day of the second treatment period.

The present disclosure also provides a method or use for suppressing one or more sex hormones in a subject having prostate cancer that includes administering to the subject at least once daily for 24 consecutive weeks or greater for the treatment period, an oral formulation comprising at least about 80 mg of Compound 1, or a corresponding amount of a pharmaceutically acceptable salt thereof, in a dosage form to achieve a PK profile in which mean $C_{max}$ may increase at least 2 fold when measured from the first to last day of the treatment period.

The present disclosure further provides a method or use for suppressing one or more sex hormones in a subject having prostate cancer, which includes: administering to the subject for at least one day for a first treatment period, or oral load dose formulation comprising about 240 mg to about 480 mg of Compound 1, or a corresponding amount of a pharmaceutically acceptable salt thereof; and administering to the subject at least once daily for 24 consecutive weeks or greater for a second treatment period, an oral maintenance dose formulation comprising about 80 mg to about 160 mg of Compound 1, or a corresponding amount of a pharmaceutically acceptable salt thereof, and the oral maintenance dose formulation has a PK profile in which mean $C_{max}$ may increase at least 2 fold when measured from the first day of the first treatment period to last day of the second treatment period.

In some embodiments, several benefits may result from pre-prandial administration of an oral formulation comprising Compound 1, or a corresponding amount of a pharmaceutically acceptable salt thereof. In some embodiments, mean $C_{max}$ may be higher with pre-prandial administration than with post-prandial administration. Also, mean plasma $AUC_{(0\text{-}tau)}$ may be higher with pre-prandial administration than with post-prandial administration after at least 30 minutes.

Several benefits may result from treating prostate cancer by administering oral formulations comprising Compound 1, or a pharmaceutically acceptable salt thereof, to a subject in need of treatment. In some embodiments, mean $C_{max}$ may be achieved between 1 and 2 hours ($T_{max}$) after beginning treatment. Mean plasma $T_{1/2}$ may be 30 to 70 hours measured at day 14 after beginning treatment. Steady state may be reached within 10 days after beginning treatment. Less than 4% of Compound 1 may be excreted unchanged in urine of a subject, measured at day 14 after beginning treatment. Medical castration levels of less than or equal to 50 ng/dl (1.73 nmol/L) serum testosterone may be achieved and maintained from day 14 to day 28 after beginning treatment.

Additional benefits that may result from treating prostate cancer by administering oral formulations comprising Compound 1, or a pharmaceutically acceptable salt thereof, to a subject include, for example, mean plasma $AUC_{(0\text{-}tau)}$ may increase 1.5 to 2.5 fold (150% to 250%) from day 1 to day 14 after beginning treatment. In some embodiments, mean $C_{max}$ may increase 1.5 to 2.5 fold (150% to 250%) from day 1 to day 14 after beginning treatment.

Additional benefits that may result from treating prostate cancer by administering oral formulations comprising Compound 1, or a pharmaceutically acceptable salt thereof, to a subject include, for example, mean plasma $AUC_{(0\text{-}tau)}$ may increase 1.5 to 2.5 fold (150% to 250%) from day 1 to day 14 after beginning treatment. In some embodiments, mean $C_{max}$ may increase 1.5 to 2.5 fold (150 to 250%) from day 1 to day 14 after beginning treatment.

In accordance with this disclosure, the mean plasma $T_{1/2}$ of Compound 1 may be at least 15 hours, at least about 30 hours, or at least about 35 hours, measured at the end of the treatment period. In some embodiments, the mean plasma $T_{1/2}$ of Compound 1 may be about 35 hours to about 45 hours, such as about 37 hours to about 42 hours, measured at the end of the treatment period.

Following administering oral maintenance dose formulations comprising about 80 mg or about 120 mg per day for 25 consecutive weeks of the Compound 1, or a corresponding amount of a pharmaceutically acceptable salt thereof, formulation, median trough plasma concentration ($C_{min}$) of unchanged Compound 1 may range between 1.0 ng/ml and 9.0 ng/ml, particularly between 2.0 ng/mL and 8.0 ng/mL, and more particularly between 2.5 ng/ml and 7.5 ng/mL, for the 80 mg dose, and between 2.0 ng/ml and 14.0 ng/mL, particularly between 4.0 ng/mL and 12.0 ng/mL, and more particularly between 4.5 ng/ml and 11.5 ng/ml, for the 120 mg dose.

In some embodiments, $C_{min}$ may be maintained constant over the treatment period.

As described herein, in some embodiments, the absorption of Compound 1 in plasma may be decreased and delayed following a single dose administered 30 minutes after the start of a standard U.S. Food and Drug Administration (FDA) high fat, high-calorie breakfast (approx. 800-1000 calories, 50% from fat) compared to fasting conditions. Median $T_{max}$ may increase under fed conditions. Mean $C_{max}$ and mean plasma $AUC_{\infty}$ may be reduced under fed conditions compared with fasted conditions, indicating a clinically meaningful effect of food on the oral bioavailability of Compound 1. When Compound 1, or a pharmaceutically acceptable salt thereof, may be administered daily 30 minutes prior to ingestion of a standardized morning meal (approx. 600 calories, 27% from fat), systemic exposure to Compound 1 may be reduced to a lesser extent and no obvious changes in the rate of absorption are observed when compared to fasting conditions. In some embodiments, subjects should take oral formulations comprising Compound 1, or a pharmaceutically acceptable salt thereof, upon arising in the morning, on an empty stomach, and start eating approximately 30 minutes after dosing whenever possible.

Following administration of oral maintenance dose formulations comprising about 80 mg or about 120 mg of Compound 1, or a corresponding amount of a pharmaceutically acceptable salt thereof ("Compound 1 formulation"), per day for 13 consecutive weeks having the following excipients: 244 mg or 549 mg of mannitol, 40 mg or 90 mg of microcrystalline cellulose, 12 mg or 27 mg of hydroxypropyl cellulose, 20 mg or 45 mg of croscarmellose sodium, 4 mg or 10 mg of magnesium stearate, 14.24 mg or 35.6 mg of hypromellose 2910, 1.6 mg or 3.6 mg of titanium dioxide, and 0.16 mg or 0.36 mg of ferric oxide, the change from baseline (i.e., the subject's serum PSA level prior to treatment commencing) in the mean serum PSA concentration at 13 consecutive weeks (i.e., week 13, day 1) may be a reduction from 10.6004 ng/L to 1.0823 ng/L (i.e., 10.6 fold (1060%) reduction) for the 80 mg dose, and a reduction from 6.6275 ng/L to 0.5849 ng/L (i.e., 11.3 fold (1130%) reduction) for the 120 mg dose. The change from baseline in the mean serum PSA concentration may result in a 6.5 to 15.5 fold (650% to 1550%), particularly a 7.5 to 14.5 fold (750% to 1450%), and more particularly a 8.0 to 12 fold (800% to 1200%), reduction for the 80 mg dose and a 7.5 to 16.5 fold (750% to 1650%), particularly a 8.5 to 15.5 fold (850% to 1550%), and more particularly a 9.0 to 13 fold (900% to 1300%), reduction for the 120 mg dose. Rates of PSA reduction achieved by the Compound 1, or a pharmaceutically acceptable salt thereof, formulations may be comparable to leuprolide acetate and degarelix, but the Compound 1, or a pharmaceutically acceptable salt thereof, formulations provide greater ease of use.

Following administration of oral maintenance dose formulations comprising about 80 mg or about 180 mg of Compound 1, or a corresponding amount of a pharmaceutically acceptable salt thereof ("Compound 1 formulation"), per day for 16 consecutive days, the change from baseline (i.e., the subject's serum LH level prior to treatment commencing) in the mean serum LH concentration at the end of 16 consecutive days, namely end of treatment, may be a reduction from 3.90 IU/L to 0.23 IU/L (i.e., 13.8 fold (1380%) reduction) for 180 mg dose, and a reduction from 4.57 IU/L to 0.33 IU/L (i.e., 17 fold (1700%) reduction) for 80 mg dose. The change from baseline in the mean serum LH concentration may result in a 10 to 18 fold (1000% to 1800%), particularly a 12 to 16 fold (1200% to 1600%), and more particularly a 12.5 to 15.5 fold (1250% to 1550%), reduction for the 80 mg dose, and a 14 to 20 fold (1400% to 2000%), particularly a 15 to 19 fold (1500% to 1900%), and more particularly a 15.5 to 18.5 fold (1550% to 1850%), reduction for the 180 mg dose.

Following administration of oral maintenance dose formulations comprising about 80 mg or about 180 mg of Compound 1, or a corresponding amount of a pharmaceutically acceptable salt thereof ("Compound 1 formulation"), per day for 16 consecutive days, the change from baseline (i.e., the subject's serum testosterone level prior to treatment commencing) in the mean serum testosterone concentration at the end of 16 consecutive days may be a reduction from 10.40 nmol/L to 0.3565 nmol/L (i.e., 29 fold (2900%) reduction) for the 80 mg dose, and a reduction from 10.40 nmol/L to 0.4320 nmol/L (i.e., 24 fold (2400%) reduction) for the 180 mg dose. The change from baseline in the mean serum testosterone concentration may result in a 25 to 33 fold (2500% to 3300%), particularly a 27 to 31 fold (2700% to 3100%), and more particularly a 27.5 to 30.5 fold (2750% to 3050%), reduction for the 80 mg dose, and a 20 to 28 fold (2000% to 2800%), particularly a 22 to 26 fold (2200% to 2600%), and more particularly a 22.5 to 25.5 fold (2250% to 2550%), reduction for the 180 mg dose. Rates of testosterone suppression achieved by the Compound 1, or a pharmaceutically acceptable salt thereof, formulations may be comparable to leuprolide acetate and degarelix, but the Compound 1, or a pharmaceutically acceptable salt thereof, formulations provide greater ease of use.

Following administration of oral maintenance dose formulations comprising about 80 mg or about 180 mg of Compound 1, or a corresponding amount of a pharmaceutically acceptable salt thereof ("Compound 1 formulation"), per day for 16 consecutive days, change from baseline in mean serum FSH concentration at the end of 16 consecutive days may be a reduction from 6.07 IU/L to 0.67 IU/L (i.e., 9.1 fold (910%) reduction) for the 80 mg dose, and a reduction from 3.88 IU/L to 0.33 IU/L (i.e., 11.8 fold (1180%) reduction) for the 180 mg dose. The change from baseline in mean serum FSH concentration may result in a 5 to 13 fold (500% to 1300%), particularly a 7 to 11 fold (700% to 1100%), and more particularly a 7.5 to 10.5 fold (750% to 1050%), reduction for the 80 mg dose, and a 8 to 16 fold (800% to 1600%), particularly a 10 to 14 fold (1000% to 1400%), and more particularly a 10.5 to 13.5 fold (1050% to 1350%), reduction for the 180 mg dose.

Following administration of oral maintenance dose formulations comprising about 80 mg or about 180 mg of Compound 1, or a corresponding amount of a pharmaceutically acceptable salt thereof ("Compound 1 formulation"), per day for 16 consecutive days, the change from baseline (i.e., the subject's serum DHT level prior to treatment commencing) in the mean serum DHT concentration at the end of the 16 consecutive days may be a reduction from 1.883 nmol/L to 1.095 nmol/L (i.e., 1.7 fold (170%) reduction) for the 80 mg dose, and a reduction from 1.882 nmol/L to 0.865 nmol/L (i.e., 2.2 fold (220%) reduction) for the 180 mg dose. The change from baseline in the mean serum DHT concentration may result in a 1.1 to 5 fold (110% to 500%), particularly a 1.1 to 3 fold (110% to 300%), and more particularly a 1.1 to 2.5 fold (110% to 250%), reduction for the 80 mg dose, and a 1.1 to 6 fold (110% to 600%), particularly a 1.1 to 4 fold (110% to 400%), and more particularly a 1.1 to 3.5 fold (110% to 350%), reduction for the 180 mg dose.

The following non-limiting examples are provided to illustrate the disclosure.

EXAMPLES

Example 1: Production of Compound 1

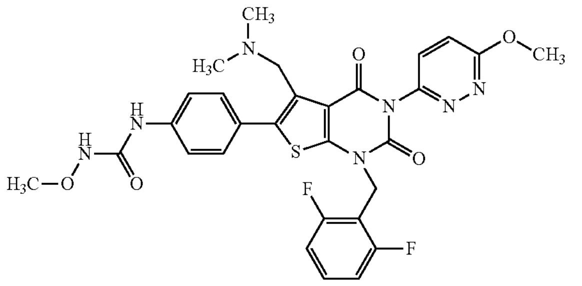

N-(4-(1-(2,6-difluorobenzyl)-3-(6-methoxy-3-pyridazinyl)-5-((methylamino) methyl)-2,4-dioxo-1,2,3,4-tetrahydrothieno[2,3-d]pyrimidin-6-yl)phenyl)-N'-methoxyurea (150 mg, 0.259 mmol) was dissolved in DMF (4 mL), and methyl iodide (0.010 mL, 0.164 mmol) was added thereto. The reaction mixture was stirred at room temperature for 1 hour, combined with an aqueous solution of sodium hydrogen carbonate and extracted with ethyl acetate. The organic layer was washed with brine, dried over magnesium sulfate and concentrated under reduced pressure. The residue was purified by silica gel column chromatography (eluent: ethyl acetate/methanol=40/1), and recrystallized from dichloromethane/methanol/diethyl ether to give the title compound (17.3 mg, 17%) as colorless crystals. $^1$H-NMR ($CDCl_3$) δ: 2.15 (6H, s), 3.6-3.8 (2H, m), 3.82 (3H, s), 4.18 (3H, s), 5.35 (2H), 6.92 (2H, t, J=8.2 Hz), 7.12 (1H, d, J=8.8 Hz), 7.2-7.65 (7H, m), 7.69 (1H, s).

Example 2: Production of Film Coated Tablets of Compound 1

Film coated tablets were prepared by using the compound obtained in Example 1 (120 mg), mannitol (366 mg), microcrystalline cellulose (120 mg), hydroxypropyl cellulose (18 mg), croscarmellose sodium (30 mg), magnesium stearate (6 mg), and sufficient quantity of purified water. Water was removed during processing. In a fluid bed dryer granulator (LAB-1, Powrex Corporation), the compound obtained in Example 1, mannitol, precisely D-mannitol, and microcrystalline cellulose were preheated and mixed, an aqueous solution of hydroxypropyl cellulose was sprayed, and the mixture was dried to give a granulated powder. To the obtained granulated powder was added croscarmellose sodium and magnesium stearate, and they were mixed in a bag to give a mixed powder. The mixed powder was tableted by a rotary tableting machine (compact 10 tableting machine, Kikusui Seisakusho Ltd.) with a 6.0 mmφ pounder to give core tablets. The core tablets were placed in a film coating machine (DRC-200, Powrex Corporation), a film coating solution with a composition of hypromellose 2910 (21.36 mg), titanium dioxide (2.4 mg), and red ferric oxide (0.24 mg) was sprayed to give film coated tablets. The obtained film coated tablets were placed in a glass bottle, which was tightly sealed and preserved at 60° C. for 2 weeks.

Example 3: Production of Film Coated Tablets of Compound 1

Film coated tablets were prepared by using the compound obtained in Example 1 (360 mg), mannitol (1098 mg), microcrystalline cellulose (360 mg), hydroxypropyl cellulose (54 mg), croscarmellose sodium (90 mg), magnesium stearate (18 mg), and sufficient quantity of purified water. Water was removed during processing. In a fluid bed dryer granulator (LAB-1, Powrex Corporation), the compound obtained in Example 1, mannitol, precisely D-mannitol, and microcrystalline cellulose were preheated and mixed, an aqueous solution of hydroxypropyl cellulose was sprayed, and the mixture was dried to give a granulated powder. To the obtained granulated powder was added croscarmellose sodium and magnesium stearate, and they were mixed in a bag to give a mixed powder. The mixed powder was tableted by a rotary tableting machine (compact 10 tableting machine, Kikusui Seisakusho Ltd.) with a 6.0 mmφ pounder to give core tablets. The core tablets were placed in a film coating machine (DRC-200, Powrex Corporation), a film coating solution with a composition of hypromellose 2910 (64.08 mg), titanium dioxide (7.2 mg), and red ferric oxide (0.72 mg) was sprayed to give film coated tablets. The obtained film coated tablets were placed in a glass bottle, which was tightly sealed and preserved at 60° C. for 2 weeks.

Example 4: Production of Film Coated Tablets of Compound 1

Film coated tablets were prepared by using the compound obtained in Example 1 (120 mg), mannitol (153 mg), sodium starch glycolate (Type A) (15 mg), hydroxypropyl cellulose (9 mg), magnesium stearate (3 mg), and a sufficient quantity of purified water. Again, water was removed during processing. In a fluid bed dryer granulator (LAB-1, Powrex Corporation), the compound obtained in Example 1, D-mannitol, and sodium starch glycolate were preheated and mixed, an aqueous solution of hydroxypropyl cellulose was sprayed, and the mixture was dried to give a granulated powder. To the obtained granulated powder, magnesium stearate was added, and they were mixed in a bag to give a mixed powder. The mixed powder was tableted by a rotary tableting machine (compact 10 tableting machine, Kikusui Seisakusho Ltd.) with a 6.0 mmφ pounder to give core tablets. The core tablets were placed in a film coating machine (DRC-200, Powrex Corporation), a film coating solution with a composition of hypromellose 2910 (10.68 mg), titanium dioxide (1.2 mg), ferric oxide (0.12 mg), and a sufficient quantity of carnauba wax, was sprayed to give film coated tablets. The obtained film coated tablets were placed in a glass bottle, which was tightly sealed and preserved at 60° C. for 2 weeks.

Example 5: Production of Film Coated Tablets of Compound 1

Film coated tablets were prepared by using the compound obtained in Example 1 (360 mg), mannitol (459 mg), sodium starch glycolate (Type A) (45 mg), hydroxypropyl cellulose (27 mg), magnesium stearate (9 mg), and a sufficient quantity of purified water. Again, water was removed during processing. In a fluid bed dryer granulator (LAB-1, Powrex Corporation), the compound obtained in Example 1, D-mannitol, and sodium starch glycolate were preheated and mixed, an aqueous solution of hydroxypropyl cellulose was sprayed, and the mixture was dried to give a granulated powder. To the obtained granulated powder, magnesium stearate was added, and they were mixed in a bag to give a mixed powder. The mixed powder was tableted by a rotary tableting machine (compact 10 tableting machine, Kikusui Seisakusho Ltd.) with a 6.0 mmφ pounder to give core tablets. The core tablets were placed in a film coating machine (DRC-200, Powrex Corporation), a film coating solution with a composition of hypromellose 2910 (32.04 mg), titanium dioxide (3.6 mg), ferric oxide (0.36 mg), and a sufficient quantity of carnauba wax, was sprayed to give film coated tablets. The obtained film coated tablets were placed in a glass bottle, which was tightly sealed and preserved at 60° C. for 2 weeks.

Example 6: A Study to Evaluate the Effect of Compound 1 on Pharmacokinetics and Pharmacodynamics in Men with Non-metastatic Prostate Cancer This study consisted of two parts: Part A, a dose-rising phase, and Part B, an expansion phase. Whether or not the study would proceed to the next cohort or to Part B was determined through assessment of tolerability at the present dose, based on the incidence of adverse effects during the evaluation period.

The Compound 1 formulation was taken orally once a day for 28 days. The 120 mg Compound 1 formulation comprised a core tablet of Compound 1 (120 mg), mannitol (366 mg), microcrystalline cellulose (60 mg), hydroxypropyl cellulose (18 mg), croscarmellose sodium (30 mg), and magnesium stearate (6 mg). The core tablets were coated with a film coating comprising hypromellose 2910 (21.36 mg), titanium dioxide (2.4 mg), and red ferric oxide (0.06 mg). The amounts of the excipients in the core tablet and film coating were adjusted accordingly based on the amount of Compound 1 in the core tablet (e.g., for the 360 mg tablet, the amount of excipient added to the core tablet and film coating is three times the amount added to the 120 mg tablet).

Subjects in Cohort 1 received a load dose of 320 mg and a maintenance dose of 80 mg; subjects in Cohort 2 received a load dose of 320 mg and a maintenance dose of 120 mg; subjects in Cohort 3 received a load dose of 320 mg and a maintenance dose of 160 mg; and subjects in Cohort 4 received a load dose of 360 mg and a maintenance dose of 120 mg. Subjects being switched to treatment with GnRH agonists (e.g., leuprolide acetate) or GnRH antagonists (e.g., degarelix) go through a 1-week follow-up period after receiving their last dose of the Compound 1 formulation.

If tolerability was confirmed in Cohort 2, then the study proceeded to Cohort 3 and Part B simultaneously. However, if tolerability was not confirmed in Cohort 2, then an additional cohort was conducted, where subjects received a load or loading dose of Compound 1 of 320 mg and a maintenance dose of 40 mg. Cohort 4 was conducted after tolerability was confirmed in Cohort 3.

In Part B, subjects were randomized in a 1:1 ratio (15 patients each) to either the 80 mg group (load dose of Compound 1 320 mg and maintenance of 80 mg orally once-daily) or 120 mg group (load dose of Compound 1 320 mg and maintenance dose of 120 mg orally once-daily) to evaluate the safety of the Compound 1 formulation. In addition to the safety assessments, efficacy assessments were also performed according to the study schedule, and the Compound 1 formulation was administered until each subject met the discontinuation criteria.

The serum concentrations of testosterone and other pharmacodynamic parameters involved in the testosterone synthetic pathway, such as LH, FSH, DHT and SHBG, were measured during 28 days of the treatment period in Part A and for up to 96 weeks in Part B. Assay methods of serum testosterone, LH and FSH are chemiluminescent immunoassay (CLIA) (lower limits of quantitation [LLOQ] were 0.04 ng/mL, 0.10 mIU/mL, and 0.10 mIU/mL, respectively), DHT was radioimmunoassay (RIA) of ammonium sulfate salting out (LLOQ was 0.02 ng/mL), and SHBG was two-side CLIA (LLOQ was 2.0 nmol/L).

For Part A, the mean serum testosterone concentration of each dose level of Compound 1 is shown in FIG. 1, and individual changes in the serum testosterone concentration of each dose level of the study drug is presented in FIG. 2. The serum testosterone concentration rapidly decreased after the first dose in all dose levels (maintenance dose of 80 mg, 120 mg or 160 mg). The mean serum testosterone concentration fell to below medical castration levels (i.e., below 50 ng/dL) within the first 3 days of dosing. The serum testosterone concentration achieved medical castration levels between Day 2 and Day 14 and was maintained thereafter up to 3 days after the last dose on Day 28 in all subjects.

For Part A, the mean serum LH, FSH, DHT and SHBG concentrations for each dose level of the study drug are graphically shown in FIGS. 3-6, respectively. The serum LH, FSH and DHT concentrations were rapidly suppressed, similar to the serum testosterone concentration, in all dose levels. There were no particular changes between the baseline (i.e., the subject's serum hormone levels prior to treatment commencing) and postdose serum SHBG concentrations.

Figure 7:
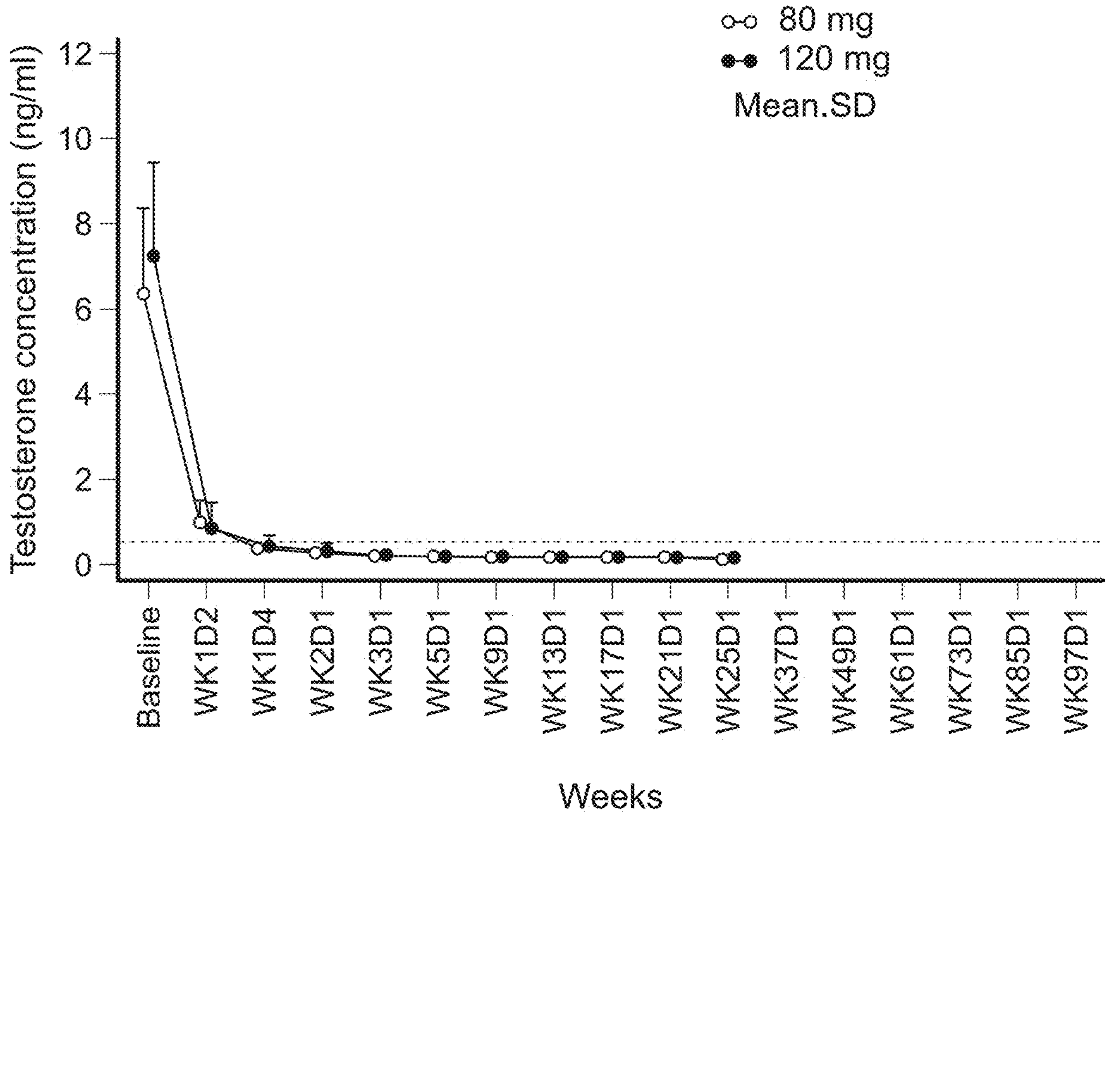
FIG. 7 graphically depicts mean serum testosterone concentrations for a treatment period (Part B) in accordance with Example 6.
Figure 8B:
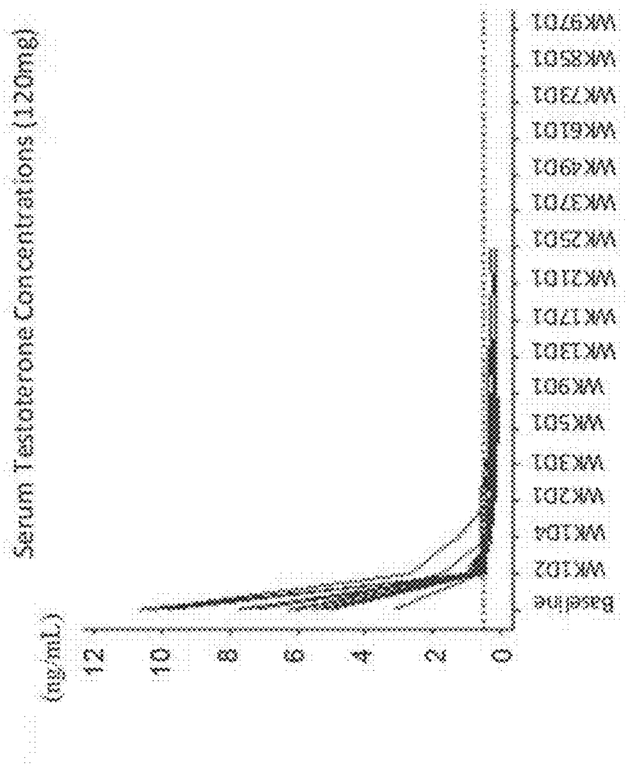
FIGS. 8A and 8B graphically depict mean serum testosterone concentrations for a treatment period (Part B) for 80 mg Compound 1 and 120 mg Compound 1 in accordance with Example 6.
Figure 8A:
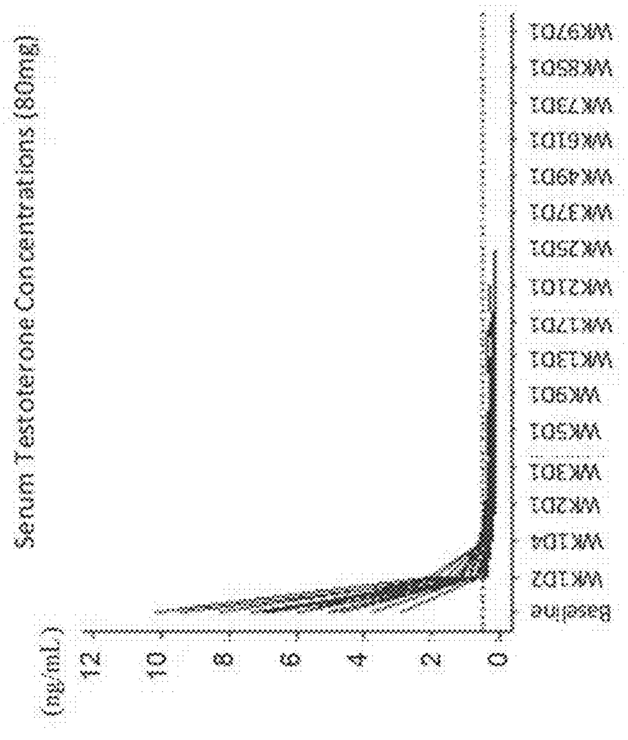
Figure 9:
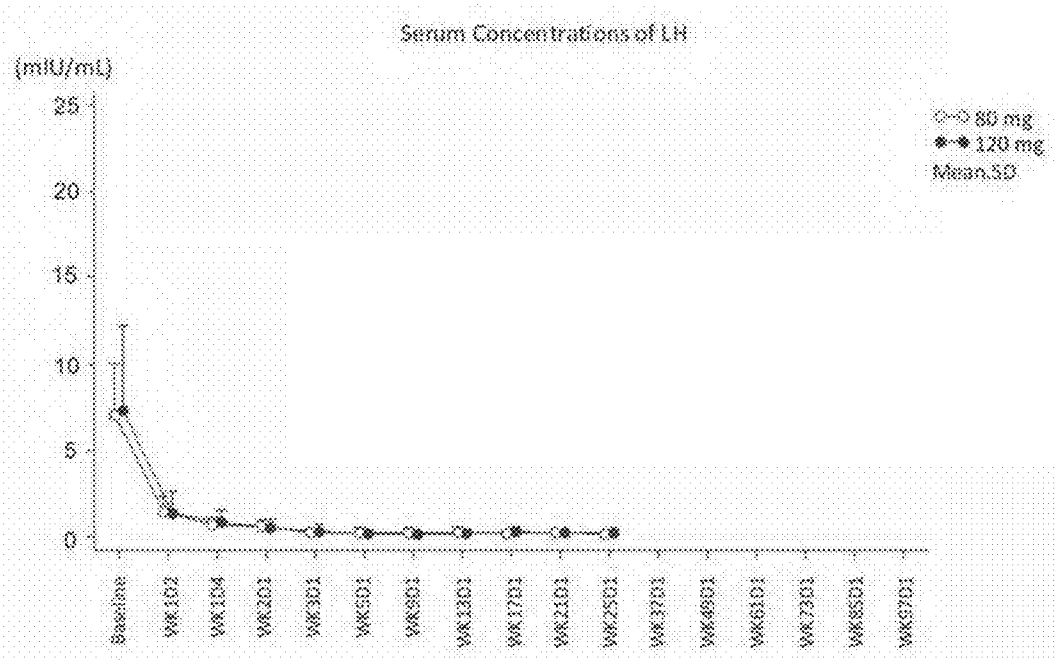
FIG. 9 graphically depicts mean serum LH concentrations for a treatment period (Part A) in accordance with Example 6.
Figure 10:
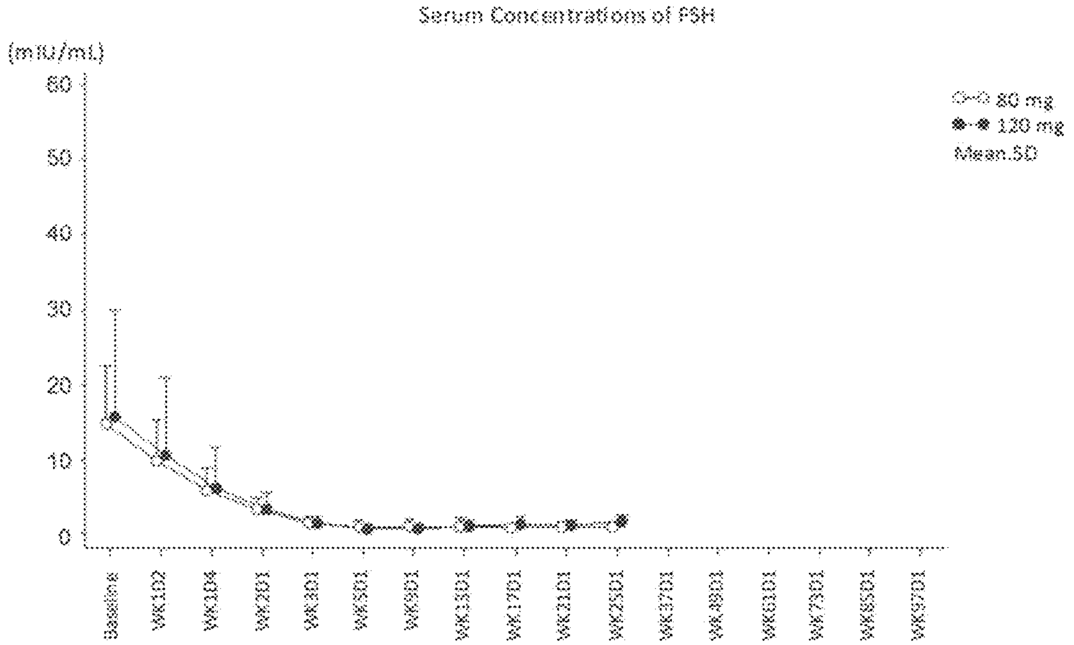
FIG. 10 graphically depicts mean serum FSH concentrations for a treatment period (Part A) in accordance with Example 6.
Figure 11:
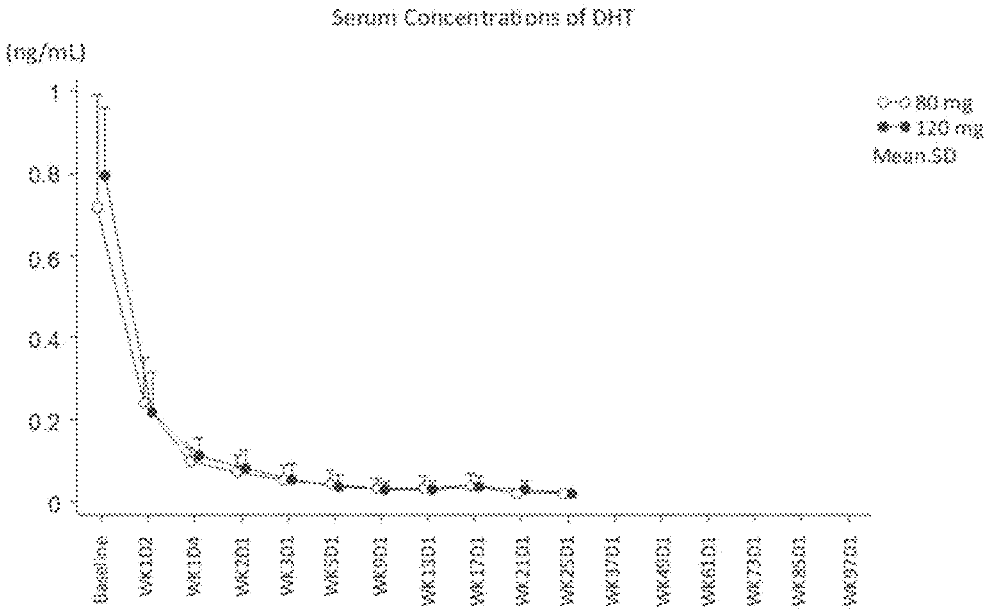
FIG. 11 graphically depicts mean serum DHT concentrations for a treatment period (Part A) in accordance with Example 6.
Figure 12:
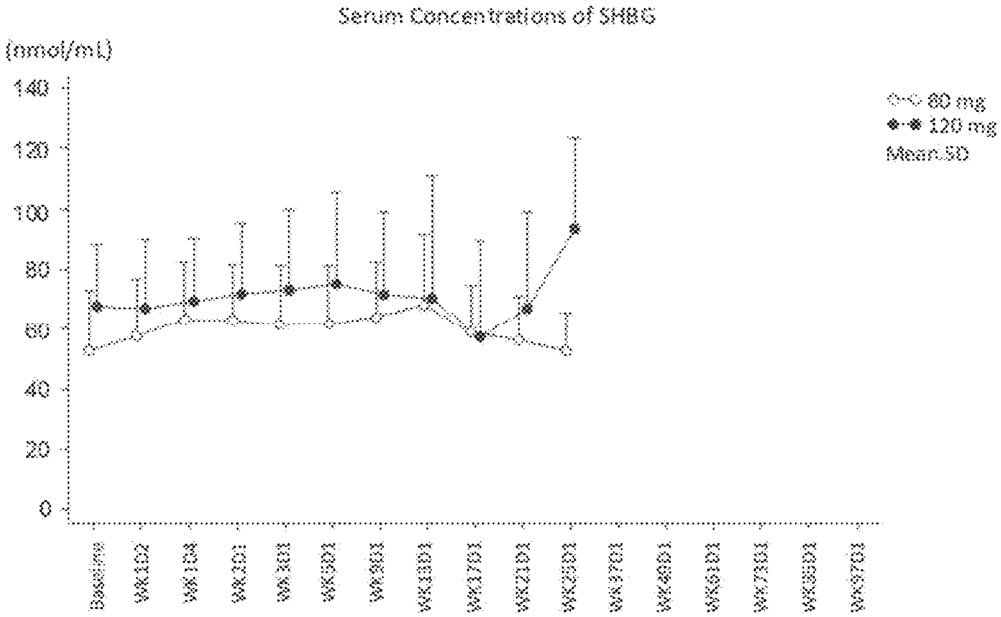
FIG. 12 graphically depicts mean serum sex hormone-binding globulin (SHGB) concentrations at maintenance doses of 80 mg or 120 mg or a treatment period (Part A) in accordance with Example 6.

For Part B, the mean serum testosterone concentration for each dose level of the study drug is shown in FIG. 7, and changes in the serum testosterone concentration for each dose level of the study drug is shown in FIG. 8A and FIG. 8B, and summary statistics of serum testosterone concentrations is shown in FIG. 2. The serum testosterone concentration was rapidly suppressed after the first dose in all dose levels (maintenance dose of 80 mg or 120 mg). The mean serum testosterone concentration was suppressed to below medical castration levels (i.e., below 50 ng/dL) within the first 4 days of dosing. In all subjects, the serum testosterone concentration reached medical castration levels between Day 2 and Week 3. Medical castration levels were maintained in all subjects throughout the evaluation period.

For Part B, the mean serum LH, FSH, DHT and SHBG concentrations for each dose level of the study drug are shown graphically in FIGS. 9-12, respectively. The serum LH, FSH and DHT concentrations were rapidly suppressed, similar to the serum testosterone concentration, in all dose levels. There were no particular changes in the baseline and postdose serum SHBG concentrations.

To evaluate the clinical efficacy of Compound 1 on prostate cancer, the serum concentration of PSA, the established diagnostic marker for prostate cancer, was measured during the 28 days of treatment period in Part A and for up to 96 weeks in Part B. The assay method of PSA was a chemiluminescent enzyme immunoassay (CLEIA) and LLOQ was 0.008 ng/mL.

For Part A, at Day 28, the mean and median percentage changes from baseline in the serum PSA concentration were −76.37% and −77.50%, respectively, in Cohort 1, −60.10% and −72.30%, respectively, in Cohort 2, and −32.10% and −50.50%, respectively, in Cohort 3. For Part A, summary statistics of serum PSA and change from baseline in PSA are tabulated in FIG. 13.

For Part B, the mean and median percentage changes from baseline in the serum PSA concentration at Week 13 Day 1 (LOCF) were-89.47% and −97.20%, respectively, in the 80 mg group and −93.11% and −95.80%, respectively, in the 120 mg group. For Part B, summary statistics of serum PSA and change from baseline in PSA are tabulated in FIG. 14.

Following administering to Week 13 Day 1 in Part B, the change from baseline in mean serum PSA concentration at Week 13 Day 1 is 10.6 fold (1060%) reduction for 80 mg dosage (reduced from 10.6004 ng/L to 1.0823 ng/L), and 11.3 fold (1130%) reduction for 180 mg dosage (reduced from 6.6275 ng/L to 0.5849 ng/L).

To preliminarily assess the pharmacokinetics of Compound 1, the plasma concentration of unchanged Compound 1 was measured by validated LC-MS/MS method (LLOQ: 0.01 ng/mL) in patients with prostate cancer when the study drug was repeatedly administered.

Figure 15A:
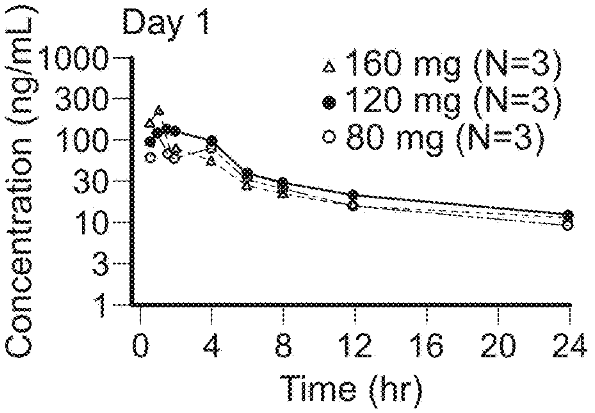
FIGS. 15A, 15B, and 15C graphically depict mean plasma concentrations of unchanged Compound 1 for a treatment period (Part A) in accordance with Example 6.
Figure 15B:
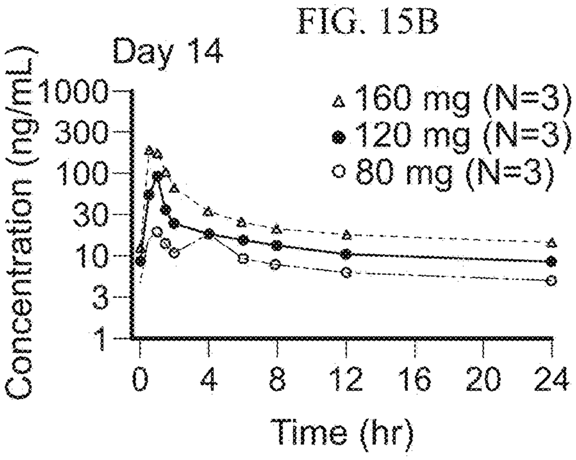
Figure 15C:
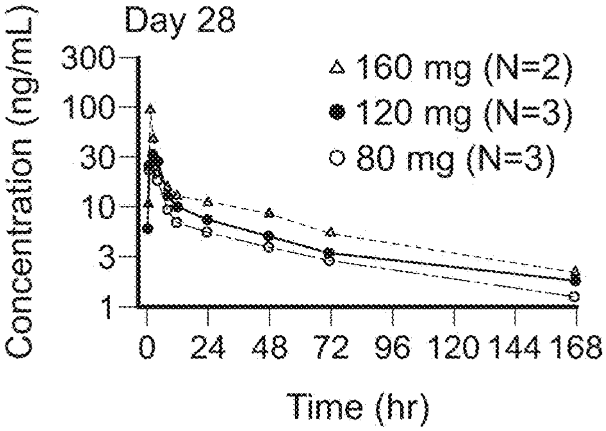

For Part A, the Compound 1 formulation was administered once-daily for 28 days. The profiles of plasma unchanged Compound 1 concentration-time at Day 1 (loading dose) and Days 14 and 28 (maintenance dose) are shown in FIG. 15A-15C, and preliminary pharmacokinetic parameters are summarized in FIG. 16.

At Day 1, a load dose of 320 mg was orally administered. The plasma concentration of unchanged Compound 1 rapidly increased after administration across dosing cohorts. The median maximum drug concentration-time ($T_{max}$) was 1.0 hour or 1.5 hours. There were little differences in mean $C_{max}$ or mean plasma $AUC_{24}$ among the cohorts. After Day 2, a maintenance dose of 80 to 160 mg was repeatedly administered once-daily. At Days 14 and 28, the plasma concentration of unchanged Compound 1 rapidly increased after administration in all cohorts. The median $T_{max}$ was 0.5-2.0 hours. The mean $C_{max}$, $C_{trough}$ and mean plasma $AUC_{24}$ generally increased proportionately with dose. At Day 28, the mean plasma $T_{1/2}$ was 66.5-78.1 hours, and there were little differences among the cohorts.

Figure 17A:
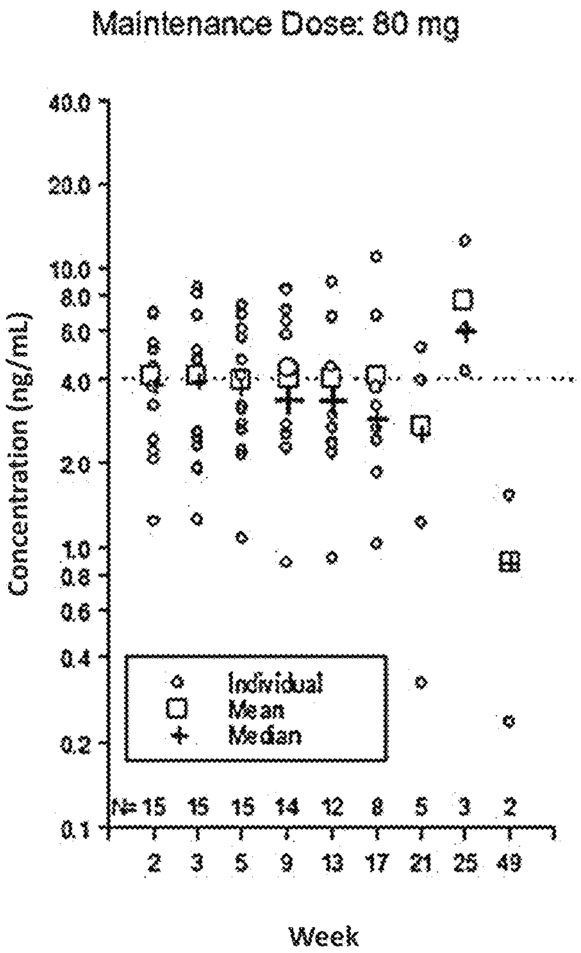
FIGS. 17A and 17B graphically depict mean plasma trough concentrations of unchanged Compound 1 for a treatment period (Part B) in accordance with Example 6.
Figure 17B:
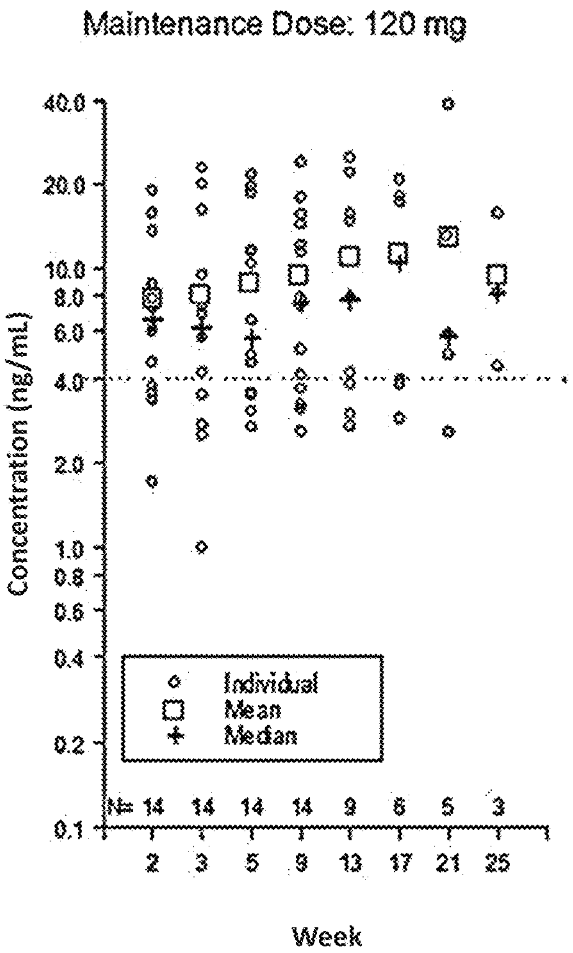

For Part B, a maintenance dose of 80 mg or 120 mg (starting with a loading dose of 320 mg on Day 1 for both cases) was repeatedly administered once-daily. The mean trough plasma concentration of unchanged Compound 1 between Week 2 and Week 25 is shown in FIGS. 17A and 17B. The median trough plasma concentration of unchanged Compound 1 ranged between 2.60 ng/ml and 6.09 ng/mL in the 80 mg group (n=3-15) and between 5.72 ng/mL and 10.7 ng/ml in the 120 mg group (n=3-14) and were maintained almost constant over time in both groups.

Example 7: A Double Blind, Randomized, Placebo-Controlled, Study to Evaluate the Effect of Compound 1 on Pharmacokinetics and Pharmacodynamics in Healthy Men for Testosterone Lowering Aim: To evaluate the PK, PD, safety and tolerability of Compound 1 in healthy male subjects following single and once daily doses for 2 and 4 weeks.

Key findings: PK was dosed proportionally over 80-360 mg range. The food effect with 180 mg dose was similar to that observed with 40 mg dose, demonstrating that the food effect is dose independent. The ANOVA results showed that the $C_{max}$ and $AUC_{0\text{-}inf}$ ratios of least square means (90% CI) of fed versus fasted state were 48.25 (22.62-102.90) and 52.74 (29.99-92.76), respectively. A 360 mg single dose resulted in castrate levels (<50 ng/dL) within 24 hours post dose. 360 mg Day 1 and 40 mg day 2 to 14 resulted in rapid castration level and sustained castration level. 320 mg day 1, 160 mg day 2, and 40 mg day 3 to 28 did not maintain castrate level. 80 mg once daily took up to 21 days to reach castrate level.

This was a randomized, double-blind, placebo-controlled, single and multiple dose, study in healthy men to evaluate the safety, tolerability, pharmacokinetics, and efficacy for testosterone lowering of Compound 1, an oral GnRH antagonist. The study had 4 parts: Part 1 (inpatient) included single dose administration of the Compound 1 formulation across 4 dose cohorts plus placebo and included a fed/fasted arm; Part 2 (inpatient) included multiple dose administration of the Compound 1 formulation for 14 days across 5 dose cohorts plus placebo; and Parts 3 and 4 (outpatient) included once-daily (QD), multiple dose administration of the Compound 1 formulation for 28 days across 2 dose cohorts (total of 4 dose levels), plus placebo.

The Compound 1 formulation was supplied as light red-colored, film-coated tablets, each containing active Compound 1. The 120 mg Compound 1 formulation comprised a core tablet of Compound 1 (120 mg), mannitol (366 mg), microcrystalline cellulose (60 mg), hydroxypropyl cellulose (18 mg), croscarmellose sodium (30 mg), and magnesium stearate (6 mg). The core tablets were coated with a film coating comprising hypromellose 2910 (21.36 mg), titanium dioxide (2.4 mg), and red ferric oxide (0.06 mg). The amounts of the excipients in the core tablet and film coating were adjusted accordingly based on the amount of Compound 1 in the core tablet (e.g., for the 360 mg tablet, the amount of excipient added to the core tablet and film coating is three times the amount added to the 120 mg tablet).

In Part 1, a single oral dose of 80 mg, 120 mg, 180 mg, and 360 mg Compound 1 formulation was administered. In Part 2, 80 mg, 180 mg, 40 mg, and 20 mg Compound 1 formulation was administered for 14 days. The 40 mg dose was administered once per day with a single load dose of 360 mg on Day 1 of the 14 days of treatment administration. For the 20 mg dosages, one 20 mg dose was administered with loading doses of 320 mg on Day 1, 240 mg on Day 2, and 160 mg on Day 3, and the other 20 mg dose was administered with loading doses of 320 mg on Day 1 and 160 mg on Day 2. Parts 3 and 4 of the study administered 40 mg or 160 mg, and 60 mg or 80 mg Compound 1 formulation QD for 28 days, respectively. The 40 mg dose was administered with loading doses of 320 mg and 160 mg on Days 1 and 2 of treatment, respectively.

Part 1 included single oral dose administration; Part 2 included 14 days of daily treatment; and Parts 3 and 4 included 28 days of daily treatment.

Blood (approximately 4 mL) and urine samples were collected for the determination of the plasma (Parts 1 through 4) and urine (Parts 1 and 2) concentrations of Compound 1. Samples were analyzed using validated liquid chromatography with tandem mass spectrometry (LC/MS/MS) methods. The LLOQ was 0.0100 ng/ml for plasma and 0.500 ng/ml for urine.

The main pharmacodynamic variables included serum concentrations of LH and testosterone, measured at regular intervals following single- and multiple dose administration of the Compound 1 formulation in Parts 1 through 4. FSH, DHT, and insulin-like growth factor 1 (IGF-1; Parts 3 and 4 only) were measured in a subset of samples. Serum testosterone was assayed using a conventional immunoassay for screening (LLOQ=0.4 nmol/L). A validated LC/MS/MS method, with an LLOQ of 0.173 nmol/L and a ULOQ of 10.425 nmol/L, was used for all subsequent baseline (i.e., the subject's serum hormone levels prior to treatment commencing) and postdose measurements.

Individual Compound 1 plasma and urine concentration-time data obtained in Parts 1 and 2 were analyzed using noncompartmental methods (WinNonlin Enterprise version 5.2) to characterize the single- and multiple dose pharmacokinetics of the Compound 1 formulation and to evaluate the effect of food on the Compound 1 formulation pharmacokinetics. Individual plasma and/or urine concentrations and single- and multiple dose PK parameters of the Compound 1 formulation were listed and summarized descriptively by study part, study day, and dose level. Dose-proportionality of PK parameters of the Compound 1 formulation after single and multiple dosing were first explored graphically by plotting individual dose-normalized exposure parameters: dose-adjusted observed mean $C_{max}$/D, dose-adjusted mean plasma $AUC_{0\text{-}tlqc}$/D and dose-adjusted mean plasma $AUC_{0\text{-}\infty}$/D, or dose-adjusted over the dosing interval mean plasma $AUC_{0\text{-}tau}$/D versus dose. Then, a formal assessment was performed using both analysis of variance (ANOVA) and power model approaches. In Part 1 (Cohort 3), ANOVA was performed on In-transformed PK parameters [mean plasma $AUC_{0\text{-}tlqc}$, mean plasma $AUC_{0\text{-}\infty}$, and mean $C_{max}$] of Compound 1 to assess the effect of food on Compound 1 oral bioavailability. In Part 2, steady state attainment was determined based on visual inspection of mean observed predose plasma concentration during multiple dosing ($C_{trough}$) versus time profiles at each dose level. Noncompartmental analysis of Part 3 and 4 data were not planned given the limited number of postdose samples collected per subject on Days 1 and 28.

Pharmacodynamic measures included serum concentrations of testosterone, DHT, LH, and FSH. In Part 2, the number and percentage of subjects with average serum testosterone levels less than 0.69 nmol/L occurring during the second week of dosing were tabulated. In Parts 3 and 4, the number and percentage of subjects with serum testosterone levels consistently less than 0.69 nmol/L from Day 14 through Day 28 were tabulated.

Figure 18A:
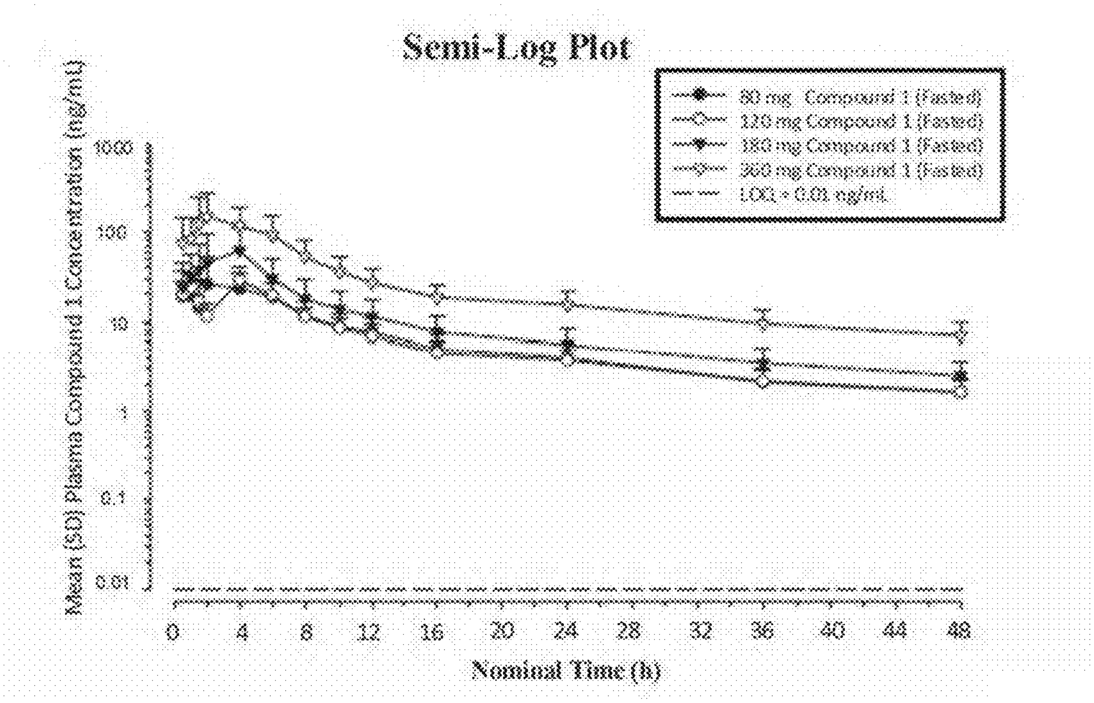
FIGS. 18A and 18B graphically depict mean plasma concentration-time profiles of Compound 1 after single oral dose administration (Part 1) in accordance with Example 7.
Figure 18B:
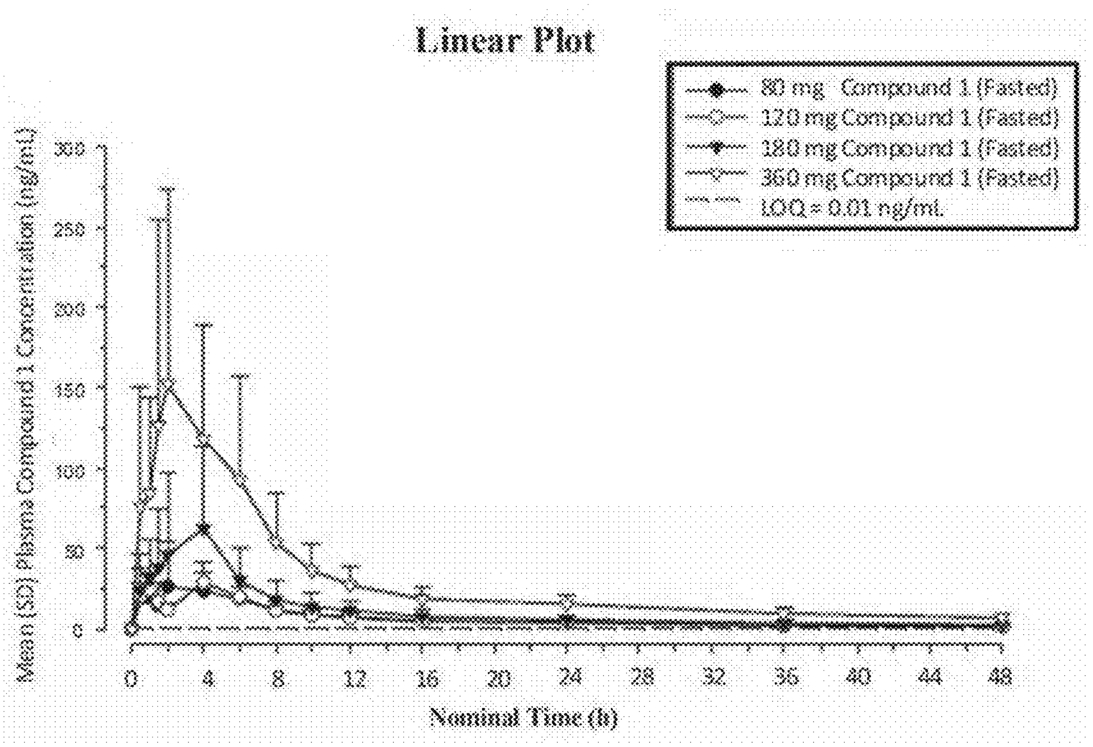
Figure 19:
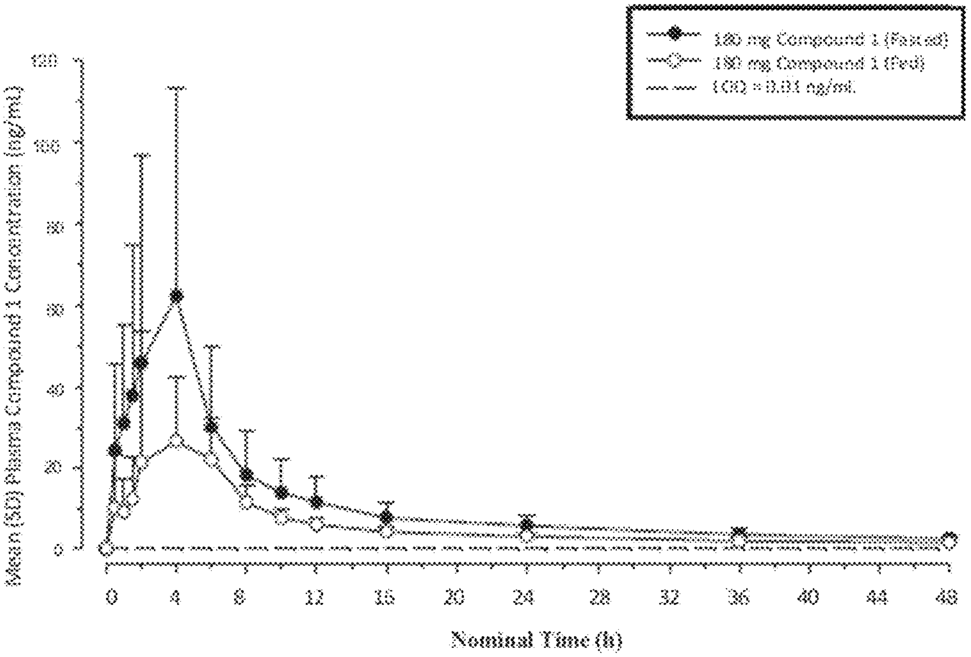
FIG. 19 graphically depicts mean plasma concentration-time profiles of Compound 1 after single oral dose administration (Part 1) under fasted and fed conditions in accordance with Example 7.

In Part 1, single dose pharmacokinetics of Compound 1 were evaluated in healthy male subjects at 4 dose levels (80, 120, 180, and 360 mg) under fasted conditions and at 1 dose level (180 mg) 30 minutes after ingestion of a standard, FDA-recommended, high fat, high-calorie breakfast (fed conditions). Mean plasma concentration-time profiles of Compound 1 are presented in FIGS. 18A, 18B, and 19. A summary of relevant plasma and urine PK parameters is in FIG. 20.

Figure 21A:
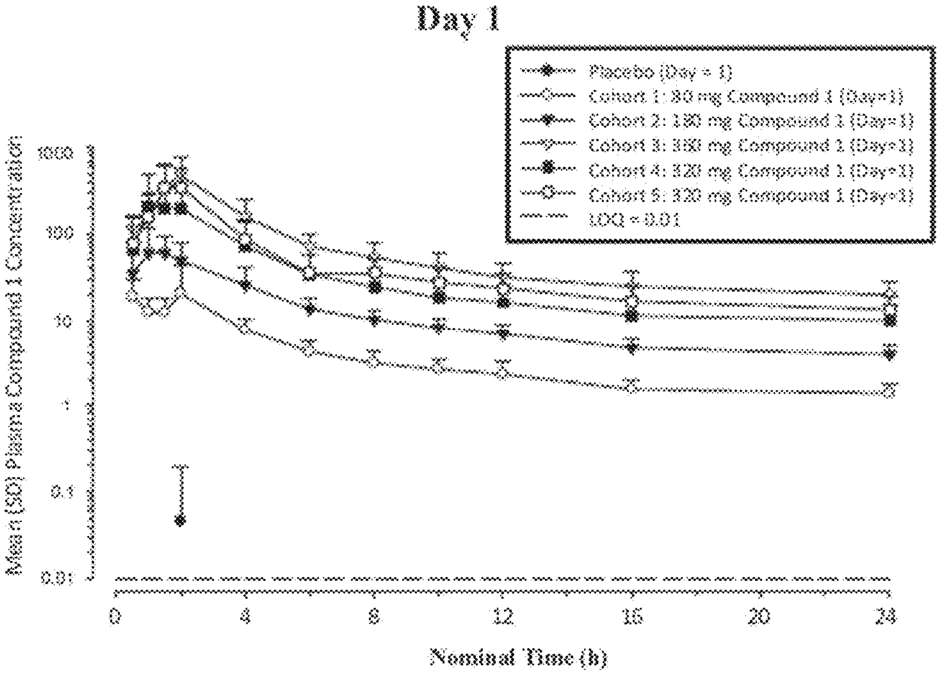
FIGS. 21A and 21B graphically depict mean plasma concentration-time profiles of Compound 1 after single and multiple oral dose administration (Part 2) in accordance with Example 7.
Figure 21B:
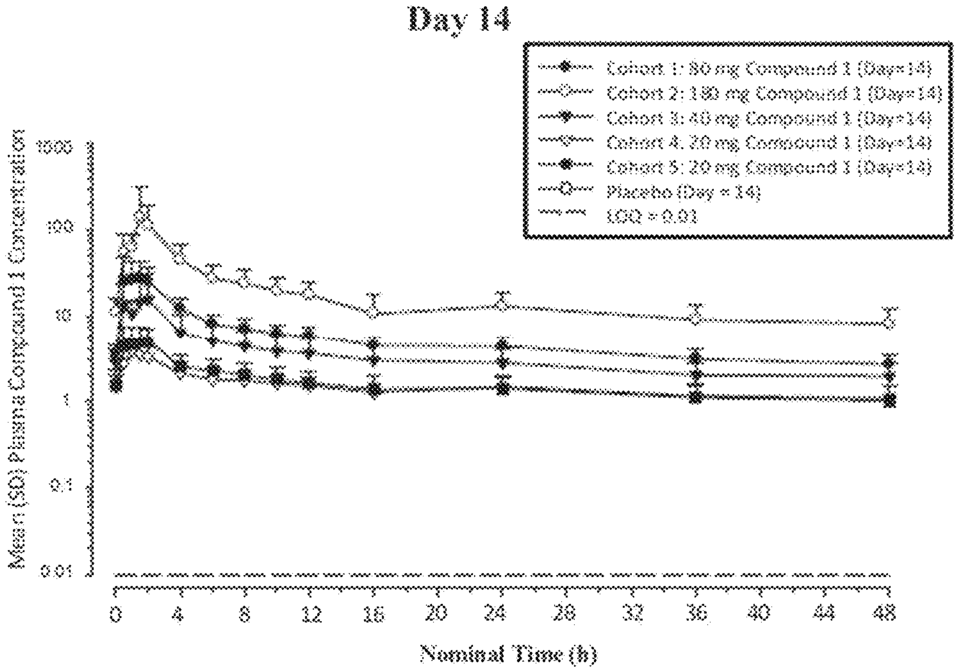

In Part 2, multiple dose pharmacokinetics of Compound 1 were evaluated in healthy male subjects at 4 dose regimens (20, 40, 80, and 180 mg) given QD for 14 days; of these doses, 3 included a loading dose administered during the first 1, 2, or 3 days. Mean Compound 1 plasma concentration-time profiles on Days 1 and 14 are presented graphically in FIGS. 21A and 21B. Summaries of all relevant plasma and urine PK parameters obtained on Days 1 and 14 are presented in FIGS. 22 and 23, respectively.

On Days 1 and 14, Compound 1 was administered to healthy, adult, male subjects 30 minutes prior to the ingestion of a standardized morning meal was readily absorbed in plasma. Observed peak concentrations typically occurred within 1 to 2 hours after dosing. When comparing the absorption profiles of a single 180 mg dose administered in the fasted state (Part 1) or 30 minutes prior to ingestion of a standardized meal (Part 2, Day 1), it was noted that mean plasma $AUC_{0-24}$ decreased to a lesser extent (approximately 28%) while no changes were observed in the rate of absorption (mean $C_{max}$ and $T_{max}$) of Compound 1.

Compound 1 was readily absorbed in plasma following single and multiple oral administration. The absorption phase was somewhat erratic, with individual first time to $T_{max}$ values ranging from 0.5 to 12 hours postdose (median ~2 hours) across all doses studied. Co-administration with food decreased mean $C_{max}$ and mean plasma $AUC_{0-\infty}$ by approximately 50% and delayed absorption (median $T_{max}$ 5 hours) when compared to fasting conditions. When dosing 30 minutes prior to ingestion of a standardized meal, the rate of absorption was unchanged while the Compound 1 systemic exposure (mean plasma AUC) was reduced on average by approximately 28%.

The absorption of Compound 1 in plasma was decreased and delayed following a single 180 mg dose administered 30 minutes after the start of a standard U.S. FDA high fat, high-calorie breakfast (approx. 800-1000 calories, 50% from fat) compared to fasting conditions. Median $T_{max}$ increased from 1.75 to 5.00 hours under fed conditions. The mean $C_{max}$ and mean plasma $AUC_{\infty}$ ratios (and associated 90% CI) of least square means of fed versus fasted state were 48.25% (22.62%, 102.90%) and 52.74% (29.99%, 92.76%), respectively, indicating a clinically meaningful effect of food on the oral bioavailability of Compound 1. In the 14 day inpatient multiple dose Part 2, the Compound 1 formulation was administered daily 30 minutes prior to ingestion of a standardized morning meal (approx. 600 calories, 27% from fat). Under these conditions, systemic exposure to Compound 1 was reduced to a lesser extent (approximately 28% on average) and no obvious changes in the rate of absorption were observed when compared to fasting conditions. Consequently, in the 28 day outpatient multiple dose Parts 3 and 4, subjects were instructed to take the Compound 1 formulation upon arising in the morning, on an empty stomach, and start eating approximately 30 minutes after dosing whenever possible.

In general, approximate dose-proportional increases in mean $C_{max}$ and mean plasma $AUC_{0-\infty}$ were observed after single doses of 80 mg to 360 mg. At steady state, mean plasma $AUC_{0-tau}$ increased in a dose-proportional manner following multiple doses of Compound 1 over the dose range of 20 to 180 mg QD, while mean $C_{max}$ increased slightly more than dose-proportionately. It was noted that there was a moderate to large interindividual variability in the Compound 1 systemic exposures across all study parts.

After attaining mean $C_{max}$, plasma Compound 1 concentrations declined in a multi-exponential manner with a mean plasma $T_{1/2}$ ranging from 19.1 to 21.7 hours after single dosing and from 35.8 (180 mg QD) to 64.5 hours (20 mg QD) after repeat dosing. Steady state was reached within 11 to 14 days following the start of QD dosing. The observed accumulation factor, based on mean plasma $AUC_{0-tau}$, was 1.92 and 2.16 for the 80 mg and 180 mg QD dose regimens, respectively.

Less than 4% of Compound 1 was excreted unchanged in urine after single and repeat dosing. Mean renal clearance of Compound 1 represented a small portion of its total clearance, thus indicating that renal excretion plays a minor role in the elimination of Compound 1.

Figure 25:
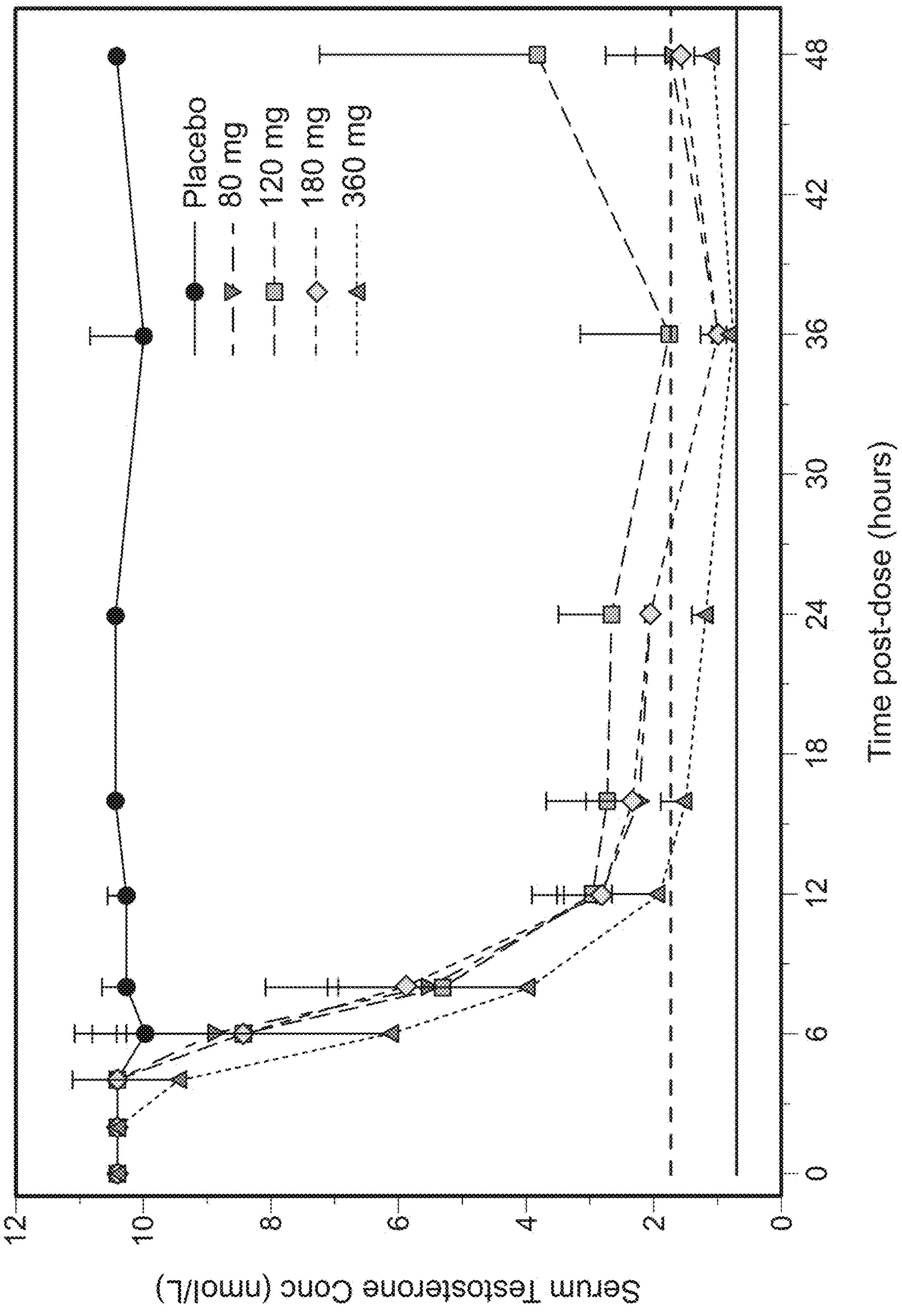
FIG. 25 graphically depicts mean time-course of serum testosterone lowering following a single dose administration of Compound 1 (Part 1) in accordance with Example 7.

Clinically-relevant mean serum testosterone suppression was noted to have occurred 4 to 6 hours following single doses of 80 mg, 120 mg, 180 mg and 360 mg of Compound 1, and this was maintained through 36 hours postdose. Mean serum LH concentration profiles were similar to testosterone for these 4 doses. Mean serum LH concentration-time data (IU/L) for the treatment period (Part 1) is presented in FIG. 24. Mean time-course of serum testosterone lowering following a single dose administration of Compound 1 (Part 1) is shown graphically in FIG. 25. Mean serum testosterone concentration-time data (nmol/L) for the treatment period (Part 1) is presented in FIG. 26.

Mean serum FSH concentration-time data (IU/L) for the treatment period (Part 1) is presented in FIG. 27. The mean serum FSH concentration profile was similar across respective dose cohorts at corresponding time points for the 80, 120, 180, and 360 mg groups. Mean serum FSH concentrations began to decrease 2 hours postdose to a low at 48 hours.

Mean serum DHT concentration-time data (nmol/L) for the treatment period (Part 1) is resented in FIG. 28. The mean serum DHT concentration profile was similar across respective dose cohorts at corresponding time points for the 80, 120, 180, and 360 mg groups. Mean serum DHT concentrations began to decrease 2 hours postdose. Decreases in DHT were more profound in the 180 and 360 mg dose cohorts, with minor and variable further reductions occurring after the 12 hour time point.

Following 14 days of daily dosing, mean serum LH and testosterone and concentration profiles were similar for the 80 mg, 180 mg, and 40 mg Compound 1 dose cohorts. Concentrations decreased from 2 to 6 hours postdose through Day 14. Either 1 to 3-day loading dose regimens or doses of 180 mg QD resulted in rapid reductions in serum testosterone concentrations over the first 48 hours following start of dosing. However, the daily maintenance dose was a major determinant of sustained serum testosterone suppression. The profound castration threshold (defined for this study as average serum testosterone levels <0.69 nmol/L) was achieved with multiple dosing for 14 days at doses of 40, 80, and 180 mg; however, 20 mg QD was insufficient in maintaining adequate suppression of serum LH and testosterone concentration levels during the second week.

There was no increase in the incidence of adverse events (AEs) was observed with increasing dose of Compound 1. The most common treatment emergent adverse events (TEAEs) observed across all dose cohorts were bradycardia, hot flush, and headache. The most common drug-related TEAE was hot flash. There were no deaths, serious adverse events (SAEs), or severe AEs following single dose treatment or multiple dose treatment with the Compound 1 formulation for 14 or 28 days.

Safety results showed that single and multiple doses of the Compound 1 formulation administered were safe and well tolerated.

Compound 1 was readily absorbed in plasma following single and multiple dose oral administration. After attaining mean $C_{max}$, typically occurring within 1 to 2 hours after repeat dosing, plasma Compound 1 concentrations declined in a multi-exponential manner with a mean disposition phase. Mean plasma $T_{1/2}$ was approximately 36 to 65 hours across the 20 to 180 mg QD dose range. Moderate to large interindividual variability in Compound 1 systemic exposures was apparent across all study parts.

At steady state, mean plasma $AUC_{0-tau}$ increased in a dose-proportional manner following multiple doses of Compound 1 over the dose range of 20 to 180 mg QD, while mean $C_{max}$ increased slightly more than dose-proportionately. Steady state conditions were reached within 10 to 14 days and Compound 1 systemic exposure increased approximately 2 fold (200%) following QD dosing.

Co-administration with food decreased Compound 1 systemic exposure (mean $C_{max}$ and mean plasma $AUC_{0-\infty}$) by approximately 50% and delayed absorption when compared to fasting conditions.

Effective medical castration was consistently achieved at maintenance doses of 80 mg, 160 mg and 180 mg QD. Only load doses of 180 mg or greater led to serum testosterone levels below the medical castration limit of 1.73 nmol/L within 24 to 48 hours. While a large variability in the pharmacodynamics response was apparent across cohorts, higher doses of Compound 1 produced more robust serum testosterone suppression. The recommended safe and effective dose regimen based on this study would be ≥80 mg QD Compound 1 for sustained castration during the treatment period.

Consistent with the mechanism of action of GnRH antagonists, Compound 1 caused an immediate and effective suppression of gonadotropins (LH, FSH) and serum testosterone as a result of competitive binding for the pituitary GnRH receptors.

Figure 30:
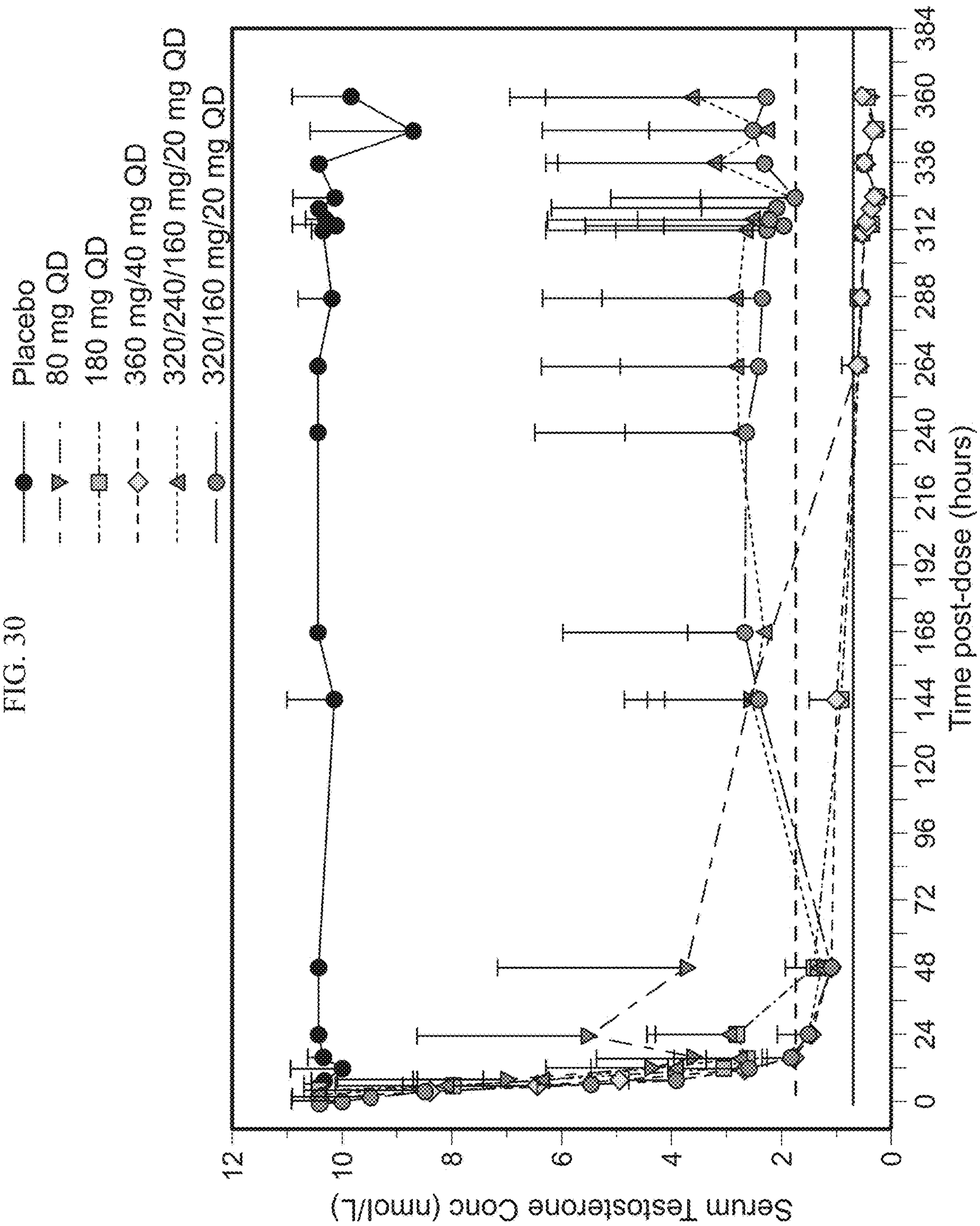
FIG. 30 graphically depicts mean time-course of serum testosterone lowering following a multiple dose administration of Compound 1 (Part 2) in accordance with Example 7.

Mean serum LH concentration-time data (IU/L) for the treatment period (Part 2) is presented in FIG. 29. Mean time-course of serum testosterone lowering following a multiple oral dose administration of Compound 1 (Part 2) is depicted graphically in FIG. 30. Mean serum testosterone concentration-time data (nmol/L) for the treatment period (Part 2) is tabulated in FIGS. 31A and 31B.

Mean serum FSH concentration-time data (IU/L) for the treatment period (Part 2) is presented in FIG. 32. Postdose mean serum FSH concentration profiles were similar across respective dose cohorts at corresponding time points for the 80, 180, 40 and 20 mg groups, in which they decreased from 24 hours postdose through Day 14 (end of dosing).

Mean serum DHT concentration-time data (nmol/L) for the treatment period (Part 2) is presented in FIG. 33. The mean serum DHT concentration profiles were generally consistent with serum testosterone.

Following administering of 80 mg and 180 mg of the Compound 1 formulation for 16 days in Part 2, the change from baseline in mean serum LH concentration at the end of 16 days of treatment was 13.8 fold (1380%) reduction for 80 mg dosage (reduced from 4.57 IU/L to 0.33 IU/L), and 17 fold (1700%) reduction for 180 mg dosage (reduced from 3.90 IU/L to 0.23 IU/L).

Following administering for 16 days in Part 2, the change from baseline in mean serum testosterone concentration at the end of 16 days of treatment is 29 fold (2900%) reduction for 80 mg dosage (reduced from 10.40 nmol/L to 0.3565 nmol/L), and 24 fold (2400%) reduction for 180 mg dosage (reduced from 10.40 nmol/L to 0.4320 nmol/L).

Following administering for 16 days in Part 2, the change from baseline in mean serum FSH concentration at the end of 16 days is 9.1 fold (910%) reduction for 80 mg dosage (reduced from 6.07 IU/L to 0.67 IU/L), and 11.8 fold (1180%) reduction for 180 mg dosage (reduced from 3.88 IU/L to 0.33 IU/L).

Following administering for 16 days in Part 2, the change from baseline in mean serum dihydrotestosterone concentration at the end of 16 days is 1.7 fold (170%) reduction for 80 mg dosage (reduced from 1.883 nmol/L to 1.095 nmol/L), and 2.2 fold (220%) reduction for 180 mg dosage (reduced from 1.882 nmol/L to 0.865 nmol/L).

In healthy, older men in Parts 3 and 4 of the study, effective medical castration was consistently achieved over 14 and 28 days dosing at daily doses of 40 mg to 180 mg (14 days) and 80 mg to 160 mg (28 days). Use of a load dose for up to 3 days (or daily doses of 160 mg or higher) resulted in below castration levels of serum testosterone (50 ng/dL or 1.73 nmol/L) within 24 to 48 hours.

Figure 35:
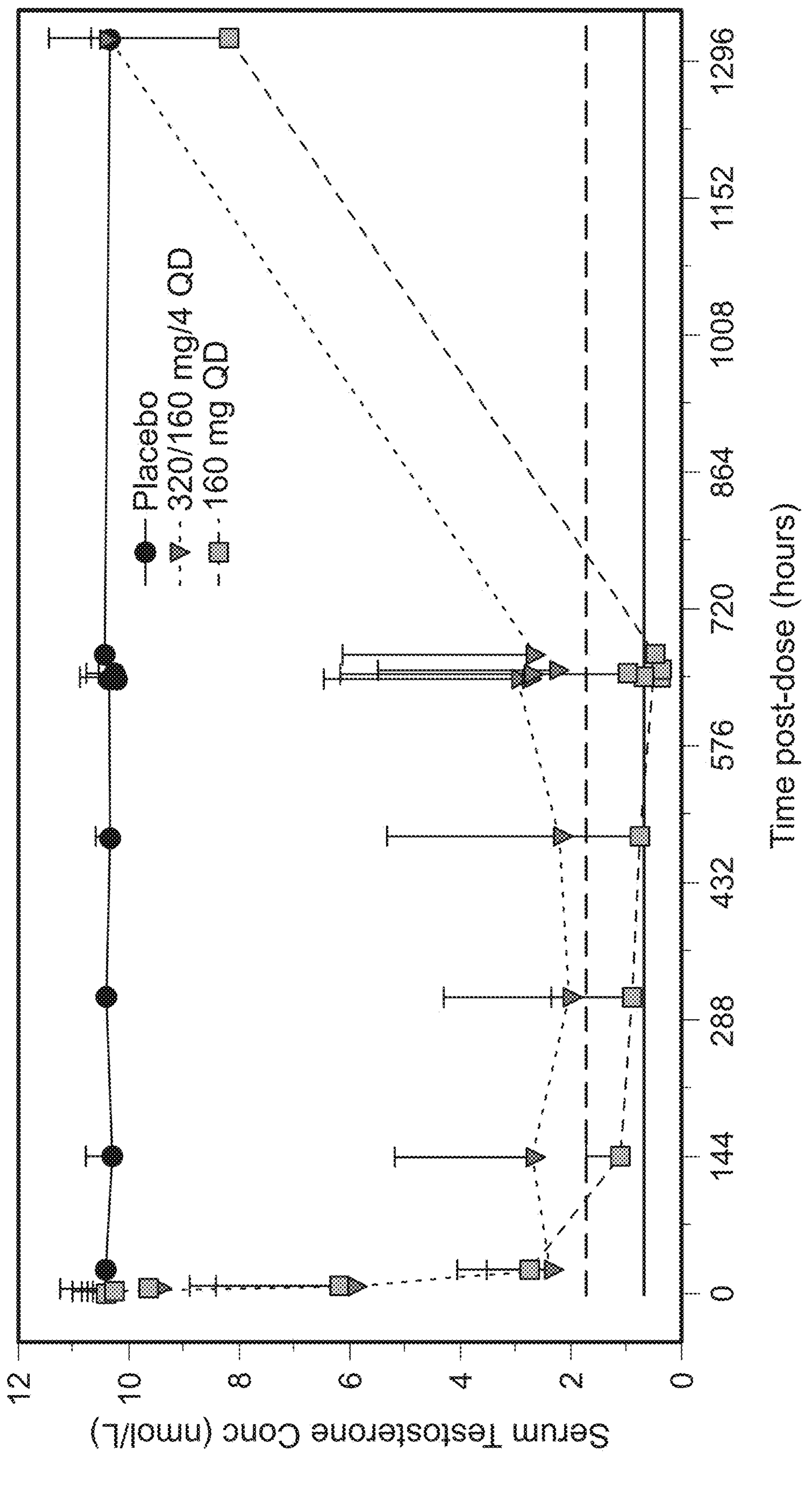
FIG. 35 graphically depicts mean time-course of serum testosterone lowering following a multiple dose administration of Compound 1 (Part 3) in accordance with Example 7.
Figure 40:
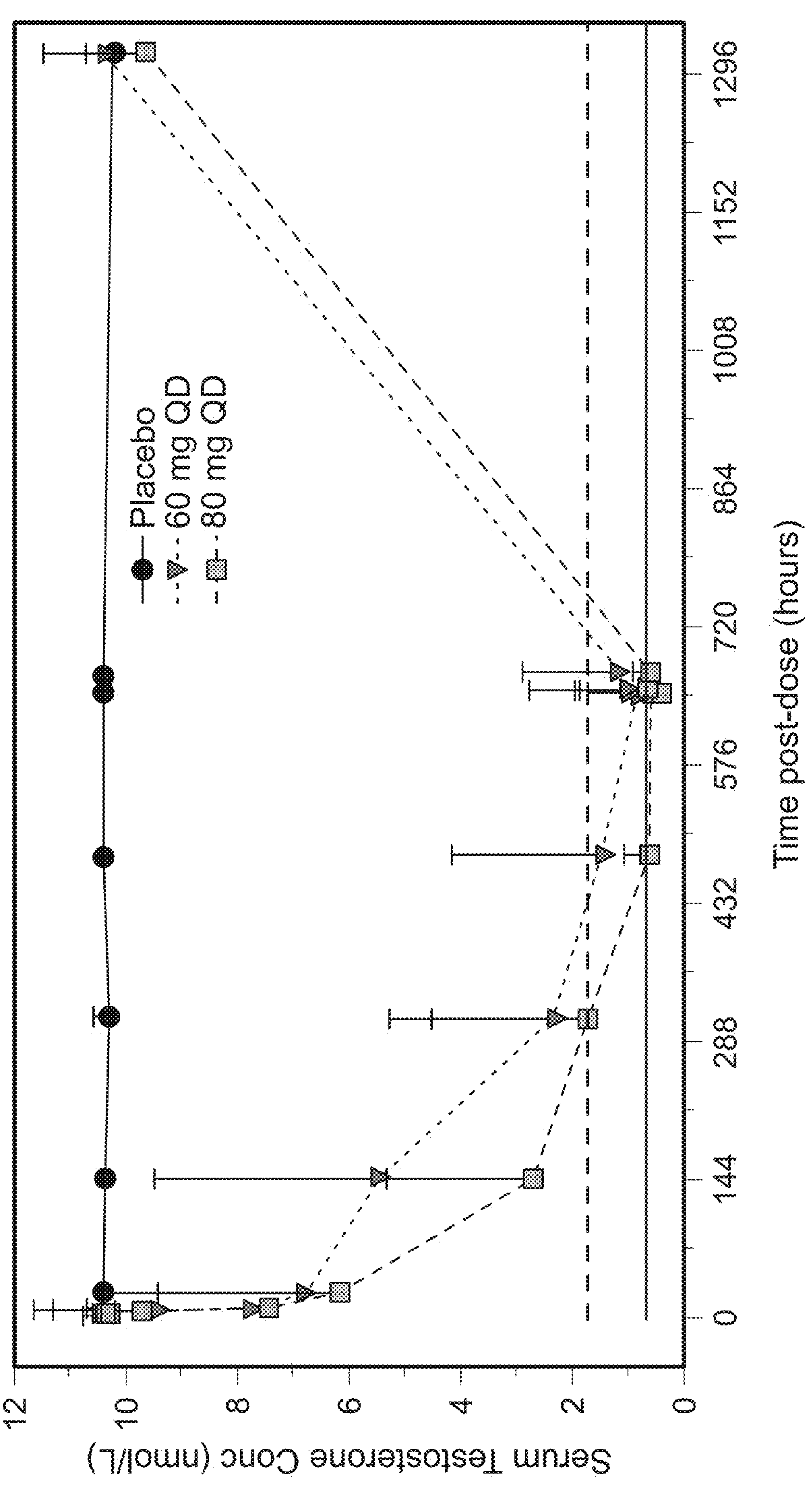
FIG. 40 graphically depicts mean time-course of serum testosterone lowering following a multiple dose administration of Compound 1 (Part 4) in accordance with Example 7.
Figure 44A:
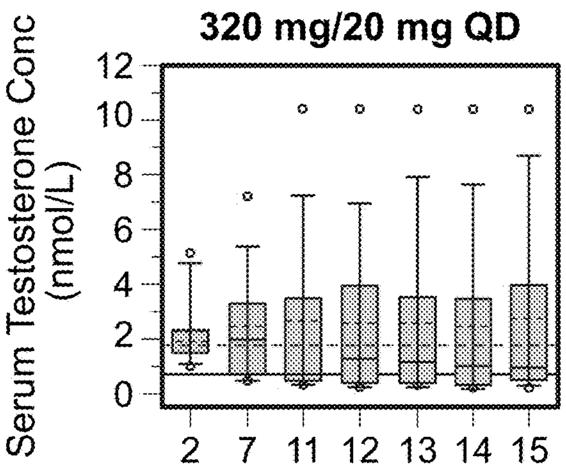
FIGS. 44A, 44B, 44C, and 44D graphically depict time-course of serum testosterone suppression following treatment (Part 2) with Compound 1 in healthy men for 14 days in accordance with Example 7.
Figure 44B:
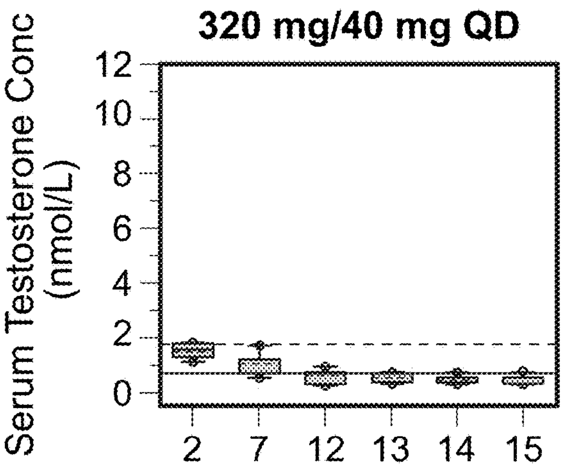
Figure 44C:
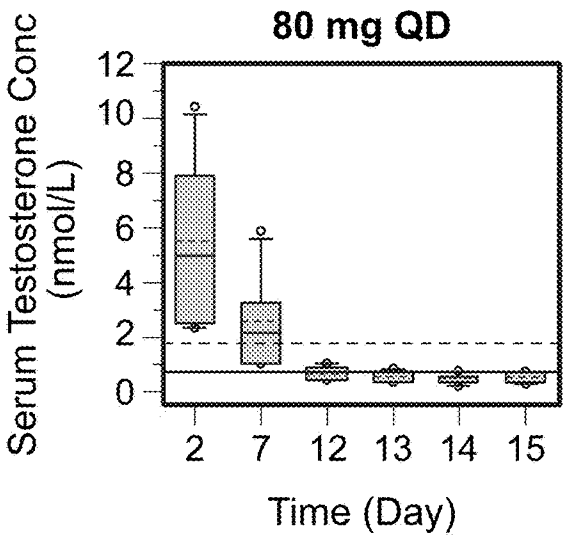
Figure 44D:
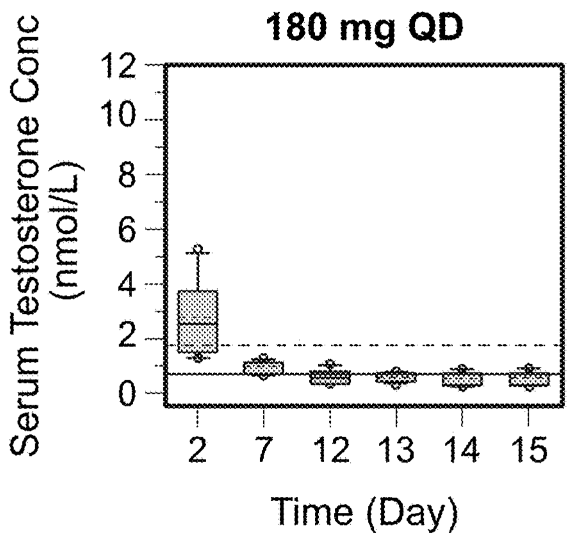

Mean serum LH concentration-time data (IU/L) for the treatment period (Part 3) is presented in FIG. 34, and for the treatment period (Part 4) is presented in FIG. 39. Mean time-course of serum testosterone lowering following a multiple oral dose administration of Compound 1 (Part 3) is shown in FIG. 35, and administration of Compound 1 (Part 4) is shown in FIG. 40. Mean serum testosterone concentration-time data (nmol/L) for the treatment period (Part 3) is presented in FIG. 36, and for the treatment period (Part 4) is presented in FIG. 41.

Mean serum FSH concentration-time data (IU/L) for the treatment period (Part 3) is presented in FIG. 37, and for the treatment period (Part 4) is presented in FIG. 42.

Mean serum DHT concentration-time data (nmol/L) for the treatment period (Part 3) is presented in FIG. 38, and for the treatment period (Part 4) is presented in FIG. 43.

In dosing for 28 days, both 160 mg (Part 3) and 80 mg (Part 4) were effective at achieving medical (<1.73 nmol/L) and profound (<0.69 nmol/L) castration during the third and fourth weeks of repeat administration. However, the 40 mg QD dose was ineffective in maintaining castration between Days 14 and 28. The results at 60 mg QD were intermediate to those of 40 and 80 mg and suggested that the likely minimal, fully effective maintenance dose for medical castration would be at 80 mg QD or above.

Consistent with the observed dose-dependent suppression of serum testosterone across the 20 to 180 mg QD studied dose range, the magnitude of the serum testosterone lowering-response was correlated with individual Compound 1 plasma trough concentrations; the higher the Compound 1 systemic exposure, the greater the number of subjects achieving and maintaining medical castration throughout the treatment period. Median Compound 1 trough concentrations of greater than 4 ng/mL, which were associated with maintenance doses of 80 mg or greater, reduced serum testosterone to below medical castration levels of 1.73 nmol/L in all subjects with the majority having serum testosterone levels decreased to below the profound castration threshold of 0.69 nmol/L after 28 days of treatment with the Compound 1 formulation.

Figure 45:
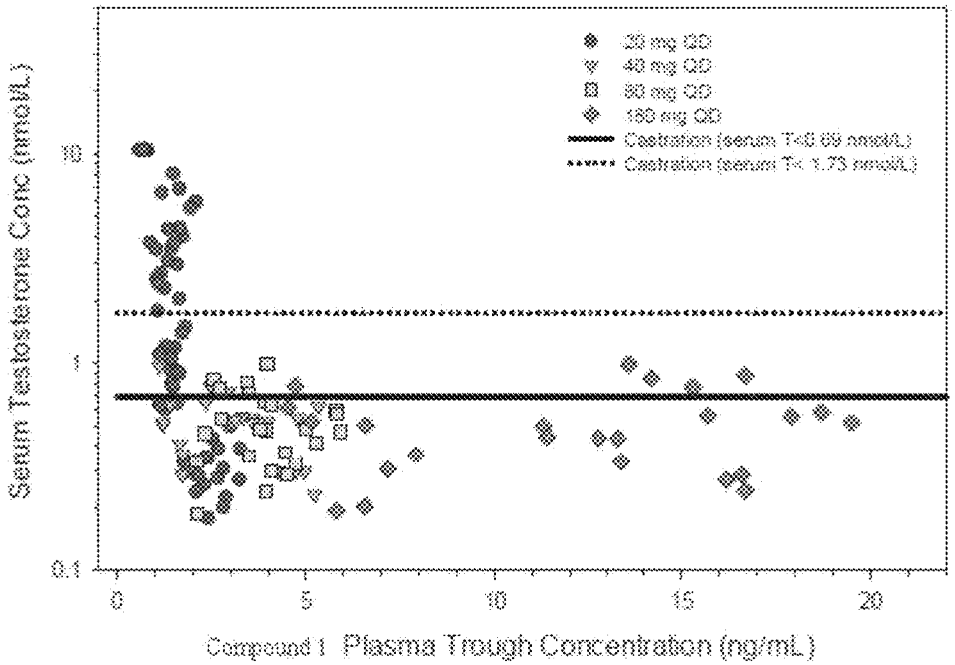
FIG. 45 graphically depicts the correlation between serum testosterone suppression and Compound 1 steady state exposure in healthy men (Part 2) in accordance with Example 7.
Figure 46A:
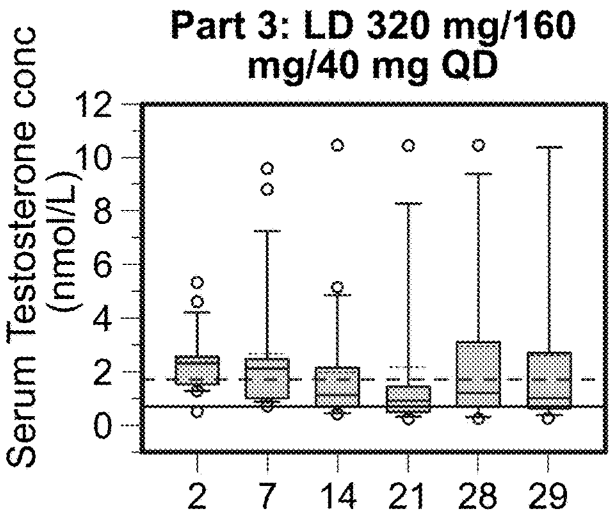
FIGS. 46A, 46B, 46C, and 46D graphically depict the time-course of serum testosterone suppression following treatment (Parts 3 and 4) with Compound 1 in healthy men for 28 days in accordance with Example 7.
Figure 46B:
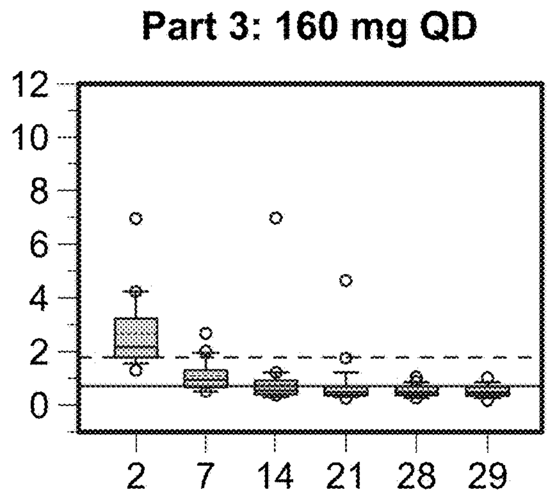
Figure 46C:
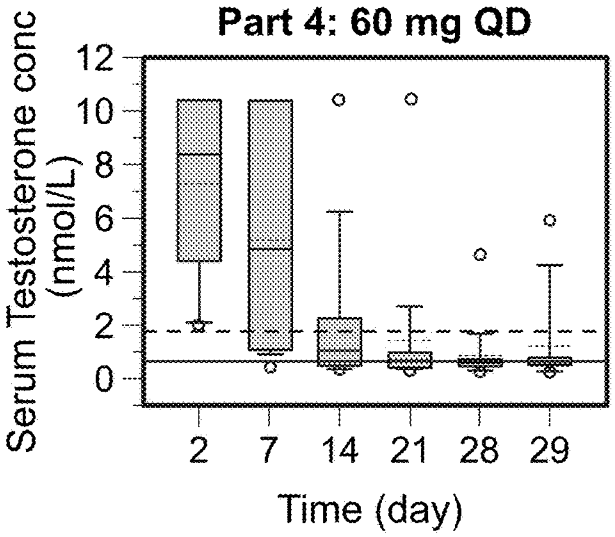
Figure 46D:
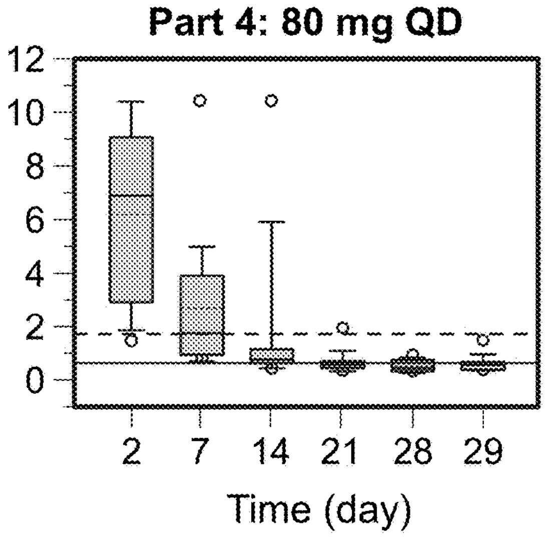
Figure 47A:
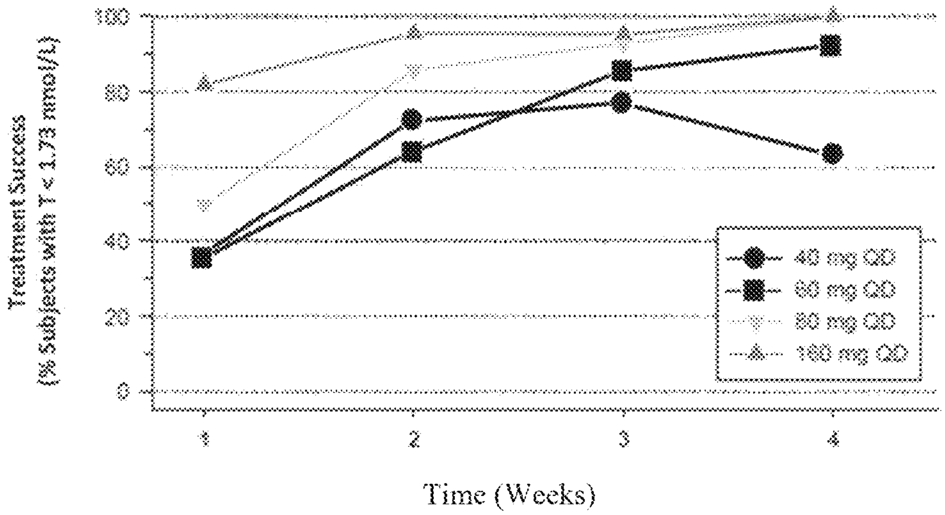
FIGS. 47A and 47B graphically depict the percent of subjects reaching serum testosterone below castration levels after 28 days of treatment (Parts 3 and 4) with Compound 1 in accordance with Example 7.
Figure 47B:
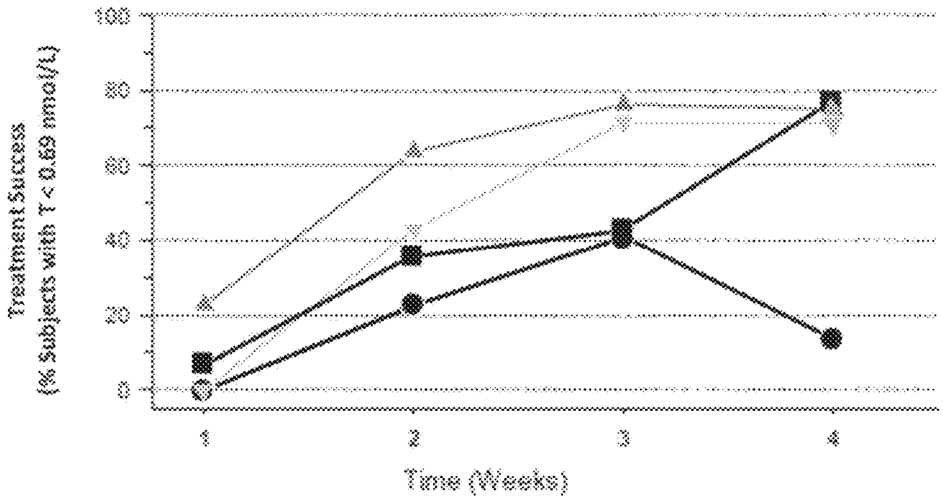
Figure 48:
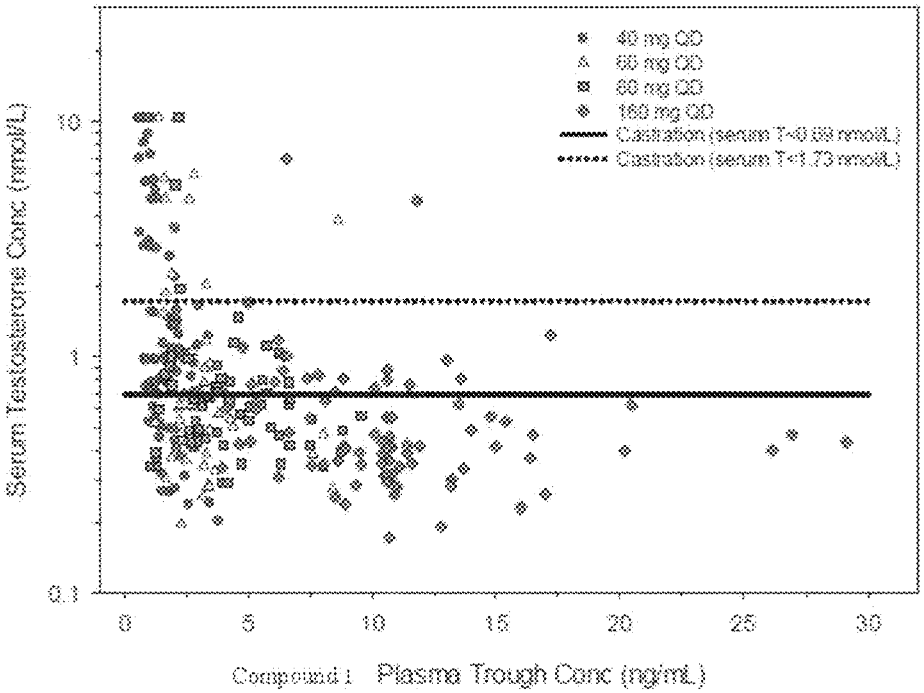
FIG. 48 graphically depicts the correlation between serum testosterone suppression and Compound 1 steady state exposure in healthy men (Parts 3 and 4) in accordance with Example 7.

The time-course of serum testosterone suppression following treatment (Part 2) with Compound 1 in healthy men for 14 days is shown in FIG. 44A-44D. The correlation between serum testosterone suppression and Compound 1 steady state exposure in healthy men (Part 2) is shown is FIG. 45, and in healthy men (Parts 3 and 4) is shown is FIG. 48. The time-course of serum testosterone suppression following treatment (Parts 3 and 4) with Compound 1 in healthy men for 28 days is shown in FIG. 46A-46D. The percent of subjects reaching serum testosterone below castration levels after 28 days of treatment (Parts 3 and 4) with Compound 1 is shown in FIGS. 47A and 47B.

Compound 1 was well tolerated, with no AEs of symptomatic significance unless directly related to the effects of acute medical castration. Mild to moderate transaminase elevations were observed without symptoms or changes in total bilirubin. Changes in QT/QTc intervals were consistent with those described in the literature with other medical castration agents.

Example 8: A Study to Evaluate the Effect of Compound 1 in Men with Advanced Prostate Cancer for Testosterone Lowering and PSA Response In this study, patients with advanced prostate cancer who require first-line androgen deprivation therapy (ADT)

received either 80 mg or 120 mg daily of oral Compound 1 formulation (with a load dose of 320 mg on Day 1) or leuprolide acetate 22.5 mg SC. The 120 mg Compound 1 formulation comprised a core tablet of Compound 1 (120 mg), mannitol (366 mg), microcrystalline cellulose (60 mg), hydroxypropyl cellulose (18 mg), croscarmellose sodium (30 mg), and magnesium stearate (6 mg). The core tablets were coated with a film coating comprising hypromellose 2910 (21.36 mg), titanium dioxide (2.4 mg), and red ferric oxide (0.06 mg). The amounts of the excipients in the core tablet and film coating were adjusted accordingly based on the amount of Compound 1 in the core tablet (e.g., for a 360 mg tablet, the amount of excipient added to the core tablet and film coating is three times the amount added to the 120 mg tablet).

The Compound 1 formulation or conventional leuprolide acetate was administered for up to 48 weeks. For treatment with Compound 1, study visits occurred at baseline (week 1), day 1 of weeks 2, 3, and 5, and then every 4 weeks until week 49 (the end of the 48-week core study period). All patients who completed >12 weeks of Compound 1 therapy were followed off-treatment for 12 weeks with assessments at 4 (end of treatment, EOT), 8 (follow-up visit), and 12 (end of study, EOS) weeks. For patients receiving leuprolide acetate (leuprorelin), on-treatment study visits occurred at baseline (day 1, week 1), day 1 of weeks 2, 3, and 5, and then every 4 weeks until week 25, and then at 12 week intervals (week 37 and 49). Patients on leuprorelin received their final injection at week 37, day 1, and the week 49, day 1 visit was considered the end of leuprorelin exposure. Patients receiving leuprorelin at visits at 16 (EOT), 20 (follow-up visit), and 24 (EOS) weeks after the last leuprorelin injection.

Eligible men were aged ≥18 years with a histologically confirmed diagnosis of prostate adenocarcinoma, and were candidates for ADT for the management of hormone-sensitive prostate cancer with one of the following clinical disease states: advanced localized disease not suitable for primary surgical or radiation therapy; evidence of PSA biochemical or clinical relapse following primary surgery or radiation therapy of curative intent; or newly diagnosed metastatic disease that was asymptomatic and without visceral involvement. Additional inclusion criteria at screening included: eugonadal serum testosterone >150 ng/dl (5.2 nmol/L); serum PSA concentration >2 ng/ml (or, when applicable, >0.2 ng/ml following radical prostatectomy or >2 ng/mL above the post-radiotherapy nadir following radiotherapy); body mass index ≥18.0 at screening and/or baseline (i.e., the subject's BMI prior to treatment commencing); and Eastern Cooperative Oncology Group (ECOG) performance status of 0 or 1. Patients with advanced, localized MON1 or M1 disease with clinically significant symptoms or visceral involvement, who required immediate GnRH therapy, chemotherapy, or radiation therapy were not eligible for the trial.

The time-course and intensity of serum testosterone lowering observed in patients in this study receiving the Compound 1 formulation was similar to that observed in the study in healthy older men in Example 7. Serum testosterone levels were measured at each visit. On average, in patients receiving the Compound 1 formulation, serum testosterone decreased to below the medical castration threshold of 50 ng/dL (1.73 nmol/L) by Day 4 (end of Day 3) visit, and to below the profound castration threshold of 20 ng/dl (0.69 nmol/L) by the Week 5 Day 1 visit. In contrast, in patients receiving leuprolide acetate, serum testosterone levels rose during the first 1-2 weeks of therapy then declined to castration levels by Week 5 Day 1. In the Compound 1 groups, median serum testosterone was suppressed below the profound castration threshold (<20 ng/dL) from weeks 5-49. The most common adverse event was hot flush in 31 (55%), 35 (65%), and 15 (63%) patients in the Compound 1 80 mg, Compound 1 120 mg, leuprorelin groups, respectively.

Quality of life (QoL) was assessed throughout the study and the follow-up period. The 25-item Prostate Cancer Module of the European Organization for Research and Treatment of Cancer Quality of Life Questionnaire (EORTC QLQ-PR25), Aging Male Survey (AMS), and core 30-item EORTC Quality of Life Questionnaire (EORTC QLQ-C30) were completed at screening, day 1 of weeks 5, 13, 25, 37, and 49, and, if applicable, at the follow-up visits.

Figure 52:
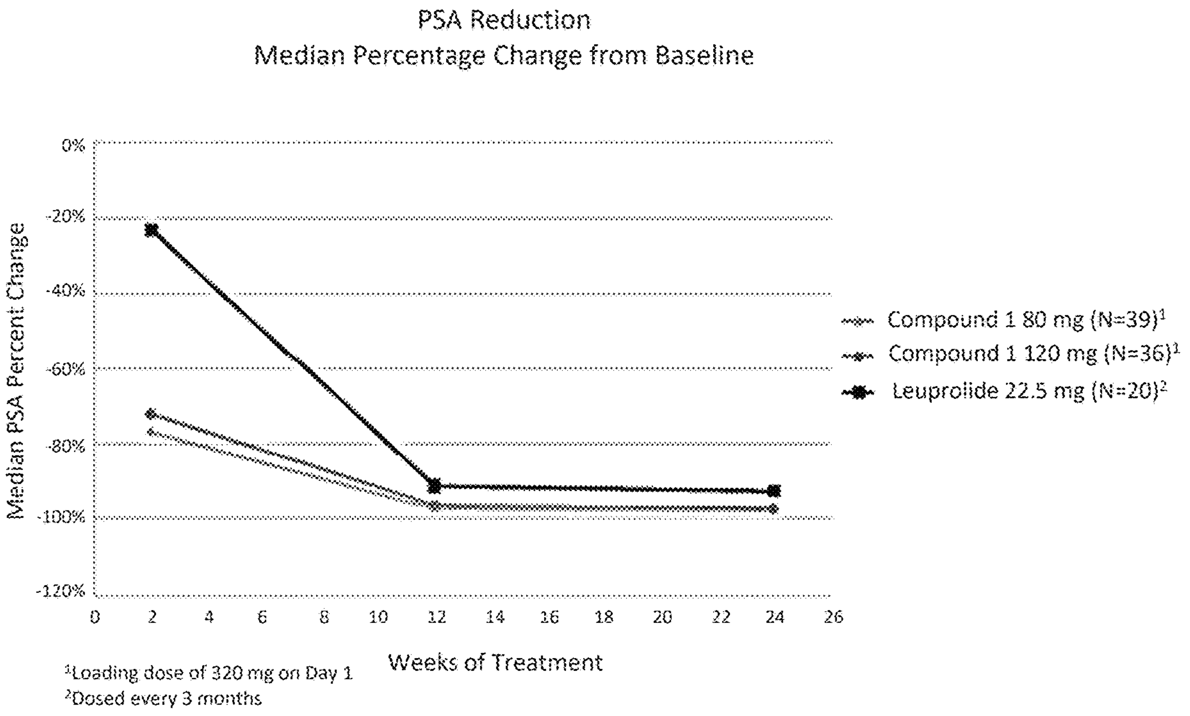
FIG. 52 graphically depicts the PSA reduction provided in Example 8.

PSA levels were measured at each visit. On average, in patients receiving the Compound 1 formulation, PSA levels decreased to less than 0.4 ng/ml by the Week 13 Day 1 visit and to less than 0.2 ng/ml by the Week 21 Day 1 visit. Following initiation of treatment, the PSA response was more rapid in patients receiving Compound 1 compared with leuprorelin (FIG. 52). Patients receiving Compound 1 also achieved PSA nadir more quickly than patients receiving leuprolide acetate (Table 1). Eighty-three percent of patients receiving Compound 1 had a ≥50% serum PSA reduction after 4 weeks of treatment versus only 20% of patients receiving leuprolide. Eight percent of patients receiving Compound 1 had a ≥90% serum PSA reduction after 4 weeks of treatment versus 0% of patients receiving leuprolide.

TABLE 1

Median Time from First Dose to PSA Nadir

| | Compound 1 80 mg QD (N = 56) | Compound 1 120 mg QD (N = 54) | Leuprolide Q12W (N = 24) |
|---|---|---|---|
| Median time from first dose to PSA nadir Weeks (range) | 16.1 (1.60-24.70) | 12.3 (2.00-24.60) | 20.5 (8.00-24.60) |

FSH levels were also measured at each visit. Compound 1 caused greater suppression of FSH compared to leuprorelin (leuprolide acetate). This was seen at both the 80 mg and 120 mg doses of Compound 1 (Table 2). Median FSH was ~4.2 mIU/mL with leuprolide (agonist) after 48 weeks of treatment. Although FSH did drop with leuprolide, it was not sustained suppression. However, with Compound 1 (antagonist), median FSH was 1.62 mIU/mL after 48 weeks of treatment, and this was far more sustained over the 48 weeks. FSH dropped from >10 mIU/mL at baseline to the 0.6-1.6 mIU/mL range for Compound 1, 120 mg dose over the course of 48 weeks.

TABLE 2

FSH Levels (IU/L) over Time

| | Compound 1 | | | Leuprorelin |
|---|---|---|---|---|
| | 80 mg QD (N = 56) n (%) | 120 mg QD (N = 54) n (%) | Total (N = 110) n (%) | Q12W (N = 24) n (%) |
| Baseline (b) | | | | |
| n | 56 | 54 | 110 | 24 |
| Mean (Std Dev) | 14.729 (14.3473) | 15.830 (12.8724) | 15.269 (13.5920) | 19.688 (19.1894) |
| Median | 9.550 | 11.050 | 9.850 | 14.500 |
| Min. Max | 2.80, 77.60 | 2.80, 68.60 | 2.80, 77.60 | 2.00, 79.40 |
| Week 2, Day 1 | | | | |
| n | 52 | 52 | 104 | 22 |
| Mean (Std Dev) | 3.112 (3.0612) | 3.183 (2.8956) | 3.147 (2.9653) | 7.650 (5.4542) |
| Median | 2.100 | 2.300 | 2.150 | 5.150 |
| Min. Max | 0.30, 13.90 | 0.30, 16.10 | 0.30, 16.10 | 0.60, 18.80 |
| Week 5, Day 1 | | | | |
| n | 54 | 52 | 106 | 24 |
| Mean (Std Dev) | 1.248 (2.6737) | 1.035 (1.0479) | 1.143 (2.0379) | 2.946 (1.4428) |
| Median | 0.400 | 0.600 | 0.550 | 2.550 |
| Min. Max | 0.30, 17.40 | 0.30, 5.70 | 0.30, 17.40 | 0.90, 6.30 |
| Week 13, Day 1 | | | | |
| n | 52 | 50 | 102 | 24 |
| Mean (Std Dev) | 1.137 (2.4242) | 0.908 (0.8104) | 1.025 (1.8164) | 4.625 (2.5594) |
| Median | 0.500 | 0.600 | 0.500 | 3.600 |
| Min. Max | 0.30, 16.90 | 0.30, 3.10 | 0.30, 16.90 | 0.40, 11.50 |
| Week 25, Day 1 | | | | |
| n | 49 | 48 | 97 | 23 |
| Mean (Std Dev) | 1.090 (0.9932) | 1.344 (0.9675) | 1.215 (0.9838) | 5.043 (2.8221) |
| Median | 0.800 | 1.200 | 0.900 | 4.400 |
| Min. Max | 0.30, 6.10 | 0.30, 4.00 | 0.30, 6.10 | 1.90, 14.50 |
| Week 49, Day 1 | | | | |
| n | 46 | 42 | 88 | 20 |
| Mean (Std Dev) | 1.802 (1.3956) | 1.938 (1.2169) | 1.867 (1.3077) | 5.145 (2.8201) |
| Median | 1.450 | 1.600 | 1.500 | 4.250 |
| Min. Max | 0.30, 8.00 | 0.30, 4.60 | 0.30, 8.00 | 2.10, 10.70 |

LLQ = lower limit of quantification,
Max = maximum,
Min = minimum.
Q12W = once every 12 weeks,
QD = once daily,
Std Dev = standard deviation.
(a) Baseline was defined as the value collected at the time closest to, but prior to, the start of study drug administration. The value <0.1 mIU/mL (LLQ) was imputed as 0.1 mIU/mL.
(b) Baseline was defined as the value collected at the time closest to, but prior to, the start of study drug administration. The value <0.3 IU/L (LLQ) was imputed as 0.3 IU/L.

Results of this study indicated that the time-course and intensity of serum testosterone lowering observed in patients receiving the Compound 1 formulation was similar to that observed during the study in healthy older men in Example 7. On average, in patients receiving the Compound 1 formulation, serum testosterone decreased to below the medical castration threshold of 50 ng/dL (1.7 nmol/L) by Day 4 (end of Day 3) visit, and to below the profound castration threshold of 20 ng/dL (0.7 nmol/L) by the Week 5 Day 1 visit. In contrast, in patients receiving leuprolide acetate, serum testosterone levels rose during the first 1 to 2 weeks of therapy then declined to castrate levels by Week 5 Day 1. No serum testosterone surge or resultant tumor flare occurred after Compound 1 treatment initiation. The more rapid reduction in PSA over the first 2 weeks with Compound 1 administration, compared with the delayed PSA response with leuprorelin, illustrates the rapid onset of action and therapeutic effect of Compound 1-mediated GnRH antagonism. Available data at the end of 24 weeks dosing showed that PSA % responses exceed 90% in most patients.

The median serum testosterone levels at EOT (4 weeks after the end of treatment) were 72.9 ng/dL for 120 mg Compound 1 versus 9.8 ng/dl with leuprorelin (Tables 3 and 4). At the follow-up visit, 8 weeks after stopping treatment, the median serum testosterone levels were 329.8 ng/dL for 120 mg Compound 1 versus 9.8 ng/dL with leuprorelin. At EOS, 12 weeks after stopping treatment, the median serum testosterone levels were 322.8 ng/dl for 120 mg Compound 1 versus 13.5 ng/dl with leuprorelin. The serum testosterone levels after stopping treatment with Compound 1 were above medical castration levels (50 ng/dL or 1.7 nmol/L) after 4 weeks after the end of treatment.

TABLE 3

| Testosterone Levels During Follow-Up Visits | | | | | | |
|---|---|---|---|---|---|---|
| Median testosterone, | Compound 1 | | | | Leuprorelin | |
| ng/dL (range) | n | 80 mg QD | n | 120 mg QD | n | Q12W |
| EOT | 14 | 90 · 0 (10 · 9-929 · 4) | 21 | 72 · 9 (4 · 3-362 · 9) | 18 | 9 · 8 (3 · 5-106. 0) |
| Follow-up visit | 8 | 379 · 7 (17 · 9-480 · 7) | 11 | 329 · 8 (21 · 9-646 · 6) | 15 | 9 · 8 (4 · 3-265 · 0) |
| EOS | 15 | 153 · 8 (2 · 9-490 · 8) | 15 | 322 · 8 (3 · 7-602 · 5) | 14 | 13 · 5 (4 · 3-332 · 9) |

D = day.
EOS = end of study.
EOT = end of treatment.
Q12W = once every 12 weeks.
QD = once daily.

TABLE 4

| Testosterone Values (nmol/L) During Follow-Up | | | | |
|---|---|---|---|---|
| | Compound 1 | | | Leuprorelin |
| | 80 mg QD (N = 56) n (%) | 120 mg QD (N = 54) n (%) | Total (N = 110) n (%) | Q12W (N = 24) n (%) |
| Baseline(a) | | | | |
| n | 55 | 54 | 109 | 24 |
| Mean (Std Dev) | 13.755 (4,7256) | 15.139 (5.4871) | 14,441 (5.1404) | 11.363 (5,0204) |
| Median | 12.700 | 14.350 | 13.600 | 11.120 |
| Min, Max | 5.03, 27.20 | 4.51, 27.03 | 4.51, 27.20 | 4.30, 24.01 |
| Week 49, Day 1 | | | | |
| n | 44 | 38 | 82 | 20 |
| Mean (Std Dev) | 0.526 (0.4621) | 0.443 (0.2745) | 0.487 (0.3867) | 0.478 (0.6313) |
| Median | 0.380 | 0.365 | 0.380 | 0.300 |
| Min, Max | 0.11, 2.08 | 0.10, 1.42 | 0.10, 2.08 | 0.10, 3.05 |
| End of Treatment | | | | |
| n | 14 | 21 | 35 | 18 |
| Mean (Std Dev) | 7.211 (9.2178) | 3.592 (3.7809) | 5.039 (6.6432) | 0.641 (0.9616) |
| Median | 3.125 | 2.530 | 2.530 | 0.340 |
| Min, Max | 0.38, 32.27 | 0.15, 12.60 | 0.15, 32.27 | 0.12, 3.75 |
| Follow-Up | | | | |
| n | 8 | 11 | 19 | 15 |
| Mean (Std Dev) | 11.004 (5.9971) | 12.886 (6.1331) | 12.094 (5.9829) | 0.992 (2.2948) |
| Median | 13.185 | 11.450 | 11.970 | 0.340 |
| Min, Max | 0.62, 16.69 | 0.76, 22.45 | 0.62, 22.45 | 0.15, 9.20 |
| End of Study | | | | |
| n | 15 | 15 | 30 | 14 |
| Mean (Std Dev) | 6.933 (6.4298) | 9.565 (7.6479) | 8.249 (7.0702) | 1.695 (3.0345) |
| Median | 5.340 | 11.210 | 7.425 | 0.470 |
| Min, Max | 0.10, 17.04 | 0.13, 20.92 | 0.10, 20.92 | 0.15, 11.56 |

LLQ = lower limit of quantitation,
Max = maximum,
Min = minimum,
Q12W = once every 12 weeks,
QD = once daily,
Std Dev = standard deviation.
(a)Baseline was defined as the value collected at the time closest to, but prior to, the start of study drug administration.
The value <0.10 nmol/L (LLQ) was imputed as 0.10 mmol/L.

In patients with 12 week recovery data following discontinuation of 48 weeks of Compound 1 treatment, consistent with testosterone recovery data, QOL, such as AMS (Tables 5 and 6, lower AMS score is better) and sexual activity scores from the EORTC QLQ-PR25 appeared to improve more in the Compound 1 group than the leuprorelin group.

TABLE 5

| AMS Total Score-During Treatment | | | | | | |
|---|---|---|---|---|---|---|
| | Compound 1 | | | | Leuprorelin | |
| Mean (95% CI) | 80 mg QD (N = 56) | | 120 mg QD (N = 54) | | Q12W (N = 24) | |
| AMS total score | | | | | | |
| Baseline | 55 | 29.8 (27.1-32.6) | 53 | 29.9 (27.6-32.3) | 24 | 28.3 (24.2-32.3) |
| Percent change from baseline | | | | | | |
| W5, D1 | 54 | 3.9 (−2.8-10.6) | 52 | 10.9 (2.6-19.1) | 24 | 10.1 (−1.4-21.6) |
| W13, D1 | 52 | 14.8 (8.1-21.5) | 51 | 17.3 (7.7-26.8) | 24 | 21.9 (6.5-37.3) |
| W25, D1 | 49 | 20.3 (10.1-30.4) | 48 | 20.4 (10.4-30.3) | 23 | 47.0 (23.1-70.9) |
| W37, D1 | 47 | 24.1 (14.2-34.1) | 46 | 24.5 (13.9-35.1) | 22 | 49.4 (22.3-76.5) |
| W49, D1 | 46 | 30.1 (18.8-41.4) | 41 | 24.4 (13.8-35.0) | 21 | 60.0 (32.5-87.4) |

TABLE 6

| AMS Total Score-After Treatment | | | | | | |
|---|---|---|---|---|---|---|
| | Compound 1 | | | | Leuprorelin | |
| Mean (95% CI) | 80 mg QD (N = 56) | | 120 mg QD (N = 54) | | Q12W (N = 24) | |
| EOT** | 13 | 30.5 (−2.4-63.3) | 16 | 39.2 (21.8-56.5) | 13 | 61.0 (22.7-99.2) |
| Follow-up | 5 | 31.8 (−10.2-73.9) | 8 | 25.2 (−12.2-62.5) | 14 | 53.8 (18.2-89.4) |
| EOS | 14 | 21.9 (8.9-34.9) | 12 | 25.3 (−6.1-56.7) | 16 | 49.9 (21.0-78.7) |

AMS = aging male survey.
CI = confidence interval.
D = day.
EOS = end of study.
EOT = end of treatment.
Q12W = once every 12 weeks.
QD = once daily.
Data presented as mean (95% CI) change from baseline and percent change from baseline at specified timepoints for AMS scores. For AMS total baseline scores, a high number indicates worsening or increased number of symptoms.
*Baseline was defined as the value collected at the time closest to, but prior to, the start of study drug administration.
**EOT, Follow-up and EOS quality-of-life scores include only the patients who did not enter the extension phase or who did not start alternative or continued ADT after the W49D1 study visit.

Efficacy and safety analyses were conducted using a safety population (received ≥1 dose of study drug). The safety population included 56, 54, and 24 patients in the Compound 1 80 mg, Compound 1 120 mg, and leuprorelin groups, respectively. Safety was assessed by recording the incidence, severity, and types of treatment-emergent adverse events; by physical examination (including slit lamp examination of the anterior eye); and by evaluating changes from baseline in weight, vital signs, 12-lead electrocardiogram (ECG), and clinical laboratory parameters. All adverse events and serious adverse events were recorded throughout the entire study period and for 30 days after the last dose of Compound 1 or for 12 weeks plus 30 days after the last leuprorelin injection. Adverse events were coded using the Medical Dictionary for Regulatory Activities version 19.0 and graded according to National Cancer Institute Common Terminology Criteria version 4.03 (Tables 7 and 8). Safety-related haematology, chemistry, and urinalysis measurements were taken at each study visit and analysed at a central laboratory (LabCorp). Phospholipidosis was assessed as part of the safety assessments. The overall safety profile of Compound 1 appeared similar to that seen in the smaller observational leuprorelin cohort and did not suggest 'off-target' or non-ADT-related side effects that might impact either patient compliance or long-term maintenance. Intensive ophthalmologic evaluation of Compound 1-treated patients was performed to assess for the presence of phospholipidosis, an adverse effect of Compound 1 treatment observed in rats in non-clinical toxicity studies. Although cataracts appeared in the Compound 1 groups, only Compound 1-treated and not leuprorelin-treated patients underwent comprehensive eye examinations, which included slit-lamp evaluations. A small increase in mean corrected QT interval, of unknown clinical significance, occurred in all treatment arms, confirming prior observations in patients receiving ADT.

TABLE 7

Summary of Treatment-Emergent Adverse Events (Safety Population) and Most Frequently Reported (≥10%) Adverse Events

| n (%) | Compound 1 80 mg QD (N = 56) | Compound 1 120 mg QD (N = 54) | Leuprorelin Q12W (N = 24) |
|---|---|---|---|
| Any adverse event | 53 (95) | 50 (93) | 23 (96) |
| Grade ≥3 adverse event | 5 (9) | 4 (7) | 2 (8) |
| Drug-related adverse event | 44 (79) | 45 (83) | 18 (75) |
| Serious adverse event | 6 (11) | 1 (2) | 2 (8) |
| Adverse event resulting in study drug discontinuation | 2 (4) | 2 (4) | 0 |
| Death | 1 (2) | 0 (0) | 1 (4) |

| Most frequent adverse events, n (%) | Grade ≤2 | Grade ≥3 | Grade ≤2 | Grade ≥3 | Grade ≤2 | Grade ≥3 |
|---|---|---|---|---|---|---|
| Patients with any cause adverse event | 48 (86) | 5 (9) | 46 (85) | 4 (7) | 21 (88) | 2 (8) |
| Hot flush | 31 (55) | 0 | 35 (65) | 0 | 15 (63) | 0 |
| Fatigue | 11 (20) | 0 (0) | 17 (32) | 0 | 7 (29) | 0 |
| Cataract* | 5 (9) | 0 | 11 (20) | 0 | NA | NA |
| Increased ALT | 5 (9) | 1 (2) | 3 (6) | 0 | 4 (17) | 0 |
| Arthralgia | 5 (9) | 0 | 3 (6) | 1 (2) | 1 (4) | 0 |

ALT = alanine aminotransferase.

NA = not available.

Q12W = once every 12 weeks.

QD = once daily.

A treatment-emergent adverse event was defined as any adverse event that occurred after administration of the first dose of treatment drug and through 30 days after the last dose of Compound 1, or 12 weeks plus 30 days following the last dose of leuprorelin. The percentage is based on the total number of patients in the safety population of the 48-week core period.

*Ophthalmology examinations were performed only in patients treated with Compound 1.

TABLE 8

Overall Grade ≥3 Adverse Events in the 48-week Treatment Period

| n (%) | Compound 1 80 mg QD (N = 56) | Compound 1 120 mg QD (N = 54) | Leuprorelin Q12W (N = 24) |
|---|---|---|---|
| Patients with at least 1 Grade ≥3 adverse events | 9 (16) | 8 (15) | 2 (8) |
| Alanine aminotransferase increased | 2 (4) | 0 | 0 |
| Aspartate aminotransferase increased | 2 (4) | 0 | 0 |
| Death | 0 | 1 (2) | 0 |
| Sudden death | 0 | 1 (2) | 0 |
| Acute coronary syndrome | 0 | 1 (2) | 0 |
| Arthralgia | 0 | 1 (2) | 0 |
| Atrial flutter | 0 | 1 (2) | 0 |
| Bladder cancer | 1 (2) | 0 | 0 |
| Cerebral haemorrhage | 1 (2) | 0 | 0 |
| Cerebrovascular accident | 1 (2) | 0 | 0 |
| Cervical vertebral fracture | 1 (2) | 0 | 0 |
| Fatigue | 1 (2) | 0 | 0 |
| Gamma-glutamyltransferase increased | 1 (2) | 0 | 0 |
| Hypercalcaemia | 0 | 1 (2) | 0 |
| Hypertension | 0 | 1 (2) | 0 |
| Hypotension | 1 (2) | 0 | 0 |
| Inguinal hernia | 0 | 1 (2) | 0 |
| Joint dislocation | 1 (2) | 0 | 0 |
| Metastases to bone | 1 (2) | 0 | 0 |
| Musculoskeletal pain | 0 | 1 (2) | 0 |
| Non-cardiac chest pain | 0 | 1 (2) | 0 |
| Osteoarthritis | 0 | 1 (2) | 0 |
| Procedural pain | 0 | 1 (2) | 0 |
| Sepsis | 1 (2) | 0 | 0 |
| Syncope | 0 | 1 (2) | 0 |
| Transient ischaemic attack | 1 (2) | 0 | 0 |
| Urinary tract infection | 1 (2) | 0 | 0 |
| Diabetes mellitus | 0 | 0 | 1 (4) |
| Myocardial infarction | 0 | 0 | 1 (4) |

Example 9: A Study to Evaluate the Effect of Compound 1 in Men with Prostate Cancer Requiring ADT as Neoadjuvant and Adjuvant to External Beam Radiation Treatment External beam radiotherapy (EBRT) is a standard treatment option for intermediate/high-risk prostate cancer. The addition of androgen deprivation therapy (ADT) as an adjuvant/neoadjuvant, such as gonadotrophin-releasing hormone (GnRH) analogs, to EBRT has demonstrated prolonged overall survival. This study investigated the efficacy and safety of the oral formulations comprising Compound 1, or a pharmaceutically acceptable salt thereof.

Eligible male patients were aged ≥18 years with a histologically confirmed diagnosis of localized, intermediate-risk prostate cancer, for whom 6-month neoadjuvant and adjuvant androgen deprivation therapy (ADT) to external beam radiation therapy (EBRT) was indicated. The criteria for establishing intermediate-risk prostate cancer included the presence of one of the following, without any high-risk feature: T2b-T2c disease, Gleason score 7, or prostate-specific antigen (PSA) 10-20 ng/mL. Additional inclusion criteria included: EBRT scheduled to begin ≥12 weeks after baseline visit; screening serum testosterone >150 ng/dL (5.2 nmol/L); screening PSA concentration >2 ng/ml; body mass index ≥18.0 at screening or baseline (i.e., the subject's BMI prior to treatment commencing); Eastern Cooperative Oncology Group performance status of 0 or 1 at screening. Based on investigator discretion and clinical assessment of the patient's overall medical and disease status, participation was allowed for older patients with high-risk disease (e.g., based on Gleason score or tumor status) who were deemed likely to benefit from 6 months of neoadjuvant/adjuvant ADT. Most patients had intermediate-risk disease. However, a few patients, based on Gleason score or tumor, node, and metastasis staging system, were technically of higher than intermediate risk.

Patients with prior or current use of a gonadotropin-releasing hormone analog or androgen receptor antagonist as first-line hormone therapy (unless total treatment duration was <6 months and was completed ≥1 year prior to planned baseline visit), history of another malignancy in the 2 years prior to first dose of study drug, or previous malignancy with evidence of residual disease, were excluded. Additional exclusion criteria included presence of a clinically significant underlying disease.

In this study, patients received oral Compound 1 formulation 120 mg QD (with 320 mg load dose on Day 1) or degarelix 80 mg SC once every 4 weeks (Q4W) (with 240 mg load dose on Day 1). Both treatment arms received treatment for 24 weeks. Patients remained on treatment for at least 12 weeks before the start of external beam radiation treatment (EBRT), which was initiated for most patients between Week 13, Day 1 and Week 15, Day 1. EBRT began no later than day 1, week 17.

The 120 mg Compound 1 formulation comprised a core tablet of Compound 1 (120 mg), mannitol (366 mg), microcrystalline cellulose (60 mg), hydroxypropyl cellulose (18 mg), croscarmellose sodium (30 mg), and magnesium stearate (6 mg). The core tablets were coated with a film coating comprising hypromellose 2910 (21.36 mg), titanium dioxide (2.4 mg), and red ferric oxide (0.06 mg). The amounts of the excipients in the core tablet and film coating were adjusted accordingly based on the amount of Compound 1 in the core tablet (e.g., for the 360 mg tablet, the amount of excipient added to the core tablet and film coating is three times the amount added to the 120 mg tablet).

Patients were evaluated every 4 weeks during the treatment period (including day 1, week 25), at end of treatment (defined as week 29), during follow-up (week 33), and at end of study (EOS). The EOS visit was defined as week 37, or 12 (Compound 1) or 16 (degarelix) weeks after the last dose of study drug, whichever was soonest.

Samples for testosterone, luteinizing hormone (LH), FSH, and PSA concentrations were taken at screening, on day 1 of the first week (additionally days 2 and 4 for testosterone and LH), and on day 1 of weeks 2, 3, 5, 9, 13, 17, 21, 25, 29, 33, and 37 thereafter. On average, in patients receiving the Compound 1 formulation, PSA levels decreased to <0.2 ng/ml by the Week 13 Day 1 visit. By Day 4, LH levels were low for both the Compound 1 and degarelix treated groups (Compound 1:0.462 mIU/mL; degarelix: 0.499 mIU/mL). FSH levels at this time point were not available; however, a decrease from the levels before administration of Compound 1 or degarelix (Compound 1:11.826 IU/L; degarelix: 11.716 IU/L) was noted at Week 2, Day 1 (Compound 1:2.363 IU/L; degarelix: 2.519 IU/L) for both groups. Suppression of FSH was less profound than that of LH, but consistent with the literature, and was greater than that observed with GnRH agonists. Mean levels of LH and FSH remained low through the Week 25, Day 1 Visit for both groups (Compound 1, LH: 0.325 IU/L; degarelix, LH: 0.342 IU/L; Compound 1, FSH: 1.475 IU/L; degarelix, FSH: 1.471 IU/L).

Quality of Life (QoL) was assessed via the core 30-item European Organisation for Research and Treatment of Cancer quality of life questionnaire (EORTC QLQ-C30), the 25-item prostate cancer module EORTC questionnaire (EORTC QLQ-PR25), and the aging male survey (AMS). QoL assessments were completed at screening, on day 1 of weeks 1, 5, 13, and 25, and at weeks 29, 33, and 37.

The time-course and intensity of serum testosterone lowering observed in patients in this study receiving the Compound 1 formulation was similar to that observed during the study in healthy older men in Example 7 and during the study in patients with prostate cancer in Example 8. Serum testosterone levels were measured at each visit. On average, in patients receiving the Compound 1 formulation, serum testosterone decreased to below the medical castration threshold of 50 ng/dL (1.73 nmol/L) by Day 4 (end of Day 3) visit, and to below the profound castration threshold of 20 ng/dl (0.69 nmol/L) by the Week 5 Day 1 visit.

For this study, serum testosterone lowering over Day 1 through Day 15 showed a rapid reduction over the first 24 hours and on average below medical castration levels of serum testosterone 72 hours (Week 1 Day 4) following start of dosing (or loading dose injection). The serum testosterone lowering effect of Compound 1 120 mg daily over 25 weeks was as sustained as that with the degarelix injectable antagonist analog. At the end of 8 weeks of dosing (before the start of radiation therapy), in patients with hormone-sensitive cancer in whom the prostate gland and tumor remain in situ, PSA % responses were less than observed in the study in Example 8, but nonetheless exceed 89% in most patients. The PSA responses in both the Compound 1 formulation and degarelix treatment groups appear similar. The proportion of patients achieving PSA values less than 0.2 ng/ml by the end of 12 weeks was 6 of 30 patients for the Compound 1 formulation arm versus 1 of 20 patients for the degarelix arm.

Rates for medical castration (less than 50 ng/dL) and profound castration (less than 20 ng/dL) were determined over the course of 24 weeks overall, for subjects who received at least 12 weeks of treatment, and for subjects who received at least 24 weeks of treatment. Overall, both medical castration and profound castration rates over 24 weeks were higher for Compound 1 (95% and 82%, respectively) compared with the degarelix group (89% and 68%, respectively), as shown in FIG. 49. In subjects who had at least 12 weeks of treatment, castration rates were similar overall. In subjects who had at least 24 weeks of treatment, the trend of higher castration rates with Compound 1 treatment (98% and 84% for medical castration and profound castration, respectively) compared to degarelix (86% and 71% for medical castration and profound castration, respectively) continued as shown in FIG. 49.

Time to achieve medical castration level serum testosterone (less than 50 ng/dL [1.73 nmol/L] and less than 20 ng/dL [0.69 nmol/L) and the estimated time to serum testosterone recovery (including estimated percentage of patients who had recovered to baseline value and the percentage who recovered to greater than 280 ng/dL during 12 weeks off treatment) were determined.

The time to castration appeared to be similar between treatment groups. Median time to medical castration (≤50 ng/dL) was 4 days (95% CI: 2-4) for the Compound 1 group and 3 days (95% CI: 2-4) for the degarelix group. Median time to profound castration (≤20 ng/dL) was 15 days (95% CI: 8-15) for the Compound 1 group and 12 days (95% CI: 8-15) for the degarelix group.

Figure 50:
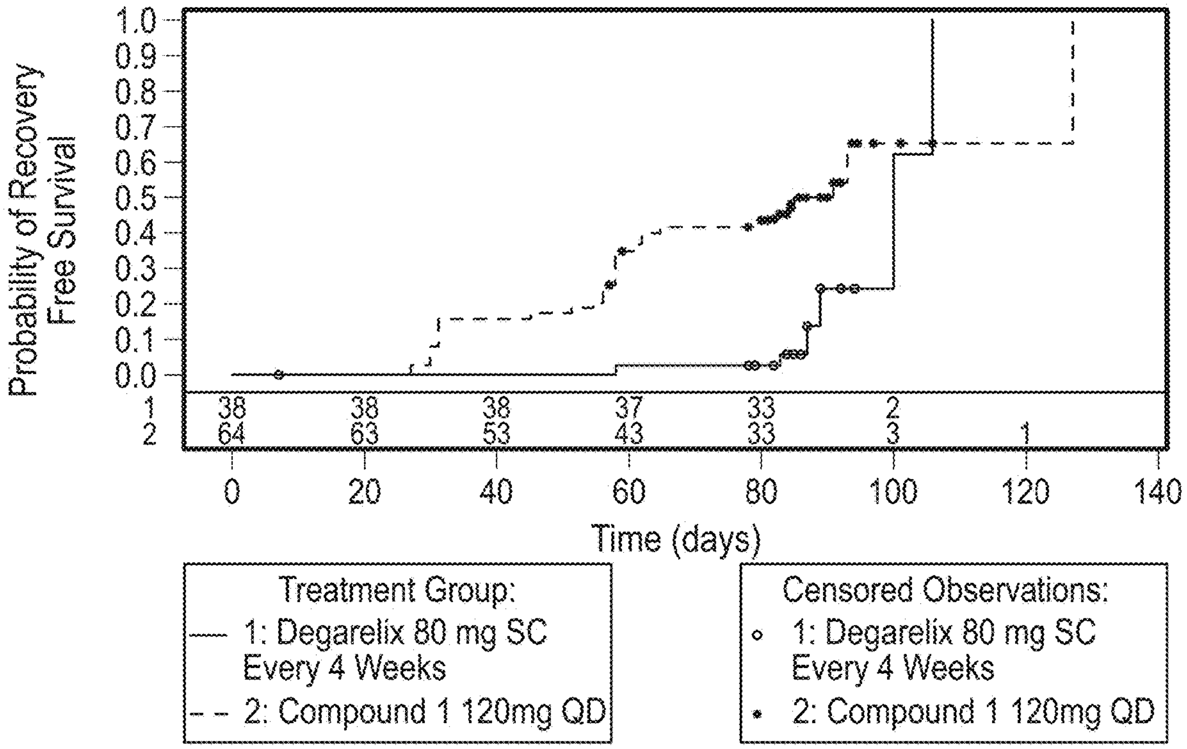
FIG. 50 graphically depicts a Kaplan-Meier survival curve for time to serum testosterone recovery (i.e., the subject's serum testosterone level prior to treatment commencing or >280 ng/dL) in accordance with Example 9. ADT=androgen deprivation therapy, QD=daily, SC=subcutaneous. (a) Time to serum testosterone recovery was defined as the time from 1 day after the last dose of Compound 1 or 4 weeks plus 1 day after the last dose of degarelix to serum testosterone recovery. Serum testosterone recovery was defined as back to the subject's serum testosterone level prior to treatment commencing or >280 ng/dL whichever occurs first. It was censored for patients starting alternative ADT without recovery at the last serum testosterone lab assessment before the start of ADT.
Figure 53:
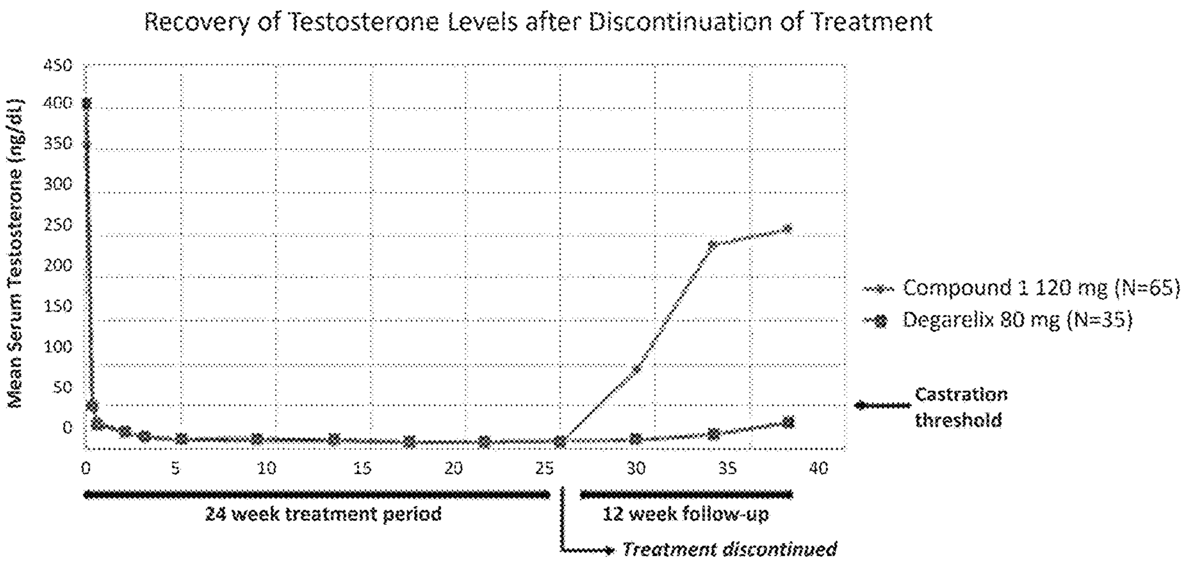
FIG. 53 graphically depicts the recovery of serum testosterone levels provided in Example 9.

After removal of therapy, mean serum testosterone levels in the degarelix group remained low through the end of study. For the Compound 1 group, serum testosterone levels increased to approximately 10 nmol/L at the follow-up visit and at end of study (1.7 nmol/L is the medical castration level). As depicted in FIG. 50, time to serum testosterone recovery to baseline levels or greater than 280 ng/dL was more rapid for Compound 1 compared with the degarelix group. Twelve weeks after treatment, approximately 43% of subjects achieve pre-treatment serum testosterone levels or a serum testosterone level at or above 280 ng/dl by 12 weeks versus only 5.3% with degarelix (Table 9). Results were similar for patients who received at least 12 weeks or 24 weeks of treatment. Based on achievement of baseline serum testosterone levels or greater than 280 ng/dL for serum testosterone concentrations, the Compound 1 group showed quicker achievement of these levels compared to the degarelix group (FIG. 53).

TABLE 9

Testosterone Values and Time to Testosterone Recovery (Baseline Levels or >280 ng/dL [9.72 nmol/L]) for Overall Safety Population

| | Compound 1 120 mg QD (N = 65) | Degarelix 80 mg Q4W (N = 38) |
|---|---|---|
| Baseline[b] | | |
| n | 65 | 38 |
| Mean (Std Dev) | 14.067 (6.7100) | 14.567 (5.5680) |
| Median | 12.350 | 14.020 |
| Min. Max | 5.17, 44.76 | 4.79, 32.55 |
| Week 25, Day 1 | | |
| n | 64 | 37 |
| Mean (Std Dev) | 0.395 (0.5584) | 0.582 (1.5107) |
| Median | 0.280 | 0.310 |
| Min. Max | 0.11, 4.34 | 0.10, 9.47 |
| EOT | | |
| n | 61 | 38 |
| Mean (Std Dev) | 5.117 (5.7671) | 0.576 (1.2218) |
| Median | 3.260 | 0.335 |
| Min. Max | 0.10, 28.42 | 0.10, 7.81 |
| Follow-Up | | |
| n | 62 | 37 |
| Mean (Std Dev) | 9.889 (6.3879) | 1.206 (1.9330) |
| Median | 8.275 | 0.560 |
| Min. Max | 0.35, 32.24 | 0.11, 9.13 |
| EOS | | |
| n | 61 | 38 |
| Mean (Std Dev) | 9.661 (5.4611) | 3.038 (4.0224) |
| Median | 8.920 | 1.040 |
| Min. Max | 0.33, 29.81 | 0.13, 13.15 |
| Time to testosterone recovery (days) | | |
| Number with events, n (%) | 34 (52) | 6 (16) |
| Number censored, n (%) | 30 (46) | 32 (84) |
| $25^{th}$ percentile (95% CI) | 57 (45.62) | 100 (87.106) |
| Median (95% CI) | 91 (62.127) | 100 (100.106) |
| $75^{th}$ percentile (95% CI) | 127 (93.127) | 106 (100.106) |
| Min. Max | 7*.127 | 58.106 |
| Kaplan-Meier estimates[c] (95% CI) | | |
| 4 weeks from last dose[d] | 0.03 (0.00.0.08) | 0.00 (0.00.0.00) |
| 8 weeks from last dose[d] | 0.24 (0.13.0.34) | 0.00 (0.00.0.00) |
| 12 weeks from last dose[d] | 045 (0.33.0.58) | 0.06 (0.00.0.13 |

TABLE 9-continued

Testosterone Values and Time to Testosterone Recovery (Baseline Levels or >280 ng/dL [9.72 nmol/L]) for Overall Safety Population

| | Compound 1 120 mg QD (N = 65) | Degarelix 80 mg Q4W (N = 38) |
|---|---|---|
| Percent recovery (95% CI)[e] | | |
| 4 weeks from last dose[d] | 3.1 (0.4.10.7) | NE |
| 8 weeks from last dose[d] | 23.1 (13.5.35.2) | NE |
| 12 weeks from last dose[d] | 43.1 (30.8.56.0) | 5.3 (0.6.17.7) |

(a) Time to testosterone recovery was defined as the time from 1 day after the last dose of Compound 1 or 4 weeks plus 1 day after the last dose of degarelix to testosterone recovery. Testosterone recovery was defined as back to Baseline or >280 ng/dL, whichever occurs first. It was censored for patients starting alternative ADT without recovery at the last testosterone lab assessment before the start of ADT.

[b]Baseline was defined as the value collected at the time closest to, but prior to, the start of study drug administration. The value <0.10 nmol/L (LLQ) was imputed as 0.10 nmol/L.

[c]Probability of event (n = number of patients at risk).

[d]4, 8 or 12 weeks from 1 day after the last dose of Compound 1 or 4, 8 or 12 weeks plus 1 day after the last dose of degarelix.

A summary of time to serum testosterone recovery based on Kaplan-Meier estimates for the overall safety population is provided in FIG. 51. The median (95% CI) number of days to recovery was 91 (62, 127) days for the Compound 1 group and 100 (100, 106) days for the degarelix group. Patients treated with Compound 1 had a higher probability of achieving serum testosterone recovery throughout the study compared with patients treated with degarelix as shown in FIG. 51. For patients who received at least 12 weeks of treatment, the results were the same as the results for the overall safety population. For patients who received treatment for at least 24 weeks, results were relatively similar to overall results for both groups; however, for the Compound 1 group, the median (95% CI) number of days to recovery was 86 (58, 93) days and the percent recovery (95% CI) by 12 weeks from the last dose was 46.0% (31.8%, 60.7%). When serum testosterone recovery was estimated separately by return to baseline or greater than 280 ng/dL, there was a higher probability for achievement of >280 ng/dL compared with achievement of baseline serum testosterone levels for the Compound 1 group.

Following discontinuation of therapy at the end of 24 weeks, patients were followed for an additional 12 weeks to evaluate serum testosterone recovery and associated changes in PSA and quality of life. At the end of the follow-up period approximately half of the patients receiving Compound 1 had recovered either to baseline testosterone values or to greater than 280 ng/dL, whichever was less, compared to only 6% of patients receiving degarelix. In the degarelix group there was relatively little LH recovery and median serum testosterone remained <50 ng/dL at the end of study visit; serum testosterone met the definition of recovery in only 6 of 38 patients. Patient-reported outcomes were similar in both treatment arms during the first 12 weeks of treatment, consistent with acute medical castration. There was a trend towards more rapid relief from hormonal and sexual related symptoms in the Compound 1-treated group (e.g., hot flashes).

The median testosterone at the week 28/EOT visit was 93.9 ng/dL (Table 10). This was 4 weeks after stopping Compound 1. Thus, median testosterone at 4 weeks after stopping treatment was well above the 50 ng/dL castration threshold. In comparison, the median testosterone was 9.6 ng/dl for degarelix at the same time point (week 28/EOT), 16.1 ng/dl at 8 weeks out (Week 32/follow-up), and 30.0 ng/dL at 12 weeks out (Week 36/EOS). Thus, with injectable GnRH antagonist (degarelix), testosterone was still suppressed under the castration threshold 12 weeks after 24 week study (16 weeks after that last monthly injection of degarelix).

TABLE 10

| Recovery of LH and Testosterone over Time from Associated PSA Levels | | | | | | |
|---|---|---|---|---|---|---|
| | Compound 1 120 mg QD (N = 65) | | | Degarelix 80 mg Q4W (N = 38) | | |
| | Median LH, mlU/mL (range) | Median testosterone, ng/dL (range) | Median PSA, µg/L (range) | Median LH, mlU/mL (range) | Median testosterone, ng/dL (range) | Median PSA, µg/L (range) |
| Baseline | 4.7 (0.8-32.2) | 355.7 (148.9-1289.1) | 7.3 (2.6-31.5) | 4.8 (1.3-42.0) | 403.8 (138.0-937.4) | 7.3 (2.5-88.9) |
| Week 24 | 0.1 (0.1-3.9) | 8.1 (3.2-125.0) | 0.07 (0.07-1.6) | 0.1 (0.1-3.7) | 8.9 (2.9-272.7) | 0.1 (0.07-1.9) |
| Week 28/EOT visit | 3.1 (0.2-15.7) | 93.9 (2.9-818.5) | 0.07 (0.07-1.5) | 0.2 (0.1-2.8) | 9.6 (2.9-224.9) | 0.07 (0.07-2.1) |
| Week 32/ follow-up | 8.3 (0.1-32.4) | 238.3 (10.1-928.5) | 0.2 (0.07-3.2) | 0.5 (0.1-7.7) | 16.1 (3.2-262.9) | 0.07 (0.07-2.2) |
| Week 36/EOS | 10.7 (0.1-38.7) | 256.9 (9.5-858.5) | 0.2 (0.07-2.3) | 1.4 (0.1-15.7) | 30.0 (3.7-378.7) | 0.07 (0.07-2.0) |

EOS = end of study.
EOT = end of treatment.
LH = luteinizing hormone.
PSA = prostate-specific antigen.
Q4W = once every 4 weeks.
QD = once daily.

From EOT through the EOS, QOL such as AMS and sexual activity scores appeared to improve more in the Compound 1 than the degarelix group, consistent with the observed pattern of testosterone recovery (Table 11). Following discontinuation of study drug treatment at the end of Week 24 (or 4 weeks after the final injection of degarelix at Week 21, Day 1), the recovery of testosterone and associated changes in PSA were followed for an additional 12 weeks. Nearly half of patients receiving Compound 1 had recovered by 8 weeks of follow-up to either baseline values or >280 ng/dL, with little apparent recovery over the subsequent 4 weeks (12 weeks follow-up). In contrast, only 6% of patients receiving degarelix had recovered by the 12-week Follow-up time point. There were minimal differences in change of PSA during the recovery period, about a 0.2 to 0.4 ng/mL increase in patients receiving Compound 1. Based on relative stability between the 8 and 12-week Follow-up time point, this recovery may have been related to PSA secretion from residual normal prostate rather than neoplastic tissue. The results suggest that the rapid recovery of testosterone in the Compound 1 group following 24 weeks neoadjuvant adjuvant to EBRT treatment for intermediate risk prostate cancer poses no significant risk regarding long term treatment outcomes.

TABLE 11

| Change in QoL During Treatment (from Baseline to Week 25) or Recovery (from Week 25 to Week 36) | | | | | | |
|---|---|---|---|---|---|---|
| | Global health/QoL* | | Sexual activity | | Hormonal treatment-related symptoms† | |
| | Compound 1 120 mg QD (N = 65) | Degarelix 80 mg Q4W (N = 38) | Compound 1 120 mg QD (N = 65) | Degarelix 80 mg Q4W (N = 38) | Compound 1 120 mg QD (N = 65) | Degarelix 80 mg Q4W (N = 38) |
| Change from baseline (day 1) to week 25 | | | | | | |
| n | 60 | 38 | 60 | 38 | 60 | 38 |
| Mean (SD) | −10.1 (18.9) | −7.5 (13.7) | −19.7 (29.4) | −11.8 (36.3) | 13.4 (12.1) | 12.9 (10.4) |
| Change from week 25 to week 36 | | | | | | |
| n | 58 | 38 | 58 | 38 | 58 | 38 |
| Mean (SD) | 2.3 (16.6) | 0.7 (15.5) | 12.1 (21.8) | 6.6 (22.8) | −5.0 (10.3) | −1.2 (9.1) |
| Change from baseline to | | | | | | |

TABLE 11-continued

Change in QoL During Treatment (from Baseline to Week 25) or Recovery (from Week 25 to Week 36)

| | Global health/QoL* | | Sexual activity | | Hormonal treatment-related symptoms† | |
|---|---|---|---|---|---|---|
| | Compound 1 120 mg QD (N = 65) | Degarelix 80 mg Q4W (N = 38) | Compound 1 120 mg QD (N = 65) | Degarelix 80 mg Q4W (N = 38) | Compound 1 120 mg QD (N = 65) | Degarelix 80 mg Q4W (N = 38) |
| week 36 (EOS) | | | | | | |
| n | 62 | 38 | 62 | 38 | 62 | 38 |
| Mean (SD) | −7.7 (17.8) | −6.8 (16.0) | −7.3 (30.0) | −5.3 (34.7) | 8.5 (11.3) | 11.7 (10.2) |

EOS = end of study.
Q4W = once every 4 weeks.
QD = once daily.
QoL = quality of life.
SD = standard deviation.
*Higher scores of hormonal treatment-related symptoms reflect worse QoL.
†Higher scores of global health/QoL and sexual activity reflect better QoL.

In summary, this study demonstrated rapid and sustained suppression of serum testosterone levels for the 24 week treatment duration. Importantly, in this study, the serum testosterone recovery following the last dose of treatment was more rapid in the Compound 1 arm than in the degarelix arm.

Example 10: Phase 1, Open-Label, Randomized, Three-Way Crossover Study Evaluating the Relative Bioavailability and Effect of Food on Compound 1 Tablet Formulations in Healthy Subjects This was an open-label, randomized, 3-way crossover, single-dose study designed to evaluate the oral bioavailability of two Compound 1 tablet formulation candidates (T4 Formulation B and T4 Formulation C) relative to a third Compound 1 tablet formulation (T2 Formulation), and the effect of food on the PK of Compound 1 following oral administration of the T4 Formulations B and C. There were five single-dose treatment regimens:

Regimen A: Compound 1, 120 mg dose T2 Formulation under fasted conditions.

Regimen B: Compound 1, 120 mg T4 Formulation B under fasted conditions.

Regimen C: Compound 1, 120 mg T4 Formulation B under fed conditions (standard US Food and Drug Administration [FDA] high-fat, high-calorie breakfast).

Regimen D: Compound 1, 120 mg T4 Formulation C under fasted conditions.

Regimen E: Compound 1, 120 mg T4 Formulation C under fed conditions (standard US FDA high-fat, high-calorie breakfast).

Screening assessments were performed within 28 days before the Day 1 dose of Compound 1. Following confirmation of eligibility, subjects were randomly assigned to a sequence in one of two treatment arms:

Arm 1: T2 Formulation (Regimen A to serve as a reference group) and T4 Formulation B (Regimens B and C).

Arm 2: T2 Formulation (Regimen A to serve as a reference group) and T4 Formulation C (Regimens D and E).

In each study arm, each subject participated in 3 treatment periods with a 10-day washout interval between each dose. Subjects received a single 120 mg oral dose of Compound 1 on Day 1, Day 11, and Day 21, per the assigned arm and sequence, followed by serial blood sampling for PK assessments at predetermined time points up to 120 hours postdose. During each of the 3 treatment periods, subjects were confined to the clinical site for a total of 4 days. Each eligible subject was to check into the clinical site on the evening of Day-1 and undergo baseline safety assessments.

Subjects were confined to the clinical site from Day −1 through Day 4. Following the Day 4 (72 hours postdose) PK blood sampling, subjects were discharged from the clinical site. Subjects were instructed to return to the study clinic on the morning of Day 5 for the 96-hour PK assessment and on the morning of Day 6 for the 120-hour PK assessment. Subjects were to return to the study clinic on the evening of Day 10 and were confined from Day 10 through Day 14. Following the Day 14 (72 hours postdose) PK blood sampling, subjects were discharged from the clinical site. Subjects were instructed to return to the study clinic on the morning of Day 15 for the 96-hour PK assessment and the morning of Day 16 for the 120-hour PK assessment. Subjects were to return to the study clinic on the evening of Day 20 and were confined from Day 20 through Day 24. Following the Day 24 (72 hours postdose) PK blood sampling, subjects were discharged from the clinical site. Subjects were instructed to return to the study clinic on the morning of Day 25 for the 96-hour PK assessment on the morning of Day 26 for the 120-hour PK assessment. Study drug was administered in the morning of Days 1, 11, and 21 in either the fed or fasted state. During confinement, subjects received standardized meals scheduled at the same time each day. For each subject, vital signs, physical examinations, adverse event (AE) assessments, laboratory values (chemistry, hematology, and urinalysis), and 12-lead electrocardiograms (ECGs) were obtained to evaluate the safety and tolerability of Compound 1. Subjects were considered to have completed the study if they completed each of the 3 treatment periods and the End-of-Study (EOS) assessment (30 days after the last dose of study drug). Subjects could discontinue participation in the study at any time. Each subject must have been a healthy adult male, aged 18-55 years (inclusive) to be included in this study. Tables 12 and 13 summarize treatment Arm 1 and treatment Arm 2 of the study.

TABLE 12

| Treatment Period Sequences for Arm 1 | | | |
|---|---|---|---|
| Sequence | Period[a] 1 | Period[a] 2 | Period[a] 3 |
| 1 | Regimen A[b] | Regimen B[c] | Regimen C[d] |
| 2 | Regimen A | Regimen C | Regimen B |
| 3 | Regimen B | Regimen A | Regimen C |
| 4 | Regimen B | Regimen C | Regimen A |
| 5 | Regimen C | Regimen A | Regimen B |
| 6 | Regimen C | Regimen B | Regimen A |

[a]The length of each treatment period was 10 days. Subjects received single doses of Compound 1 on the first day of each treatment period (i.e., Day 1, Day 11, and Day 21).
[b]Regimen A: Compound 1, 120 mg dose (80 mg + 40 mg tablets) T2 Formulation under fasted conditions.
[c]Regimen B: Compound 1, 120 mg (1 × 120 mg tablet) T4 Formulation B under fasted conditions.
[d]Regimen C: Compound 1, 120 mg (1 × 120 mg tablet) T4 Formulation B under fed conditions (standard US FDA high-fat, high-calorie breakfast).

TABLE 13

| Treatment period sequences for Arm 2 | | | |
|---|---|---|---|
| Sequence | Period[a] 1 | Period[a] 2 | Period[a] 3 |
| 1 | Regimen A[b] | Regimen D[c] | Regimen E[d] |
| 2 | Regimen A | Regimen E | Regimen D |
| 3 | Regimen D | Regimen A | Regimen E |
| 4 | Regimen D | Regimen E | Regimen A |
| 5 | Regimen E | Regimen A | Regimen D |
| 6 | Regimen E | Regimen D | Regimen A |

[a]The length of each treatment period was 10 days. Subjects received single doses of Compound 1 on the first day of each treatment period (i.e., Day 1, Day 11, and Day 21).
[b]Regimen A: Compound 1, 120 mg dose (80 mg + 40 mg tablets) T2 Formulation under fasted conditions.
[c]Regimen D: Compound 1, 120 mg (1 × 120 mg tablet) T4 Formulation C under fasted conditions.
[d]Regimen E: Compound 1, 120 mg (1 × 120 mg tablet) T4 Formulation C under fed conditions (standard US FDA high-fat, high-calorie breakfast).

A total of 54 subjects enrolled in and completed the study. There were 27 subjects in each arm of the study. All 54 subjects were included in the safety population and the PK-evaluable population. No major protocol deviations occurred for any subject during this study. One subject had a minor protocol deviation related to a dose administration interval that occurred greater than 30 minutes after the start of breakfast. In Period 3, the subject was administered the T4 Formulation B under fed conditions; the starting time of Compound 1 dose administration following the start of breakfast was 31 minutes and 3 seconds. All of the PK parameters for this subject following oral administration of T4 Formulation B under fed conditions were generally similar to the mean values of PK parameters in this treatment group; therefore, the PK parameters of this subject were included in the descriptive and ANOVA statistical analyses. Tables 14 and 15 below provide summaries of some pharmacokinetic parameters following administration of the different formulations.

TABLE 14

Summary Statistics of Plasma Pharmacokinetic Parameters of Compound 1 Following Single Oral Administration of 120 mg Compound 1 as T4 Formulation B or C Tablet Compared to T2 Formulation Tablets Under Fasted Conditions

| Parameter | Arm 1 | | Arm 2 | |
|---|---|---|---|---|
| (unit) Statistic | T2 Form. | T4 Form. B | T2 Form. | T4 Form. C |
| N | 27 | 26 | 27 | 27 |
| $t_{max}$ (h) | | | | |
| Median | 2.01 | 3.00 | 3.00 | 3.00 |
| Min, Max | 0.500, | 0.502, | 0.499, | 0.499, |

TABLE 14-continued

Summary Statistics of Plasma Pharmacokinetic Parameters of Compound 1 Following Single Oral Administration of 120 mg Compound 1 as T4 Formulation B or C Tablet Compared to T2 Formulation Tablets Under Fasted Conditions

| Parameter | Arm 1 | | Arm 2 | |
|---|---|---|---|---|
| (unit) Statistic | T2 Form. | T4 Form. B | T2 Form. | T4 Form. C |
| | 6.00 | 12.0 | 6.02 | 12.0 |
| $C_{max}$ (ng/ml) | | | | |
| GM | 46.7 | 42.0 | 52.0 | 43.5 |
| CV % | 115 | 153 | 93.3 | 147 |
| $AUC_{120}$ (ng · h/mL) | | | | |
| GM | 447 | 440 | 532 | 415 |
| CV % | 64.7 | 83.3 | 55.4 | 85.1 |
| AUC∞ (ng · h/mL) | | | | |
| GM | 476 | 467 | 563 | 440 |
| CV % | 63.5 | 82.8 | 55.1 | 84.8 |
| $t_{1/2z}$ (h) | | | | |
| Mean | 36.3 | 36.1[a] | 34.9 | 35.5 |
| SD | 4.40 | 4.90 | 4.13 | 4.22 |
| Min, Max | 28.8, 46.5 | 27.4, 44.7 | 29.2, 44.8 | 25.4, 46.0 |

CV = geometric coefficient of variation;
GM = geometric mean.
[a]N = 27.

TABLE 15

Summary Statistics of Plasma Pharmacokinetic Parameters of Compound 1 Following Single Oral Administration of 120 mg Compound 1 as T4 Formulation B or C Tablet Under Fed Conditions

| Parameter (unit) Statistic | T4 Formulation B | T4 Formulation C |
|---|---|---|
| N | 27 | 27 |
| $t_{max}$ (h) | | |
| Median | 3.00 | 3.00 |
| Min, Max | 0.500, 8.00 | 1.00, 8.00 |
| $C_{max}$ (ng/ml) | | |
| GM | 33.0 | 41.2 |
| CV % | 116 | 106 |
| $AUC_{120}$ (ng · h/mL) | | |
| GM | 350 | 386 |
| CV % | 65.0 | 52.4 |
| AUC∞ (ng · h/mL) | | |
| GM | 372 | 409 |
| CV % | 64.1 | 51.8 |
| $t_{1/2z}$ (h) | | |
| Mean | 35.1 | 35.4 |
| SD | 4.11 | 2.97 |
| Min, Max | 29.9, 45.7 | 29.9, 42.2 |

CV = geometric coefficient of variation;
GM = geometric mean.

All subjects included in this study were healthy men, a majority of who were white (81%) and Hispanic or Latino (65%). The overall mean (SD) age of study subjects was 38.9 (10.8) years, with an age range from 19 to 55 years. The overall mean (SD) weight and BMI of subjects was 83.4 (12.7) kg and 27.2 (3.2) kg/m$^2$, respectively. Demographic characteristics were similar between treatment arms. No subjects were excluded from the PK-evaluable population;

therefore, the demographics for this population were the same as the safety population. The formulation information for various formulations used in this example, and other exemplary formulations, is provided in Table 16.

TABLE 16

| | | | Exemplary Formulations | | | |
|---|---|---|---|---|---|---|
| | Function | 1-20 mg (T1) | 40 mg (T2) | 40 mg (T3) | 40 mg (T4-B) | 120 mg (T4-B) | 120 mg (T4-C) |
| Compound 1 | DS | 1-20 | 40 | 40 | 40 | 120 | 120 |
| Mannitol | Diluent | 80-61 | 122 | 122 | 51 | 153 | 234 |
| Microcrystalline cellulose | Diluent | 10 | 20 | 40 | — | — | 30 |
| Polyethylene Glycol 8000 | Lubricant | — | — | — | — | — | 1.8 |
| Hydroxypropyl cellulose | Binder | 3 | 6 | 6 | 3 | 9 | 11.4 |
| Croscarmellose sodium | Disintegrant | 5 | 10 | 10 | — | — | 19.05 |
| Sodium starch glycolate | Disintegrant | — | — | — | 5 | 15 | — |
| Magnesium stearate | Lubricant | 1 | 2 | 2 | 1 | 3 | 3.75 |
| Purified water* | solvent | q.s | q.s | q.s | q.s | q.s | q.s |
| Sub total (Core tablets) | | 100 | 220 | 220 | 100 | 300 | 420 |
| Hypromellose 2910 | Film coating | 2.93 | 7.12 | 7.12 | 3.56 | 10.68 | 13.5 |
| Polyethylene glycol 8000 | plasticizer | 0.67 | — | — | — | — | — |
| Titanium dioxide | Pigment | 0.33 | 0.8 | 0.8 | 0.4 | 1.2 | 1.5 |
| Ferric oxide, red | Colorant | 0.07 | 0.02 | 0.02 | 0.04 | 0.12 | 0.15 |
| Ferric oxide, yellow | Colorant | — | — | 0.06 | — | — | — |
| Purified water* | | q.s | q.s | q.s | q.s | q.s | q.s |
| Sub total (FC layer) | | 4 | 8 | 8 | 4 | 12 | 15.15 |
| Total | | 104 | 228 | 228 | 104 | 312 | 435.15 |
| Carnauba Wax | | — | — | 0.012 | 0.004 | 0.008 | q.s |

Figure 54:
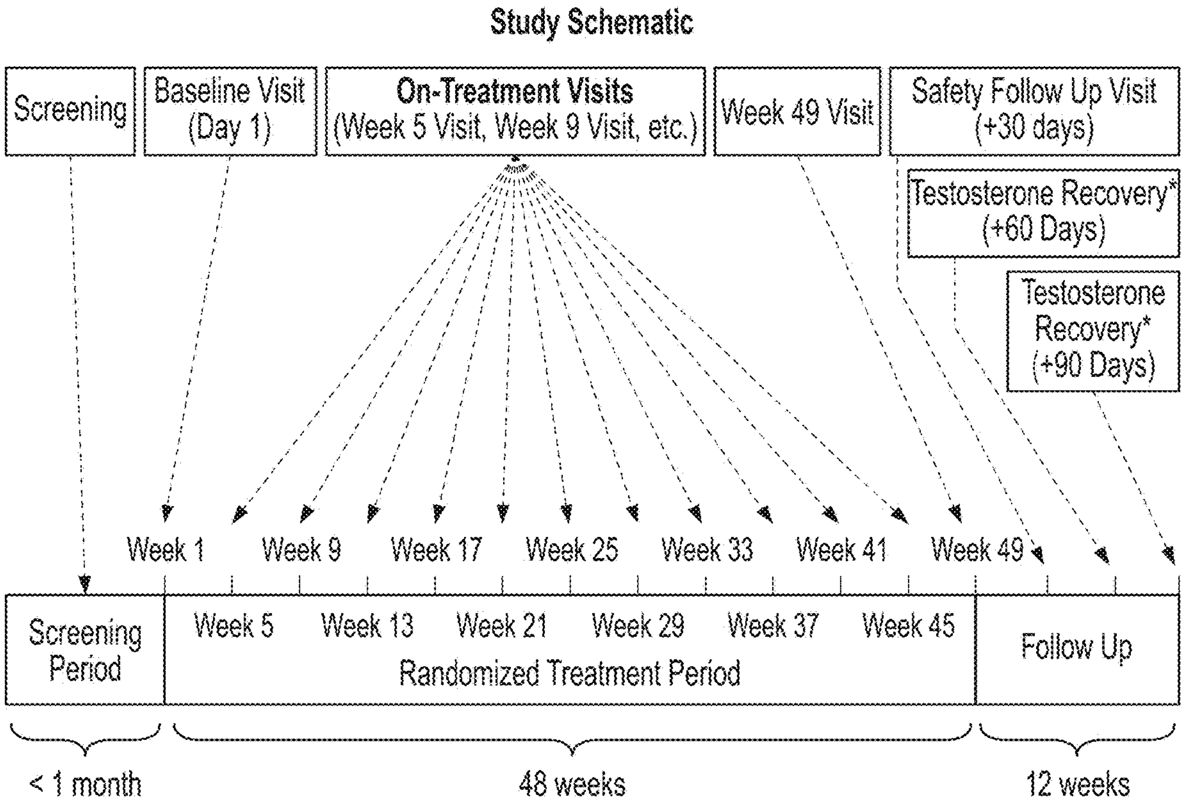
FIG. 54 graphically depicts the clinical trial detailed in Example 11. Compound 1 will be dosed daily (Day 1 to Week 48, Day 7). Leuprolide acetate will be dosed every 12 weeks (Day 1; Week 13, Day 1; Week 25, Day 1; and Week 37, Day 1). *The +60 days and +90 days testosterone recovery visits will happen with a subset of patients.

Example 11: A Study to Evaluate the Safety and Efficacy of Compound 1 in Patients with Androgen-Sensitive Advanced Prostate Cancer This study is a phase 3 multinational randomized, open-label, parallel-group study to evaluate the safety and efficacy of Compound 1, or a pharmaceutically acceptable salt thereof, in patients with androgen-sensitive advanced prostate cancer who require at least 1 year of continuous androgen deprivation therapy (FIG. 54). Compound 1 is an oral gonadotropin-releasing hormone (GnRH) receptor antagonist that lowers testosterone by inhibiting pituitary release of follicle-stimulating hormone (FSH) and luteinizing hormone (LH). Compound 1 120 mg orally once daily or leuprolide acetate depot suspension, 22.5 mg (or 11.25 mg in some Asian countries), every 3-months (3-M) will be administered to patients with prostate cancer who require androgen deprivation therapy. This study will evaluate the ability of Compound 1, or a pharmaceutically acceptable salt thereof, to achieve and maintain serum testosterone suppression to castrate levels (≤50 ng/dL [1.7 nmol/L]) for 48 weeks in patients with androgen-sensitive advanced prostate cancer.

To be eligible for the study, a patient must be, in the opinion of the investigator, a candidate for at least 1 year of continuous androgen deprivation therapy for the management of androgen-sensitive advanced prostate cancer and must not be a candidate for surgical therapy. Eligible patients include those with evidence of biochemical relapse (rising PSA) following local primary intervention with curative intent, newly diagnosed metastatic disease (excluding metastases to the brain), and/or advanced localized disease.

Patients may receive radiotherapy, cryotherapy or high frequency ultrasound no sooner than 2 months after initiation of androgen deprivation therapy. Patients may be included if they have not previously received androgen deprivation therapy for more than 12 months, and if the androgen deprivation therapy was completed at least 12 months prior to baseline. Patients previously treated with taxanes or expected to receive taxanes after initiation of androgen deprivation therapy are excluded, as are patients receiving androgen deprivation therapy adjuvant or neoadjuvant to radiotherapy as primary definitive therapy. Baseline serum testosterone must be ≥150 ng/dl (5.2 nmol/L) to be enrolled.

Patients enrolled in this study will be randomized 2:1 to receive oral Compound 1 120 mg once daily following a loading dose of 360 mg on Day 1 or leuprolide acetate 3-M depot 22.5 mg (or 11.25 mg in some Asian countries), plus an antiandrogen for the first 4 weeks or longer if indicated in the opinion of the investigator. Randomization will be stratified by geographic region, presence of metastatic disease, and age.

Approximately 1125 patients will be enrolled in this study from approximately 200 study centers in North and South America, Europe, and the Asia-Pacific region. The study includes a Screening Period of up to 28 days, a Treatment Period of 48 weeks, and a Follow-up Period of up to 90 days (with visits at 30 and 60 days after the treatment period ends). Additionally, unscheduled follow-up visit(s) may be arranged for patients with study-related safety concerns as needed. Eligible patients will receive study treatment for 48 weeks. During that time, testosterone and PSA will be assessed monthly and patient-reported outcomes (European Organisation of Research and Treatment of Cancer [EORTC] QLQ-C30, European Quality of Life 5-Dimension 5-Level questionnaire [EuroQol EQ-5D-5L]) will be assessed approximately every 3 months during the Treatment Period and more frequently during the Follow-up Period. Additional serum endocrine evaluations will include: LH, FSH, dihydrotestosterone, and sex hormone binding globulin. Compound 1 pharmacokinetic (PK) samples will be collected throughout the study. Full PK profiles will be determined in a subset of patients in Asia. Time to testosterone recovery will be measured in approximately 100 patients randomized to Compound 1 and approximately 50 patients randomized to leuprolide acetate who complete 48 weeks of treatment and who do not plan to start alternative androgen deprivation therapy within the following 12 weeks (or within 24 weeks following the last injection of leuprolide acetate 3-M depot). Safety assessments will include treatment-emergent adverse events, vital signs, physical examinations, clinical laboratory tests, 12-lead electrocardiograms (ECG), and visual acuity tests.

Patients with disease progression during the treatment period, in the setting of testosterone suppression to castrate levels (testosterone level ≤50 ng/dL [1.7 nmol/L]), should remain on study and may receive additional oral therapy, systemic antineoplastic, and/or radiotherapy as prescribed by the investigator.

The primary endpoint of the study is sustained castration rate defined as the cumulative probability of testosterone suppression to ≤50 ng/dL (1.7 nmol/L) while on study treatment from Week 5 Day 1 (Study Day 29) through Week 49 Day 1 (Study Day 337).

Secondary Endpoints Include:

- Castration rate defined as the cumulative probability of testosterone suppression to ≤50 ng/dL (1.7 nmol/L) prior to dosing on Week 1 Day 4, prior to dosing on Week 2, and prior to dosing on Week 3;
- Profound castration rate defined as the cumulative probability of testosterone suppression to ≤20 ng/dL (0.7 nmol/L) while on study treatment from Week 25 Day 1 through Week 49 Day 1;
- Time to testosterone recovery in the first 100 patients randomized to Compound 1, or a pharmaceutically acceptable salt thereof, and the first 50 patients randomized to leuprolide acetate who complete 48 weeks of treatment and who do not plan to start alternative androgen deprivation therapy within the following 12 weeks (or within 24 weeks following the last injection of leuprolide acetate 3-M depot);
- Proportion of patients with confirmed PSA response by Prostate Cancer Clinical Trials Working Group 3 guidelines at the Week 2 and 5 visits;
- Proportion of patients with PSA concentration <0.2 ng/ml (0.2 μg/L) at the Week 25 visit;
- Absolute values and changes from baseline in the scores of the EORTC-QLQ-C30 global health domain, and the EORTC-QLQ-PR25 sexual activity and hormonal-treatment-related symptom subdomains, at regular intervals during treatment, and as applicable during the Follow-up and/or at End of Treatment visits;
- Absolute values and changes from baseline of the remaining domains in the EORTC QLQ-C30 and EORTC QLQ-PR25, as well as the EuroQol EQ-5D-5L questionnaire, at regular intervals during treatment, and as applicable during the Follow-up visits;
- Incidence of adverse events;
- Incidence of abnormalities in clinical laboratory data;
- Endocrine marker effects of Compound 1 and leuprolide acetate as measured as absolute value and change from baseline for: LH at the Week 2, Week 3, and Week 5 visits, and then every 4 weeks until the last follow-up visit; FSH at the Week 5, Week 13, Week 25, Week 37, and Week 49 visits; Dihydrotestosterone at the Week 5, Week 13, Week 25, Week 37, and Week 49 visits; and Sex hormone binding globulin at the Week 13, Week 25, and Week 49 visits;
- Predose Compound 1 plasma concentrations;
- Single and repeat-dose plasma Compound 1 PK parameters such as maximum plasma concentration ($C_{max}$), area under the concentration-time curve from time 0 to the end of the dosing interval ($AUC_{0-\tau}$), and time to maximum plasma concentration ($t_{max}$) in a subset of patients from Asia during the Day 1 visit.

Exploratory Endpoints Include:

- Overall survival defined as time from randomization to date of death prior to data cutoff date; and
- The presence of polymorphisms in germline genes related to the hypothalamic-pituitary-androgen pathway, prostate cancer risk, or to drug metabolizing enzymes and transporter proteins that might be implicated in the drug disposition, safety, or efficacy of Compound 1.

EXEMPLARY EMBODIMENTS

Some embodiments of this disclosure relate to Embodiment I, as follows:

Embodiment I-1. A method for treating prostate cancer in a subject in need of an increase in serum testosterone levels to a level above 50 ng/dL, the method comprising administering to the subject once-daily an oral formulation comprising about 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, wherein when the once-daily administration is suspended for a suspension period, the subject experiences an increase of serum testosterone levels.

Embodiment I-2. A method for treating prostate cancer in a subject in need thereof, the method comprising:

- administering to the subject once-daily an oral formulation comprising about 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof;
- suspending administration of the oral formulation for a suspension period to allow for an increase of serum testosterone levels; and
- resuming administering to the subject once-daily the oral formulation at the end of the suspension period.

Embodiment I-3. The method of embodiment I-1, wherein after the suspension period, administration is not resumed.

Embodiment I-4. The method of embodiment I-2, wherein the serum testosterone level increases to above medical castration level.

Embodiment I-5. The method of any one of the preceding embodiments, wherein the serum testosterone level increases to greater than about 55 ng/dL.

Embodiment I-6. The method of any one of the preceding embodiments, wherein the serum testosterone level increases to greater than about 350 ng/dL.

Embodiment I-7. The method of any one of embodiments I-1 through I-3, wherein the serum testosterone level increases to about 300 ng/dL to about 600 ng/dL.

Embodiment I-8. The method of any one of the preceding embodiments, wherein the serum testosterone level increases to the subject's serum testosterone level prior to administration of the oral formulation.

Embodiment I-9. The method of embodiment I-8, wherein the serum testosterone level increases to the subject's serum testosterone level prior to administration of the oral formulation within 7 days of the beginning of the suspension period.

Embodiment I-10. The method of embodiment I-8, wherein the serum testosterone level increases to the subject's serum testosterone level prior to administration of the oral formulation within 45 days of the beginning of the suspension period.

Embodiment I-11. The method of any one of the preceding embodiments, wherein the serum testosterone level increase occurs within 7 days of the beginning of the suspension period.

Embodiment I-12. The method of any one of the preceding embodiments, wherein the prostate cancer is hormone dependent prostate cancer.

Embodiment I-13. The method of any one of the preceding embodiments, wherein the prostate cancer is advanced prostate cancer.

Embodiment I-14. The method of any one of the preceding embodiments, wherein the prostate cancer is metastatic, non-metastatic, locally advanced, advanced hormone sensitive, advanced castration resistant, or recurrent.

Embodiment I-15. The method of any one of the preceding embodiments, wherein said administering comprises administration once-daily of an oral load dose formulation of from about 240 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for 1-3 days at the beginning of treatment.

Embodiment I-16. The method of any one of the preceding embodiments, wherein said administering comprises administration once-daily of an oral load dose formulation of from about 240 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for 1-3 days at the beginning of treatment after the suspension period.

Embodiment I-17. The method of any one of the preceding embodiments, wherein said administering comprises administration once-daily of an oral maintenance dose formulation of from about 80 mg to about 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-18. The method of embodiment I-17, wherein the oral maintenance dose formulation administration begins on the day after administering the last dose of the oral load dose formulation.

Embodiment I-19. The method of any one of embodiments I-1 through I-18, wherein said suspension period is up to 52 weeks.

Embodiment I-20. The method of any one of embodiments I-1 through I-18, wherein said suspension period is up to 36 weeks.

Embodiment I-21. The method of any one of embodiments I-1 through I-18, wherein said suspension period is up to 24 weeks.

Embodiment I-22. The method of any one of embodiments I-1 through I-18, wherein said suspension period is up to 12 weeks.

Embodiment I-23. The method of any one of embodiments I-1 through I-18, wherein said suspension period is up to 8 weeks.

Embodiment I-24. The method of any one of embodiments I-1 through I-18, wherein said suspension period is up to 4 weeks.

Embodiment I-25. The method of any one of the preceding embodiments, wherein the suspension period is discontinued when the subject's prostate-specific antigen (PSA) level is ≥20% of the subject's PSA level of the nadir during treatment.

Embodiment I-26. The method of any one of the preceding embodiments, wherein the suspension period is discontinued when the subject's PSA level is ≥50% of the subject's PSA level prior to treatment.

Embodiment I-27. The method of any one of the preceding embodiments, wherein the suspension period is discontinued when the subject's PSA level is greater than the subject's PSA level at the beginning of the suspension period.

Embodiment I-28. The method of any one of the preceding embodiments, wherein the suspension period is discontinued when the subject experiences return of symptoms of prostate cancer.

Embodiment I-29. The method of any one of the preceding embodiments, wherein the suspension period is discontinued when the subject's PSA level is ≥3 ng/mL.

Embodiment I-30. The method of any one of the preceding embodiments, wherein the suspension period is discontinued when the subject's PSA level is ≥10 ng/ml.

Embodiment I-31. The method of any one of the preceding embodiments, wherein the suspension period is discontinued when the subject's PSA level is ≥20 ng/mL.

Embodiment I-32. The method of any one of the preceding embodiments, wherein the suspension period is discontinued when the subject's PSA level is ≥30 ng/ml.

Embodiment I-33. The method of any one of the preceding embodiments, wherein the oral formulation is administered for 12 consecutive weeks or greater.

Embodiment I-34. The method of any one of the preceding embodiments, wherein the oral formulation is administered for 24 consecutive weeks or greater.

Embodiment I-35. The method of any one of the preceding embodiments, wherein the oral formulation is administered for 48 consecutive weeks or greater.

Embodiment I-36. The method of any one of the preceding embodiments, wherein the oral formulation is administered for 52 consecutive weeks or greater.

Embodiment I-37. The method of any one of the preceding embodiments, wherein the oral formulation is administered for 72 consecutive weeks or greater.

Embodiment I-38. The method of any one of the preceding embodiments, wherein the oral formulation is administered for 96 consecutive weeks or greater.

Embodiment I-39. The method of any one of embodiments I-1 through I-32, wherein administration is suspended after at least 24 consecutive weeks of treatment.

Embodiment I-40. The method of embodiment I-39, wherein administration is suspended after at least 36 consecutive weeks of treatment.

Embodiment I-41. The method of embodiment I-39, wherein administration is suspended after at least 52 consecutive weeks of treatment.

Embodiment I-42. The method of any one of the preceding embodiments, wherein the subject is in need of an increase in serum testosterone levels due to an intercurrent illness, receiving radiation therapy, while bedridden, having suffered an injury, having a surgical procedure or other invasive procedure, or a desire for a period of restored sexual function.

Embodiment I-43. The method of any one of embodiments I-1 through I-41, wherein the subject is in need of an increase in serum testosterone levels due to an intercurrent illness or surgical or other invasive procedure with projected full recovery time of at least two weeks.

Embodiment I-44. The method of embodiment I-42 or I-43, wherein administration is suspended prior to the surgical or other invasive procedure or radiation therapy.

Embodiment I-45. The method of embodiment I-42 or I-43, wherein administration is suspended after the surgical or other invasive procedure, injury, or radiation therapy.

Embodiment I-46. The method of any one of embodiments I-42 through I-45, wherein administration is suspended during the surgical or other invasive procedure, injury, or radiation therapy.

Embodiment I-47. The method of embodiment I-42 or I-43, wherein administration occurs prior to and during the surgical or other invasive procedure or radiation therapy and administration is suspended after the surgery or other invasive procedure or radiation therapy.

Embodiment I-48. The method of any one of embodiments I-42 through I-47, wherein the surgical procedure is heart surgery, knee replacement, hip replacement, abdominal surgery, pelvic surgery, vascular surgery, spine surgery, or an emergency procedure due to injury.

Embodiment I-49. The method of any one of embodiments I-42 through I-48, wherein the subject is identified as at risk for acute postoperative frailty.

Embodiment I-50. The method of embodiment I-42 or I-43, wherein administration is suspended during the intercurrent illness or while the subject is bedridden.

Embodiment I-51. The method of any one of embodiments I-43 through I-49, wherein administration resumes after the subject is recovered from the intercurrent illness, is no longer bedridden, has resumed normal activities of daily living, or has regained a normal level of function.

Embodiment I-52. The method of any one of the preceding embodiments, wherein the serum testosterone level is above medical castration levels within 7 days of the suspension of administration.

Embodiment I-53. The method of any one of embodiments I-15 through I-52, wherein the oral load dose formulation comprises about 240 mg, about 360 mg, or about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-54. The method of embodiment I-53, wherein the oral load dose formulation comprises about 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-55. The method of any one of embodiments I-17 through I-54, wherein the oral maintenance dose formulation comprises about 80 mg, about 120 mg, or about 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-56. The method of embodiment I-55, wherein the oral maintenance dose formulation comprises about 120 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-57. The method any one of embodiments I-17 through I-54, wherein the oral load dose formulation comprises about 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and is administered once on day 1 of treatment, and the oral maintenance formulation comprises about 120 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and is administered once-daily.

Embodiment I-58. The method of any one of embodiments I-1 through I-14 or I-19 through I-52, wherein the oral formulation comprises about 80 mg to about 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-59. The method of any one of the preceding embodiments, wherein the administering is pre-prandial.

Embodiment I-60. The method of any one of the preceding embodiments, wherein the administering is at least 1 hour before eating or at least 2 hours after eating.

Embodiment I-61. The method of any one of embodiments I-1 through I-58, wherein the administering is at least 30 minutes before eating or while subject is fasting.

Embodiment I-62. The method of any one of the preceding embodiments, wherein the oral formulation, oral load dose formulation and oral maintenance dose formulation are immediate release formulations.

Embodiment I-63. The method of any one of embodiments I-17 through I-52, wherein the oral maintenance dose formulation comprises 102 mg to 204 mg of mannitol, 6 mg to 12 mg of hydroxypropyl cellulose, 10 mg to 20 mg of sodium starch glycolate, and 2 mg to 4 mg of magnesium stearate.

Embodiment I-64. The method of any one of the preceding embodiments, further comprising administering an anti-androgen.

Embodiment I-65. The method of embodiment I-64, wherein the anti-androgen is selected from the group consisting of flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine.

Embodiment I-66. The method of any one of the preceding embodiments, further comprising administering a CYP17 lyase inhibitor.

Embodiment I-67. The method of embodiment I-66, wherein the CYP17 lyase inhibitor is abiraterone.

Embodiment I-68. The method of any one of the preceding embodiments, wherein the subject's serum testosterone level is suppressed prior to and after the suspension of administration.

Embodiment I-69. The method of any one of embodiments I-1 through I-63 or I-66 through I-68, wherein the method does not comprise administration of an anti-androgen.

Embodiment I-70. The method of any one of the preceding embodiments, wherein the method does not comprise administration of prednisone.

Embodiment I-71. The method of any one of embodiments I-1 through I-69, wherein the method further comprises administration of prednisone.

Embodiment I-72. The method of any one of the preceding embodiments, further comprising the step of suspending administration for a subsequent suspension period after completion of the suspension period and resumption of administration.

Embodiment I-73. The method of embodiment I-72, wherein the subsequent suspension period occurs at least 12 weeks after resuming once-daily administration of the oral formulation comprising about 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-74. The method any one of the preceding embodiments, wherein the prostate cancer is castration-resistant metastatic prostate cancer.

Embodiment I-75. The method any one of the preceding embodiments, wherein the prostate cancer is castration-resistant non-metastatic prostate cancer.

Embodiment I-76. The method any one of the preceding embodiments, wherein the prostate cancer is hormone-sensitive metastatic prostate cancer.

Embodiment I-77. The method any one of the preceding embodiments, wherein the prostate cancer is hormone-sensitive non-metastatic prostate cancer.

Embodiment I-78. The method of any one of the preceding embodiments, wherein within about 4 to about 8 days of first administering the oral formulation, or oral load dose formulation and oral maintenance dose formulation, the serum testosterone levels in the subject are at or below medical castration level.

Embodiment I-79. The method of embodiment I-78, wherein within 4 days of first administering the oral formulation, or oral load dose formulation and oral maintenance dose formulation, the serum testosterone levels in the subject are at or below medical castration level.

Embodiment I-80. An oral formulation comprising about 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for use in a method of treating prostate cancer in a subject in need thereof.

Embodiment I-81. The formulation for use according to Embodiment I-80, wherein the subject is in need of an increase in serum testosterone levels to a level above 50 ng/dL.

Embodiment I-82. The formulation for use according to Embodiment I-80 or Embodiment I-81, wherein the method comprises administering the oral formulation to the subject once daily.

Embodiment I-83. The formulation for use according to any one of Embodiment I-80 to Embodiment I-82, wherein when the once daily administration is suspended for a suspension period, the subject experiences an increase of serum testosterone levels.

Embodiment I-84. The formulation for use according to Embodiment I-83, wherein after the suspension period, administration is not resumed.

Embodiment I-85. An oral formulation comprising about 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for use in a method for treating prostate cancer in a subject in need thereof, the method comprising:

administering the oral formulation to the subject once daily;

suspending administration of the oral formulation for a suspension period to allow for an increase of serum testosterone levels; and resuming administering to the subject once daily the oral formulation at the end of the suspension period.

Embodiment I-86. The formulation for use according to Embodiment I-85, wherein the increase in serum testosterone level is an increase to above medical castration level.

Embodiment I-87. The formulation for use according to any one of Embodiments I-80 to I-86, wherein the increase in serum testosterone level is an increase to greater than about 55 ng/dL.

Embodiment I-88. The formulation for use according to any one of Embodiments I-80 to I-87, wherein the increase in serum testosterone level is an increase to greater than about 350 ng/dL.

Embodiment I-89. The formulation for use according to any one of Embodiments I-80 to I-86, wherein the increase in serum testosterone level is an increase to about 300 ng/dL to about 600 ng/dL.

Embodiment I-90. The formulation for use according to any one of Embodiments I-80 to I-89, wherein the prostate cancer is hormone dependent prostate cancer.

Embodiment I-91. The formulation for use according to any one of Embodiments I-80 to I-90, wherein the prostate cancer is advanced prostate cancer.

Embodiment I-92. The formulation for use according to any one of Embodiments I-80 to I-91, wherein the prostate cancer is metastatic, non-metastatic, locally advanced, advanced hormone sensitive, advanced castration resistant, or recurrent.

Embodiment I-93. The formulation for use according to any one of Embodiments I-80 to I-92, wherein said administering comprises administration once daily of an oral load dose formulation of from about 240 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for 1-3 days at the beginning of treatment.

Embodiment I-94. The formulation for use according to any one of Embodiments I-80 to I-93, wherein said administering comprises administration once daily of an oral load dose formulation of from about 240 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, for 1-3 days at the beginning of treatment after the suspension period.

Embodiment I-95. The formulation for use according to any one of Embodiments I-80 to I-94, wherein said administering comprises administration once daily of an oral maintenance dose formulation of from about 80 mg to about 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-96. The formulation for use according to Embodiment I-95, wherein the oral maintenance dose formulation administration begins on the day after administering the last dose of the oral load dose formulation.

Embodiment I-97. The formulation for use according to any one of Embodiments I-80 to I-96, wherein said suspension period is up to 52 weeks.

Embodiment I-98. The formulation for use according to any one of Embodiments I-80 to I-96, wherein said suspension period is up to 36 weeks.

Embodiment I-99. The formulation for use according to any one of Embodiments I-80 to I-96, wherein said suspension period is up to 24 weeks.

Embodiment I-100. The formulation for use according to any one of Embodiments I-80 to I-96, wherein said suspension period is up to 12 weeks.

Embodiment I-101. The formulation for use according to any one of Embodiments I-80 to I-96, wherein said suspension period is up to 8 weeks.

Embodiment I-102. The formulation for use according to any one of Embodiments I-80 to I-96, wherein said suspension period is up to 4 weeks.

Embodiment I-103. The formulation for use according to any one of Embodiments I-80 to I-102, wherein the suspension period is discontinued when the subject's prostate-specific antigen (PSA) level is ≥20% of the subject's PSA level of the nadir during treatment.

Embodiment I-104. The formulation for use according to any one of Embodiments I-80 to I-103, wherein the suspension period is discontinued when the subject's PSA level is ≥50% of the subject's PSA level prior to treatment.

Embodiment I-105. The formulation for use according to any one of Embodiments I-80 to I-104, wherein the suspension period is discontinued when the subject's PSA level is greater than the subject's PSA level at the beginning of the suspension period.

Embodiment I-106. The formulation for use according to any one of Embodiments I-80 to I-105, wherein the suspension period is discontinued when the subject experiences return of symptoms of prostate cancer.

Embodiment I-107. The formulation for use according to any one of Embodiments I-80 to I-106, wherein the suspension period is discontinued when the subject's PSA level is ≥3 ng/ml.

Embodiment I-108. The formulation for use according to any one of Embodiments I-80 to I-107, wherein the suspension period is discontinued when the subject's PSA level is ≥10 ng/ml.

Embodiment I-109. The formulation for use according to any one of Embodiments I-80 to I-108, wherein the suspension period is discontinued when the subject's PSA level is ≥20 ng/ml.

Embodiment I-110. The formulation for use according to any one of Embodiments I-80 to I-109, wherein the suspension period is discontinued when the subject's PSA level is ≥30 ng/ml.

Embodiment I-111. The formulation for use according to any one of Embodiments I-80 to I-110, wherein the oral formulation is administered for 12 consecutive weeks or greater.

Embodiment I-112. The formulation for use according to any one of Embodiments I-80 to I-111, wherein the oral formulation is administered for 24 consecutive weeks or greater.

Embodiment I-113. The formulation for use according to any one of Embodiments I-80 to I-112, wherein the oral formulation is administered for 48 consecutive weeks or greater.

Embodiment I-114. The formulation for use according to any one of Embodiments I-80 to I-113, wherein the oral formulation is administered for 52 consecutive weeks or greater.

Embodiment I-115. The formulation for use according to any one of Embodiments I-80 to I-114, wherein the oral formulation is administered for 72 consecutive weeks or greater.

Embodiment I-116. The formulation for use according to any one of Embodiments I-80 to I-115, wherein the oral formulation is administered for 96 consecutive weeks or greater.

Embodiment I-117. The formulation for use according to any one of Embodiments I-80 to I-110, wherein administration is suspended after at least 24 consecutive weeks of treatment.

Embodiment I-118. The formulation for use according to Embodiment I-117, wherein administration is suspended after at least 36 consecutive weeks of treatment.

Embodiment I-119. The formulation for use according to Embodiment I-117, wherein administration is suspended after at least 52 consecutive weeks of treatment.

Embodiment I-120. The formulation for use according to any one of Embodiments I-93 to I-119, wherein the oral load dose formulation comprises about 240 mg, about 360 mg, or about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-121. The formulation for use according to Embodiment I-120, wherein the oral load dose formulation comprises about 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-122. The formulation for use according to any one of Embodiments I-95 to I-121, wherein the oral maintenance dose formulation comprises about 80 mg, about 120 mg, or about 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-123. The formulation for use according to Embodiment I-122, wherein the oral maintenance dose formulation comprises about 120 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-124. The formulation for use according to any one of Embodiments I-95 to I-121, wherein the oral load dose formulation comprises about 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and is administered once on day 1 of treatment, and the oral maintenance formulation comprises about 120 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and is administered once daily.

Embodiment I-125. The formulation for use according to any one of Embodiments I-80 to I-92 or Embodiments I-97 to I-119, wherein the oral formulation comprises about 80 mg to about 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-126. The formulation for use according to any one of Embodiments I-80 to I-125, wherein the administering is pre-prandial.

Embodiment I-127. The formulation for use according to any one of Embodiments I-80 to I-126, wherein the administering is at least 1 hour before eating or at least 2 hours after eating.

Embodiment I-128. The formulation for use according to any one of Embodiments I-80 to I-125, wherein the administering is at least 30 minutes before eating or while subject is fasting.

Embodiment I-129. The formulation for use according to any one of Embodiments I-80 to I-128, wherein the oral formulation, oral load dose formulation and oral maintenance dose formulation are immediate release formulations.

Embodiment I-130. The formulation for use according to any one of Embodiments I-95 to I-119, wherein the oral maintenance dose formulation comprises 102 mg to 204 mg of mannitol, 6 mg to 12 mg of hydroxypropyl cellulose, 10 mg to 20 mg of sodium starch glycolate, and 2 mg to 4 mg of magnesium stearate.

Embodiment I-131. The formulation for use according to any one of Embodiments I-80 to I-130, wherein the method further comprises administering an anti-androgen.

Embodiment I-132. The formulation for use according to Embodiment I-131, wherein the anti-androgen is selected from the group consisting of flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), and cimetidine.

Embodiment I-133. The formulation for use according to any one of the Embodiments I-80 to I-132, wherein the method further comprises administering a CYP17 lyase inhibitor.

Embodiment I-134. The formulation for use according to Embodiment I-133, wherein the CYP17 lyase inhibitor is abiraterone.

Embodiment I-135. The formulation for use according to any one of Embodiments I-80 to I-130 or I-133 to I-134, wherein the method does not comprise administration of an anti-androgen.

Embodiment I-136. The formulation for use according to any one of Embodiments I-80 to I-135, wherein the method does not comprise administration of prednisone.

Embodiment I-137. The formulation for use according to any one of Embodiments I-80 to I-135, wherein the method further comprises administration of prednisone.

Embodiment I-138. The formulation for use according to any one of Embodiments I-80 to I-137, wherein the method further comprises the step of suspending administration for a subsequent suspension period after completion of the suspension period and resumption of administration.

Embodiment I-139. The formulation for use according to Embodiment I-138, wherein the subsequent suspension period occurs at least 12 weeks after resuming once daily administration of the oral formulation comprising about 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment I-140. The formulation for use according to any one of Embodiments I-80 to I-139, wherein the prostate cancer is castration-resistant metastatic prostate cancer.

Embodiment I-141. The formulation for use according to any one of Embodiments I-80 to I-140, wherein the prostate cancer is castration-resistant non-metastatic prostate cancer.

Embodiment I-142. The formulation for use according to any one of Embodiments I-80 to I-141, wherein the prostate cancer is hormone-sensitive metastatic prostate cancer.

Embodiment I-143. The formulation for use according to any one of Embodiments I-80 to I-142, wherein the prostate cancer is hormone-sensitive non-metastatic prostate cancer.

Embodiment I-144. Use of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a pharmaceutically acceptable salt thereof, for the manufacture of a medicament for the treatment of prostate cancer.

Embodiment I-145. The use according to Embodiment I-144, wherein the prostate cancer is hormone dependent prostate cancer.

Embodiment I-146. The use according to Embodiment I-144, wherein the prostate cancer is advanced prostate cancer.

Embodiment I-147. The use according to Embodiment I-144, wherein the prostate cancer is metastatic, non-metastatic, locally advanced, advanced hormone sensitive, advanced castration resistant, or recurrent.

Embodiment I-148. The use according to Embodiment I-144, wherein the prostate cancer is castration-resistant metastatic prostate cancer.

Embodiment I-149. The use according to Embodiment I-144, wherein the prostate cancer is castration-resistant non-metastatic prostate cancer.

Embodiment I-150. The use according to Embodiment I-144, wherein the prostate cancer is hormone-sensitive metastatic prostate cancer.

Embodiment I-151. The use according to Embodiment I-144, wherein the prostate cancer is hormone-sensitive non-metastatic prostate cancer.

Embodiment I-152. The use according to any one of Embodiments I-144 to I-151, wherein the medicament comprises 80 mg to about 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of the pharmaceutically acceptable salt thereof.

Some embodiments of this disclosure relate to Embodiment II, as follows:

Embodiment II-1. The method of any one of embodiments I-1 through I-78, wherein a PK profile in which mean plasma $AUC_{(0-tau)}$ increases at least 1.5 fold when measured from the first to last day of administration is achieved.

Embodiment II-2. The method of any one of embodiments I-1 through I-78, wherein a PK profile in which mean $C_{max}$ increases at least 2 fold when measured from the first to last day of administration is achieved.

Embodiment II-3. The method according to embodiment II-1, wherein the increase is at least 1.5 fold is 2 fold or greater.

Embodiment II-4. The method of any one of embodiments II-1 through II-3, wherein the administering is without any fasting requirement.

Embodiment II-5. The method of any one of embodiments II-1 through II-3, wherein mean $C_{max}$ is higher with preprandial administration than with postprandial administration.

Embodiment II-6. The method of any one of embodiments II-1 through II-3, wherein mean plasma $AUC_{(0-tau)}$ is higher with preprandial administration than with postprandial administration after at least 30 minutes.

Embodiment II-7. The method of any one of embodiments I-1 through I-78 or embodiments II-1 through II-6, wherein the oral formulation includes at least one excipient that improves stability while maintaining load capacity.

Embodiment II-8. The method of any one of embodiments I-1 through I-78 or embodiments II-1 through II-7, wherein the oral formulation is a tablet.

Embodiment II-9. The method of any one of embodiments II-1 through II-3, wherein mean plasma $T_{1/2}$ is about 37 to about 42 hours measured at the end of administration.

Embodiment II-10. The method of any one of embodiments II-1 through II-3, wherein mean $C_{max}$ is achieved between 1 and 2 hours ($T_{max}$) after beginning administration.

Embodiment II-11. The method of any one of embodiments II-1 through II-3, wherein steady state is reached within 10 days after beginning administration.

Embodiment II-12. The method of any one of embodiments II-1 through II-3, wherein prostate-specific antigen (PSA) is suppressed in the subject to a level less than or equal to 4 ng/mL.

Embodiment II-13. The method of any one of embodiments II-1 through II-3, wherein prostate-specific antigen (PSA) is suppressed in the subject to a level less than or equal to 2 ng/mL.

Embodiment II-14. The method of any one of embodiments II-1 through II-3, wherein less than 4% of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof is excreted unchanged in urine of the subject, measured at day 14 or day 28 after commencing administration.

Embodiment II-15. The method of any one of embodiments II-1 through II-3, wherein medical castration levels of less than or equal to 50 ng/dl (1.73 nmol/L) serum testosterone are achieved and maintained from day 14 to day 28 after commencing administration.

Embodiment II-16. The method of any one of embodiments II-1 through II-15, wherein following administering once-daily an oral load dose formulation of 360 mg, or a corresponding amount of a pharmaceutically acceptable salt thereof, and oral maintenance dose formulations of 120 mg, or a corresponding amount of a pharmaceutically acceptable salt thereof, for 48 consecutive weeks, medical castration levels of less than or equal to 50 ng/dl (1.73 nmol/L) serum testosterone are achieved by the beginning of week 5 and maintained through the end of week 48.

Embodiment II-17. The method of any one of embodiments II-1 through II-15, wherein following administering once-daily oral maintenance dose formulations of 80 mg or 120 mg, or a corresponding amount of a pharmaceutically acceptable salt thereof, for 13 consecutive weeks, change from baseline in mean serum PSA concentration at the end of 13 consecutive weeks is a 8 to 12 fold reduction for the 80 mg dose and a 9 to 13 fold reduction for the 120 mg dose.

Embodiment II-18. The method of any one of embodiments II-1 through II-15, wherein following administering once-daily oral maintenance dose formulations of 80 mg or 120 mg, or a corresponding amount of a pharmaceutically acceptable salt thereof, for 25 consecutive weeks, median trough plasma concentration ($C_{min}$) of unchanged N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof ranges between 2.0 ng/mL and 8.0 ng/mL for the 80 mg dose and between 4.0 ng/mL and 12.0 ng/ml for the 120 mg dose.

Embodiment II-19. The method of any one of embodiments II-1 through II-3, wherein the administering results in $C_{min}$ being maintained constant over administration.

Embodiment II-20. The method of any one of embodiments II-1 through II-15, wherein following administering once-daily oral maintenance dose formulations of 80 mg or 180 mg, or a corresponding amount of a pharmaceutically acceptable salt thereof, for 16 consecutive days, change from baseline in mean serum luteinizing hormone (LH) concentration at the end of 16 consecutive days is a 12 to 16 fold reduction for the 80 mg dose and a 15 to 19 fold reduction for the 180 mg dose.

Embodiment II-21. The method of any one of embodiments II-1 through II-15, wherein following administering once-daily oral maintenance dose formulations of 80 mg or 180 mg, or a corresponding amount of a pharmaceutically acceptable salt thereof, for 16 consecutive days, change from baseline in mean serum testosterone concentration at the end of 16 consecutive days is a 27 to 31 fold reduction for the 80 mg dose and a 22 to 26 fold reduction for the 180 mg dose.

Embodiment II-22. The method of any one of embodiments II-1 through II-15, wherein following administering once-daily oral maintenance dose formulations of 80 mg or 180 mg, or a corresponding amount of a pharmaceutically acceptable salt thereof, for 16 consecutive days, change from baseline in mean serum follicle stimulating hormone (FSH) concentration at the end of 16 consecutive days is a 7 to 11 fold reduction for the 80 mg dose and a 10 to 14 fold reduction for the 180 mg dose.

Embodiment II-23. The method of any one of embodiments II-1 through II-15, wherein following administering once-daily oral maintenance dose formulations of 80 mg or 180 mg, or a corresponding amount of a pharmaceutically acceptable salt thereof, for 16 consecutive days, change from baseline in mean serum dihydrotestosterone (DHT) concentration at the end of 16 consecutive days is a 1.1 to 3 fold reduction for the 80 mg dose and a 1.1 to 4 fold reduction for the 180 mg dose.

Embodiment II-24. The method of any one of embodiments II-1 through II-3, wherein the administering is such that there is no stimulation of sex hormones, and thereby clinical flare is prevented or minimized.

Embodiment II-25. A method for treating hormone dependent prostate cancer in a subject, the method comprising:

administering to the subject once-daily for at least one day for a first treatment period, an oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; and administering to the subject once-daily for 24 consecutive weeks or greater for a second treatment period, an oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof;

wherein the oral maintenance dose formulation has a PK profile in which mean plasma $AUC_{(0-tau)}$ increases at least 1.5 fold when measured from the first day of the first treatment period to last day of the second treatment period.

Embodiment II-26. A method for treating hormone dependent prostate cancer in a subject, the method comprising:

administering to the subject once-daily for at least one day for a first treatment period, an oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; and administering to the subject once-daily for 24 consecutive weeks or greater for a second treatment period, an oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof;

wherein the oral maintenance dose formulation has a PK profile in which mean $C_{max}$ increases at least 2 fold when measured from the first day of the first treatment period to last day of the second treatment period.

Embodiment II-27. A method for suppressing one or more sex hormones in a subject having hormone dependent prostate cancer, the method comprising:

administering to the subject once-daily for at least one day for a first treatment period, an oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; and administering to the subject once-daily for 24 consecutive weeks or greater for a second treatment period, an oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof;

wherein the oral maintenance dose formulation has a PK profile in which mean plasma $AUC_{(0-tau)}$ increases at least 1.5 fold when measured from the first day of the first treatment period to last day of the second treatment period.

Embodiment II-28. A method for suppressing one or more sex hormones in a subject having hormone dependent prostate cancer, the method comprising:

administering to the subject once-daily for at least one day for a first treatment period, an oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof; and administering to the subject once-daily for 24 consecutive weeks or greater for a second treatment period, an oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof;

wherein the oral maintenance dose formulation has a PK profile in which mean $C_{max}$ increases at least 2 fold when measured from the first day of the first treatment period to last day of the second treatment period.

Embodiment II-29. The method of embodiments II-25 or II-27, wherein at least 1.5 fold is 2 fold or greater.

Embodiment II-30. The method of any one of embodiments II-25 through II-29, wherein the first treatment period is 1 day or greater.

Embodiment II-31. The method of any one of embodiments II-25 through II-29, wherein the first treatment period is 2 days or greater.

Embodiment II-32. The method of any one of embodiments II-25 through II-29, wherein the first treatment period is 3 days or greater.

Embodiment II-33. The method of any one of embodiments II-25 through II-29, wherein the second treatment period is 52 consecutive weeks or greater.

Embodiment II-34. The method of any one of embodiments II-25 through II-29, wherein the second treatment period is 72 consecutive weeks or greater.

Embodiment II-35. The method of any one of embodiments II-25 through II-29, wherein the second treatment period is 96 consecutive weeks or greater.

Embodiment II-36. The method of any one of embodiments II-25 through II-29, wherein the administering is preprandial.

Embodiment II-37. The method of any one of embodiments II-25 through II-29, wherein the administering is at least 1 hour before eating or at least 2 hours after eating.

Embodiment II-38. The method of any one of embodiments II-25 through II-29, wherein the administering is at least 30 minutes before eating or while subject is fasting.

Embodiment II-39. The method of any one of embodiments II-25 through II-29, wherein the administering is without any fasting requirement.

Embodiment II-40. The method of any one of embodiments II-25 through II-29, wherein mean $C_{max}$ is higher with preprandial administration than with postprandial administration.

Embodiment II-41. The method of any one of embodiments II-25 through II-29, wherein mean plasma $AUC_{(0-tau)}$ is higher with preprandial administration than with postprandial administration after at least 30 minutes.

Embodiment II-42. The method of any one of embodiments II-25 through II-29, wherein the oral load dose formulation and the oral maintenance dose formulation are tablets.

Embodiment II-43. The method of any one of embodiments II-25 through II-29, wherein the oral load dose formulation and the oral maintenance dose formulation have an immediate release profile.

Embodiment II-44. The method of any one of embodiments II-25 through II-29, wherein mean plasma $T_{1/2}$ is about 37 to about 42 hours measured at the end of administration.

Embodiment II-45. The method of any one of embodiments II-25 through II-29, wherein mean $C_{max}$ is achieved between 1 and 2 hours ($T_{max}$) after beginning administration.

Embodiment II-46. The method of any one of embodiments II-25 through II-29, wherein steady state is reached within 10 days after beginning administration.

Embodiment II-47. The method of any one of embodiments II-25 through II-29, wherein serum testosterone is suppressed in the subject to a castration level that is less than or equal to 50 ng/dL (1.73 nmol/L).

Embodiment II-48. The method of any one of embodiments II-25 through II-29, wherein serum testosterone is suppressed in the subject to a profound castration level that is less than or equal to 20 ng/dl (0.69 nmol/L).

Embodiment II-49. The method of any one of embodiments II-25 through II-29, wherein prostate-specific antigen (PSA) is suppressed in the subject to a level less than or equal to 4 ng/mL.

Embodiment II-50. The method of any one of embodiments II-25 through II-29, wherein prostate-specific antigen (PSA) is suppressed in the subject to a level less than or equal to 2 ng/mL.

Embodiment II-51. The method of any one of embodiments II-25 through II-29, wherein the oral load dose formulation is 240 mg, or 360 mg, or 480 mg, or a corresponding amount of a pharmaceutically acceptable salt thereof, and the oral maintenance dose formulation is 80 mg, or 120 mg, or 160 mg, or a corresponding amount of a pharmaceutically acceptable salt thereof.

Embodiment II-52. The method of any one of embodiments II-25 through II-29, wherein the oral load dose formulation is 360 mg, or a corresponding amount of a pharmaceutically acceptable salt thereof, and the oral maintenance dose formulation is 120 mg, or a corresponding amount of a pharmaceutically acceptable salt thereof.

Embodiment II-53. The method of any one of embodiments II-25 through II-29, wherein the oral load dose formulation is 360 mg, or a corresponding amount of a pharmaceutically acceptable salt thereof, and is administered on day 1 of the first treatment period, and the oral maintenance dose formulation is 120 mg, or a corresponding amount of a pharmaceutically acceptable salt thereof, administered starting on day 1 or day 2 of the second treatment period.

Embodiment II-54. The method of any one of embodiments II-25 through II-29, wherein less than 4% of the N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof is excreted unchanged in urine of the subject, measured at day 14 or day 29 after commencing the first treatment period.

Embodiment II-55. The method of any one of embodiments II-25 through II-28, wherein medical castration levels of less than or equal to 50 ng/dL (1.73 nmol/L) serum testosterone are achieved and maintained from day 14 to day 28 after commencing treatment.

Embodiment II-56. The method of any one of embodiments II-25 through II-29, wherein following administering once-daily a single oral load dose formulation of 360 mg, or a corresponding amount of a pharmaceutically acceptable salt thereof, and oral maintenance dose formulations of 120 mg, or a corresponding amount of a pharmaceutically acceptable salt thereof, for 48 consecutive weeks, medical castration levels of less than or equal to 50 ng/dl (1.73 nmol/L) serum testosterone are achieved by the beginning of week 5 and maintained through the end of week 48.

Embodiment II-57. The method of any one of embodiments II-25 through II-29, wherein following administering once-daily oral maintenance dose formulations of 80 mg or 120 mg, or a corresponding amount of a pharmaceutically acceptable salt thereof, for 13 consecutive weeks, change from baseline in mean serum PSA concentration at the end of 13 consecutive weeks is a 8 to 12 fold reduction for the 80 mg dose and a 9 to 13 fold reduction for the 120 mg dose.

Embodiment II-58. The method of any one of embodiments II-25 through II-29, wherein following administering once-daily oral maintenance dose formulations of 80 mg or 120 mg, or a corresponding amount of a pharmaceutically acceptable salt thereof, for 25 consecutive weeks, median trough plasma concentration ($C_{min}$) of unchanged N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof ranges between 2.0 ng/ml and 8.0 ng/mL for the 80 mg dose and between 4.0 ng/ml and 12.0 ng/ml for the 120 mg dose.

Embodiment II-59. The method of any one of embodiments II-25 through II-29, wherein the administering results in $C_{min}$ being maintained constant over the second treatment period.

Embodiment II-60. The method of any one of embodiments II-25 through II-29, wherein following administering once-daily oral maintenance dose formulations of 80 mg or 180 mg, or a corresponding amount of a pharmaceutically acceptable salt thereof, for 16 consecutive days, change from baseline in mean serum luteinizing hormone (LH) concentration at the end of 16 consecutive days is a 12 to 16 fold reduction for the 80 mg dose and a 15 to 19 fold reduction for the 180 mg dose.

Embodiment II-61. The method of any one of embodiments II-25 through II-29, wherein following administering once-daily oral maintenance dose formulations of 80 mg or 180 mg, or a corresponding amount of a pharmaceutically acceptable salt thereof, for 16 consecutive days, change from baseline in mean serum testosterone concentration at the end of 16 consecutive days is a 27 to 31 fold reduction for the 80 mg dose and a 22 to 26 fold reduction for the 180 mg dose.

Embodiment II-62. The method of any one of embodiments II-25 through II-29, wherein following administering once-daily oral maintenance dose formulations of 80 mg or 180 mg, or a corresponding amount of a pharmaceutically acceptable salt thereof, for 16 consecutive days, change from baseline in mean serum follicle stimulating hormone (FSH) concentration at the end of 16 consecutive days is a 7 to 11 fold reduction for the 80 mg dose and a 10 to 14 fold reduction for the 180 mg dose.

Embodiment II-63. The method of any one of embodiments II-25 through II-29, wherein following administering once-daily oral maintenance dose formulations of 80 mg or 180 mg, or a corresponding amount of a pharmaceutically acceptable salt thereof, for 16 consecutive days, change from baseline in mean serum dihydrotestosterone (DHT) concentration at the end of 16 consecutive days is a 1.1 to 3 fold reduction for the 80 mg dose and a 1.1 to 4 fold reduction for the 180 mg dose.

Embodiment II-64. The method of any one of embodiments II-25 through II-29, wherein the subject has advanced hormone dependent prostate cancer.

Embodiment II-65. The method of any one of embodiments II-25 through II-29, wherein administering can be suspended for a period of 4 weeks or less to 24 weeks or greater, after at least 24 consecutive weeks, of administration.

Embodiment II-66. The method of embodiment II-65, wherein, after administering is suspended, return to baseline serum testosterone levels in subjects is achieved within 4 weeks to 12 weeks, after the last dose.

Embodiment II-67. The method of embodiment II-65, wherein, after administering is restarted, return to castration levels in subjects are achieved within 24 hours to 48 hours.

Embodiment II-68. The method of any one of embodiments II-25 through II-29, wherein the administering is such that there is no stimulation of sex hormones, and thereby clinical flare is prevented or minimized.

Embodiment II-69. The method of any one of embodiments II-25 through II-29, wherein the prostate cancer is advanced prostate cancer.

Embodiment II-70. The method of any one of embodiments II-25 through II-29, wherein the treating is palliative and the prostate cancer is advanced prostate cancer.

Embodiment II-71. A dosage pack comprising:

a once-daily oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and excipients; and a once-daily oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and excipients;

wherein the once-daily oral maintenance dose formulation has a PK profile in which mean plasma $AUC_{(0\text{-}tau)}$ increases at least 1.5 fold when measured from the first to last day of a treatment period, wherein the treatment period of the once-daily oral maintenance dose formulations is for 24 consecutive weeks or greater.

Embodiment II-72. A dosage pack comprising:

a once-daily oral load dose formulation having from 240 mg to 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and excipients; and a once-daily oral maintenance dose formulation having 80 mg to 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and excipients;

wherein the once-daily oral maintenance dose formulation has a PK profile in which mean $C_{max}$ increases at least 2 fold when measured from the first to last day of a treatment period, wherein the treatment period of the once-daily oral maintenance dose formulations is for 24 consecutive weeks or greater.

Embodiment II-73. The dosage pack of embodiment II-71, wherein the at least 1.5 fold is 2 fold or greater.

Embodiment II-74. The dosage pack of embodiment II-71 or II-72, wherein the oral load dose formulation comprises 306 mg to 612 mg of mannitol, 18 mg to 36 mg of hydroxypropyl cellulose, 30 mg to 60 mg of sodium starch glycolate, and 6 mg to 12 mg of magnesium stearate.

Embodiment II-75. The dosage pack of embodiment II-74, wherein the oral load dose formulation further comprises 21.36 mg to 42.72 mg of hypromellose 2910, 2.4 mg to 4.8 mg of titanium dioxide, 0.24 mg to 0.48 mg of ferric oxide, and a sufficient quantity of carnauba wax.

Embodiment II-76. The dosage pack of embodiment II-71 or II-72, wherein the oral maintenance dose formulation comprises 102 mg to 204 mg of mannitol, 6 mg to 12 mg of hydroxypropyl cellulose, 10 mg to 20 mg of sodium starch glycolate, and 2 mg to 4 mg of magnesium stearate.

Embodiment II-77. The dosage pack of embodiment II-76, wherein the oral maintenance dose formulation further comprises 7.12 mg to 14.24 mg of hypromellose 2910, 0.8 mg to 1.6 mg of titanium dioxide, 0.08 mg to 0.16 mg of ferric oxide, and a sufficient quantity of carnauba wax.

Embodiment II-78. The dosage pack of embodiment II-75 or II-77, wherein the oral load dose formulation and the oral maintenance dose formulation include at least one excipient that improves stability while maintaining load capacity.

Embodiment II-79. The dosage pack of embodiment II-74 or II-76, wherein the sodium starch glycolate in the oral load dose formulation and the oral maintenance dose formulation improves stability and load capacity of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea or a pharmaceutically acceptable salt thereof in the oral load dose formulation and the oral maintenance dose formulation.

Embodiment II-80. The dosage pack of embodiment II-71 or II-72, wherein the oral load dose formulation has 240 mg, or 360 mg, or 480 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment II-81. The dosage pack of embodiment II-71 or II-72, wherein the oral maintenance dose formulation has 80 mg, or 120 mg, or 160 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment II-82. The dosage pack of embodiment II-71 or II-72, wherein the oral load dose formulation has 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof, and the oral maintenance dose formulation has 120 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea, or a corresponding amount of a pharmaceutically acceptable salt thereof.

Embodiment II-83. The dosage pack of embodiment II-71 or II-72, wherein the oral load dose formulation and the oral maintenance dose formulation are tablets.

Embodiment II-84. The dosage pack of embodiment II-71 or II-72, wherein the oral load dose formulation and the oral maintenance dose formulation have an immediate release profile.

Embodiment II-85. The dosage pack of embodiment II-71 or II-72, further comprising at least one of an anti-androgen or CYP17 lyase inhibitor.

Embodiment II-86. The dosage pack of embodiment II-85, wherein the anti-androgen comprises enzalutamide, bicalutamide, enzalutamide or flutamide, and the CYP17 lyase inhibitor comprises abiraterone.

Embodiment II-87. The dosage pack of embodiment II-71 or II-72, which is used for treating hormone dependent prostate cancer.

What is claimed is:

1. A method of treating prostate cancer in a subject in need thereof, the method comprising:

(i) orally administering a loading dose of 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea to the subject; and (ii) about one day after administering the loading dose, orally administering a 120 mg dose of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea to the subject once a day for a treatment period of 24 consecutive weeks or greater;

wherein one or more adverse cardiovascular events associated with Androgen Deprivation Therapy (ADT) in the subject are reduced.

2. The method of claim 1, wherein the prostate cancer is advanced prostate cancer.

3. The method of claim 1, wherein the reduction of one or more adverse cardiovascular events associated with ADT in the subject with prostate cancer is as compared to treatment with leuprolide.

4. The method of claim 1, wherein the subject is administered the maintenance dose once a day for a treatment period of 48 consecutive weeks or greater.

5. The method of claim 1, wherein the one or more adverse cardiovascular events is a myocardial infarction.

6. The method of claim 3, wherein the one or more adverse cardiovascular events is a myocardial infarction.

7. The method of claim 1, further comprising:

discontinuing administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea to the subject, wherein the subject's serum testosterone concentration is at least about 280 ng/dl within about 90 days after discontinuing.

8. The method of claim 1, wherein the 120 mg dose is administered with food.

9. A method of treating prostate cancer in a subject in need thereof, the method comprising:

(i) orally administering a loading dose of 360 mg of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea to the subject; and (ii) about one day after administering the loading dose, orally administering a 120 mg dose of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea to the subject once a day for a treatment period of 24 consecutive weeks or greater;

wherein the subject is at risk of a cardiovascular event associated with Androgen Deprivation Therapy (ADT).

10. The method of claim 9, wherein the prostate cancer is advanced prostate cancer.

11. The method of claim 9, wherein the administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea decreases the likelihood of developing a cardiovascular event in the subject with prostate cancer.

12. The method of claim 9, wherein the administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea decreases the likelihood of experiencing a cardiovascular event in the subject with prostate cancer.

13. The method of claim 11, wherein the decrease in likelihood of developing a cardiovascular event in the subject with prostate cancer is as compared to treatment with leuprolide.

14. The method of claim 13, wherein the cardiovascular event is a myocardial infarction.

15. The method of claim 12, wherein the decrease in likelihood of experiencing a cardiovascular event in the subject with prostate cancer is as compared to treatment with leuprolide.

16. The method of claim 15, wherein the cardiovascular event is a myocardial infarction.

17. The method of claim 9, wherein the subject is administered the maintenance dose once a day for a treatment period of 48 consecutive weeks or greater.

18. The method of claim 9, further comprising:

discontinuing administration of N-(4-(1-(2,6-difluorobenzyl)-5-((dimethylamino)methyl)-3-(6-methoxy-3-pyridazinyl)-2,4-dioxo-1,2,3,4-tetrahydrothieno[2,3-d]pyrimidin-6-yl)phenyl)-N'-methoxyurea to the subject, wherein the subject's serum testosterone concentration is at least about 280 ng/dL within about 90 days after discontinuing.

19. The method of claim 9, wherein the 120 mg dose is administered with food.

20. The method of claim 9, wherein the cardiovascular event is a myocardial infarction.

* * * * *